(12) United States Patent
Bell et al.

(10) Patent No.: US 10,759,804 B2
(45) Date of Patent: Sep. 1, 2020

(54) COMPOUNDS AND THEIR USE AS INHIBITORS OF N-MYRISTOYL TRANSFERASE

(71) Applicant: Imperial College Innovations Limited, London (GB)

(72) Inventors: Andrew Simon Bell, London (GB); Edward William Tate, London (GB); Robin John Leatherbarrow, London (GB); Jennie Ann Hutton, London (GB); James Antony Brannigan, York (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 0 days.

(21) Appl. No.: 15/739,166

(22) PCT Filed: Jun. 29, 2016

(86) PCT No.: PCT/GB2016/000134
§ 371 (c)(1),
(2) Date: Dec. 22, 2017

(87) PCT Pub. No.: WO2017/001812
PCT Pub. Date: Jan. 5, 2017

(65) Prior Publication Data
US 2018/0370974 A1    Dec. 27, 2018

(30) Foreign Application Priority Data

Jun. 29, 2015  (GB) .................................. 1511382.2

(51) Int. Cl.
| | | |
|---|---|---|
| *C07D 231/56* | (2006.01) | |
| *C07D 401/12* | (2006.01) | |
| *C07D 487/04* | (2006.01) | |
| *C07D 403/12* | (2006.01) | |
| *C07D 471/04* | (2006.01) | |
| *C07D 417/12* | (2006.01) | |
| *A61P 31/18* | (2006.01) | |
| *A61P 33/06* | (2006.01) | |
| *A61P 3/10* | (2006.01) | |
| *A61P 31/16* | (2006.01) | |
| *A61P 35/00* | (2006.01) | |

(52) U.S. Cl.
CPC .............. *C07D 487/04* (2013.01); *A61P 3/10* (2018.01); *A61P 31/16* (2018.01); *A61P 31/18* (2018.01); *A61P 33/06* (2018.01); *A61P 35/00* (2018.01); *C07D 231/56* (2013.01); *C07D 401/12* (2013.01); *C07D 403/12* (2013.01); *C07D 417/12* (2013.01); *C07D 471/04* (2013.01)

(58) Field of Classification Search
CPC ........................... C07D 231/56; C07D 401/04
See application file for complete search history.

(56) References Cited

U.S. PATENT DOCUMENTS

| | | |
|---|---|---|
| 2,917,511 A | 12/1959 | Bicking |
| 3,050,525 A | 8/1962 | Bicking |
| 3,145,215 A | 8/1964 | Kirchner |
| 3,457,269 A | 7/1969 | Kirchner |
| 3,678,059 A | 7/1972 | Gschwend et al. |
| 3,705,175 A | 12/1972 | Magdanyi et al. |
| 4,886,808 A | 12/1989 | King |
| 5,017,573 A | 5/1991 | Kon et al. |
| 5,037,844 A | 8/1991 | Hamminga et al. |
| 5,190,953 A | 3/1993 | Munson, Jr. et al. |
| 5,246,945 A | 9/1993 | Kikuchi et al. |

(Continued)

FOREIGN PATENT DOCUMENTS

| | | |
|---|---|---|
| EP | 0261964 A2 | 3/1988 |
| EP | 0494774 A1 | 7/1992 |

(Continued)

OTHER PUBLICATIONS

Abstract Book, "Emerging Paradigms in Anti-Infective Drug Design," London School of Hygiene and Tropical Medicine, British Society for Parasitology and Royal Society of Chemistry (Biological & Medicinal Chemistry Sector) Symposium, Sep. 17th and 18th, 2012, (76 pages).

Armour, D., "Discovery of a Novel Series of Non-Peptidic Fungal N-Myristoyl Transferase (NMT) Inhibitors," Slides from Pfizer, 221 ACS meeting, 2001, Medi 349, (21 pages).

Basta et al., "Modeling of the human rhinovirus C capsid suggests a novel topography with insights on receptor preference and immunogenicity," Virology, 2014, 448, pp. 176-184.

(Continued)

*Primary Examiner* — Susanna Moore
(74) *Attorney, Agent, or Firm* — Kilyk & Bowersox, P.L.L.C.

(57) ABSTRACT

This invention provides compounds of formula (I) and salts thereof, which have activity as inhibitors of N-myristoyl transferase (NMT). The invention also relates to uses of such compounds as medicaments, in particular in the treatment of a disease or disorder in which inhibition of N-myristoyl transferase provides a therapeutic or prophylactic effect, including protozoan infections (such as malaria and leishmaniasis), viral infections (such as human rhinovirus and HIV), and hyperproliferative disorders (such as B-cell lymphoma).

24 Claims, 3 Drawing Sheets

(56) References Cited

U.S. PATENT DOCUMENTS

| | | |
|---|---|---|
| 5,665,725 A | 9/1997 | Moltzen et al. |
| 5,684,003 A | 11/1997 | Kikuchi et al. |
| 5,798,367 A | 8/1998 | Catlow et al. |
| 5,861,414 A | 1/1999 | Allen et al. |
| 5,914,405 A | 6/1999 | Wilson |
| 5,985,867 A | 11/1999 | Rodgers et al. |
| 6,069,152 A | 5/2000 | Schaus et al. |
| 6,096,746 A | 8/2000 | Suzuki et al. |
| 6,303,625 B1 | 10/2001 | Hoekstra et al. |
| 6,376,491 B1 | 4/2002 | Aoki et al. |
| 6,458,781 B1 | 10/2002 | Connor et al. |
| 8,557,841 B2 | 10/2013 | Yu et al. |
| 2002/0103229 A1 | 8/2002 | Bhagwat et al. |
| 2002/0119972 A1 | 8/2002 | Leftheris et al. |
| 2002/0161022 A1 | 10/2002 | Reich et al. |
| 2003/0096838 A1 | 5/2003 | McClure et al. |
| 2003/0109550 A1 | 6/2003 | Clare et al. |
| 2003/0149034 A1 | 8/2003 | Lee et al. |
| 2003/0153507 A1 | 8/2003 | Canan-Koch et al. |
| 2003/0207883 A1 | 11/2003 | Renhowe et al. |
| 2004/0009968 A1 | 1/2004 | Binch et al. |
| 2004/0014764 A1 | 1/2004 | Smith et al. |
| 2004/0014802 A1 | 1/2004 | Dutruc-Rosset et al. |
| 2004/0053958 A1 | 3/2004 | Dombroski et al. |
| 2004/0058912 A1 | 3/2004 | Aissaoui et al. |
| 2004/0106667 A1 | 6/2004 | Damour et al. |
| 2004/0138286 A1 | 7/2004 | Imazaki et al. |
| 2004/0157877 A1 | 8/2004 | Dombroski et al. |
| 2004/0176325 A1 | 9/2004 | Munson et al. |
| 2004/0204591 A1 | 10/2004 | Kucera et al. |
| 2005/0070546 A1 | 3/2005 | Arrington et al. |
| 2005/0075365 A1 | 4/2005 | Braganza et al. |
| 2006/0004000 A1 | 1/2006 | D'Orchymont et al. |
| 2006/0035922 A1 | 2/2006 | Mathias et al. |
| 2006/0100248 A1 | 5/2006 | Garthwaite et al. |
| 2006/0135589 A1 | 6/2006 | Berdino et al. |
| 2006/0135764 A1 | 6/2006 | Fatheree et al. |
| 2006/0142345 A1 | 6/2006 | Kephart et al. |
| 2006/0281789 A1 | 12/2006 | Shiotsu et al. |
| 2006/0287324 A1 | 12/2006 | Sun et al. |
| 2007/0197522 A1 | 8/2007 | Edwards et al. |
| 2008/0039457 A1 | 2/2008 | Zhuo et al. |
| 2009/0082348 A1 | 3/2009 | Ohta et al. |
| 2009/0124612 A1 | 5/2009 | Albrecht et al. |
| 2009/0203690 A1 | 8/2009 | Akritopoulou-Zanze et al. |
| 2009/0209577 A1 | 8/2009 | Rucker et al. |
| 2009/0215817 A1 | 8/2009 | Rucker et al. |
| 2009/0247504 A1 | 10/2009 | Churcher et al. |
| 2009/0270402 A1 | 10/2009 | Calderwood et al. |
| 2009/0291968 A1 | 11/2009 | Georges et al. |
| 2009/0318436 A1 | 12/2009 | Albrecht et al. |
| 2010/0113421 A1 | 5/2010 | Williams et al. |
| 2010/0120731 A1 | 5/2010 | Vidal Juan et al. |
| 2010/0222331 A1 | 9/2010 | Engelhardt et al. |
| 2010/0240662 A1 | 9/2010 | Moon et al. |
| 2011/0039891 A1 | 2/2011 | Hagihara et al. |
| 2011/0124626 A1 | 5/2011 | Pooni et al. |
| 2013/0039906 A1 | 2/2013 | Do et al. |
| 2013/0280245 A1 | 10/2013 | Cai et al. |
| 2013/0303529 A1 | 11/2013 | Albrecht et al. |
| 2013/0310373 A1 | 11/2013 | Matsushima et al. |
| 2014/0031360 A1 | 1/2014 | Wang et al. |
| 2014/0227284 A1 | 8/2014 | Berthiaume et al. |
| 2014/0378474 A1 | 12/2014 | Flohr et al. |
| 2016/0002224 A1 | 1/2016 | Acton, III et al. |
| 2016/0060224 A1 | 3/2016 | Brand et al. |
| 2017/0081315 A1 | 3/2017 | Berger et al. |
| 2018/0237416 A1 | 8/2018 | Hood et al. |

FOREIGN PATENT DOCUMENTS

| | | | |
|---|---|---|---|
| EP | 0517984 | A1 | 12/1992 |
| EP | 0623621 | A1 | 11/1994 |
| EP | 0765873 | B1 | 4/2002 |
| EP | 1674464 | A1 | 6/2006 |
| GB | 2208862 | A | 4/1989 |
| GB | 2345486 | A | 7/2000 |
| JP | S63-310891 | A | 12/1988 |
| JP | H03-223280 | A | 10/1991 |
| JP | H05-230057 | A | 9/1993 |
| JP | H06-135960 | A | 5/1994 |
| JP | H11-279156 | A | 10/1999 |
| WO | 9204025 | A1 | 3/1992 |
| WO | 9205174 | A1 | 3/1992 |
| WO | 9303725 | A1 | 3/1993 |
| WO | 9961426 | A1 | 12/1999 |
| WO | 0063215 | A2 | 10/2000 |
| WO | 0102369 | A2 | 1/2001 |
| WO | 2004077682 | A2 | 9/2004 |
| WO | 2005014554 | A1 | 2/2005 |
| WO | 2008040995 | A1 | 4/2008 |
| WO | 2008153858 | A1 | 12/2008 |
| WO | 2011019738 | A1 | 2/2011 |
| WO | 2012095781 | A1 | 7/2012 |
| WO | 2013083991 | A1 | 6/2013 |
| WO | 2013133556 | A1 | 9/2013 |

OTHER PUBLICATIONS

Bell et al., "Selective Inhibitors of Protozoan Protein N-myristoyltransferases as Starting Points for Tropical Disease Medicinal Chemistry Programs," Plos Neglected Tropical Diseases, 2012, vol. 6, Issue 4, e1625, pp. 1-9.

Bell et al., Slides from "Selective Inhibitors of Protozoan Protein N-myristoyltransferases as Starting Points for Tropical Disease Medicinal Chemistry Programs," Emerging Paradigms in Anti-Infective Drug Design, London School of Hygiene and Tropical Medicine, Sep. 18, 2012, (16 pages).

Bell et al., "Discovery of Fungicidal N-Myristoyl Transferase (NMT) Inhibitors," Slides from Pfizer, 221 ACS meeting, 2001, Medi 350, (20 pages).

Boezio, et al., "Discovery and optimization of potent and selective triazolopyridazine series of c-Met inhibitors," Bioorganic & Medicinal Chemistry Letters 19, 2009, pp. 6307-6312.

Bowyer et al., "Molecules incorporating a benzothiazole core scaffold inhibit the N-myristoyltransferase of Plasmodium falciparum," Biochem. J., 2007, 408, pp. 173-180.

Bowyer et al., "N-Myristoyltransferase: a Prospective Drug Target for Protozoan Parasites," ChemMedChem, 2008, 3, pp. 402-408.

Brand et al., "Discovery of a Novel Class of Orally Active Trypanocidal N-Myristoyltransferase Inhibitors," Journal of Medicinal Chemistry, 2012, 55, pp. 140-152.

Brand et al., "Lead Optimization of a Pyrazole Sulfonamide Series of Trypanosoma brucei N-Myristoyltransferase Inhibitors: Identification and Evaluation of CNS Penetrant Cmopounds as Potential Treatments for Stage 2 Human African Trypanosomiasis," Journal of Medicinal Chemistry, 2014, 57, pp. 9855-9869.

Brannigan et al., "Diverse modes of binding in structures of Leishmania major N-myristoyltransferase with selective inhibitors," IUCrJ, 2014, 1, pp. 250-260.

Brannigan et al., "N-Myristoyltransferase from Leishmania donovani: Structural and Functional Characterisation of a Potential Drug Target for Visceral Leishmaniasis," J. Mol. Biol., 2010, 396, pp. 985-999.

Bryant et al., "Myristoylation-dependent replication and assembly of human immunodeficiency virus 1," Proc. Natl. Acad. Sci. USA, 1990, vol. 87, pp. 523-527.

Davis et al., "Recombinant VP4 of Human Rhinovirus Induces Permeability in Model Membranes," Journal of Virology, 2008, vol. 82, No. 8, pp. 4169-4174.

Devadas et al., "Design and Synthesis of Novel Imidazole-Substituted Dipeptide Amides as Potent and Selective Inhibitors of Candida albicans MyristoylCoA:Protein N-Myristoyltransferase and Identification of Related Tripeptide Inhibitors with Mechanism-Based Antifungal Activity," Journal of Medicinal Chemistry, 1997, vol. 40, No. 16, pp. 2609-2625.

Devadas et al., "Design and Synthesis of Potent and Selective Dipeptide Inhibitors of Candida albicans Myristoyl-CoA:Protein N-Myristoyltransferase," Journal of Medicinal Chemistry, 1995, vol. 38, No. 11, pp. 1837-1840.

(56) References Cited

OTHER PUBLICATIONS

Duronio et al., "Disruption of the Yeast N-Myristoyl Transferase Gene Causes Recessive Lethality," Science, 1989, vol. 243, pp. 796-800.

Ebara et al., "FTR1335 Is a Novel Synthetic Inhibitor of Candida albicans N-Myristoyltransferase with Fungicidal Activity," Biol. Pharm. Bull., 2005, vol. 28, No. 4, pp. 591-595.

Ebiike et al., "Design and Synthesis of Novel Benzofurans as a New Class of Antifungal Agents Targeting Fungal N-Myristoyltransferase. Part 2,"Bioorganic & Medicinal Chemistry Letters 12, 2002, pp. 607-610.

Fang et al., "N-Myristoyltransferase Is a Cell Wall Target in Aspergillus fumigatus," ACS Chem. Biol., 2015, 10, pp. 1425-1434.

Farazi et al., "The Biology and Enzymology of Protein N-Myristoylation," The Journal of Biological Chemistry, 2001, vol. 276, No. 43, pp. 39501-39504.

Frearson et al., "N-myristoyltransferase inhibitors as new leads to treat sleeping sickness," Nature, 2010, vol. 464, pp. 728-732 (7 pages).

Galvin et al., "A Target Repurposing Approach Identifies N-myristoyltransferase as a New Candidate Drug Target in Filarial Nematodes," PLOS Neglected Tropical Diseases, 2014, vol. 8, Issue 9, e3145, pp. 1-13.

Giang et al., "A Second Mammalian N-Myristoyltransferase," The Journal of Biological Chemistry, 1998, vol. 273, No. 12, pp. 6595-6598.

Goncalves et al., "A fluorescence-based assay for N-myristoyltransferase activity," Anal Biochem., 2012, 421(1), pp. 1-7.

Goncalves et al., "Discovery of Plasmodium vivax N-Myristoyltransferase Inhibitors: Screening, Synthesis, and Structural Characterization of their Binding Mode," Journal of Medicinal Chemistry, 2012, 55, pp. 3578-3582.

Gottlinger et al., "Role of capsid precursor processing and myristoylation in morphogenesis and infectivity of human immunodeficiency virus type 1," Proc. Natl. Acad. Sci. USA, 1989, vol. 86, pp. 5781-5785.

Grundt et al., "Analogues of the dopamine D2 receptor antagonist L741,626: Binding, function, and SAR," Bioorganic & medicinal Chemistry Letters 17, 2007, pp. 745-749.

Gunaratne et al., "Characterization of N-myristoyltransferase from Plasmodium falciparum," Biochem. J., 2000, 348, pp. 459-463.

Herrera et al., "Validation of N-myristoyltransferase as Potential Chemotherapeutic Target in Mammal-Dwelling Stages of Trypanosoma cruzi," PLOS Neglected Tropical Diseases, 2016, DOI:10.1371/journal.pntd.0004540, pp. 1-20.

Hutton et al., "Structure-Based Design of Potent and Selective Leishmania N-Myristoyltransferase Inhibitors," Journal of Medicinal Chemistry, 2014, 57, pp. 8664-8670.

Johnson et al., "Genetic and Biochemical Studies of Protein N-Myristoylation," Annu. Rev. Biochem., 1994, 63, pp. 869-914.

Kawasaki et al., "Design and Synthesis of Novel Benzofurans as a New Class of Antifungal Agents Targeting Fungal N-Myristoyltransferase. Part 3" Bioorganic & Medicinal Chemistry Letters 13, 2003, pp. 87-91.

Lee et al., "Synthesis and biological evaluation of 3,5-diaminoindazoles as cyclin-dependent kinase inhibitors," Bioorganic & Medicinal Chemistry Letters 18, 2008, pp. 2292-2295.

Liu et al., "Novel benzothiazole derivatives with broad antifungal spectrum: design, synthesis and structure-activity relationships," Med. Chem. Commun., 2013, 4, pp. 1551-1651.

Lodge et al., "Comparison of Myristoyl-CoA:Protein N-Myristoyltransferases from Three Pathogenic Fungi: Cryptococcus neoformans, Histoplasma capsulatum, and Candida albicans," The Journal of Biological Chemistry, 1994, vol. 269, No. 4, pp. 2996-3009.

Masubuchi et al., "Design and Synthesis of Novel Benzofurans as a New Class of Antifungal Agents Targeting Fungal N-Myristoyltransferase. Part 1," Bioorganic & Medicinal Chemistry Letters 11, 2001, pp. 1833-1837.

Masubuchi et al., "Synthesis and Biological Activities of Benzofuran Antifungal Agents Targeting Fungal N-Myristoyltransferase," Bioorganic & Medicinal Chemistry 11, 2003, pp. 4463-4478.

McIlhinney et al., "Immunocytochemical Characterization and Subcellular Localization of Human Myristoyl-CoA:Protein N-Myristoyltransferase in HeLa Cells," Experimental Cell Research, 1996, 223, pp. 348-356.

Music et al., "Reactions of Acylglycines With Heteroarylhydrazines," Heterocyclic Communications, 2005, vol. 11, Nos. 3-4, pp. 321-324.

Music et al., "Synthesis of Benzoylaminomethyl and Aminomethyl Substituted Fused 1,2,4-Triazoles," Synthetic Communications, 2001, 31(10), pp. 1511-1519.

Nagarajan et al., "Conformationally Constrained [p-(omega-Aminoalkyl)phenacetyl]-L-seryl-L-lysyl Dipeptide Amides as Potent Peptidomimetic Inhibitors of Candida albicans and Human Myristoyl-CoA:Protein N-Myristoyl Transferase," J. Med. Chem., 1997, vol. 40, No. 10, pp. 1422-1438.

Olaleye et al., "Peptiodomimetic inhibitors of N-myristoyltransferase from human malaria and leishmaniasis parasites," Organic & Biomolecular Chemistry, 2014, DOI: 10.1039/c4ob01669f, (6 pages).

Panethymitaki et al., "Characterization and selective inhibition of myristoyl-CoA:protein N-myristoyltransferase from Trypansoma brucei and Leishmania major," Biochem. J., 2006, 396, pp. 277-285.

Price et al., "Myristoyl-CoA:Protein N-Myristoyltransferase, an Essential Enzyme and Potential Drug Target in Kinetoplastid Parasites," The Journal of Biological Chemistry, 2003, vol. 278, No. 9, pp. 7206-7214.

Rackham et al., "Discovery of high affinity inhibitors of Leishmania donovani N-myristoyltransferase," Med. Chem. Commun., 2015, DOI: 10.1039/c5md00241a, (6 pages).

Rackham et al., "Discovery of Novel and Ligand-Efficient Inhibitors of Plasmodium falciparum and Plasmodium vivax N-myristoyltransferase," Journal of Medicinal Chemistry, 2013, 56, pp. 371-375.

Resh, M., "Interaction of tyrosine kinase oncoproteins with cellular membranes," Biochimca et Biophysica Acta, 1993, 1155, pp. 307-322.

Robinson et al., "Identification and structure solution of fragment hits against kinetoplastid N-myristoyltransferase," Acta Cryst., 2015, F71, pp. 586-593.

Rudnick et al., "Kinetic and Structural Evidence for a Sequential Ordered Bi Bi Mechanism of Catalysis by Saccharomyces cervisiae Myristoyl-CoA:Protein N-Myristoyltransferase," The Journal of Biological Chemistry, 1991, vol. 266, No. 15, pp. 9732-9739.

Sheng et al., "Design, synthesis and antifungal activity of isoteric analogues of benzoheterocyclic N-myristoyltransferase inhibitors," European Journal of Medicinal Chemistry, 2010, 45, pp. 3531-3540.

Sheng et al., "Homology modeling and molecular dynamics simulation of N-myristoyltransferase from protozoan parasites: active site characterization and insights into rational inhibitor design," J Comput Aided Mol Des, 2009, 23, pp. 375-389.

Sikorski et al., "Selective Peptidic and Peptidomimetic Inhibitors of Candida albicans MyristoylCoA : Protein N-Myristoyltransferase: A New Approach to Antifungal Therapy," Biopolymers, 1997, 43, pp. 43-71.

Snyder et al., "The Synthesis of an Indazole Analog of DL-Tryptophan," JACS, 1952, vol. 74, pp. 2009-2012.

Snyder et al., "The Synthesis of DL-alpha-Amino-beta-(6-methyl-3-indazolyl)-propionic Acid," JACS, 1954, vol. 76, 1298-1301.

Sogabe et al., "Crystal Structures of Candida albicans N-Myristoyltransferase with Two Distinct Inhibitors," Chemistry & Biology, 2002, vol. 9, pp. 1119-1128.

Tate et al., "Peptide-based inhibitors of N-myristoyl transferase generated from a lipid/combinatorial peptide chimera library," Signal Transduction, 2006, 6, pp. 160-166.

Wang et al., "Expeditious one-pot synthesis of C3-piperazinyl-substituted quinolines: key precursors to potent c-Met Inhibitors," Org. Biomol. Chem., 2011, 9, pp. 5930-5933.

Wiegand et al., "The Candida albicans Myristoyl-CoA:Protein N-Myristoyltransferase Gene," The Journal of Biological Chemistry, 1992, vol. 267, No. 12, pp. 8591-8598.

(56) References Cited

OTHER PUBLICATIONS

Wright et al., "Validation of N-myristoyltransferase as an antimalarial drug target using an integrated chemical biology approach," Nature Chemistry, 2013, DOI: 10.1038/NCHEM.1830, pp. 1-10.

Wu et al., "Multisubstituted quinoxalines and pyrido[2,3-d]pyrimidines: Synthesis and SAR study as tyrosine kinase c-Met inhibitors," Bioorganic & Medicinal Chemistry Letters 22, 2012, pp. 6368-6372.

Yamazaki et al., "Synthesis of potent and selective inhibitors of Candida albicans N-myristoyltransferase based on the benzothiazole structure," Bioorganic & Medicinal Chemistry 13, 2005, pp. 2509-2522.

Yu et al., "Design and Synthesis of Inhibitors of Plasmodium falciparum N-Myristoyltransferase, A Promising Target for Antimalarial Drug Discovery," Journal of Medicinal Chemistry, 2012, 55, pp. 8879-8890.

Yu et al., "Discovery of pyridyl-based inhibitors of Plasmodium falciparum N-myristoyltransferase," Med. Chem. Commun., 2015, DOI: 10.1039/c5md00242g, (6 pages).

International Search Report and Written Opinion issued in corresponding International Patent Application No. PCT/GB2016/000134 dated Aug. 30, 2016 (13 pages).

Wu et al., "A Versatile Linkage Strategy for Solid-Phase Synthesis of N,N-Dimethyltryptamines and beta-Carbolines," Organic Letters, vol. 4, No. 23, 2002, pp. 4033-4036.

| Example | EC50 (µM) |
|---|---|
| | Hela |
| 30 | 0.038 ± 0.002 |
| 33 | 2.301 ± 0.690 |

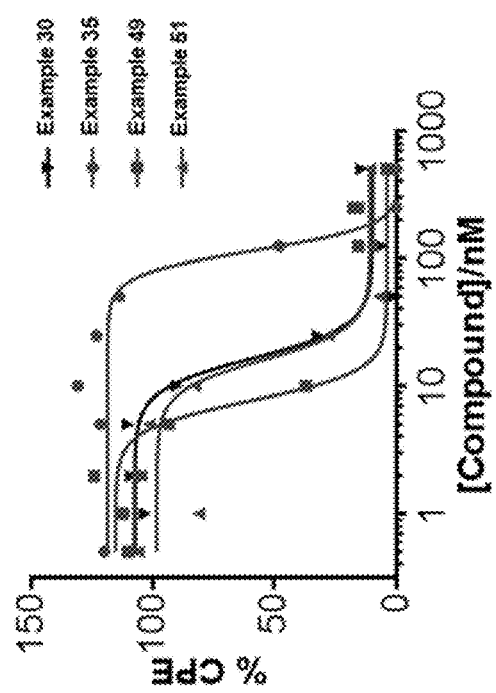
Fig. 5a
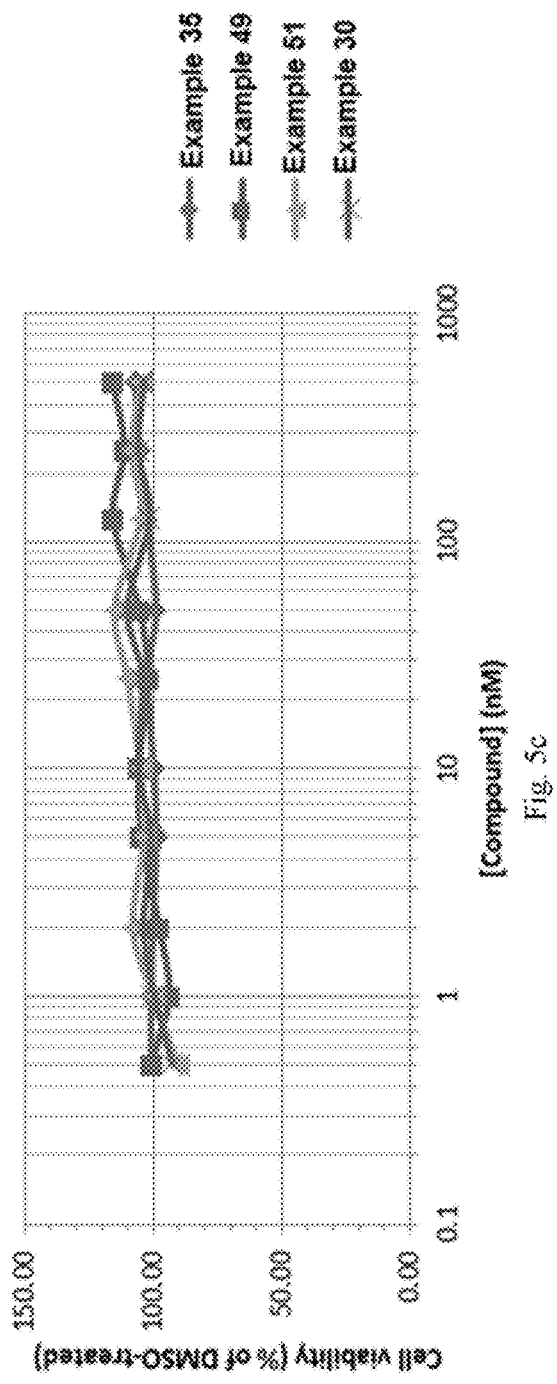
Fig. 5b
Fig. 5c ated protein.
COMPOUNDS AND THEIR USE AS INHIBITORS OF N-MYRISTOYL TRANSFERASE This application is a National Stage Application of PCT/GB2016/000134, filed Jun. 29, 2016, which claims priority to United Kingdom Patent Application No. 1511382.2, filed Jun. 29, 2015.

FIELD OF INVENTION

This invention relates to compounds of formula (I) and salts thereof which have activity as inhibitors of N-myristoyl transferase (NMT). The invention also relates to uses of such compounds as medicaments, in particular in the treatment of a disease or disorder in which inhibition of N-myristoyl transferase provides a therapeutic or prophylactic effect. Such diseases include protozoan infections (such as malaria and leishmaniasis), viral infections (such as human rhinovirus and HIV), and hyperproliferative disorders (such as B-cell lymphoma).

BACKGROUND TO THE INVENTION

N-myristoyl transferase (NMT) is a monomeric enzyme, which is ubiquitous in eukaryotes. NMT catalyses an irreversible co-translational transfer of myristic acid (a saturated 14-carbon fatty acid) from myristoyl-Coenzyme A (myr-CoA) to a protein substrate containing an N-terminal glycine with formation of an amide bond (Farazi, T. A., G. Waksman, and J. I. Gordon, *J. Biol. Chem.*, 2001. 276(43): p. 39501-39504). N-myristoylation by NMT follows an ordered Bi-Bi mechanism. Myr-CoA binds to NMT in the first NMT binding pocket prior to the binding of a protein substrate (Rudnick, D. A., C. A. McWherter, W. J. Rocque, et al., *J. Biol. Chem.*, 1991. 266(15): p. 9732-9739.). The bound myr-CoA facilitates the opening of a second binding pocket where the protein substrate binds. Following binding of the protein substrate, transfer of myristate to the protein substrate takes place via a nucleophilic addition-elimination reaction, finally with the release of CoA and the myristoylated protein.

NMT plays a key role in protein trafficking, mediation of protein-protein interactions, stabilization of protein structures and signal transduction in living systems. Inhibition of the NMT enzyme has the potential to disrupt multi-protein pathways, which is an attractive characteristic to reduce the risk of the development of resistance in, for example, treatment or prophylaxis of microbial infections and hyperproliferative disorders.

Biochemical analysis has shown high conservation of myr-CoA binding sites, but divergent peptide binding specificities between human and fungal and parasitic NMTs (Johnson, D. R., R. S. Bhatnagar, J. I. Gordon, et al., *Annu. Rev. Biochem.*, 1994. 63: p. 869-914.). As a consequence, NMT can be viewed as a target with the potential for the development of selective non-peptidic inhibitors.

NMT fungal and mammalian enzymes from various sources have been well characterized, see for example the following references: *Saccharomyces cerevisiae* (Duronio, R. J., D. A. Towler, R. O. Heuckeroth, et al., *Science,* 1989. 243(4892): p. 796-800), *Candida albicans* (Wiegand, R. C., C. Carr, J. C. Minnerly, et al., *J. Biol. Chem.*, 1992. 267(12): p. 8591-8598) and *Cryptococcus neoformans* (Lodge, J. K., R. L. Johnson, R. A. Weinberg, et al., *J. Biol. Chem.*, 1994. 269(4): p. 2996-3009), human NMT1 (McIlhinney, R. A. J. and K. McGlone, *Exp. Cell Res.*, 1996. 223: p. 348-356) and human NMT2 (Giang, D. K. and B. F. Cravatt, *J. Biol. Chem.*, 1998. 273: p. 6595-6598).

NMT has also been characterised in protozoan parasites. See for example the following references: *Plasmodium falciparum* (Pf) (Gunaratne, R. S., M. Sajid, I. T. Ling, et al., *Biochem. J.,* 2000. 348: p. 459-463), *Plasmodium vivax* (Pv), *Leishmania major* (Lm) (Price, H. P., M. R. Menon, C. Panethymitaki, et al., *J. Biol. Chem.*, 2003. 278(9): p. 7206-7214.), *Leishmania donovani* (Ld) (Branningan, J. A., B. A. Smith, Z. Yu, et al., *J. Mol. Biol.*, 2010. 396: p. 985-999) and *Trypanosoma brucei* (Tb) (Price, H. P., M. R. Menon, C. Panethymitaki, et al., *J. Biol. Chem.*, 2003. 278(9): p. 7206-7214.

Several myristoylated proteins have been observed in protozoans and their functions have been determined. These proteins and the processes in which they are involved suggest that N-myristoylation may play a role in multiple pathways in the biology of parasites. Inhibition of myristoylation could thus disrupt multiple pathways. The potential for the development of resistance should thus be smaller than for some other targets. To date, only a single isoform of NMT has been found in each protozoan organism investigated. If it is correct that there is only a single isoform, then that will also assist in reducing the potential for the development of resistance.

Inhibition of human NMT has also been suggested as a target for treating or preventing various diseases or disorders, for example hyperproliferative disorders (cancers, e.g. human colorectal cancer, gallbladder carcinoma, brain tumors, lymphomas such as B-cell lymphoma) (Resh M D. 1993. Biochem. Biophys. Acta 1115, 307-22), and viral infections such as HIV (Gottlinger H G, Sodroski J G, Haseltine W A. 1989. Proc. Nat. Acad. Sci. USA 86:5781-85; Bryant M L, Ratner L. 1990. Proc. Natl. Acad. Sci. USA 87:523-27) and human rhinovirus (HRV) (Davis M P, Bottley, G, Beales L P, Killington, R A, Rowlands D J, Tuthill, T J, 2008 Journal of Virology 82 4169-4174).

As described above, there are two binding pockets in NMT. One is the myr-CoA binding pocket and the other is the peptide binding pocket. Most NMT inhibitors reported to date target the peptide binding pocket. Most NMT inhibitors developed to date have been targeted to fungal N-myristoyl transferases.

Compounds active as inhibitors of NMT have previously been disclosed, see for example WO00/37464 (Roche), WO2010/026365 (University of Dundee), and WO2013/083991 (Imperial Innovations Limited). In addition, Bell et al disclosed the results of a high throughput screening study carried out to identify inhibitors of NMT, and disclosed the compound N,N-dimethyl-1-(5-(o-tolyl)-1H-indazol-3-yl) methanamine as having activity against *Plasmodium falciparum* NMT (PLoS Neglected Tropical Diseases, 2012, 6, e1625). A further indazole-containing analogue (1-(5-(4-fluoro-2-methylphenyl)-1H-indazol-3-yl)-N,N-dimethylmethanamine) was disclosed as part of a presentation "Selective inhibitors of protozoan protein N-myristoyl transferases" on 18 Sep. 2012 during a Symposium "Emerging Paradigms in Anti-Infective Drug Design" held at the London School of Hygiene and Tropical Medicine.

However, there remains a need in the art for further compounds active as inhibitors of N-myristoyl transferase.

SUMMARY OF THE INVENTION

The invention provides an inhibitor of N-myristoyl transferase (NMT) which is a compound of formula (I) or a salt thereof,

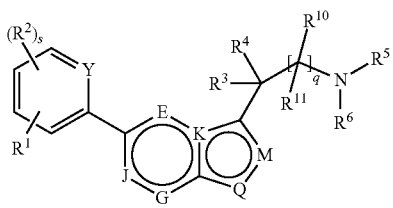

(I)

wherein:
Y is selected from the group consisting of —CH—, —C(R²)— and —N—;
R¹ is a group of formula —X-L-A;
X is selected from the group consisting of —O—, —N(H)— and —S—, or is absent;
L is selected from the group consisting of —(CHR¹²)$_m$— and —(CHR¹²)$_m$O—, or is absent;
m is 1, 2 or 3;
A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —OCH₃, —OCF₃, —CN, —C$_{1-4}$alkyl optionally substituted by up to 3 halogen, hydroxyl, or —OC$_{1-4}$alkyl groups, —S(O)C$_{1-4}$ alkyl, —S(O)₂Cl$_{1-4}$alkyl, —C(O)N(R⁹)₂, —C(O)N(R¹³)C$_{1-4}$alkylOC$_{1-4}$alkyl, —C(O)N(C$_{1-4}$alkylOC$_{1-4}$ alkyl)₂, —CH₂C(O)N(R⁹)₂, —CH₂C(O)N(R¹³)C$_{1-4}$alkylOC$_{1-4}$alkyl, —CH₂C(O)N(C$_{1-4}$alkylOC$_{1-4}$alkyl)₂, —S(O)₂NHC$_{1-4}$alkyl, —S(O)₂ N(C$_{1-4}$alkyl)₂, —NHC$_{1-4}$alkyl, —N(C$_{1-4}$alkyl)₂, —NHC(O)C$_{1-4}$ alkyl, —NHC(O)CF₃, —NHS(O)₂C$_{1-4}$ alkyl, CH₂N(R¹³)₂, CH₂N(R¹³)C(O)C$_{1-4}$alkyl, CH₂N(R¹³)S(O)₂C$_{1-4}$alkyl, —CH₂S(O)₂C$_{1-4}$alkyl, and CO₂H;
s is 0, 1, 2, or 3;
each R² is independently selected from the group consisting of —F, —Cl, —Br, —OCH₃, —OCF₃, —CN, —C$_{1-4}$alkyl optionally substituted by up to 3 halogen or hydroxyl groups, —S(O)C$_{1-4}$alkyl, —S(O)₂C$_{1-4}$alkyl, —S(O)₂NH-C$_{1-4}$alkyl, —S(O)₂N(C$_{1-4}$alkyl)₂, —NHC$_{1-4}$alkyl, —N(C$_{1-4}$alkyl)₂, —NHC(O)C$_{1-4}$alkyl, —NHC(O)CF₃, and —NHS(O)₂C$_{1-4}$alkyl;
E, J and G are each independently nitrogen or C(R⁷);
K is carbon or nitrogen;
when K is carbon, either Q is N(R⁸) and M is nitrogen or C(R⁷), or Q is nitrogen and M is N(R⁸);
when K is nitrogen, Q is nitrogen or C(R⁷) and M is nitrogen or C(R⁷);
and further wherein at least 2 of E, J, G, K, Q and M are selected from the group consisting of carbon and C(R⁷);
q is 0 or 1;
R³ is hydrogen or methyl; R⁴ is hydrogen or methyl;
R⁵ is hydrogen or C$_{1-6}$alkyl optionally substituted by up to 3 —F, —Cl, —Br, —OH, —OCH₃, —OCF₃ or —CN groups; R⁸ is hydrogen or C$_{1-6}$alkyl optionally substituted by up to 3 —F, —Cl, —Br, —OH, —OCH₃, —OCF₃ or —CN groups; or the R⁵ and R⁶ groups and the N they are bonded to form a 4 to 7 membered non-aromatic heterocycle, the heterocycle optionally comprising 1 or 2 further heteroatoms selected from N, O and S, optionally substituted by up to 3 —F, —Cl, —Br, —OH, —OCH₃, —OCF₃ or —CN groups;
when present R¹⁰ is hydrogen or methyl;
when present R¹¹ is hydrogen or methyl;
or the R³ group and the R⁵ group and the intervening atoms form a 3 to 7 membered non-aromatic heterocycle composed of the intervening atoms and bond, or the intervening atoms and —(CHR$^a$)$_r$—; or the R¹⁰ group and the R⁵ group and the intervening atoms form a 3 to 7 membered non-aromatic heterocycle composed of the intervening atoms and —(CHR$^a$)$_r$—;
r is 1, 2, 3, 4 or 5; R$^a$ is hydrogen or methyl;
each R⁷ is independently selected from the group consisting of hydrogen, halogen, C$_{1-4}$ alkoxy, and C$_{1-4}$alkyl optionally substituted with 1, 2 or 3 halogens; and R⁸ is selected from the group selected from hydrogen and C$_{1-4}$alkyl;
each R⁹ is independently selected from the group consisting of hydrogen and C$_{1-4}$alkyl, or two R⁹ groups and the N they are bonded to form a 4 to 7 membered non-aromatic heterocycle, the heterocycle optionally comprising 1 or 2 further heteroatoms selected from N, O and S;
each R¹² is independently selected from the group consisting of hydrogen, C$_{1-6}$alkyl optionally substituted by up to 3 —F, —Cl, —Br, I, —OH, —OCH₃, —OCF₃ or —CN groups, C$_{1-6}$alkenyl optionally substituted by up to 3 —F, —Cl, —Br, I, —OH, —OCH₃, —OCF₃ or —CN groups, and C$_{1-6}$ alkynyl optionally substituted by up to 3 —F, —Cl, —Br, I, —OH, —OCH₃, —OCF₃ or —CN groups; and each R¹³ is independently selected from the group consisting of hydrogen and C$_{1-4}$alkyl.

The compounds of the invention have surprisingly been found to have activity as inhibitors of N-myristoyl transferase.

The invention also provides a pharmaceutical composition comprising an NMT inhibitor according to the invention and a pharmaceutically acceptable carrier.

The invention also provides an NMT inhibitor or a pharmaceutical composition according to the invention for use as a medicament.

The invention also provides an NMT inhibitor or a pharmaceutical composition according to the invention for use in the prevention or treatment of a disease or disorder in which inhibition of N-myristoyl transferase provides a therapeutic or prophylactic effect.

The invention also provides use of an NMT inhibitor according to the invention for the manufacture of a medicament for the prevention or treatment of a disease or disorder in which inhibition of N-myristoyl transferase provides a therapeutic or prophylactic effect.

The invention also provides a method of treating or preventing a disease or disorder in which inhibition of N-myristoyl transferase provides a therapeutic or prophylactic effect in a mammal, which comprises administering to the mammal a therapeutically effective amount of an NMT inhibitor or pharmaceutical composition according to the invention.

The invention also provides a kit of parts comprising: (a) a first pharmaceutical composition comprising an NMT inhibitor according to the invention and a pharmaceutically acceptable carrier; and (b) a second pharmaceutical composition comprising a further therapeutic agent, preferably a further N-myristoyl transferase inhibitor, and a pharmaceutically acceptable carrier.

Figures 1, 2:
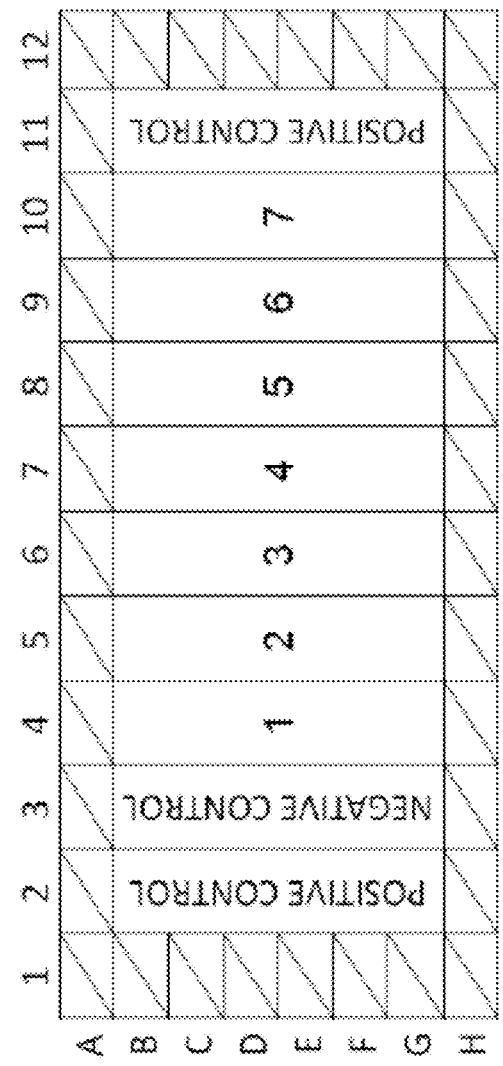
FIG. 1 shows a table containing NMT (N-myristoyl transferase) IC$_{50}$ (μM) and EC$_{50}$ (μM) values for Example compounds 1 to 51, 53 to 58, 60, 62, 63, and 66 to 101 of the invention tested for their ability to inhibit NMT of various species. Details of the assay are described at (a) below. The table further shows EC50 (μM) values for certain Example compounds of the invention tested for their ability to inhibit *Plasmodium falciparum* viability (Pf strains 3D7 or NF54 (NF54 results shown in bold text), details of which are described at (b) below. The table also shows the $EC_{50}$ (μM) results of the *P. berghei* liver stage assay for certain example compounds, details of which are described at (g) below. The table further shows the results of how certain Example compounds of the invention performed in a mouse malaria model. The percentage reduction in the parasite burden for mice treated with a compound of the invention over control mice is indicated in the table. Details of the mouse malaria model are provided at (c) below. The table also shows $EC_{50}$ values for certain Example compounds of the invention tested for their ability to inhibit metabolic activity in BL-41 cells. Details of the assay are described at (d) below.

FIG. 2 shows a representation of a 96-well plate used to determine the inhibitory effects of Example compounds of the invention in a metabolic activity assay using HeLa and/or BL-41 cells.

Figures 3, 4:
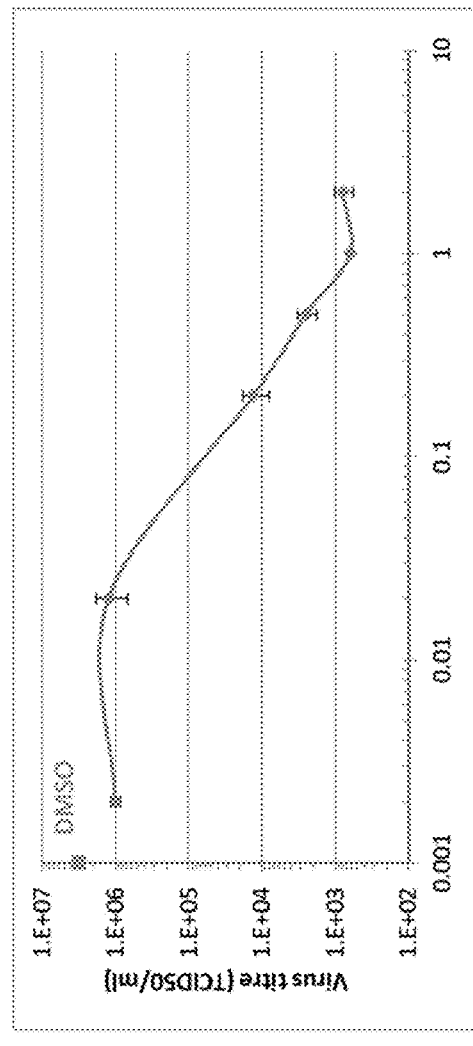

FIG. 3 shows a table containing $EC_{50}$ values for Example compounds 30 and 33 of the invention tested for their ability to inhibit metabolic activity in HeLa cells. Details of the assay are described at (d) below.

FIG. 4 shows the effect of Example 30 on rhinovirus production in HeLa cells. Details of the assay are described at (e) below.

FIG. 5a-5c show the results for Examples 30, 35, 49 and 50 when tested in a rhinovirus replication assay in the human HeLa Ohio cell line, details of which are described at (f) below. FIGS. 5a and 5b show the virus-induced cytopathic effect (CPE) measured by a Metabolic Activity Assay (MTS assay) 2 days post-infection. The cell viability of the inhibitor-treated but uninfected cells was measured in parallel by MTS 2 days post-treatment, and the results are shown in FIG. 5c.

DETAILED DESCRIPTION OF THE INVENTION

The present invention provides compounds that are NMT inhibitors. The term "NMT inhibitor" as used herein is intended to cover any moiety which binds to NMT and inhibits its activity.

The inhibitors may act as competitive inhibitors, or partial competitive inhibitors. The inhibitor may bind to NMT at the myr-CoA binding pocket or at the peptide binding pocket (or inhibit NMT through another mechanism). Compounds of the present invention preferably bind and inhibit NMT through the peptide binding pocket.

Definitions

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "alkylene" means both straight and branched chain divalent hydrocarbon radical. Examples of alkyl groups include methylene, ethylene, n-propylene, iso-propylene, n-butylene, t-butylene, i-butylene, sec-butylene, pentylene and hexylene groups. Among unbranched alkyl groups, there are preferred methylene, ethylene, n-propylene, iso-propylene, n-butylene groups. Among branched alkyl groups, there may be mentioned t-butylene, i-butylene, 1-ethylpropylene and 1-ethylbutylene groups As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkenylene" refers to a straight or branched chain divalent hydrocarbon radical with at least one carbon carbon double bond. Examples of alkenylene groups include ethenylene, 1-propenylene, 2-propenylene and but-2-enylene.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl, 1-propynyl and 2-propynyl.

As used herein, the term "alkynylene" means both straight and branched chain divalent hydrocarbon radical with at least one carbon carbon triple bond. Examples of alkynylene groups include ethynylene, 1-propynylene, 2-propynylene, butynylene, pentynylene and hexynylene.

As used herein, the term "carbocycle" is intended to mean any 3- to 13-membered carbon ring system, which may be saturated, partially unsaturated, or aromatic. The carbon ring system may be monocyclic or contain more than one ring (e.g. the ring system may be bicyclic). Examples of monocyclic saturated carbocycles include cyclopropyl, cyclobutyl, cyclopentyl, cyclohexyl, cycloheptyl, cyclooctyl. Examples of bicyclic saturated carbocycles include bicyclooctane, bicyclononane, bicyclodecane (decalin) and bicyclooctane. A further example of a saturated carbocycle is adamantane. Examples of monocyclic non-saturated carbocycles include cyclobutene, cyclopentene, cyclopentadiene, cyclohexene. Examples of aromatic carbocycles include phenyl and naphthyl. Further examples of aromatic carbocycles include tetrahydronaphthyl (tetralin) and indane.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo [2. 2.1]hept-2-yl. Preferably, the cycloalkyl group is monocyclic.

As used herein, the term "cycloalkylene" means a 3- to 7-membered non-aromatic alicyclic divalent hydrocarbon radical, Examples of cycloalkylene include cyclopropylene, cyclobutylene and cyclopentylene. Other examples of monocyclic cycloalkyl groups are cyclohexylene and cycloheptylene. Preferably, the cycloalkylene group is monocyclic.

As used herein, the term "halogen" or "halo" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the term "heterocyclyl" (or heterocycle) means an aromatic or a non-aromatic cyclic group of carbon atoms wherein from one to four of the carbon atoms is/are replaced by one or more heteroatoms independently selected from nitrogen, oxygen or sulfur. A heterocyclyl (or heterocycle) group may, for example, be monocyclic or bicyclic. In a bicyclic heterocyclyl (or heterocycle) group there may be one or more heteroatoms in each ring, or only in one of the rings. A heteroatom may be S, O or N, and is preferably O or N.

Examples of monocyclic non-aromatic heterocyclyl (or heterocycle) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of monocyclic aromatic heterocyclyl (or heterocycle) groups include furanyl, thienyl, pyrrolyl, oxazolyl, thiazolyl, imidazolyl, oxadiazolyl, thiadiazolyl, pyridyl, triazolyl, triazinyl, tetrazolyl, pyridazyl, isothiazolyl, isoxazolyl, pyrazinyl, pyrazolyl and pyrimidinyl.

Examples of bicyclic aromatic heterocyclyl groups (or heterocycle) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridyl, pyridopyrimidinyl, isoquinolinyl and benzodroxazole. Further examples of bicyclic aromatic heterocyclyl groups include those in which one of the rings is aromatic and the other is non-aromatic, such as dihydrobenzofuranyl, indanyl, indolinyl, isoindolinyl, tetrahydroisoquinolinyl, tetrahydroquinolyl and benzoazepanyl.

The compounds of the invention may contain chiral (asymmetric) centers. The molecule as a whole may be chiral. The individual stereoisomers (enantiomers and diastereoisomers) and mixtures of these are within the scope of the present invention.

For the avoidance of doubt, an embodiment or preferred aspect of any one feature of the NMT inhibitors of the invention may be combined with any embodiment or preferred aspect of another feature of the NMT inhibitors of the invention to create a further embodiment.

In one preferred embodiment of the invention, X is selected from the group consisting of —O—, —N(H)— and —S—. In another preferred embodiment L is selected from the group consisting of —(CHR$^{12}$)$_m$— and —(CHR$^{12}$)$_m$O—. Most preferably X is selected from the group consisting of —O—, —N(H)— and —S— and L is selected from the group consisting of —(CHR$^{12}$)$_m$— and —(CHR$^{12}$)$_m$O—.

In another preferred embodiment E, J, G and M are each C(R$^7$), and K and Q are each nitrogen. In another preferred embodiment q is 1, R$^{10}$ is hydrogen and R$^{11}$ is hydrogen. In a especially preferred embodiment, q is 1, R$^{10}$ is hydrogen and R$^{11}$ is hydrogen and E, J, G and M are each C(R$^7$), and K and Q are each nitrogen.

In one preferred embodiment of the invention, A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —OCH$_3$, —OCF$_3$, —CN, —C$_{1-6}$alkyl optionally substituted by up to 3 halogen, hydroxyl, or —OC$_{1-4}$alkyl groups, —S(O)C$_{1-4}$alkyl, —S(O)$_2$C$_{1-4}$alkyl, —C(O)N(R$^9$)$_2$, —CH$_2$C(O)N(R$^9$)$_2$, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —CH$_2$NHC(O)C$_{1-4}$alkyl, —NHC(O)CF$_3$ and —NHS(O)$_2$C$_{1-4}$alkyl.

In another preferred embodiment of the invention, A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —OCH$_3$, —OCF$_3$, —CN, —C$_{1-6}$alkyl optionally substituted by up to 3 halogen, hydroxyl, or —OC$_{1-4}$alkyl groups, —S(O)C$_{1-4}$alkyl, —S(O)$_2$C$_{1-4}$alkyl, —C(O)N(R$^9$)$_2$, —CH$_2$C(O)N(R$^9$)$_2$, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —CH$_2$NHC(O)C$_{1-4}$alkyl, —NHC(O)CF$_3$, —NHS(O)$_2$C$_{1-4}$alkyl, CH$_2$NH$_2$, CH$_2$NHC$_{1-4}$alkyl, CH$_2$NC$_{1-4}$alkylC(O)C$_{1-4}$alkyl, CH$_2$NHS(O)$_2$C$_{1-4}$alkyl, —CH$_2$S(O)$_2$C$_{1-4}$alkyl, CH$_2$NC$_{1-4}$alkylS(O)$_2$C$_{1-4}$alkyl.

In one preferred embodiment of the NMT inhibitor of the invention, the compound has the formula (IA)

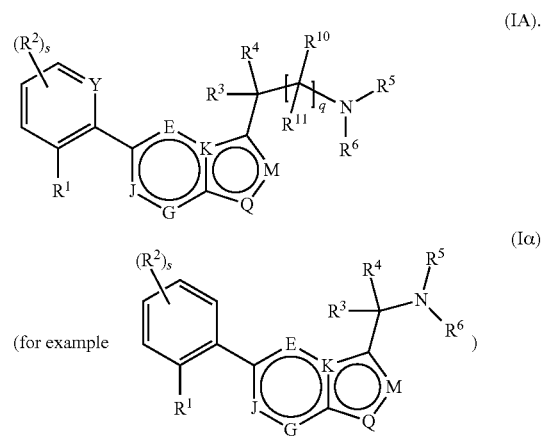

wherein R$^1$, R$^2$, s, E, J G, K, Q, M, q, R$^3$, R$^4$, R$^5$ and R$^6$, R$^7$, R$^8$, R$^9$, R$^{10}$ and R$^{11}$ are as defined in formula (I).

In another preferred embodiment of the NMT inhibitor of the invention, the compound has the formula (IB)

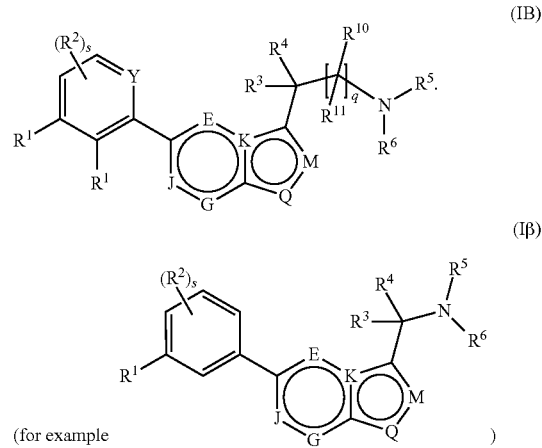

wherein R$^1$, R$^2$, s, E, J, G, K, Q, M, R$^3$, R$^4$, R$^5$ and R$^6$ are as defined in formula (I).

In one preferred embodiment of the NMT inhibitor of the invention, the NMT inhibitor has the formula (IA*):

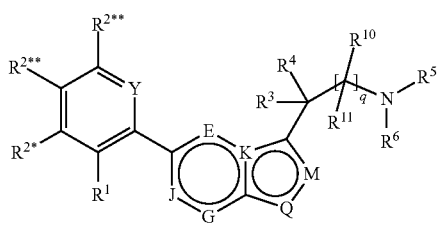

(IA*)

wherein each $R^{2*}$ is independently selected from the group consisting of —F, —Cl, —Br, —OCH$_3$, —OCF$_3$, —CN, —C$_{1-4}$alkyl optionally substituted by up to 3 halogen or hydroxyl groups, —S(O)C$_{1-4}$alkyl, —S(O)$_2$C$_{1-4}$alkyl, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —NHC(O)CF$_3$, and —NHS(O)$_2$C$_{1-4}$alkyl (preferably selected from the group consisting of —F, —Cl, —Br, —OCH$_3$, —OCF$_3$, —CN, —C$_{1-4}$alkyl optionally substituted by up to 3 halogen or hydroxyl groups; more preferably selected from the group consisting of —F and —Cl; most preferably —F); and $R^{2}$ is selected from the group consisting of —H, —F, —Cl, —Br, —OCH$_3$, —OCF$_3$, —CN, —C$_{1-4}$alkyl optionally substituted by up to 3 halogen or hydroxyl groups, —S(O)C$_{1-4}$alkyl, —S(O)$_2$C$_{1-4}$alkyl, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —NHC(O)CF$_3$, and —NHS(O)$_2$C$_{1-4}$alkyl (preferably selected from the group consisting of —H, —F, —Cl, —Br, —OCH$_3$, —OCF$_3$, —CN, —C$_{1-4}$alkyl optionally substituted by up to 3 halogen or hydroxyl groups; more preferably selected from the group consisting of —H, —F and —Cl). More preferably the compound has the formula (IA*):

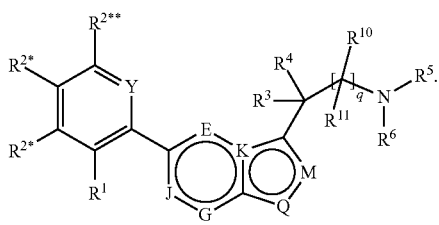

(IA***)

Compounds of formula (IA*) and (IA***) are surprisingly highly active, and their high potency makes them especially viable for use as HsNMT inhibitors.

In another embodiment the NMT inhibitor of the invention is a compound of formula (I) (or for example (IA) or (IA")), with the proviso the compound is not a compound of formula (IA*). In another embodiment the NMT inhibitor of the invention is a compound of formula (I) (or for example (IA) or (IA")), with the proviso the compound is pot a compound of formula (IA***).

In another embodiment the NMT inhibitor of the invention is a compound of formula (IA**) or (IB):

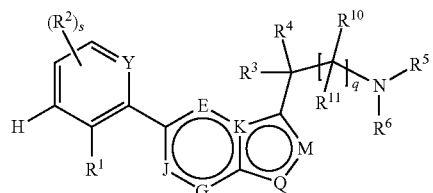

(IA**)

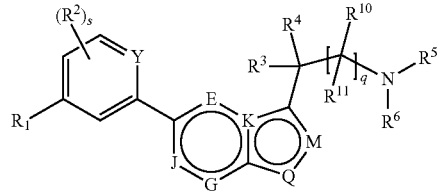

(IB)

wherein s is 0, 1 or 2 for formula (IA**); and s is 0, 1, 2 or 3 for (IB).

At least two of the variable ring atoms in the core bicyclic moiety of formula (I) are carbon. In other words, at least two of E, J, G, K, Q and M are selected from the group consisting of C(R$^7$) and carbon (with it being possible for E, J, G, Q and M to be C(R$^7$), and it being possible for K to be carbon).

At least one of the variable ring atoms in the core bicyclic moiety of formula (I) is nitrogen. In other words at least one of E, J, G, K, Q and M is selected from the group consisting of nitrogen and N(R$^8$). By way of explanation, K is either carbon or nitrogen and, where K is carbon, either Q is N(R$^8$) and M is nitrogen or C(R$^7$), or Q is nitrogen and M is N(R$^8$).

In one preferred embodiment of the NMT inhibitor of the invention, E, J and G are each C(R$^7$), K is carbon, Q is N(R$^8$), and M is nitrogen.

In one preferred embodiment of the NMT inhibitor of the invention, E, J and G are each C(R$^7$), and K, Q and M are each nitrogen.

In one preferred embodiment of the NMT inhibitor of the invention, E and G are each C(R$^7$), and J, K, Q and M are each nitrogen.

In one preferred embodiment of the NMT inhibitor of the invention, J and G are each C(R$^7$), and E, K, Q and M are each nitrogen.

In one preferred embodiment of the NMT inhibitor of the invention, E, J, G and M are each C(R$^7$), and K and Q are each nitrogen.

More preferably, E, J and G are each C(R$^7$), K is carbon, Q is N(R$^8$), and M is nitrogen; E, J and G are each C(R$^7$), and K, Q and M are each nitrogen; or E, J, G and M are each C(R$^7$), and K and Q are each nitrogen. Most preferably E, J and G are each C(R$^7$), K is carbon, Q is N(R$^8$), and M is nitrogen; or E, J and G are each C(R$^7$), and K, Q and M are each nitrogen.

In certain embodiments Y is —CH— or —C(R$^{2'}$)—; preferably Y is —CH—. In another embodiment Y is —N—.

In one preferred embodiment, s is 0, 1 or 2, and, where present, each R$^2$ is independently selected from the group consisting of —F, —Cl, —Br, —OCH$_3$, —OCF$_3$, —CN, and —C$_{1-4}$alkyl optionally substituted by up to 3 halogen or hydroxyl groups. More preferably R$^2$ is F or Cl.

In one preferred embodiment, A is an aromatic carbocycle or heterocycle selected from the group consisting of phenyl, pyridinyl, quinolinyl, imidazolyl, benzimidazolyl, pyrazolyl, thiazolyl, 1,2,3-triazolyl and 1,2,4-triazolyl, said aromatic carbocycle or heterocycle being optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups; $C(O)N(R^9)_2$ (for example —$C(O)N(H)C_{1-4}$alkyl or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring)), —$CH_2C(O)N(R^9)_2$ (for example —$CH_2C(O)N(H)C_{1-4}$alkyl), —$CH_2C(O)N(R^9)_2$ (for example —$CH_2C(O)N(H)C_{1-4}$alkyl), —$C(O)N(R^{13})C_{1-4}$alkyl$OC_{1-4}$alkyl (for example —$C(O)N(H)C_{1-4}$alkyl$OC_{1-4}$alkyl), —$N(R^9)C(O)C_{1-4}$alkyl, —$CH_2N(R^{13})_2$, $CH_2N(R^9)C(O)C_{1-4}$alkyl or $CH_2N(R^{13})S(O)_2C_{1-4}$alkyl; and more preferably $C(O)N(R^9)_2$ (for example —$C(O)N(H)C_{1-4}$alkyl), or —$CH_2C(O)N(R^9)_2$ (for example —$CH_2C(O)N(H)C_{1-4}$alkyl). Preferably A is selected from the group consisting optionally substituted pyrazolyl and thiazolyl.

In one preferred embodiment, A is optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups (preferably one —$OC_{1-4}$alkyl group; more preferably one —$OCH_3$ group); $C(O)N(R^9)_2$ (for example —$C(O)N(H)C_{1-4}$alkyl or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring)), —$CH_2C(O)N(R^9)_2$ (for example —$CH_2C(O)N(H)C_{1-4}$alkyl), —$CH_2C(O)N(R^9)_2$ (for example —$CH_2C(O)N(H)C_{1-4}$alkyl), —$C(O)N(R^{13})C_{1-4}$alkyl$OC_{1-4}$alkyl (for example —$C(O)N(H)C_{1-4}$alkyl$OC_{1-4}$alkyl), —$N(R^9)C(O)C_{1-4}$alkyl, —$CH_2N(R^{13})_2$, $CH_2N(R^9)C(O)C_{1-4}$alkyl or $CH_2N(R^{13})S(O)_2C_{1-4}$alkyl I; preferably $C(O)N(R^9)_2$ (for example —$C(O)N(H)C_{1-4}$alkyl), —$CH_2C(O)N(R^9)_2$ (for example —$CH_2C(O)N(H)C_{1-4}$alkyl). Preferably A is selected from the group consisting optionally substituted pyrazolyl and thiazolyl.

In certain preferred embodiments, A is optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups (preferably one —$OC_{1-4}$alkyl group; more preferably one —$OCH_3$ group); —$C(O)N(H)C_{1-4}$alkyl (for example —$C(O)N(H)CH_3$) or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring), —$CH_2C(O)N(H)C_{1-4}$ alkyl, —$CH_2C(O)N(H)Cl_{1-4}$alkyl, —$C(O)N(H)C_{1-4}$alkyl $OC_{1-4}$alkyl, —$N(R^9)C(O)C_{1-4}$alkyl, —$CH_2N(R^{13})_2$, $CH_2N(R^9)C(O)C_{1-4}$ alkyl or $CH_2N(R^{13})S(O)_2C_{1-4}$alkyl. Preferably A is selected from the group consisting optionally substituted pyrazolyl and thiazolyl.

In even more preferred embodiments, A is optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups (preferably one —$OC_{1-4}$alkyl group; more preferably one —$OCH_3$ group); —$C(O)N(H)C_{1-4}$alkyl (for example —$C(O)N(H)CH_3$) or —$C(O)N(R^9)_2$ wherein the two $R^9$ and the N they are bonded to form a morpholine or pyrrolidine ring (preferably a morpholine ring), —$CH_2C(O)N(H)C_{1-4}$ alkyl, —$CH_2C(O)N(H)C_{1-4}$alkyl, and —$C(O)N(H)C_{1-4}$alkyl$OC_{1-4}$alkyl; and more preferably substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups; —$C(O)N(H)C_{1-4}$alkyl (for example —$C(O)N(H)CH_3$) or —$C(O)N(R^9)_2$ wherein the two $R^9$ and the N they are bonded to form a morpholine or pyrrolidine ring (preferably a morpholine ring), —$C(O)N(H)C_{1-4}$alkyl$OC_{1-4}$alkyl and $CH_2N(R^{13})S(O)_2C_{1-4}$alkyl. Preferably A is selected from the group consisting optionally substituted pyrazolyl and thiazolyl.

In one preferred embodiment, A is optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups preferably one —$OC_{1-4}$alkyl group; more preferably one —$OCH_3$ group); $C(O)N(R^9)_2$ (for example —$C(O)N(H)C_{1-4}$alkyl or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring)), —$CH_2C(O)N(R^9)_2$ (for example —$CH_2C(O)N(H)C_{1-4}$alkyl), —$CH_2C(O)N(R^9)_2$ (for example —$CH_2C(O)N(H)C_{1-4}$alkyl), —$C(O)N(R^{13})C_{1-4}$ alkyl$OC_{1-4}$alkyl (for example —$C(O)N(H)C_{1-4}$alkyl$OC_{1-4}$alkyl), —$N(R^9)C(O)C_{1-4}$alkyl, $CH_2N(R^9)C(O)C_{1-4}$alkyl and $CH_2N(R^{13})S(O)_2C_{1-4}$alkyl. Preferably A is selected from the group consisting optionally substituted pyrazolyl and thiazolyl.

In one preferred embodiment, A is substituted with 1, 2, or 3 groups, and at least one of the substituents is —$C_{1-4}$alkyl (for example methyl), wherein each —$C_{1-4}$alkyl is optionally substituted by up to 3 halogen, hydroxyl or —$OC_{1-4}$alkyl groups (preferably one —$OC_{1-4}$alkyl group; more preferably one —$OCH_3$ group); $C(O)N(R^9)_2$ (for example —$C(O)N(H)C_{1-4}$alkyl or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring)), —$CH_2C(O)N(R^9)_2$ (for example —$CH_2C(O)N(H)C_{1-4}$alkyl), —$CH_2C(O)N(R^9)_2$ (for example —$CH_2C(O)N(H)C_{1-4}$alkyl), —$C(O)N(R^{13})C_{1-4}$alkyl$OC_{1-4}$alkyl (for example —$C(O)N(H)C_{1-4}$alkyl $OC_{1-4}$alkyl), —$N(R^9)C(O)C_{1-4}$alkyl, —$CH_2N(R^{13})_2$, $CH_2N(R^9)C(O)C_{1-4}$alkyl or $CH_2N(H)S(O)_2C_{1-4}$alkyl. Preferably A is selected from the group consisting optionally substituted pyrazolyl and thiazolyl.

In one preferred embodiment, A is substituted with 1, 2, or 3 groups, and at least one of the substituents is —$CH_2N(R^{13})_2$ or $C_{1-4}$alkyl (for example methyl), wherein each —$C_{1-4}$alkyl is optionally substituted by up to 3 halogen, hydroxyl or —$OC_{1-4}$alkyl groups (preferably one —$OC_{1-4}$alkyl group; more preferably one —$OCH_3$ group).

In another preferred embodiment, A is substituted with 1, 2, or 3 groups, and at least one of the substituents is $C(O)N(R^9)_2$ (for example —$C(O)N(H)C_{1-4}$alkyl or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring)), $CH_2N(R^9)C(O)C_{1-4}$alkyl or $CH_2N(R^{13})S(O)_2C_{1-4}$alkyl (for example $CH_2N(H)S(O)_2C_{1-4}$alkyl).

It has been surprisingly found that where A is substituted with one carboxamide containing group, stability of the NMT inhibitor is improved. In one preferred embodiment A is substituted with 1, 2, or 3 groups, and at least one of the substituents is —$C(O)N(R^9)_2$, —$C(O)N(R^{13})C_{1-4}$alkylO$C_{1-4}$ alkyl, —$C(O)N(C_{1-4}$alkyl $OC_{1-4}$alkyl$)_2$, —$CH_2C(O)N(R^9)_2$, —$CH_2C(O)N(R^{13})C_{1-4}$alkylO$C_{1-4}$alkyl, —$CH_2C(O)N(C_{1-4}$alkylO$C_{1-4}$alkyl$)_2$, —$NHC(O)C_{1-4}$alkyl, —$NHC(O)CF_3$, $CH_2N(R^{13})C(O)C_{1-4}$alkyl. In another preferred embodiment, A is substituted with 1, 2, or 3 groups, and at least one of the substituents is —$C(O)N(R^9)_2$, —$C(O)N(R^{13})C_{1-4}$alkylO$C_{1-4}$alkyl, —$C(O)N(C_{1-4}$alkylO$C_{1-4}$alkyl$)_2$, —$CH_2C(O)N(R^9)_2$, —$CH_2C(O)N(R^{13})C_{1-4}$alkylO$C_{1-4}$ alkyl, —$CH_2C(O)N(C_{1-4}$alkylO$C_{1-4}$alkyl$)_2$, —$NHC(O)C_{1-4}$alkyl, —$NHC(O)CF_3$, $CH_2N(R^{13})C(O)C_{1-4}$alkyl, $CO_2H$, and $CH_2N(H)S(O)_2C_{1-4}$alkyl.

More preferably, at least one of the substituents is $C(O)N(R^9)_2$ (for example —$C(O)N(H)C_{1-4}$ alkyl or —$C(O)N(R^9)_2$ wherein the two $R^9$ groups and the N they are bonded to form a 4 to 7 membered non-aromatic heterocycle, the heterocycle optionally comprising 1 or 2 further heteroatoms selected from N, O and S (for example wherein the two $R^9$ and the N they are bonded to form a morpholine or pyrrolidine ring)), —$CH_2C(O)N(R^9)_2$ (for example —$CH_2C(O)N(H)C_{1-4}$alkyl), —$CH_2C(O)N(R^9)_2$ (for example —$CH_2C(O)N(H)C_{1-4}$alkyl), —$C(O)N(R^{13})C_{1-4}$alkylO$C_{1-4}$alkyl (for example —$C(O)N(H)C_{1-4}$alkylO$C_{1-4}$alkyl), —$N(R^9)C(O)C_{1-4}$alkyl, $CH_2N(R^9)C(O)C_{1-4}$alkyl or $CH_2N(R^{13})S(O)_2C_{1-4}$alkyl (for example $CH_2N(H)S(O)_2C_{1-4}$alkyl).

Even more preferably, at least one of the substituents is $C(O)N(R^9)_2$ (for example —$C(O)N(H)C_{1-4}$alkyl) or —$CH_2C(O)N(R^9)_2$ (for example —$CH_2C(O)N(H)C_{1-4}$alkyl). In such embodiments, preferably A is substituted pyrazolyl (such as a 4-pyrazolyl) or thiazolyl (such as a 5-thiazolyl).

In one preferred embodiment, X is O. In another preferred embodiment X is absent. In one preferred embodiment, L is —$(CH_2)_m$— or —$(CH_2)_mO$—; more preferably L is —$(CH_2)_m$—. In one preferred embodiment m is 1 or 2; preferably 2. In one preferred embodiment X is —O—; L is —$(CH_2)_m$ and m is 1 or 2.

In one preferred embodiment where, for example, the NMT inhibitor is used as a diagnostic agent for the diagnosis of a disease or disorder in which inhibition of NMT provides a therapeutic or prophylactic effect, or as reference compound in a method of discovering other inhibitors of NMT, L is —$(CHR^{12})_m$— or —$(CHR^{12})_mO$—; and one $R^{12}$ is a terminal $C_{1-6}$alkynyl optionally substituted by up to 3 —F, —Cl, —Br, I, —OH, —$OCH_3$, —$OCF_3$ or —CN groups, and more preferably one $R^{12}$ is a terminal unsubstituted $C_{1-6}$alkynyl. Preferably, when present, all other $R^{12}$ groups are hydrogen.

In one preferred embodiment $R^7$ is hydrogen or methyl, and/or $R^8$ is hydrogen or methyl. For the avoidance of doubt, when X is absent and L is present, $R^1$ is a group of formula -L-A, in which group L is directly bonded to group A and to the phenyl ring shown in formula (I). When X is present and L is absent, $R^1$ is a group of formula —X-A, in which group X is directly bonded to group A and to the phenyl ring shown in formula (I). When X and L are both absent, $R^1$ is a group of formula -A, in which group A is directly bonded to the phenyl ring shown in formula (I).

In one preferred embodiment, X is O, L is —$(CH_2)_m$—, m is 1 or 2, and A is an aromatic carbocycle or heterocycle selected from the group consisting of phenyl, pyridinyl, quinolinyl, imidazolyl, benzimidazolyl, pyrazolyl, thiazolyl, 1,2,3-triazolyl and 1,2,4-triazolyl, said aromatic carbocycle or heterocycle being optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups; —$C(O)N(R^9)_2$ (for example —$C(O)N(H)C_{1-4}$alkyl); and —$CH_2C(O)N(R^9)_2$ (for example —$CH_2C(O)N(H)C_{1-4}$alkyl). More preferably A is selected from the group consisting optionally substituted pyrazolyl and thiazolyl.

In one preferred embodiment, X is absent, L is —$(CH_2)_m$—, m is 3, and A is an aromatic carbocycle or heterocycle selected from the group consisting of phenyl, pyridinyl, quinolinyl, imidazolyl, benzimidazolyl, pyrazolyl, thiazolyl, 1,2,3-triazolyl and 1,2,4-triazolyl, said aromatic carbocycle or heterocycle being optionally substituted with 1, 2, or 3 groups independently selected from the group consisting of —$C_{1-4}$alkyl (for example methyl), wherein each —$C_{1-4}$alkyl is optionally substituted by up to 3 halogen, hydroxyl or —$OC_{1-4}$alkyl groups; —$C(O)N(R^9)_2$ (for example —$C(O)N(H)Cl_{1-4}$alkyl); and —$CH_2C(O)N(R^9)_2$ (for example —$CH_2C(O)N(H)C_{1-4}$alkyl). Preferably A is selected from the group consisting optionally substituted pyrazolyl and thiazolyl.

In one preferred embodiment, $R^3$ and $R^4$ are both hydrogen. In another preferred embodiment, $R^3$ is hydrogen and $R^4$ is methyl.

In one preferred embodiment, $R^5$ and $R^6$ are both methyl. In another embodiment, $R^5$ and $R^6$ are both hydrogen. In another embodiment, $R^5$ is hydrogen and $R^6$ is methyl.

In another embodiment, q is 0 or 1 and the $R^3$ group and the $R^5$ group and the intervening atoms form a 3 to 7 membered non-aromatic heterocycle composed of the intervening atoms and bond, or the intervening atoms and —$(CHR^a)_r$—. Preferably a 4 to 6 membered non-aromatic heterocycle is formed; and more preferably a 4 membered non-aromatic heterocycle. In embodiments where a 4 membered non-aromatic heterocycle is formed, preferably q is 1.

In another embodiment, q is 1 and the $R^{10}$ group and the $R^5$ group and the intervening atoms form a 3 to 7 membered non-aromatic heterocycle composed of the intervening atoms and —$(CHR^a)_r$—. Preferably a 4 to 6 membered non-aromatic heterocycle is formed.

It has been surprisingly found that stability, and in particular $t_{1/2}$, of the NMT inhibitors according to the invention can be improved when q is 1, and when q is 1and the $R^3$ group and the $R^5$ group and the intervening atoms form a non-aromatic heterocycle composed of the intervening atoms and —$(CHR^a)_r$—, for example when a 4 membered ring is formed wherein r is 1. Therefore, in one preferred embodiment q is 1 and the $R^3$ group and the $R^5$ group and the intervening atoms form a 4 membered non-aromatic heterocycle composed of the intervening atoms and —$(CHR^a)_r$, wherein r is 1.

It has also been surprisingly found that rapid metabolism can be achieved when q is 0. Compounds having a short $t_{1/2}$ can be advantageous to reduce side effects and/or for administration methods in which rapid metabolism is advantageous, for example delivery by inhalation. Therefore, in another preferred embodiment q is 0.

In one preferred embodiment, A is phenyl, X is —O—; L is —$(CH_2)_m$—; m is 1 or 2; s is 0; E, J and G are each $C(R^7)$; K is carbon; Q is $N(R^8)$; M is nitrogen; $R^3$ and $R^4$ are each hydrogen; $R^5$ and $R^6$ are each methyl; and $R^8$ is hydrogen.

In one preferred embodiment, A is 3-pyridinyl. In one preferred embodiment, the compound has the formula (IA') or (IB')

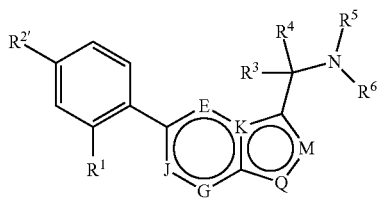
(IA')

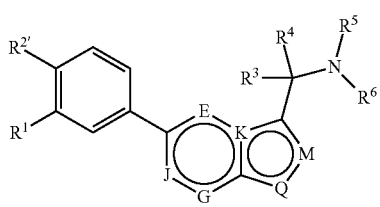
(IB')

wherein R¹ is a group of formula —X-L-A; A is 3-pyridinyl; X is —O—; L is —(CH₂)$_m$—; m is 1 or 2; R²' is hydrogen or fluorine; Q is N(R⁸); M is nitrogen; E, J and G are each C(R⁷); K is carbon; R³ and R⁴ are each hydrogen; R⁵ and R⁶ are each methyl; and R⁸ is hydrogen.

In one preferred embodiment, A is 4-quinolinyl. In one preferred embodiment, A is 4-quinolinyl; X is —O—; L is —(CH₂)$_m$—; m is 1 or 2; s is 0; E, J and G are each C(R⁷); K is carbon; Q is N(R⁸); M is nitrogen; R³ and R⁴ are each hydrogen; R⁵ and R⁶ are each methyl; and R⁸ is hydrogen.

In one preferred embodiment, A is 1-imidazolyl, said imidazolyl being optionally substituted by 1 or 2 methyl groups. In one preferred embodiment, the compound has the formula (IA') or (IB')

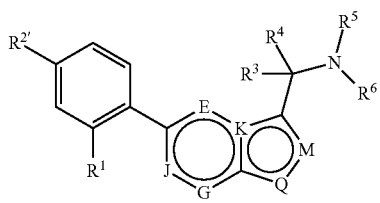
(IA')

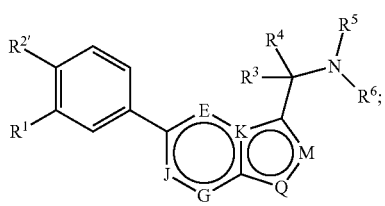
(IB')

wherein R¹ is a group of formula —X-L-A; A is 1-imidazolyl, said imidazolyl being optionally substituted by 1 or 2 methyl groups; X is —O—; L is —(CH₂)$_m$—; m is 1 or 2; R²' is hydrogen or fluorine; E, J and G are each C(R⁷); K is carbon; Q is N(R⁸); M is nitrogen; R³ and R⁴ are each hydrogen; R⁵ and R⁶ are each methyl; and R⁸ is hydrogen or methyl.

In one preferred embodiment, A is 1-benzimidazolyl. In one preferred embodiment, the compound has the formula (IA')

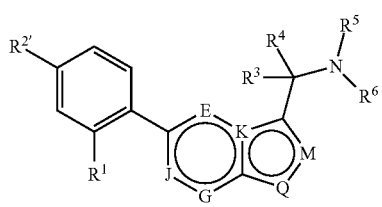
(IA')

wherein R¹ is a group of formula —X-L-A; A is 1-benzimidazolyl; X is —O—; L is —(CH₂)$_m$—; m is 1 or 2; R²' is fluorine or hydrogen; E, J and G are each C(R⁷); K is carbon; Q is N(R⁸); M is nitrogen; R³ and R⁴ are each hydrogen; R⁵ and R⁶ are each methyl; and R⁸ is hydrogen.

In one preferred embodiment, A is an optionally substituted 4-pyrazolyl, such as a 4-pyrazolyl optionally substituted by up to 3 substituents independently selected from the group consisting of —C$_{1-4}$alkyl, wherein each —C$_{1-4}$alkyl is optionally substituted by up to 3 halogen, hydroxyl or —OC$_{1-4}$alkyl groups; —C(O)N(R⁹)₂ (for example —C(O)N(H)C$_{1-4}$alkyl), and —CH₂C(O)N(R⁹)₂ (for example —CH₂C(O)N(H)C$_{1-4}$alkyl); and R⁹ where present is each selected from the group consisting of hydrogen and —C$_{1-4}$alkyl, or two R⁹ groups and the N they are bonded to from a 4 to 7 membered non-aromatic heterocycle, the heterocycle optionally comprising 1 or 2 further heteroatoms selected from N, O and S. Preferably A is 4-pyrazolyl optionally substituted by up to 3 —C$_{1-4}$alkyl; —CH₂OC$_{1-4}$alkyl, CF₂H, CF₃, C(O)N(Me)₂, —C(O)-1-pyrazole; or —C(O)-4-morpholine groups. More preferably A is 4-pyrazolyl substituted with one or two methyl groups and one —C$_{1-4}$alkyl; —CH₂OC$_{1-4}$alkyl, CF₂H, CF₃, C(O)N(Me)₂, —C(O)-1-pyrazole; or —C(O)-4-morpholine group.

In one preferred embodiment, the compound has the formula (IA″)

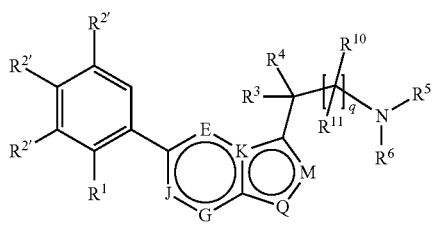
(IA″)

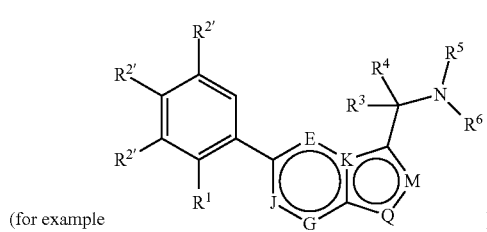
(Iα″)

(for example            )

wherein R¹ is a group of formula —X-L-A; A is 4-pyrazolyl, said pyrazolyl being optionally substituted with up to 3 methyl groups; X is —O— or absent (preferably —O—); L is —(CH₂)$_m$— or —(CH₂)$_m$—O— (preferably —(CH₂)$_m$—); m is 1, 2 or 3 (preferably 1 or 2); each R²' is independently selected from the group consisting of hydrogen, fluorine, chlorine, —CN and methyl; R³ and R⁴ are each hydrogen; R³ is hydrogen or methyl; R⁴ is hydrogen or methyl;

$R^5$ is hydrogen or methyl; $R^6$ is hydrogen or methyl; when present $R^{10}$ is hydrogen or methyl; when present $R^{11}$ is hydrogen or methyl; or the $R^3$ group and the $R^5$ group and the intervening atoms form a 3 to 7 membered non-aromatic heterocycle composed of the intervening atoms and bond, or the intervening atoms and —$(CHR^a)_r$—; or the $R^{10}$ group and the $R^5$ group and the intervening atoms form a 3 to 7 membered non-aromatic heterocycle composed of the intervening atoms and —$(CHR^a)_r$—; (more preferably at least one of $R^5$ and $R^6$ is methyl, most preferably $R^5$ and $R^6$ are both methyl); r is 1, 2, 3, 4 or 5; $R^a$ is hydrogen or methyl; $R^7$ where present is hydrogen or methyl; $R^8$ where present is hydrogen or methyl; and E, J, G, K, Q and M are as defined in formula (I). Within that embodiment, preferably i) E, J and G are each $C(R^7)$, K is carbon, Q is $N(R^6)$, M is nitrogen; and $R^8$ is hydrogen or methyl;
ii) E, J and G are each $C(R^7)$, and K, Q and M are each nitrogen;
iii) E and G are each $C(R^7)$, and J, K, Q and M are each nitrogen;
iv) J and G are each $C(R^7)$, and E, K, Q and M are each nitrogen; or
v) E, J, G and M are each $C(R^7)$, and K and Q are each nitrogen; and more preferably E, J and G are each $C(R^7)$, and K, Q and M are each nitrogen; E, J and G are each $C(R^7)$, K is carbon, Q is $N(R^8)$, M is nitrogen, and $R^8$ is hydrogen or methyl; or E, J, G and M are each $C(R^7)$, and K and Q are each nitrogen.

Also within that embodiment, preferably, Y is —CH— or —$C(R^2)$—.

Also within that embodiment, the compound may have formula (IA^)

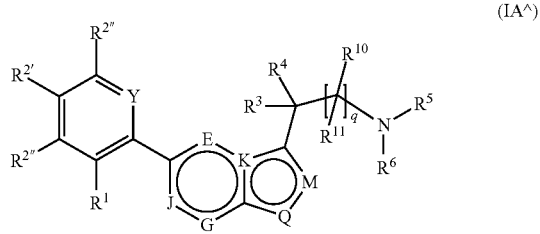

and wherein $R^{2'}$ is selected from the group consisting of fluorine, chlorine, —CN and methyl (preferably fluorine); and $R^{2''}$ is selected from the group consisting of hydrogen, fluorine, chlorine, —CN and methyl; or the compound may have formula (IA^^)

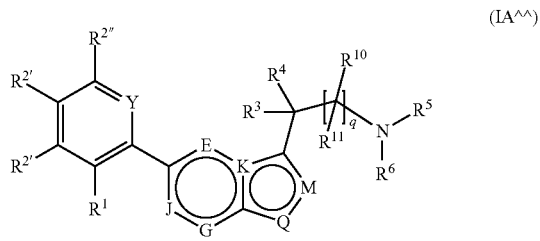

wherein $R^{2'}$ is selected from the group consisting of fluorine, chlorine, —CN and methyl (preferably fluorine); and $R^{2''}$ is selected from the group consisting of hydrogen, fluorine, chlorine, —CN and methyl; or the compound may have formula (IA^^^)

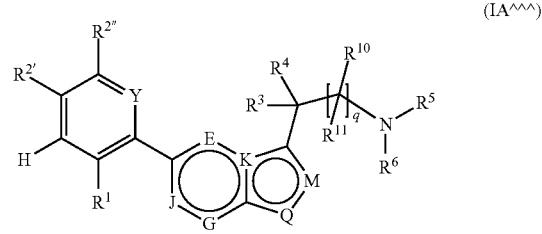

wherein $R^{2'}$ is selected from the group consisting of fluorine, chlorine, —CN and methyl (preferably fluorine); and $R^{2''}$ is selected from the group consisting of hydrogen, fluorine, chlorine, —CN and methyl.

In certain embodiments within the above-mentioned embodiment, $R^1$ is a group of formula —X-L-A; A is 4-pyrazolyl, said pyrazolyl being optionally substituted with up to 3 methyl groups; X is —O— or absent; L is —$(CH_2)_m$— or —$(CH_2)_m$—O—; m is 2; $R^{2'}$ is selected from the group consisting of fluorine, chlorine —CN and methyl (preferably fluorine); q is 0, $R^3$ is hydrogen or methyl; $R^4$ is hydrogen or methyl; $R^5$ is hydrogen or methyl; $R^6$ is hydrogen or methyl; or the $R^3$ group and the $R^5$ group and the intervening atoms form a 3 to 7 membered non-aromatic heterocycle composed of the intervening atoms and bond, or the intervening atoms and —$(CHR^a)_r$—; (more preferably $R^5$ and $R^6$ are both methyl); $R^7$ where present is hydrogen or methyl; $R^8$ where present is hydrogen or methyl; and E, J, G, K, Q and M are as defined in formula (I); and, preferably i) E, J and G are each $C(R^7)$, K is carbon, Q is $N(R^8)$, M is nitrogen; and $R^8$ is hydrogen or methyl;
ii) E, J and G are each $C(R^7)$, and K, Q and M are each nitrogen;
iii) E and G are each $C(R^7)$, and J, K, Q and M are each nitrogen;
iv) J and G are each $C(R^7)$, and E, K, Q and M are each nitrogen; or
v) E, J, G and M are each $C(R^7)$, and K and Q are each nitrogen.

In certain embodiments of the above-mentioned embodiment, $R^1$ is a group of formula —X-L-A; A is 4-pyrazolyl, said pyrazolyl being optionally substituted with up to 3 methyl groups; X is —O— or absent; L is —$(CH_2)_m$— or —$(CH_2)_m$—O—; m is 2; $R^{2'}$ is fluorine; $R^3$ and $R^4$ are each hydrogen; q is 0, $R^5$ and $R^6$ are each independently hydrogen or methyl (more preferably $R^5$ and $R^6$ are both methyl); or the $R^3$ group and the $R^5$ group and the intervening atoms form a 3 to 7 membered non-aromatic heterocycle composed of the intervening atoms and bond, or the intervening atoms and —$(CHR^a)_r$—; $R^7$ where present is hydrogen or methyl; $R^8$ is methyl; K is carbon; Q is $N(R^8)$; M is nitrogen; and E, J and G are as defined in formula (I); or $R^1$ is a group of formula —X-L-A; A is 4-pyrazolyl, said pyrazolyl being optionally substituted with up to 3 methyl groups; X is —O— or absent; L is —$(CH_2)_m$— or —$(CH_2)_m$—O—; m is 2; $R^{2'}$ is fluorine; $R^3$ and $R^4$ are each hydrogen; $R^5$ and $R^6$ are each independently hydrogen or methyl (more preferably $R^5$ and $R^6$ are both methyl); $R^7$ where present is hydrogen or methyl; Q, M and K are each nitrogen; and E, J and G are each $C(R^7)$.

In one preferred embodiment, the compound has the formula (IA')

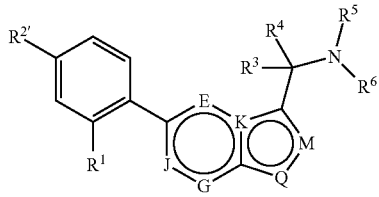

(IA')

wherein $R^1$ is a group of formula —X-L-A; A is 4-pyrazolyl, said pyrazolyl being optionally substituted with up to 3 methyl groups; X is —O— or absent; L is —(CH$_2$)$_m$— or —(CH$_2$)$_m$—O—; m is 2; $R^{2'}$ is selected from the group consisting of fluorine, chlorine —CN and methyl (preferably fluorine);

$R^3$ is hydrogen or methyl; $R^4$ is hydrogen or methyl;

$R^5$ is hydrogen or methyl; $R^6$ is hydrogen or methyl; or the $R^3$ group and the $R^5$ group and the intervening atoms form a 3 to 7 membered non-aromatic heterocycle composed of the intervening atoms and bond, or the intervening atoms and —(CHR$^a$)$_r$—; (more preferably $R^5$ and $R^6$ are both methyl); $R^7$ where present is hydrogen or methyl; $R^8$ where present is hydrogen or methyl; and E, J, G, K, Q and M are as defined in formula (I). Within that embodiment, preferably i) E, J and G are each C($R^7$), K is carbon, Q is N($R^8$), M is nitrogen; and $R^8$ is hydrogen or methyl;

ii) E, J and G are each C($R^7$), and K, Q and M are each nitrogen;

iii) E and G are each C($R^7$), and J, K, Q and M are each nitrogen;

iv) J and G are each C($R^7$), and E, K, Q and M are each nitrogen; or v) E, J, G and M are each C($R^7$), and K and Q are each nitrogen.

In one preferred embodiment, the compound has the formula (IA')

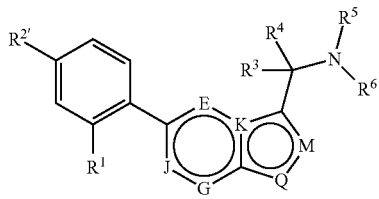

(IA')

wherein $R^1$ is a group of formula —X-L-A; A is 4-pyrazolyl, said pyrazolyl being optionally substituted with up to 3 methyl groups; X is —O— or absent; L is —(CH$_2$)$_m$— or —(CH$_2$)$_m$—O—; m is 2; $R^{2'}$ is fluorine; $R^3$ and $R^4$ are each hydrogen; $R^5$ and $R^6$ are each independently hydrogen or methyl (more preferably $R^5$ and $R^6$ are both methyl); $R^7$ where present is hydrogen or methyl; $R^8$ is methyl; K is carbon; Q is N($R^8$); M is nitrogen; and E, J and G are as defined in formula (I).

In one preferred embodiment, the compound has the formula (IA')

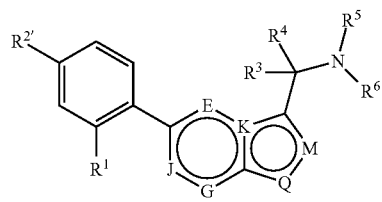

(IA')

wherein $R^1$ is a group of formula —X-L-A; A is 4-pyrazolyl, said pyrazolyl being optionally substituted with up to 3 methyl groups; X is —O— or absent; L is —(CH$_2$)$_m$— or —(CH$_2$)$_m$—O—; m is 2; $R^{2'}$ is fluorine; $R^3$ and $R^4$ are each hydrogen; $R^5$ and $R^6$ are each independently hydrogen or methyl (more preferably $R^5$ and $R^6$ are both methyl); $R^7$ where present is hydrogen or methyl; Q, M and K are each nitrogen; and E, J and G are each C($R^7$).

In one preferred embodiment, the compound has the formula (IA'''')

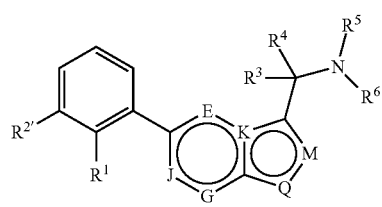

(IA'''')

wherein $R^1$ is a group of formula —X-L-A; A is 4-pyrazolyl, said pyrazolyl being optionally substituted with up to 3 methyl groups; X is —O— or absent; L is —(CH$_2$)$_m$— or —(CH$_2$)$_m$—O—; m is 2; $R^{2'}$ is selected from the group consisting of fluorine, —CN and methyl; $R^3$ and $R^4$ are each hydrogen; $R^5$ and $R^6$ are each independently hydrogen or methyl (more preferably $R^5$ and $R^6$ are both methyl); $R^7$ where present is hydrogen or methyl; $R^8$ where present is hydrogen or methyl; and E, J, G, K, Q and M are as defined in formula (I). Within that embodiment, preferably i) E, J and G are each C($R^7$), K is carbon, Q is N($R^8$), M is nitrogen; and $R^8$ is hydrogen or methyl;

ii) E, J and G are each C($R^7$), and K, Q and M are each nitrogen;

iii) E and G are each C($R^7$), and J, K, Q and M are each nitrogen;

iv) J and G are each C($R^7$), and E, K, Q and M are each nitrogen; or v) E, J, G and M are each C($R^7$), and K and Q are each nitrogen.

In one preferred embodiment, the compound has the formula (IA'''')

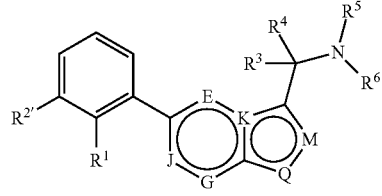

(IA'''')

wherein R¹ is a group of formula —X-L-A; A is 4-pyrazolyl, said pyrazolyl being optionally substituted with up to 3 methyl groups; X is —O— or absent; L is —(CH₂)ₘ— or —(CH₂)ₘ—O—; m is 2; R²' is fluorine; R³ and R⁴ are each hydrogen; R⁵ and R⁶ are each independently hydrogen or methyl (more preferably R⁵ and R⁶ are both methyl); R⁷ where present is hydrogen or methyl; R⁸ is methyl; K is carbon; Q is N(R⁸); M is nitrogen; and E, J and G are as defined in formula (I).

In one preferred embodiment, the compound has the formula (IA'''')

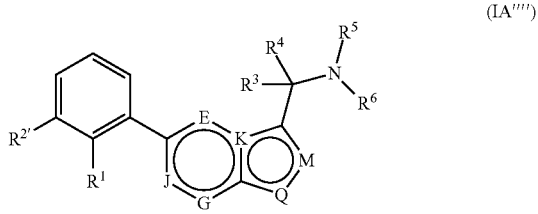

(IA'''')

wherein R¹ is a group of formula —X-L-A; A is 4-pyrazolyl, said pyrazolyl being optionally substituted with up to 3 methyl groups; X is —O— or absent; L is —(CH₂)ₘ— or —(CH₂)ₘ—O—; m is 2; R²' is fluorine; R³ and R⁴ are each hydrogen; R⁵ and R⁶ are each independently hydrogen or methyl (more preferably R⁵ and R⁶ are both methyl); R⁷ where present is hydrogen or methyl; Q, M and K are each nitrogen; and E, J and G are each C(R⁷).

In one preferred embodiment, A is an optionally substituted 5-thiazolyl, such as a 5-thiazolyl optionally substituted by 1 or 2 methyl groups. In one preferred embodiment, the compound has the formula (IA'')

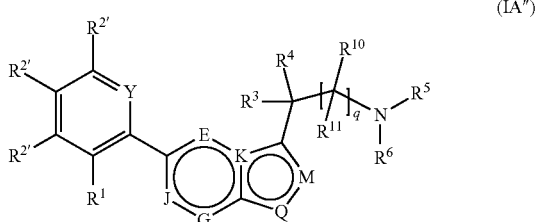

(IA'')

(for example

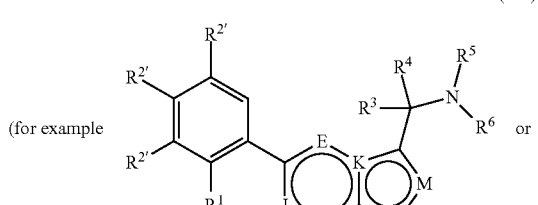

(Iα'')

)

(IA')

wherein R¹ is a group of formula —X-L-A; A is 5-thiazolyl optionally substituted with 1 or 2 methyl groups (more preferably A is 5-thiazolyl substituted with one methyl group at the 4-position; or substituted with two methyl groups, one at the 2-position and one at the 4-position); X is —O—; L is —(CH₂)ₘ—; m is 1, 2 or 3 (preferably 1 or 2); R²' is hydrogen, chlorine or fluorine (preferably fluorine); R³ is hydrogen or methyl; R⁴ is hydrogen or methyl;

R⁵ is hydrogen or methyl; R⁶ is hydrogen or methyl;

when present R¹⁰ is hydrogen or methyl;

when present R¹¹ is hydrogen or methyl;

or the R³ group and the R⁵ group and the intervening atoms form a 3 to 7 membered non-aromatic heterocycle composed of the intervening atoms and bond, or the intervening atoms and —(CHRᵃ)ᵣ—; or the R¹⁰ group and the R⁵ group and the intervening atoms form a 3 to 7 membered non-aromatic heterocycle composed of the intervening atoms and —(CHRᵃ)ᵣ—;

r is 1, 2, 3, 4 or 5; Rᵃ is hydrogen or methyl (preferably R³ and R⁴ are each independently hydrogen or methyl; and R⁵ and R⁶ are each independently hydrogen or methyl;) K is carbon; Q is N(R⁸); M is nitrogen; R⁸ is methyl; and E, J and G are as defined in formula (I).

Also within that embodiment, preferably, Y is —CH— or —C(R²')—.

Also within that embodiment, the compound may have formula (IA^)

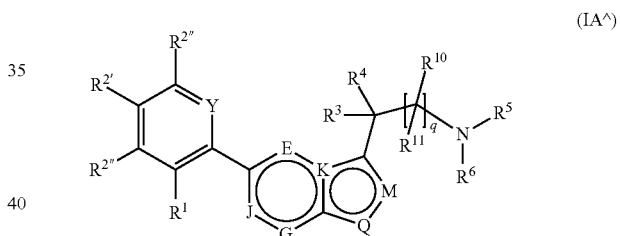

(IA^)

and wherein R²' is selected from the group consisting of fluorine and chlorine (preferably fluorine); and R²'' is selected from the group consisting of hydrogen, fluorine and chlorine; or the compound may have formula (IA^^)

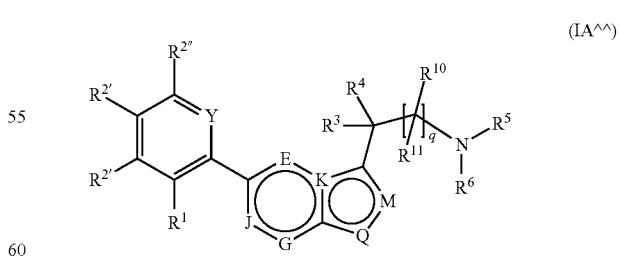

(IA^^)

wherein R²' is selected from the group consisting of fluorine and chlorine (preferably fluorine); and R²'' is selected from the group consisting of hydrogen, fluorine and chlorine; or the compound may have formula (IA^^^)

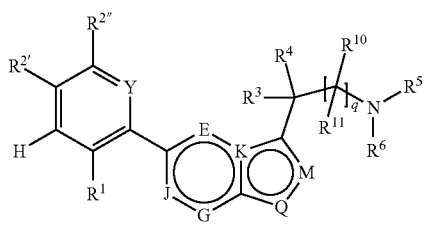

(IA^^^)

wherein R$^{2'}$ is selected from the group consisting of fluorine and chlorine (preferably fluorine); and R$^{2''}$ is selected from the group consisting of hydrogen, fluorine and chlorine.

In one preferred embodiment, the compound has the formula (IA')

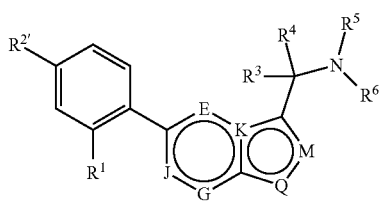

(IA')

wherein R$^1$ is a group of formula —X-L-A; A is 5-thiazolyl optionally substituted with 1 or 2 methyl groups (more preferably A is 5-thiazolyl substituted with one methyl group at the 4-position; or substituted with two methyl groups, one at the 2-position and one at the 4-position); X is —O—; L is —(CH$_2$)$_m$—; m is 1, 2 or 3 (preferably 3); R$^{2'}$ is hydrogen, chlorine or fluorine (preferably fluorine); R$^3$ is hydrogen or methyl; R$^4$ is hydrogen or methyl;

R$^5$ is hydrogen or methyl; R$^6$ is hydrogen or methyl;

when present R$^{10}$ is hydrogen or methyl;

when present R$^{11}$ is hydrogen or methyl;

or the R$^3$ group and the R$^5$ group and the intervening atoms form a 3 to 7 membered non-aromatic heterocycle composed of the intervening atoms and bond, or the intervening atoms and —(CHR$^a$)$_r$; or the R$^{10}$ group and the R$^5$ group and the intervening atoms form a 3 to 7 membered non-aromatic heterocycle composed of the intervening atoms and —(CHR$^a$)$_r$;

r is 1, 2, 3, 4 or 5; R$^a$ is hydrogen or methyl (preferably R$^3$ and R$^4$ are each independently hydrogen or methyl; and R$^5$ and R$^6$ are each independently hydrogen or methyl); K, Q and M are each nitrogen; and E, J and G are as defined in formula (I).

In one preferred embodiment, A is selected from the group consisting of optionally substituted 1,2,4-triazol-1-yl, optionally substituted 1,2,4-triazol-4-yl, optionally substituted 1,2,4-triazol-3-yl and optionally substituted 1,2,3-triazol-4-yl. Within that embodiment, preferably X is absent and L is —(CH$_2$)$_3$—. A is preferably optionally substituted 1,2,4-triazol-1-yl.

In one preferred embodiment, the compound has the formula (IA''')

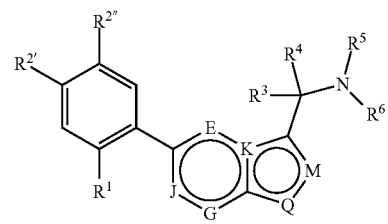

(IA'')

wherein R$^1$ is a group of formula —X-L-A; A is selected from the group consisting of optionally substituted 1,2,4-triazol-1-yl, optionally substituted 1,2,4-triazol-4-yl, optionally substituted 1,2,4-triazol-3-yl and optionally substituted 1,2,3-triazol-4-yl; X is —O— or absent; L is —(CH$_2$)$_m$—; m is 2 or 3; R$^{2'}$ is hydrogen or fluorine (more preferably R$^{2'}$ is fluorine); R$^{2''}$ is hydrogen or —OCH$_3$; R$^3$ and R$^4$ are each hydrogen; R$^5$ and R$^6$ are each methyl; K is carbon; Q is N(R$^8$); M is nitrogen; R$^8$ is methyl or hydrogen; and E, J and G are as defined in formula (I). Within that embodiment, preferably X is absent and L is —(CH$_2$)$_3$—.

In one preferred embodiment, the compound has the formula (IA''')

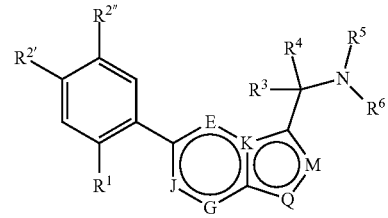

(IA''')

wherein R$^1$ is a group of formula —X-L-A; A is selected from the group consisting of optionally substituted 1,2,4-triazol-1-yl, optionally substituted 1,2,4-triazol-4-yl, optionally substituted 1,2,4-triazol-3-yl and optionally substituted 1,2,3-triazol-4-yl; X is —O— or absent; L is —(CH$_2$)$_m$—; m is 2 or 3; R$^{2'}$ is hydrogen or fluorine (more preferably R$^{2'}$ is fluorine); R$^{2''}$ is hydrogen or —OCH$_3$; R$^3$ and R$^4$ are each hydrogen; R$^5$ and R$^6$ are each methyl; K, Q and M are each nitrogen; and E, J and G are as defined in formula (I). Within that embodiment, preferably X is absent and L is —(CH$_2$)$_3$—.

In one preferred embodiment, the compound has the formula (IA''')

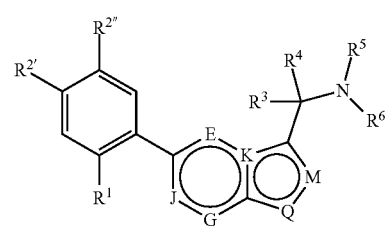

(IA''')

wherein R$^1$ is a group of formula —X-L-A; A is selected from the group consisting of optionally substituted 1,2,4-triazol-1-yl, optionally substituted 1,2,4-triazol-4-yl, optionally substituted 1,2,4-triazol-3-yl and optionally substituted 1,2,3-triazol-4-yl; X is absent; L is —(CH$_2$)$_3$—; R$^{2'}$ is fluorine; R$^{2''}$ is hydrogen or —OCH$_3$; R$^3$ and R$^4$ are each hydrogen; R$^5$ and R$^6$ are each methyl; K, Q and M are each nitrogen; and E, J and G are as defined in formula (I).

In one embodiment, the compound has the formula (IB)

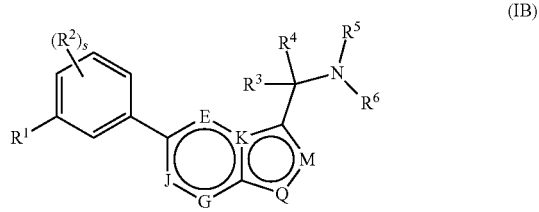

(IB)

wherein R$^1$ is a group of formula —X-L-A; X is —O—; L is —(CH$_2$)$_m$—; m is 1 or 2;
A is selected from the group consisting of optionally substituted 3-pyridinyl, 4-pyridinyl and 1-imidazolyl;
s is 0; R$^3$ and R$^4$ are each hydrogen; R$^5$ and R$^6$ are each methyl; K is carbon; Q is N(R$^8$); M is nitrogen; and R$^8$ is hydrogen; and E, J, and G are as defined in formula (I).

In one embodiment, the compound has the formula (IB)

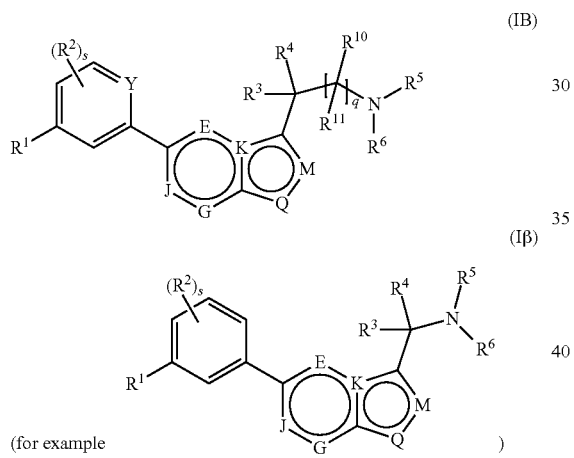

(IB)

(Iβ)

(for example             )

wherein R$^1$ is a group of formula —X-L-A; X is —O—; L is —(CH$_2$)$_m$—; m is 1 or 2;
A is selected from the group consisting of optionally substituted 3-pyridinyl, 4-pyridinyl and 1-imidazolyl;
s is 0 or 1; R$^2$ is fluorine; q is 0 or 1 (preferably q is 0); R$^3$ and R$^4$ are each hydrogen; R$^5$ and R$^6$ are each methyl; R$^{10}$ and R$^{11}$ are each hydrogen or methyl; K, Q and M are each nitrogen;
and E, J, and G are as defined in formula (I).

NMT inhibitors of the invention include, but are not limited to, the compounds specifically named in the Examples herein, and salts thereof. In one embodiment, the NMT inhibitor is any one of Example compound nos. 1 to 122 (for example, Example compound nos. 1 to 108, 1 to 101, 1 to 67, or 1 to 51), or a salt thereof. In one embodiment, the NMT inhibitor is a compound selected from the group consisting of: 17, 7, 18, 30, 29, 24, 36, 35, 33, 37, 45, 46, 47, 48, 49, and 50, or a salt thereof.

In one preferred embodiment, the NMT inhibitor compound of the invention is selection from the groups consisting of example 2, 3, 4, 6, 7, 8, 9, 10, 11, 12, 13, 17, 18, 19, 20, 22, 23, 24, 26, 28, 29, 30 and 32, 33, 34, 35, 36, 37, 38, 39, 41, 42, 43, 45, 46, 48, 49, and 50, 53, 55, 56, 57, 58, 60, 62, 63, 66, 67, 68, 69, 70, 71, 72, 74, 75, 76, 77, 78, 79, 80, 81, 82, 86, 86, 88, 89, 90, 91, 92, 93, 94, 95, and 96. In another preferred embodiment, the compound of the invention is selection from the groups consisting of example 8, 9, 17, 18, 20, 22, 24, 29, 30, 31, 32, 33, 35, 36, 39, and 48. In another preferred embodiment, the compound of the invention is selection from the groups consisting of example 7 and 8. In another preferred embodiment, the compound of the invention is selection from the groups consisting of example 7, 8, 17 and 18.

In another preferred embodiment, the compound of the invention is selection from the groups consisting of example 7, 17, 53, 56, 70, 77, 78, 85, 92, 94. In another preferred embodiment, the compound of the invention is selection from the groups consisting of example 8, 17.18, 29, 30, 35, 37, 39, 53, 55, 56, 62, 68, 70, 72, 76 and 92. In another preferred embodiment, the compound of the invention is selection from the groups consisting of example 7, 17, 18 and 30. In another preferred embodiment, the compound of the invention is selection from the groups consisting of example 17, 18, 30, 49, 50, 62, 63, 70, 76, 77, 83, 86, 94, 97, and 100. In another preferred embodiment, the compound of the invention is selection from the groups consisting of example 30, 34, 49, and 50.

In one embodiment, the NMT inhibitor is any one of the following compounds:

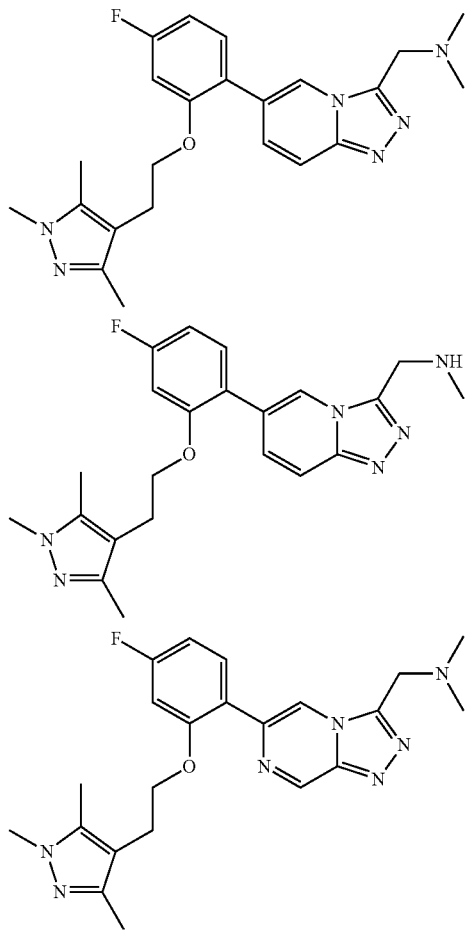

27
-continued
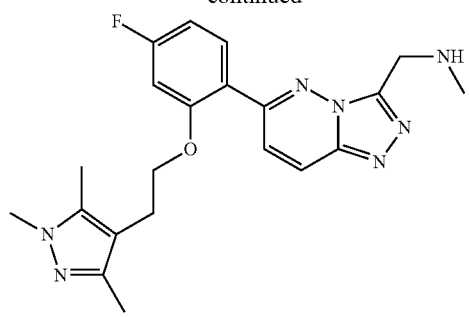
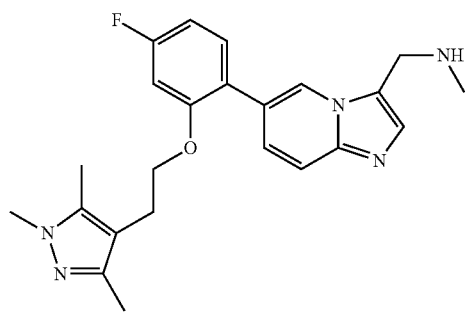
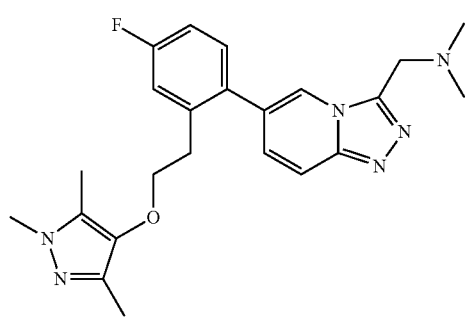
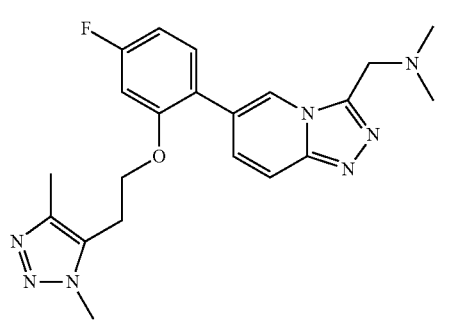
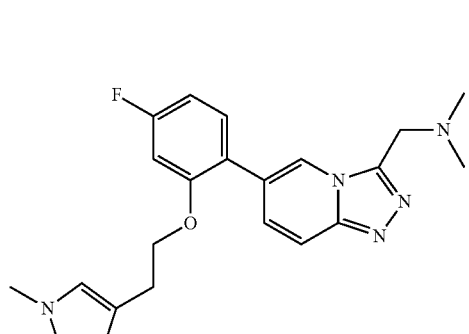
28
-continued
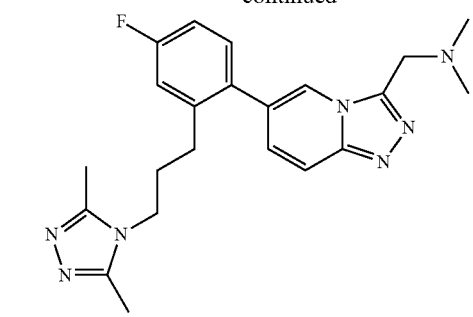
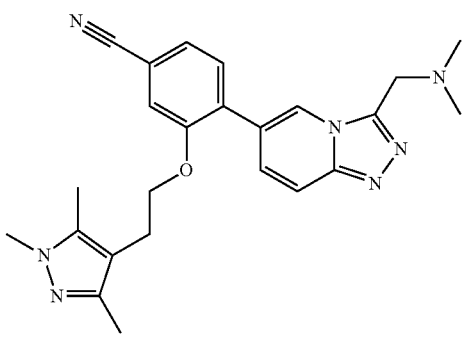
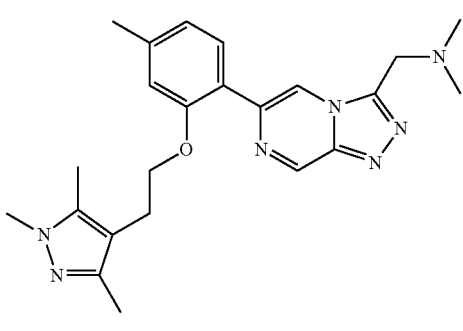
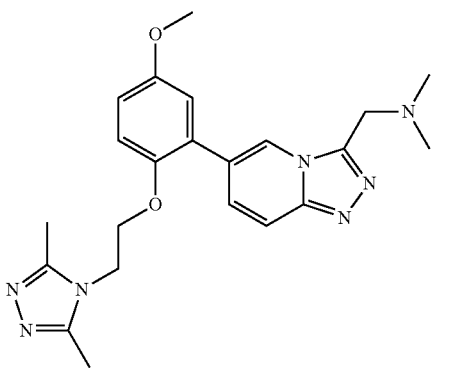

or a salt thereof. In another embodiment, the NMT inhibitor is any one of the following compounds:
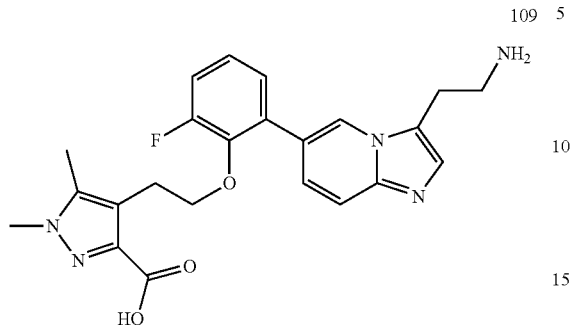
109
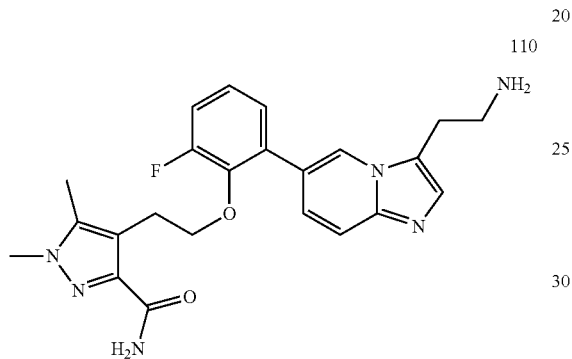
110
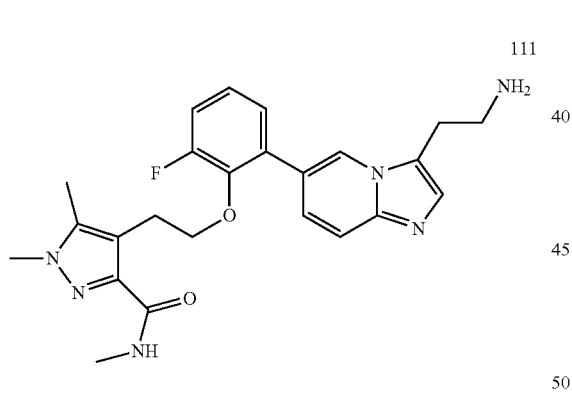
111
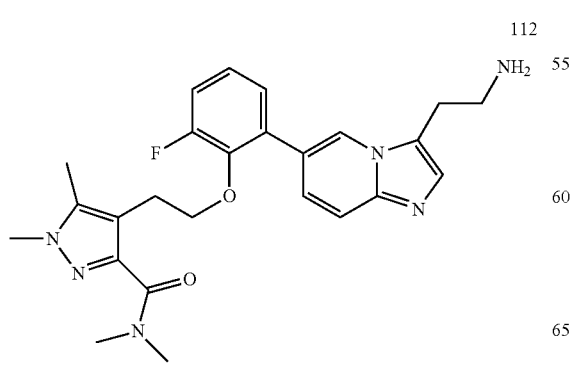
112
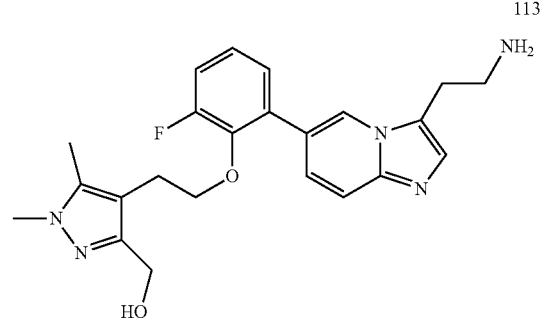
113
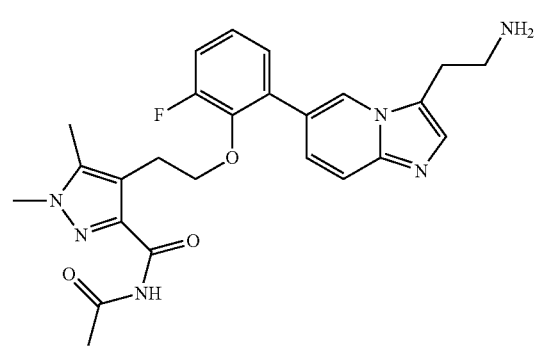
114
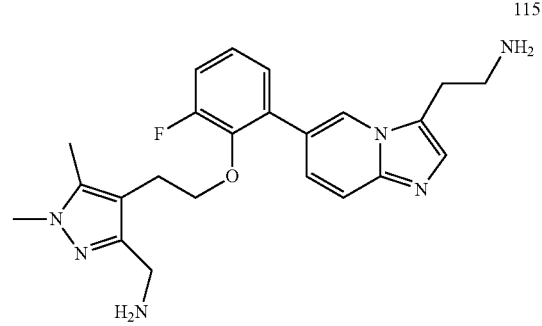
115
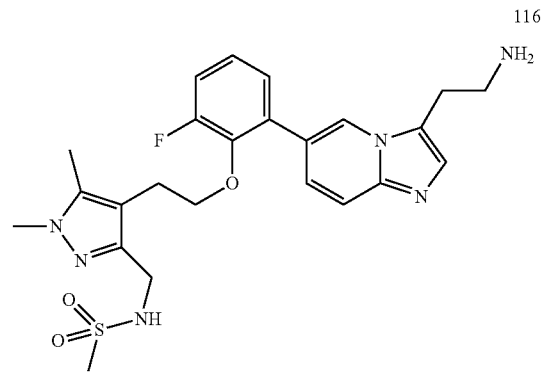
116

117

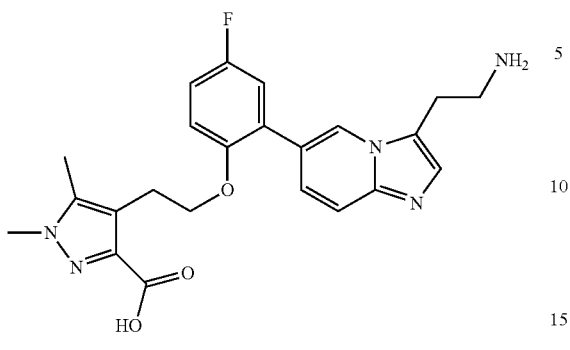

118

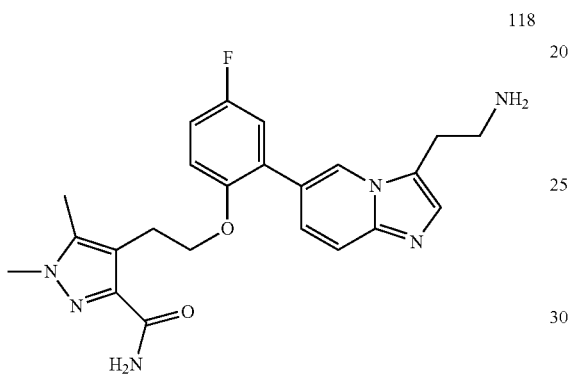

119

120

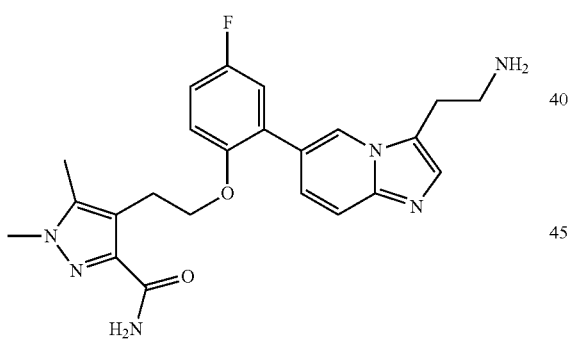

121

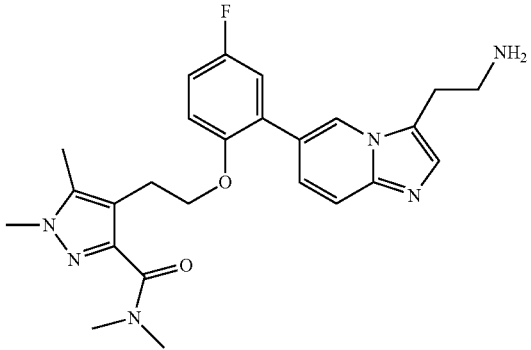

122

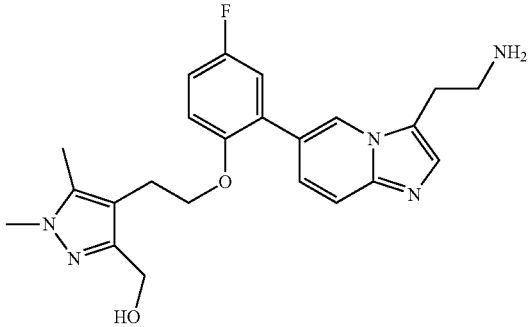

or a salt thereof.

As mentioned above, the compounds of the invention have activity as inhibitors of N-myristoyl transferase. The NMT inhibitors of the invention may be competitive inhibitors or partial competitive inhibitors of the NMT enzyme. The NMT inhibitors of the invention may thus be used in the treatment of diseases or disorders associated with NMT activity or may be used in the treatment of a disease or disorder by targeting NMT activity (for example in microbial infections, hyperproliferative diseases, picornavirus infections). Accordingly, there is provided an NMT inhibitor according to the invention, or a pharmaceutical composition comprising the NMT inhibitor and a pharmaceutically acceptable carrier, for use as a medicament. There is also provided an NMT inhibitor according to the invention, or a pharmaceutical composition comprising the NMT inhibitor and a pharmaceutically acceptable carrier, for use in the treatment or prophylaxis of a disease or disorder in which inhibition of N-myristoyl transferase provides a therapeutic or prophylactic effect.

The invention also provides a method for the treatment or prophylaxis of a disease or disorder in a subject in which inhibition of N-myristoyl transferase provides a therapeutic or prophylactic effect in a mammal, which comprises administering to the mammal a therapeutically effective amount of an NMT inhibitor according to the invention, or of a pharmaceutical composition comprising the NMT inhibitor and a pharmaceutically acceptable carrier.

The invention also provides the use of an NMT inhibitor according to the invention for the manufacture of a medicament for the treatment or prophylaxis of a disease or disorder in which inhibition of N-myristoyl transferase provides a therapeutic or prophylactic effect.

Diseases or disorders in which inhibition of N-myristoyl transferase provides a therapeutic or prophylactic effect include microbial infections; e.g. fungal infections, and protozoan infections such as malaria, leishmaniasis, human African trypanosomiasis (sleeping sickness) and American trypanosomiasis (Chagas disease).

In one preferred embodiment, the disease or disorder is a protozoan infection caused by a species of *Plasmodium*, *Leishmania* or *Trypanosoma* (for example *Plasmodium falciparum*, *Plasmodium vivax*, *Leishmania donovani*, *Leishmania major*, *Trypanosoma brucei*, *Trypanosoma cruzi*).

As mentioned above, inhibition of human NMT has also been suggested as a target for treating or preventing various diseases or disorders, for example hyperproliferative disorders (cancers, e.g. human colorectal cancer, gallbladder carcinoma, brain tumors, lymphomas such as B-cell lymphoma), and viral infections such as picornavirus infections, for example rhinovirus (HRV, also known as the common cold) or lentivirus infections for example HIV, and so NMT inhibitors of the invention find use the treatment or prevention of those disorders.

Further diseases or disorders in which inhibition of N-myristoyl transferase provides a therapeutic or prophylactic effect include neurological diseases/disorders, ischemia, osteoporosis and diabetes.

Compounds of the invention which are selective for the NMT enzyme of a particular species (e.g. *Plasmodium falciparum*, *Plasmodium vivax*, *Leishmania donovani*, *Leishmania major*, *Trypanosoma brucei*, *Trypanosoma cruzi*) over human NMT (human NMT1 and/or human NMT2) may be particularly useful in the treatment of conditions associated with those species (e.g. malaria, leishmaniasis, sleeping sickness). For example, use of a selective NMT inhibitor may result in fewer side effects compared with use of a less selective compound. In one preferred embodiment, NMT inhibitors are selective for a non-human NMT (e.g. *Plasmodium falciparum*, *Plasmodium vivax*, *Leishmania donovani*, *Trypanosoma brucei* and/or *Trypanosoma cruzi*) over human NMT (e.g. over human NMT1 and/or human NMT2). NMT inhibitors are considered selective if the ratio of human NMT $IC_{50}$ value to non-human NMT $IC_{50}$ value is greater than 5, preferably greater than 10, more preferably greater than 100, most preferably greater than 1000.

Compounds which are particularly good inhibitors of human NMT may be preferred for use in the treatment and/or prevention of viral infections (e.g. HIV, HRV) and cancers, as well as other conditions for which inhibition of human NMT has been suggested as a means of therapy.

The NMT inhibitor of the invention may be in the form of a pharmaceutically acceptable salt. Salts of compounds of the invention which are suitable for use in medicine are those wherein a counter-ion is pharmaceutically acceptable. However, salts having non-pharmaceutically acceptable counter-ions are within the scope of the present invention, for example, for use as intermediates in the preparation of the compounds of the invention and their pharmaceutically acceptable salts.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids, which may or may not in themselves be pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al., Pharmaceutical Research, 1995. 12(7): p. 954-954, and Water-Insoluble Drug Formulation, $2^{nd}$ ed. R. Liu, CRC Press, page 553, which are incorporated herein by reference. Accordingly, it will be understood by the skilled person that the NMT inhibitors of the invention may therefore be present in the form of solvates. Solvates of NMT inhibitors of the invention which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the NMT inhibitors according to the invention.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, NMT inhibitors of the present invention may be administered in a single daily dose, or the total daily dosage may be administered in divided doses of two, three or four times daily. Furthermore, preferred NMT inhibitors of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than inter-mittent throughout the dosage regimen.

While it is possible for the active ingredient to be administered alone, it is preferable for it to be present in a pharmaceutical formulation or composition. Accordingly, the invention provides a pharmaceutical formulation or composition comprising an NMT inhibitor according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), intranasal (also known as nasal administration), inhalation (including fine particle dusts or mists which may be generated by means of various types of metered dose pressurized aerosols, nebulizers or insufflators) insufflation, rectal, intraperitoneal and topical (including dermal, buccal, sublingual, and intraocular) administration, although the most suitable route may depend upon, for example, the condition and disorder of the recipient.

In certain preferred embodiments the NMT inhibitor according to the present invention is administered by intranasal, inhalation (including fine particle dusts or mists which may be generated by means of various types of metered dose pressurized aerosols, nebulizers or insufflators) or insufflation administration. Such embodiments are especially preferred for, for example, the treatment of a picornaviral infection, such as human rhinovirus infection. Such a method of administration allows for low doses of NMT inhibitor to be administered, which can lead to a reduction in side-effects. For example, a daily dose of 10 to 0.01 µg, preferably 1 to 0.01 µg, and more preferably in the region of as low as 0.1 µg (100 ng) of NMT inhibitor may be used.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present NMT inhibitors can, for example, be administered in a form suitable for immediate release or extended release. Immediate release or extended release can be achieved by the use of suitable pharmaceutical compositions comprising the present NMT inhibitors, or, particularly in the case of extended release, by the use of devices such as subcutaneous implants or osmotic pumps. The present NMT inhibitors may also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The NMT inhibitors according to the invention can also be delivered through the oral cavity by sublingual and/or buccal administration. Molded tablets, compressed tablets or freeze-dried tablets are exemplary forms which may be used. Exemplary compositions include those formulating the present NMT inhibitors with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The NMT inhibitors of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for intranasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst an NMT inhibitor of the invention may be used as the sole active ingredient in a medicament, it is also possible for the NMT inhibitor to be used in combination with one or more further therapeutic agents. Accordingly there is provided an NMT inhibitor of the invention, together with a further therapeutic ingredient, for simultaneous, sequential or separate administration.

Such further therapeutic agents may be further NMT inhibitors, for example a further NMT inhibitor according to the invention (i.e. a further compound of formula (I) or salt thereof).

Further therapeutic agents may also be different therapeutic agents; for example further therapeutic agents useful for treatment of malaria, leishmaniasis, human African trypanosomiasis (sleeping sickness) and American trypanosomiasis (Chagas disease); anti-fungal agents; anti-viral agents (including anti-HIV agents); chemotherapeutic agents (e.g. anti-lymphoma agents); antidepressants; anxiolytic agents; anti-psychotic agents; anti-osteoporosis agents; anti-ischemia agents and/or anti-diabetic agents.

In one preferred embodiment, the NMT inhibitor of the invention is administered in combination with an effective amount of a further anti-protozoan agent, for example (i) an anti-malarial agent selected from the group consisting of chloroquine, primaquine, amodiaquine, mefloquine, halofantrine, lumefantrine, pyrimethamine, sulfadoxine, artemesinin, dihydroartemesinin, artemether, artesunate, atovaquone, and proguanil; and/or (ii) an anti-leishmaniasis agent selected from the group consisting of amphotericin B, miltefosine, paromomycin, pentamidine, fexinidazole, and meglumine antimonate; and/or (iii) an anti-human African trypanosomiasis or anti-American trypanosomiasis agent selected from the group consisting of melarsoprol, suramin, pentamidine, eflornithine, nufurtimox, benznidazole, posaconazole and E1224. One or more of those further anti-protozoan agents may be used in combination with an NMT inhibitor of the invention.

In a further embodiment, the NMT inhibitor of the invention may be effectively administered in combination with an effective amount of an anti-lymphoma agent selected from the group consisting of adriamycin, bleomycin, blenoxane, dacarbazine, deltasone, cyclophosphamide, Cytoxan, DTIC, doxorubicin, etoposide, matulane, mechlorethamine, Mustargen, Mustine, Natulan, VCR, Neosar, nitrogen mustard, Oncovin, Orasone, Prednisone, procarbazine, VP-16, Velban, Velbe, Velsar, VePesid, vinblastine and vincristine.

The NMT inhibitors of the invention can be used in combination with other agents useful for the treatment or prophylaxis of a disease or disorder in which inhibition of N-myristoyl transferase provides a therapeutic or prophylactic effect. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the NMT inhibitors of the invention with other agents useful for treating or prophylaxis of a disease or disorder in which inhibition of N-myristoyl transferase provides a therapeutic or prophylactic effect includes in principle any combination with any pharmaceutical composition useful for treating or prophylaxis of a disease or disorder in which inhibition of N-myristoyl transferase provides a therapeutic or prophylactic effect.

The above further therapeutic agents, when employed in combination with the compounds of the present invention, may be used, for example, in those amounts indicated in the Physicians' Desk Reference (PDR) or as otherwise determined by one of ordinary skill in the art.

Where the NMT inhibitors of the invention are utilized in combination with one or more further therapeutic agent(s), either concurrently or sequentially, the following combination ratios and dosage ranges are preferred: when combined with a further therapeutic agent, the NMT inhibitor of the invention may for example be employed in a weight ratio to the further therapeutic agent within the range from about 10:1 to about 1:10.

The invention also provides a kit of parts comprising: (a) a first pharmaceutical composition comprising an NMT inhibitor according to the invention and a pharmaceutically acceptable carrier; and (b) a second pharmaceutical composition comprising a further therapeutic agent, preferably a further N-myristoyl transferase inhibitor, and a pharmaceutically acceptable carrier.

In one embodiment, where the NMT inhibitor of the invention is for the treatment or prevention of rhinovirus (HRV, also known as the common cold), the NMT inhibitors of the invention may be utilized in combination with one or more further therapeutic agent(s), either concurrently or sequentially, for the treatment of HRV and/or for the treatment of asthma and/or for the treatment of chronic obstructive pulmonary disease (COPD). For example, the further therapeutic agent(s) may be selected from the group consisting of: pleconaril, pirodavir, vapendavir BTA-798, V-073, rupintrivir, enviroxime, IFN-β (SNG001); corticosteroids (inhaled and oral, for example beclomethasone, fluticasone, budesonide, ciclesonide), beta agonists (for example salbutamol, levosalbutamol, terbutaline, pirbuterol, procaterol, clenbuterol, metaproterenol, fenoterol, bitolterol mesylate, ritodrine, isoprenaline, salmeterol, formoterol, bambuterol, clenbuterol, olodaterol and indacaterol) muscarinic antagonists (for example ipratropium and diphenhydramine), leukotriene receptor antagonists (for example montelukast, zafirlukast, zileuton), cromylins, PDE4 inhibitors (for example ibudilast), and anti-cytokine antibodies, such as anti-IgE (for example omalizumab), anti-IL5 (for example mepolizumab, reslizumab and benralizumab) anti-IL4 (for example dupilumab and pitrakinra).

In one embodiment, the NMT inhibitor of the invention comprises an isotope atom, preferably a radioactive isotope atom. As defined herein, an isotope atom is an atom of an element that is not the most common naturally occurring isotope. Such NMT inhibitors may find use as diagnostic agents for the diagnosis of a disease or disorder in which inhibition of NMT provides a therapeutic or prophylactic effect. Accordingly, the present invention also provides for use of an NMT inhibitor comprising an isotope atom, preferably a radioactive isotope atom, as a diagnostic agent for the diagnosis of a disease or disorder in which inhibition of NMT provides a therapeutic or prophylactic effect.

The present invention also provides an NMT inhibitor in which L is —(CHR$^{12}$)$_m$— or —(CHR$^{12}$)$_m$O—, and one R$^{12}$ is a terminal C$_{1-6}$alkynyl optionally substituted by up to 3 —F, —Cl, —Br, I, —OH, —OCH$_3$, —OCF$_3$ or —CN groups (and more preferably one R$^{12}$ is a terminal unsubstituted C$_{1-6}$alkynyl and/or when present, all other R$^{12}$ groups are hydrogen), for use as a diagnostic agent for the diagnosis of a disease or disorder in which inhibition of NMT provides a therapeutic or prophylactic effect. In such an embodiment 'click chemistry', for example using an azide analogue, can be used detect the NMT inhibitor.

The NMT inhibitors of the invention also find use as reference compounds in methods of discovering other inhibitors of NMT. Thus, the invention also provides use of an NMT inhibitor according to the invention (i.e. a compound of formula (I) or salt thereof), for example an NMT inhibitor comprising an isotope atom (preferably a radioactive isotope atom) or an NMT inhibitor in which L is —(CHR$^{12}$)$_m$— or —(CHR$^{12}$)$_m$O—, and one R$^{12}$ is a terminal C$_{1-6}$alkynyl optionally substituted by up to 3 —F, —Cl, —Br, I, —OH, —OCH$_3$, —OCF$_3$ or —CN groups, as a reference compound in a method of identifying a further inhibitor of N-myristoyl transferase. For example, such a method may involve a competitive binding experiment in which binding of an NMT inhibitor according to the invention to an NMT enzyme is reduced by the presence of a further compound which has NMT-binding characteristics, for example stronger NMT-binding characteristics than the NMT inhibitor of the invention in question (i.e the compound of formula (I) or salt thereof). In embodiments which use an NMT inhibitor in which L is —(CHR$^{12}$)$_m$— or —(CHR$^{12}$)$_m$O—, and one R$^{12}$ is a terminal C$_{1-6}$alkynyl optionally substituted by up to 3 —F, —Cl, —Br, I, —OH, —OCH$_3$, —OCF$_3$ or —CN groups, 'click chemistry', for example using an azide analogue, can be used detect the NMT inhibitor. In such an embodiment, preferably one R$^{12}$ is a terminal unsubstituted C$_{1-6}$alkynyl and/or, when present, all other R$^{12}$ groups are hydrogen Numerous synthetic routes to the compounds of the present invention can be devised by any person skilled in the art and the exemplified synthetic routes described below do not limit the invention. Many methods exist in the literature for the synthesis of heterocycles, for example: Joule, J. A.; Mills, K., Heterocyclic Chemistry, 2010, 5$^{th}$ Edition, Pub. Wiley. A number of possible synthetic routes are exemplified below. Where appropriate, any initially produced compound according to the invention can be converted into another compound according to the invention by known methods.

General Method I

The invention also provides a process for the preparation of an NMT inhibitor according to the invention, in which X and L are present; R$^4$ is hydrogen; R$^5$ and R$^6$ are each C$_{1-6}$alkyl; K is carbon; Q is N(R$^8$); M is nitrogen; and R$^8$ is hydrogen; the process comprising: (i) reacting a compound of formula (X)

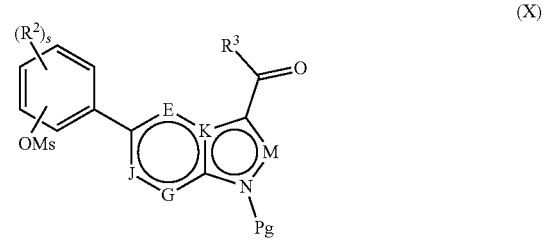

(X)

in which Ms represents —S(O)$_2$CH$_3$; Pg represents a protecting group, preferably a 2-tetrahydropyranyl group; K is carbon; M is nitrogen; and E, J, G, R$^2$, R$^3$ and s are as defined in formula (I);

with a compound of formula (XI)

HNR$^5$R$^6$ (XI)

in which R$^5$ and R$^6$ are each C$_{1-6}$alkyl;

and a source of hydride to produce a compound of formula (XII)

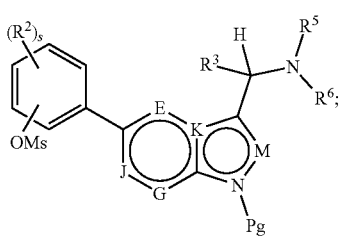 (XII)

(ii) reacting the compound of formula (XII) with a compound of formula (XIII)

A-L-XH  (XIII)

in which L and X are present, and in which A, L and X are as defined in formula (I); to produce a compound of formula (XIV)

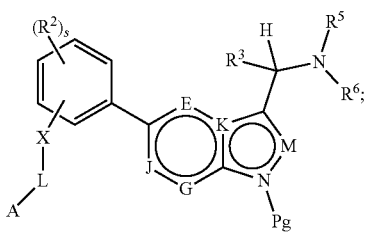 (XIV)

(iii) subjecting the compound of formula (XIV) to deprotection conditions to produce a compound of formula (I); and (iv) optionally converting the compound of formula (I) to a pharmaceutically acceptable salt thereof.

The compound of formula (X) may for example be produced by reacting a compound of formula (XIX)

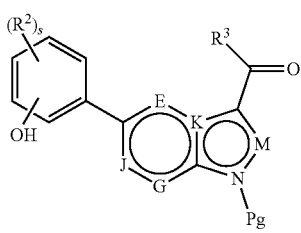 (XIX)

in which Pg represents a protecting group, preferably a 2-tetrahydropyranyl group; K is carbon; M is nitrogen; and E, J, G, R², R³ and s are as defined in formula (I); with methanesulfonyl chloride in the presence of a base such as triethylamine.

The compound of formula (XIX) may for example be produced reacting a compound of formula (XX)

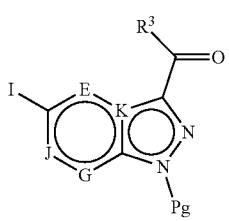 (XX)

in which Pg represents a protecting group, preferably a 2-tetrahydropyranyl group; K is carbon; M is nitrogen; and E, J, G, and R³ are as defined in formula (I);
with a compound of formula (XXI)

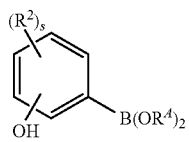 (XXI)

in which each $R^A$ independently represents hydrogen, $C_{1-6}$ alkyl, or the two $OR^A$ groups together form a —O—C(CH₃)₂—C(CH₃)₂—O— group;
under Suzuki coupling conditions; e.g. in the presence of a palladium catalyst such as tetrakis (triphenylphosphine) palladium(0) and a base such as potassium phosphate.

Where Pg represents a 2-tetrahydropyranyl group, the step of subjecting the compound of formula (XIV) to deprotection conditions to produce a compound of formula (I) may comprise contacting the compound of formula (XIV) with an acid (e.g. HCl).

General Method I as shown above was used for the synthesis of, for example, Example compounds 1, 2, 3, 4, 5, 6, 7, 8, 9, 10, 11, 12, 13, 14, 15 and 16. Full experimental details of the individual steps of the general method applicable for the synthesis of Example compounds 1, 2, 3, 4, 5, 6, 7, 8, 9, 10, 11, 12, 13, 14, 15 and 16 are described below.

General Method II

The invention also provides a process for the preparation of an NMT inhibitor according to the invention in which X and L are present; K is carbon; Q is N(R⁸); M is nitrogen; R⁴ is hydrogen; R⁸ is methyl; and R⁵ and R⁶ are each $C_{1-6}$alkyl; the process comprising: (i) reacting a compound of formula (XV)

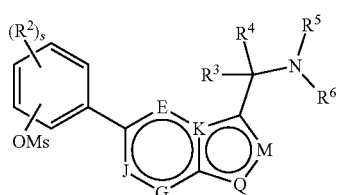 (XV)

in which Ms represents —S(O)₂CH₃; K is carbon; Q is N(R⁸); M is nitrogen; R⁸ is methyl; R⁴ is hydrogen; R⁵ and R⁶ are each $C_{1-6}$alkyl; and E, J, G, R², R³, R⁵, R⁶ and s are as defined in formula (I);
with a compound of formula (XIII)

A-L-XH  (XIII);

in which L and X are present, and in which A, L and X are as defined in formula (I); to produce a compound of formula (I); and (ii) optionally converting the compound of formula (I) to a pharmaceutically acceptable salt thereof.

The compound of formula (XV) may for example be produced by reacting a compound of formula (XXII)

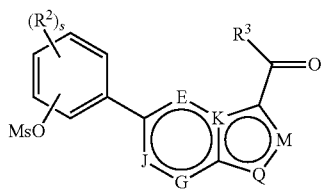

(XXII)

in which Ms represents —S(O)$_2$CH$_3$; K is carbon; Q is N(R$^8$); M is nitrogen; R$^8$ is methyl; and E, J, G, R$^2$, R$^3$ and s are as defined in formula (I);
with a compound of formula (XI)

HNR$^5$R$^6$ (XI)

in which R$^5$ and R$^6$ are each C$_{1-6}$alkyl;
and a source of hydride.

The compound of formula (XXII) may for example be produced by reacting a compound of formula (XXIII)

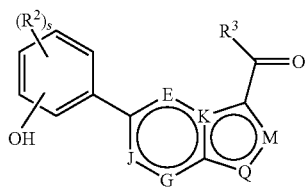

(XXIII)

in which K is carbon; Q is N(R$^8$); M is nitrogen; R$^8$ is methyl; and E, J, G, R$^2$, R$^3$ and s are as defined in formula (I);
with methanesulfonyl chloride in the presence of a base such as triethylamine.

The compound of formula (XXIII) may for example be produced by reacting a compound of formula (XXIV)

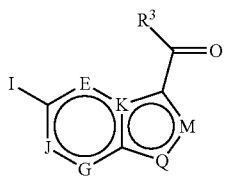

(XXIV)

in which K is carbon; Q is N(R$^8$); M is nitrogen; R$^8$ is methyl; and E, J, G and R$^3$ are as defined in formula (I);
with a compound of formula (XXI) as defined above, under Suzuki coupling conditions, e.g. in the presence of a palladium catalyst such as tetrakis (triphenylphosphine)palladium(0) and a base such as potassium phosphate.

General Method II as shown above was used for the synthesis of, for example, Example compound 20, 21, 22, 23 and 24. Full experimental details of the individual steps of the general method applicable for the synthesis of Example compound 20, 21 22, 23 and 24 are described below.

General Method III

The invention also provides a process for the preparation of an NMT inhibitor according to the invention in which X and L are present; K is carbon; Q is N(R$^8$); M is nitrogen; R$^8$ is methyl; and R$^5$ and R$^6$ are each hydrogen; the process comprising:

(i) reacting a compound of formula (XVI)

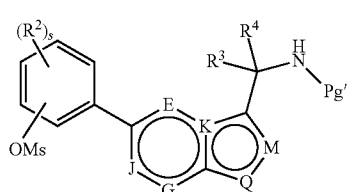

(XVI)

in which Ms represents —S(O)$_2$CH$_3$; K is carbon; Q is N(R$^8$); M is nitrogen; R$^8$ is methyl; Pg' is a protecting group, preferably a benzoyl group; and E, J, G, R$^2$, R$^3$ R$^4$ and s are as defined in formula (I);
with a compound of formula (XIII)

A-L-XH (XIII);

In which L and X are present, and in which A, L and X are as defined in formula (I); to produce a compound of formula (XVII)

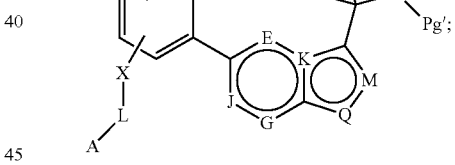

(XVII)

(ii) subjecting the compound of formula (XVII) to deprotection conditions to produce a compound of formula (I); and (iii) optionally converting the compound of formula (I) to a pharmaceutically acceptable salt thereof.

Where Pg' represents a benzoyl group, the step of subjecting the compound of formula (XVII) to deprotection conditions to produce a compound of formula (I) may comprise contacting the compound of formula (XVII) with an acid (e.g. HCl).

General Method IV

The invention also provides a process for the preparation of an NMT inhibitor according to the invention in which R$^4$ is hydrogen; K is carbon; Q is N(R$^8$); M is nitrogen; and R$^8$ is methyl; the process comprising:

(i) reacting a compound of formula (XVIII)

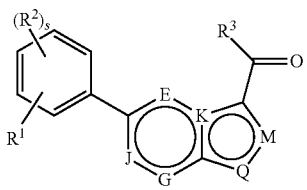
(XVIII)

in which K is carbon; Q is N(R$^8$); M is nitrogen; R$^8$ is methyl; and E, J, G, R$^1$, R$^2$, R$^3$ and s are as defined in formula (I);
with a compound of formula (XI)

HNR$^5$R$^6$  (XI)

in which R$^5$ and R$^6$ are as defined as in formula (I);
and a source of hydride to produce a compound of formula (I);
(ii) optionally converting the compound of formula (I) into a further compound of formula (I); and
(iii) optionally converting the compound of formula (I) to a pharmaceutically acceptable salt thereof.

Where L and X are present, the compound of formula (XVIII) may for example be produced by reacting a compound of formula (XXV)

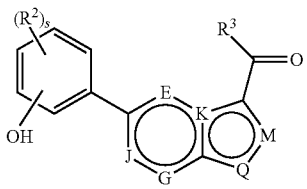
(XXV)

in which K is carbon; Q is N(R$^8$); M is nitrogen; R$^8$ is methyl; and E, J, G, R$^2$, R$^3$ and s are as defined in formula (I);
with a compound of formula (XIII)

A-L-XH  (XIII);

in which L and X are present, and in which A, L and X are as defined in formula (I); under Mitsunobu conditions, for example using triphenylphosphine and di-isopropyl azodicarboxylate.

Alternatively, where L and X are present, the compound of formula (XVIII) may for example be produced by reacting a compound of formula (XXII)

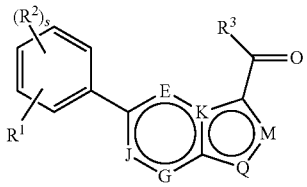
(XXII)

in which Ms represents S(O)$_2$CH$_3$; K is carbon; Q is N(R$^8$); M is nitrogen; R$^8$ is methyl; and E, J, G, R$^2$, R$^3$ and s are as defined in formula (I);
with a compound of formula (XIII)

A-L-XH  (XIII);

in which L and X are present, and in which A, L and X are as defined in formula (I).

The compound of formula (I) where R$^5$ and R$^6$ are each hydrogen may be converted into a further compound of formula (I) where R$^5$ and R$^6$ are each methyl, for example by reacting with paraformaldehyde and acetic acid, followed by sodium acetoxyborohydride.

The compound of formula (I) where R$^5$ and R$^6$ are each hydrogen may be converted into a further compound of formula (I) where R$^5$ is methyl and R$^6$ is hydrogen, for example by i) conversion of the primary amine group (i.e. —NR$^5$R$^6$, wherein both R$^5$ and R$^6$ are hydrogen) into the corresponding formyl amide (i.e. —NH—CH(O)) or into a carbamate, followed by ii) reduction (e.g. with lithium aluminium hydride) to produce the further compound of formula (I) where R$^5$ is methyl and R$^6$ is hydrogen.

General Method IV as shown above was used for the synthesis of, for example, Example compounds 17, 18, 25, 26, 29, 30. Full experimental details of the individual steps of the general method applicable for the synthesis of Example compounds 17, 18, 25, 26, 29, 30 are described below.

General Method V

The invention also provides a process for the preparation of an NMT inhibitor according to the invention in which R$^3$, R$^4$, R$^5$ and R$^6$ are each hydrogen; K is carbon; Q is N(R$^8$); M is nitrogen; and R$^8$ is methyl; the process comprising:
(i) reacting a compound of formula (XIX)

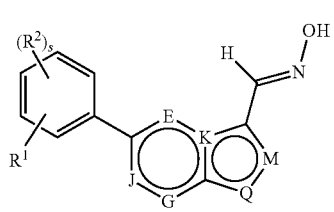
(XIX)

in which K is carbon; Q is N(R$^8$); M is nitrogen; R$^8$ is methyl; and E, J, G, R$^1$, R$^2$ and s are as defined in formula (I);
with a reducing agent to produce a compound of formula (I); and
(ii) optionally converting the compound of formula (I) to a pharmaceutically acceptable salt thereof.

The compound of formula (XIX) may for example be produced by reacting a compound of formula (XXVI)

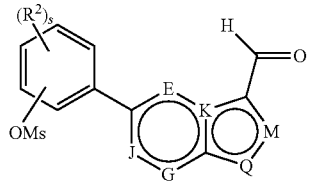
(XXVI)

in which K is carbon; Q is N(R$^8$); M is nitrogen; R$^8$ is methyl; and E, J, G, R$^1$, R$^2$ and s are as defined in formula (I);
with hydroxylamine hydrochloride and sodium acetate.

General Method V as shown above was used for the synthesis of, for example, Example compounds 31, 32 and 33. Full experimental details of the individual steps of the general method applicable for the synthesis of Example compounds 31, 32 and 33 are described below.

General Method VI

The invention also provides a process for the preparation of an NMT inhibitor according to the invention in which X and L are present; $R^5$ and $R^6$ are each $C_{1-6}$alkyl; K, Q and M are each nitrogen; the process comprising:

(i) reacting a compound of formula (XV)

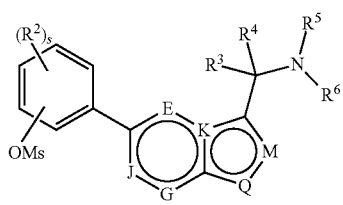
(XV)

in which Ms represents —S(O)$_2$CH$_3$; K, Q and M are each nitrogen; $R^5$ and $R^6$ are each $C_{1-6}$ alkyl; and E, J, G, $R^2$, $R^3$ $R^4$ and s are as defined in formula (I);
with a compound of formula (XIII)

A-L-XH   (XIII);

in which L and X are present, and in which A, L and X are as defined in formula (I); to produce a compound of formula (I); and
(ii) optionally converting the compound of formula (I) to a pharmaceutically acceptable salt thereof.

General Method VII

The invention also provides a process for the preparation of an NMT inhibitor according to the invention in which X and L are present; $R^5$ and $R^6$ are each hydrogen; and K, Q and M are each nitrogen; the process comprising:

(i) reacting a compound of formula (XVI)

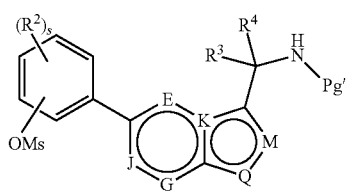
(XVI)

in which Ms represents —S(O)$_2$CH$_3$; K, Q and M are each nitrogen; Pg' is a protecting group, preferably a benzoyl group; and E, J, G, $R^2$, $R^3$, $R^4$ and s are as defined in formula (I); with a compound of formula (XIII)

A-L-XH   (XIII);

in which L and X are present, and A, L and X are as defined in formula (I); to produce a compound of formula (XVII)

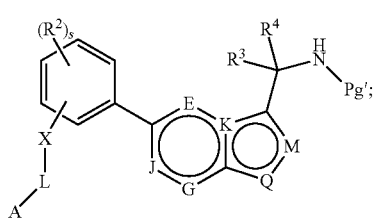
(XVII)

(ii) subjecting the compound of formula (XVII) to deprotection conditions to produce a compound of formula (I);
(iii) optionally converting the compound of formula (I) into a further compound of formula (I); and
(iv) optionally converting the compound of formula (I) to a pharmaceutically acceptable salt thereof.

Where Pg' represents a benzoyl group, the step of subjecting the compound of formula (XVII) to deprotection conditions to produce a compound of formula (I) may comprise contacting the compound of formula (XVII) with an acid (e.g. HCl).

The compound of formula (I) where $R^5$ and $R^6$ are each hydrogen may be converted into a further compound of formula (I) where $R^5$ and $R^6$ are each methyl, for example by reacting with paraformaldehyde and acetic acid, followed by sodium acetoxyborohydride.

Where Pg' is a benzoyl group, the compound of formula (XVI) may for example be produced by reaction of a compound of formula (XXVII)

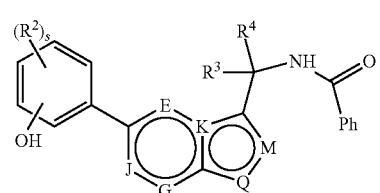
(XXVII)

in which K, Q and M are each nitrogen; and E, J, G, $R^2$, $R^3$, $R^4$ and s are as defined in formula (I);
with methanesulfonyl chloride in the presence of a base such as triethylamine.

The compound of formula (XXVII) may for example be produced by reaction of a compound of formula (XXVIII)

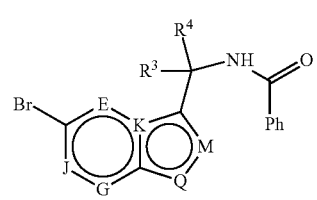
(XXVIII)

in which K, Q and M are each nitrogen; and E, J, G, $R^3$ and $R^4$ are as defined in formula (I); with a compound of formula (XXI) as defined above, under Suzuki coupling conditions, e.g. in the presence of a palladium catalyst such as tetrakis(triphenylphosphine)palladium(0) and a base such as potassium phosphate.

Where Pg' is benzoyl, where E, J, and G are each CH, and where K, Q and M are each nitrogen, the compound of formula (XXVIII) may for example be produced by reacting a compound of formula (XXIX)

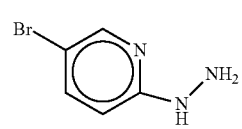
(XXIX)

with a compound of formula (XXX)

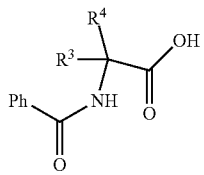

(XXX)

in which $R^3$ and $R^4$ are as defined in formula (I).

General Method VII as shown above was used for the synthesis of, for example, Example compounds 27 and 28. Full experimental details of the individual steps of the general method applicable for the synthesis of Example compounds 27 and 28 are described below.

General Method VIII

The invention also provides a process for the preparation of an NMT inhibitor according to the invention in which X is O, L is present; K is carbon; Q is $N(R^8)$; M is nitrogen; $R^4$ is hydrogen; $R^8$ is methyl; and $R^5$ and $R^6$ are each $C_{1-6}$alkyl; the process comprising: (i) reacting a compound of formula (XL)

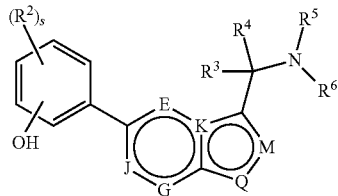

(XL)

in which; K is carbon; Q is $N(R^8)$; M is nitrogen; $R^8$ is methyl; $R^4$ is hydrogen; $R^5$ and $R^6$ are each $C_{1-6}$alkyl; and E, J, G, $R^2$, $R^3$, $R^5$, $R^6$ and s are as defined in formula (I); with a compound of formula (XLI)

A-L-O-Ts     (XLI)

in which Ts represents a para-toluene-sulfonyl group; L is present; and A and L are as defined in formula (I);
to produce a compound of formula (I); and
(ii) optionally converting the compound of formula (I) to a pharmaceutically acceptable salt thereof.

The compound of formula (XL) may for example be produced by reacting a compound of formula (XLII)

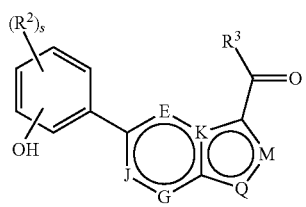

(XLII)

in which; K is carbon; Q is $N(R^8)$; M is nitrogen; $R^8$ is methyl; and E, J, G, $R^2$, $R^3$ and s are as defined in formula (I);
with a compound of formula (XI)

$HNR^5R^6$     (XI)

in which $R^5$ and $R^6$ are each $C_{1-6}$alkyl;
and a source of hydride.

General Method VIII as shown above was used for the synthesis of, for example, Example compound 19. Full experimental details of the individual steps of the general method applicable for the synthesis of Example compound 19 are described below.

Synthesis of Example Compounds

General Experimental Details

LC-MS

Compounds were purified and analysed on an LC-MS system equipped with both an XBridge prep C18 5 µm, 19×100 mm OBD column and an XBridge C18 5 µm, 4.6×100 mm column. Unless specified otherwise, all compounds were separated over a gradient of methanol in water (5-98% over 12 minutes then 98% methanol for 3 minutes), both containing 0.1% formic acid. Alternative gradient elutions started from 20 or 50% methanol for the same time periods.

Compounds requiring purification under basic conditions were purified on an LC-MS system equipped with a YMC Actus Triart C18 5 µm (20×250 mm) column or Gemini NX 5 µm C18 (100×30 mm) columns, using a gradient elution of acetonitrile in water containing 20 mM Ammonium bicarbonate (10-45% over 30 min then 95% acetonitrile for 2 minutes).

Hplc

The purity of examples 53-108 (with the exception of examples 74, 75, 79-82, 87-89 and 96) was determined by analytical hplc using an Eclipse Extend 5 µm C18 (150×4.6 mm) or Shimadzu L Column 2 ODS 5 µm C18 (150×4.6 mm) column using gradient elution of acetonitrile in water containing 10 mM ammonium acetate over 12 mins. The purity of examples 87-89 and 96 were determined by analytical hplc using a Gemini NX 3 µm C18 (50×4.6 mm) column using gradient elution of acetonitrile in water containing 0.05% formic acid over 12 mins.

Flash Column Chromatography

Compounds were purified using either an automated system using pre-packed silica cartridges and a gradient of ethyl acetate in n-hexane (typically 5-30% over 20 minutes) with UV detection or by manual columns using an appropriate solvent mixture as detailed.

NMR $^1$H NMR and $^{13}$C spectra were recorded on 400 MHz and 101 MHz respectively instruments at room temperature unless specified otherwise were referenced to residual solvent signals.

Data are presented as follows: chemical shift in ppm, integration, multiplicity (br=broad, app=apparent, s=singlet, d=doublet, t=triplet, q=quartet, p=pentet, m=multiplet) and coupling constants in Hz.

General Procedures

THP Deprotection (Method A)

The THP (tetrahydropyranyl) protected indazole was dissolved in a 1:1 mixture of THF and methanol (2 ml), then treated with a solution of HCl in isopropanol (6M, 1 ml). The reaction mixture was left at room temperature for 2 days. All volatiles were removed under reduced pressure and the residue was partitioned between ethyl acetate (20 ml) and saturated sodium carbonate solution (10 ml). The organic phase was dried over $Na_2SO_4$, concentrated under reduced pressure and the crude product purified by flash column chromatography.

THP Deprotection (Method B)

The THP protected indazole was dissolved in a 1:1 mixture of THF and methanol (2 ml), then treated with a solution of HCl in isopropanol (6M, 1 ml). The reaction mixture was heated to 40° C. at room temperature for 6 h-2 days. All volatiles were removed under reduced pressure and the residue was partitioned between ethyl acetate (20 ml) and saturated sodium carbonate solution (10 ml). The organic phase was dried over $Na_2SO_4$, concentrated under reduced pressure and the product purified by LC-MS.

Reductive Amination (Method A)

A solution of the heterocyclic carboxaldehydes (e.g. the indazolecarboxaldehyde) in DCE (dichloroethane) (5 ml) was treated with a solution of the appropriate amine in THF (3 mol equiv) followed by acetic acid (6 mol equiv). The solution was stirred at room temperature for 15 mins before being treated with solid sodium triacetoxyborohydride (3 mol equiv). The mixture was stirred overnight at room temperature then partitioned between DCM (dichloromethane) (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, then 92:3:5).

Reductive Amination (Method B)

The heterocyclic carboxaldehydes (e.g. the indazolecarboxaldehyde) was dissolved in a solution of the appropriate amine in ethanol (2 ml) and the solution stirred at room temperature overnight. Volatile material was removed under reduced pressure and residue dissolved in ethanol (5 ml), then treated with solid sodium borohydride (5 mol equiv). After stirring for 3 hours at room temperature, excess regent was destroyed by addition of 1N HCl and the mixture concentrated in vacuo. The residue was partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, then 90:5:5).

Reductive Amination (Method C)

The 3-acetylindazole was dissolved in methanol (2 ml) and treated with ammonium acetate (10 mol equiv) followed by sodium cyanoborohydride (5 mol equiv). The solution stirred and heated under reflux overnight. Volatile material was removed under reduced residue was partitioned between dichloromethane (20 ml) and saturated sodium carbonate solution (10 ml). The organic phase was dried over $Na_2SO_4$, concentrated under reduced pressure and the crude product purified by flash column chromatography by elution dichloromethane/methanol/conc.aqueous ammonia solution (97:3:0.5, then 95:5:0.5).

Reductive Amination (Method D)

A solution of the aminoalkyl heterocycles (e.g. the aminoalkylindazole) in DCE (5 ml) was treated with solid paraformaldehyde (10 mol equiv) and acetic acid (8 mol equiv). The suspension was stirred at room temperature for 15 mins before being treated with solid sodium triacetoxyborohydride (8 mol equiv). The mixture was stirred overnight at room temperature then partitioned between DCM (20 ml) and saturated sodium carbonate solution (10 ml). The organic phase was dried over $Na_2SO_4$, concentrated under reduced pressure and the crude product purified LC-MS.

Reductive Amination (Method E)

A solution of the heterocyclic carboxaldehydes (e.g. the indazolecarboxaldehyde) in THF (2 mL) was treated with a solution of the appropriate amine in THF (tetrahydrofuran) (3 mol equiv) followed by acetic acid (6 mol equiv). The solution was stirred at room temperature for 15 mins before being treated with solid sodium triacetoxyborohydride (3 mol equiv) and DCE (2 mL). The mixture was stirred overnight at room temperature then partitioned between DCM (20 mL) and saturated sodium carbonate solution (10 mL). The organic phase was dried over $Na_2SO_4$, concentrated under reduced pressure and the crude product purified by LCMS.

Mesyl Transfer (Method A)

A solution of the appropriate phenylmethane sulphonate in dry acetonitrile in a microwave vial was treated with a solution of the appropriate alcohol (1 mol equiv), followed by solid sodium t-butoxide (1 mol equiv). The vial was sealed then heated under microwave irradiation to 140° C. for 10 mins. The reaction mixture was partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, optionally by further elution with a 90:5:5 mixture).

Mesyl Transfer (Method B)

A solution of the appropriate phenylmethane sulphonate in dry DMF (N,N-dimethylformamide) (5 ml) was treated with a solution of the appropriate alcohol (1.5 mol equiv), followed by solid cesium carbonate (1.1 mol equiv). The reaction mixture was heated to 100° C. for 18 hrs, cooled to room temperature then partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, then 90:5:5) or dichloromethane/methanol/aqueous ammonia solution (95:5:0.5).

Mesyl Transfer (Method C)

A solution of the appropriate alcohol (1.0 mol equiv) was added to a suspension of sodium hydride (50% dispersion in oil, 1.9 mol equiv) in dry DMF followed by a solution of the appropriate phenylmethane sulphonate (1.0 mol equiv) in dry DMF. The reaction mixture was heated to 70° C. for 18 hrs, cooled to room temperature then partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, then 90:5:5) or dichloromethane/methanol/aqueous ammonia solution (95:5:0.5).

Mesyl Transfer (Method D)

A solution of the appropriate phenylmethane sulphonate in dry DMF in a microwave vial was treated with a solution of the appropriate alcohol (2 mol equiv), followed by solid cesium carbonate (2 mol equiv). The vial was sealed then heated under microwave irradiation to 140° C. for 10 mins. The reaction mixture was partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, optionally by further elution with a 90:5:5 mixture).

Mesyl Transfer (Method E)

A solution of the appropriate phenylmethane sulphonate in dry acetonitrile in a microwave vial was treated with a solution of the appropriate alcohol (5 mol equiv), followed by solid cesium carbonate (2 mol equiv). The vial was sealed then heated under microwave irradiation to 140° C. for 20 mins. The reaction mixture was partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, optionally by further elution with a 90:5:5 mixture).

Alkylation Using Alkyltosylate

A solution of the appropriate phenol in dry acetonitrile (0.5 ml) in a microwave vial was treated with a solution of the appropriate alcoholtosylate (1.1 mol equiv), followed by solid sodium t-butoxide (1 mol equiv). The vial was sealed then heated under microwave irradiation to 140° C. for 10 mins. The reaction mixture was partitioned between ethyl acetate (20 ml) and saturated sodium carbonate solution (10 ml). The organic phase was dried over $Na_2SO_4$, concentrated under reduced pressure and the crude product purified by flash column chromatography by elution with ethyl acetate/methanol/diethylamine (95:0:5, then 90:5:5) or dichloromethane/methanol/aqueous ammonia solution (95:5:0.5).

Benzamide Deprotection

The appropriate benzamide was dissolved in concentrated hydrochloric acid and heated under reflux overnight. The mixture was evaporated to dryness under reduced pressure, redissolved in methanol and basified with a solution of ammonia in methanol (7M, 5 ml), then re-evaporated. The crude product was purified by column chromatography on silica by elution with dichloromethane/methanol/ammonium hydroxide (90:10:1).

Boc Deprotection (Method A)

The Boc protected amine was dissolved in a 1:1 mixture of THF and methanol (2 ml), then treated with a solution of HCl in isopropanol (6M, 1 ml). The reaction mixture was stirred at room temperature overnight. All volatiles were removed under reduced pressure and the product purified by LC-MS using a gradient elution from methanol/water/formic acid (5:95:0.1 to 98:2:0.1).

Boc Deprotection (Method B)

The Boc protected amine was dissolved in dioxane and treated with a solution of HCl in dioxane (6M, 2 ml). The reaction mixture was stirred at room temperature overnight. All volatiles were removed under reduced pressure and the product triturated with ether redissolved in water and freeze dried.

Boc Deprotection (Method C)

The Boc protected amine was dissolved in dichloromethane then treated with trifluoroacetic acid at 0° C. The solution was stirred at room temperature for 3 hr. The solvent was removed under reduced pressure and the residue triturated with diethyl ether. The product was dissolved in water and freeze-dried.

Preparation of Starting Materials

All of the starting materials for making the intermediate and example compound were obtained from commercial sources or using literature methods with the exception of the following compounds.

2-(3-isobutyl-1,5-dimethyl-1H-pyrazol-4-yl)ethanol and 2-(5-isobutyl-1,3-dimethyl-1H-pyrazol-4-yl)ethanol

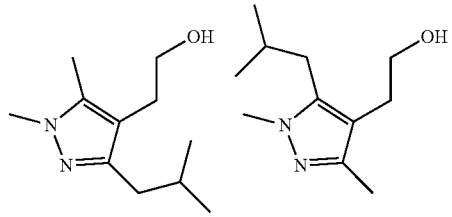

Step 1

A solution of 6-methylheptane-2,4-dione (5.0 g, 35 mmol) in DMF (20 ml) was added dropwise to a suspension of sodium hydride (50% dispersion in oil; 1.69 g, 42 mmol) in DMF (30 ml) at 0° C. The mixture was stirred for 30 mins then treated with a solution of ethyl bromoacetate (4.3 ml, 39 mmol) in DMF (20 ml). The reaction mixture was allowed to warm to room temperature, stirred overnight then quenched by addition of water (20 ml). The solvents were removed under reduced pressure and the residue partitioned between ethyl acetate (150 ml) and water (100 ml). The organic phase was dried ($Na_2SO_4$) and concentrated under reduced pressure. The crude product was purified by column chromatography by elution with ethyl acetate/hexane (5:95). Fractions containing the product were combined and evaporated to give a colourless oil (5.2 g), which was found to be an inseparable mixture of mono- and di-alkylated products.

Step 2

The mixture of ethyl 3-acetyl-6-methyl-4-oxoheptanoate and diethyl 3-acetyl-3-(3-methylbutanoyl)pentanedioate from Step 1 (5.2 g, ~2.4 mmol) was dissolved in acetic acid (50 ml) and treated with methylhydrazine (1.4 m, 2.6 mmol) dropwise over 5 min. The solution was stirred overnight at room temperature, then evaporated under reduced pressure. The residue was partitioned between ethyl acetate (100 ml) and sodium carbonate solution (2M, 100 ml). The organic phase was dried ($Na_2SO_4$) and concentrated under reduced pressure. The crude product was purified by column chromatography by elution with ethyl acetate/hexane (50:50, then 75:25 and 100:0). Fractions containing unreacted diethyl 3-acetyl-3-(3-methylbutanoyl)pentanedioate eluted first followed by fractions containing a mixture of both desired products, which were combined and evaporated. Partial separation of the regiosomeric products was achieved using column chromatography by elution with DCM/ethyl acetate (70:30, then 50:50). Fractions containing the higher and lower Rf product spots were combined separately, then analysed by NMR and were found to be 6:1 mixtures of the desired regioisomeric products. The structure of each compound was assigned by the nOe peaks between the N-methyl and the adjacent C—H groups.

The higher running spot (470 mg) was assigned as ethyl 2-(3-isobutyl-1,5-dimethyl-1H-pyrazol-4-yl)acetate $^1$H NMR (400 MHz, Chloroform-d) δ 4.11 (q, J=7.2 Hz, 2H), 3.72 (s, 3H), 3.33 (s, 2H), 2.41 (d, J=7.3 Hz, 2H), 2.19 (s, 3H), 1.98-1.84 (m, 1H), 1.24 (td, J=7.2, 1.6 Hz, 3H), 0.91 (d, J=6.8 Hz, 6H).

The lower running spot (860 mg) was assigned as ethyl 2-(5-isobutyl-1,3-dimethyl-1H-pyrazol-4-yl)acetate $^1$H NMR (400 MHz, Chloroform-d) δ 4.11 (q, J=7.1 Hz, 2H), 3.71 (s, 3H), 3.32 (s, 2H), 2.44 (d, J=7.6 Hz, 2H), 2.19 (s, 3H), 1.90-1.79 (m, 1H), 1.23 (t, J=7.1 Hz, 3H), 0.91 (d, J=6.8 Hz, 6H).

Step 3

The appropriate ethyl pyrazole acetate was dissolved in dry THF (10 ml) and was treated with a solution of lithium aluminium hydride in toluene (1M, 1 equivalent). After 3 hr at room temperature, the reaction was worked up using standard Fieser conditions (water; 15% sodium hydroxide solution; water @ x; x; 3× ml/g LAH). Solid Na$_2$SO$_4$ was added to ensure complete dryness and the mixture was filtered and concentrated under reduced pressure to give the title compounds as 6:1 mixtures of regioisomers.

2-(3-isobutyl-1,5-dimethyl-1H-pyrazol-4-yl)ethanol colourless oil (440 mg) $^1$H NMR (400 MHz, Chloroform-d) δ 3.61 (s, 3H), 3.53 (t, J=7.4 Hz, 2H), 2.54 (t, J=7.3 Hz, 2H), 2.31 (d, J=7.3 Hz, 2H), 2.10 (s, 3H), 1.90-1.79 (m, 1H), 0.84 (d, J=6.7, 3.4 Hz, 6H).

2-(5-isobutyl-1,3-dimethyl-1H-pyrazol-4-yl)ethanol colourless oil (751 mg) $^1$H NMR (400 MHz, Chloroform-d) δ 3.51 (s, 3H), 3.45 (t, J=7.7 Hz, 2H), 2.45 (t, J=7.6 Hz, 2H), 2.27 (d, J=7.4 Hz, 2H), 2.00 (s, 3H), 1.73-1.63 (m, 1H), 0.75 (d, J=6.8 Hz, 6H).

2-bromo-3-[2-(1,3,5-trimethyl-1H-pyrazol-4-yl)ethoxy]pyridine

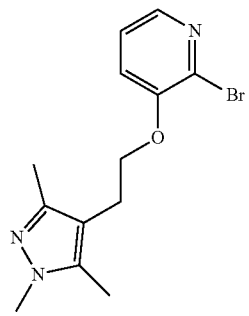 [SMILES: Cc1nn(C)c(C)c1CCOc1cccnc1Br]

Step 1

A solution of 2-bromo-3-hydroxypyridine (250 mg, 0.65 mmol) in dichloromethane (10 ml) was cooled to 0° C. then treated with triethylamine (842 µl, 6.0 mmol) followed by methanesulfonyl chloride (467 µl, 6.0 mmol). The reaction mixture was allowed to warm to room temperature and was stirred for 18 hours before being quenched with sodium bicarbonate solution (2M, 20 ml). Dichloromethane (20 ml) was added and the layers were separated. The organic phase was washed with water and brine then dried (Na$_2$SO$_4$) and concentrated under reduced pressure to give the product, 2-bromopyridin-3-yl methanesulfonate as a viscous liquid (700 mg, 97%). $^1$H NMR (400 MHz, DMSO-d6) δ 8.40 (dd, 1H), 7.99 (dd, 1H), 7.59 (dd, 1H), 3.60 (s, 3H), Step 2

According to the general method for mesyl transfer (method B), a solution of 2-bromopyridin-3-yl methanesulfonate (350 mg, 1.39 mmol) in dry DMF (5 ml) was treated with a solution of the 2-(1,3,5-trimethyl-1H-pyrazol-4-yl)ethanol (388 mg, 2.5 mmol) in dry DMF (2.0 ml), followed by solid cesium carbonate (615 mg, 1.89 mmol). The reaction mixture was heated to 100° C. overnight. The reaction mixture was partitioned between ethyl acetate (50 ml) and saturated sodium bicarbonate solution (10 ml). The organic phase was washed with water and brine, dried over Na$_2$SO$_4$, concentrated under reduced pressure and the crude product purified by flash column chromatography by elution with dichloromethane/methanol (97:3) to provide the title compound as a colourless oil (100 mg; 23%) $^1$H NMR (400 MHz, DMSO-d6) 7.94 (dd, 1H), 7.47 (dd, 1H), 7.36 (dd, 1H), 4.06 (t, 2H), 3.60 (s, 3H), 2.77 (t, 2H), 2.18 (s, 3H), 2.11 (s, 3H).

4-(2-hydroxyethyl)-N,N,1,5-tetramethyl-1H-pyrazole-3-carboxamide

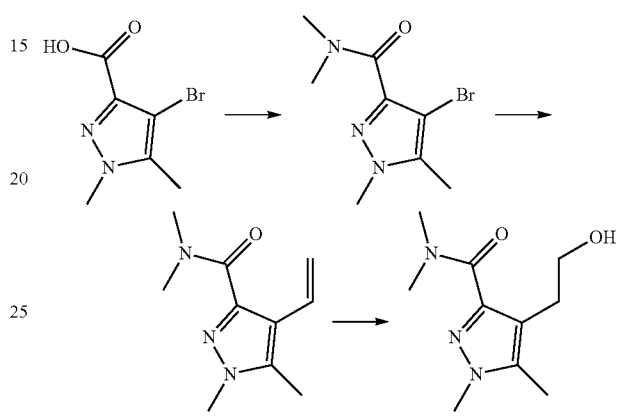

Step 1

A solution of 4-bromo-1,5-dimethyl-1H-pyrazole-3-carboxylic acid (500 mg, 2.3 mmol) in dry THF (10 ml) was treated with HATU (1.04 g, 2.7 mmol) and triethylamine (640 µl, 4.6 mmol) followed by a solution of dimethylamine in THF (2M, 113 µl, 2.5 mmol). The reaction mixture was stirred at room temperature overnight, diluted with ethyl acetate and washed with saturated sodium bicarbonate, water and brine, dried over Na$_2$SO$_4$, concentrated under reduced pressure and the crude product purified by flash column chromatography by elution with dichloromethane/methanol (98:2) to provide 4-bromo-N,N,1,5-tetramethyl-1H-pyrazole-3-carboxamide as a brown solid (500 mg, 89%). $^1$H NMR (400 MHz, DMSO-d6) 3.79 (s, 3H), 2.96 (s, 3H), 2.86 (s, 3H), 2.25 (s, 3H).

Step 2

A solution of 4-bromo-N,N, 1,5-tetramethyl-1H-pyrazole-3-carboxamide (320 mg, 1.3 mmol) in dry DMF (10 ml) was treated with tributylvinylstannane (0.76 ml, 2.6 mmol). The mixture was purged with argon for 15 min before addition of tetrakis(triphenylphosphine) palladium(0) (75 mg, 0.065 mmol). The reaction was heated to 110° C. overnight, diluted with ethyl acetate and washed with water and brine, dried over Na$_2$SO$_4$, concentrated under reduced pressure and the crude product purified by flash column chromatography by gradient elution with dichloromethane/methanol (96:4-95:5) to provide 4-ethenyl-N,N,1,5-tetramethyl-1H-pyrazole-3-carboxamide as a solid (125 mg). $^1$H NMR (400 MHz, DMSO-d6) 6.54 (dd, 1H), 5.20 (d, 1H), 5.06 (d, 1H), 3.73 (s, 3H), 2.95 (s, 3H), 2.90 (s, 3H), 2.29 (s, 3H).

Step 3

A solution of 4-ethenyl-N,N,1,5-tetramethyl-1H-pyrazole-3-carboxamide (175 mg, 0.90 mmol) in dioxane (10 ml) was cooled to 0° C. and treated with a solution of 9-BBN (0.5M in THF, 4.5 ml). The reaction was heated to 100° C. overnight. The mixture was re-cooled to 0° C., and was treated with ethanol (0.7 ml), 6N NaOH solution (0.35 ml), 50% H₂O₂ (0.6 ml). The reaction mixture was heated at 50° C. for 2 hr diluted with ethyl acetate and washed with water and brine, dried over Na₂SO₄, concentrated under reduced pressure and the crude product purified by flash column chromatography by elution with dichloromethane/methanol (97:3) to provide the title compound as a colourless oil (150 mg; 78%). ¹H NMR (400 MHz, DMSO-d6) 4.64 (t, 1H) 4.25 (q, 2H), 3.71 (s, 3H), 3.06 (s, 3H), 2.94 (s, 3H), 2.54 (t, 2H), 2.17 (s, 3H).

3, 4-Difluoro-2-Hydroxybenzene Boronic Acid

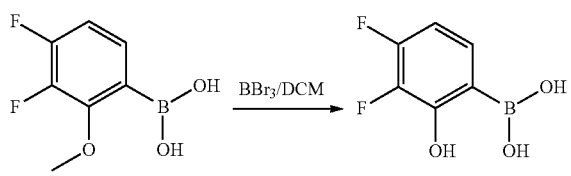

A solution of 3, 4-difluoro-2-methoxybenzene boronic acid (4.12 g, 22 mmol) in dry DCM (100 ml) was treated with a solution of boron tribromide in DCM (1M, 33 ml, 33 mmol). After stirring for 1 hr at room temperature, the reaction mixture was poured onto ice and extracted with DCM/methanol (3×100 ml). The combined organic layers were dried (Na₂SO₄), and evaporated under reduced pressure to give a purple solid. Trituration of the solid residue with DCM gave an analytical sample of the title compound as an off-white solid (400 mg) mp 130-135° C.

2,3-difluoro-6-(4,4,5,5-tetramethyl-1,3,2-dioxaborolan-2-yl)phenol

To a stirred solution of 6-bromo-2,3-difluorophenol (2.0 g, 9.60 mmol) in dioxane (20 mL), bis pinacolato diboron (2.68 g, 10.5 mmol)) and KOAc (1.69 g, 17.3 mmol) was added and degassed with argon for 15 min. PdCl₂(dppf) DCM (0.628 g, 0.7 mmol) was added and the reaction mixture was stirred at 90° C. for 16 h. The progress of the reaction was monitored by TLC. After completion of the reaction, the reaction mixture was filtered through Celite and washed with 10% MeOH in DCM. The reaction mixture was concentrated under reduced pressure. The residue was dissolved in EtOAc and organic layer was washed with brine, dried over anhydrous Na₂SO₄ and concentrated under reduced pressure. The residue was purified by column chromatography to afford 2,3-difluoro-6-(4,4,5,5-tetramethyl-1,3,2-dioxaborolan-2-yl)phenol (340 mg, 14%). ¹H NMR (400 MHz, CDCl₃) δ 6.94 (m, 1H), 6.70 (m, 1H), 1.42 &1.17 (2 s, 12H).

2-{1,5-dimethyl-3-[(pyrrolidin-1-yl)carbonyl]-1H-pyrazol-4-yl}ethan-1-ol

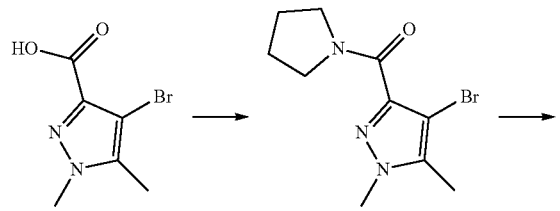

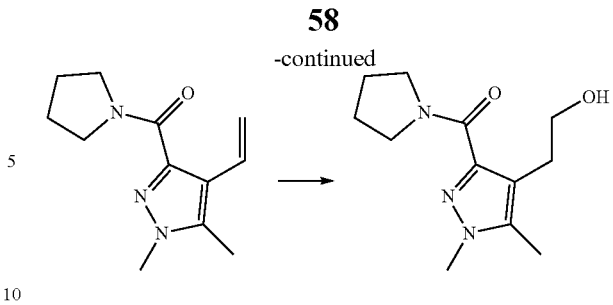

Step 1

A solution of 4-bromo-1,5-dimethyl-1H-pyrazole-3-carboxylic acid (1.0 g, 4.6 mmol) in dry THF (25 ml) was treated with triethylamine (1.9 mL, 13.7 mmol) and HATU (2.60 g, 6.8 mmol), followed by pyrrolidine (450 µL, 5.5 mmol). The reaction mixture was stirred at room temperature overnight, diluted with ethyl acetate and washed with saturated sodium bicarbonate, water and brine, dried over Na₂SO₄, concentrated under reduced pressure and the crude product purified by flash column chromatography by elution with dichloromethane/methanol (97:3) to provide 4-bromo-1,5-dimethyl-3-[(pyrrolidin-1-yl)carbonyl]-1H-pyrazole (1.0 g, 81%). ¹H NMR (400 MHz, DMSO-d₆) 3.80 (s, 3H), 3.51 (t, 2H), 3.41 (t, 2H), 2.25 (s, 3H), 1.83 (m, 4H).

Step 2

A solution of 4-bromo-1,5-dimethyl-3-[(pyrrolidin-1-yl)carbonyl]-1H-pyrazole (1.0 g, 3.5 mmol) in dry DMF (20 ml) was treated with tributylvinylstannane (2.0 mL, 9.0 mmol). The mixture was purged with argon for 15 min before addition of tetrakis(triphenylphosphine) palladium(0) (201 mg, 0.174 mmol). The reaction was heated to 110° C. overnight, diluted with ethyl acetate and washed with water and brine, dried over Na₂SO₄, concentrated under reduced pressure and the crude product purified by flash column chromatography by gradient elution with dichloromethane/methanol (97:3) to provide 4-ethenyl-1,5-dimethyl-3-[(pyrrolidin-1-yl)carbonyl]-1H-pyrazole as a gum (400 mg, 52%). ¹H NMR (400 MHz, DMSO-d6) 6.73 (dd, 1H), 5.27 (dd, 1H), 5.08 (dd, 1H), 3.75 (s, 3H), 3.45 (dt, 4H), 2.30 (s, 3H), 1.81 (m, 4H).

Step 3

A solution of 4-ethenyl-1,5-dimethyl-3-[(pyrrolidin-1-yl)carbonyl]-1H-pyrazole (400 mg, 1.8 mmol) in dioxane (20 ml) was treated with a solution of 9-BBN (0.5M in THF, 9 ml, 4.5 mmol). The reaction was heated to 100° C. overnight. The mixture was re-cooled to 0° C., and was treated with ethanol (1.6 ml), 6N NaOH solution (0.8 ml), 50% H₂O₂ (0.6 ml). The reaction mixture was heated at 50° C. for 2 hr diluted with 5% methanol/DCM and filtered. The filtrate was concentrated under reduced pressure and the crude product purified by flash column chromatography by elution with ethyl acetate/methanol (99:1) to provide the title compound as a colourless oil (170 mg; 39%). ¹H NMR (400 MHz, DMSO-d6) 3.72 (s, 3H), 3.66 (t, 2H), 3.41 (m, 4H), 2.64 (t, 2H), 2.17 (s, 3H), 1.81 (m, 4H).

4-{[4-(2-chloroethyl)-1,5-dimethyl-1H-pyrazol-3-yl]carbonyl}morpholine

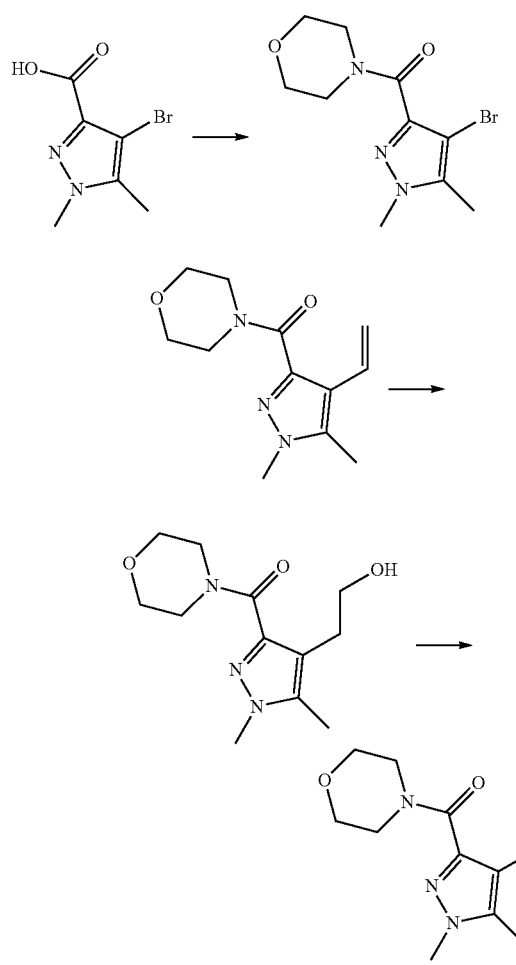

Step 1

A solution of 4-bromo-1,5-dimethyl-1H-pyrazole-3-carboxylic acid (1.0 g, 4.6 mmol) in dry THF (10 ml) was treated with triethylamine (1.27 mL, 9.1 mmol) and HATU (2.08 g, 5.5 mmol), followed by morpholine (470 µL, 5.5 mmol). The reaction mixture was stirred at room temperature overnight, diluted with DCM and washed with saturated sodium bicarbonate, water and brine, dried over $Na_2SO_4$, concentrated under reduced pressure and the crude product purified by flash column chromatography by elution with dichloromethane/methanol (97:3) to provide 4-bromo-1,5-dimethyl-3-[(morpholin-4-yl)carbonyl]-1H-pyrazole (1.2 g, 91%). $^1$H NMR (400 MHz, $CDCl_3$) 3.81 (s, 3H), 3.76 (m, 4H), 3.68 (m, 2H), 3.60 (m, 2H), 2.26 (s, 3H).

Step 2

A solution of 4-bromo-1,5-dimethyl-3-[(morpholin-4-yl)carbonyl]-1H-pyrazole (500 mg, 1.7 mmol) in dry DMF (5 ml) was treated with tributylvinylstannane (1.0 mL, 3.5 mmol). The mixture was purged with argon for 15 min before addition of tetrakis(triphenylphosphine) palladium(0) (100 mg, 0.087 mmol). The reaction was heated to 110° C. overnight, diluted with ethyl acetate and washed with potassium fluoride solution, water and brine, dried over $Na_2SO_4$, concentrated under reduced pressure and the crude product purified, by flash column chromatography by gradient elution with dichloromethane/methanol (96:4) to provide 4-[(4-ethenyl-1,5-dimethyl-1H-pyrazol-3-yl)carbonyl]morpholine (200 mg, 49%). $^1$H NMR (400 MHz, DMSO-$d_6$) 6.56 (dd, 1H), 5.27 (dd, 1H), 5.10 (dd, 1H), 3.73 (s, 3H), 3.61 (m, 4H), 3.50 (m, 2H), 3.40 (m, 2H), 2.27 (s, 3H).

Step 3

A solution of 4-[(4-ethenyl-1,5-dimethyl-1H-pyrazol-3-yl)carbonyl]morpholine (500 mg, 2.1 mmol) in dioxane (30 ml) was treated with a solution of 9-BBN (0.5M in THF, 13 ml, 6.5 mmol) under a nitrogen atmosphere. The reaction was heated to 100° C. overnight. The mixture was re-cooled to 0° C., and was treated with ethanol (1.0 ml), 6N NaOH solution (0.5 ml), 50% $H_2O_2$ (1.0 ml). The reaction mixture was heated at 50° C. for 2 hr diluted with methanol and concentrated under reduced pressure. The crude product purified by flash column chromatography by elution with ethyl acetate/methanol (95:5) to provide the title compound 2-{1,5-dimethyl-3-[(morpholin-4-yl)carbonyl]-1H-pyrazol-4-yl}ethan-1-ol (200 mg, 37%). $^1$H NMR (400 MHz, DMSO-$d_6$) 4.58 (t, 2H), 3.71 (s, 3H), 3.65-3.50 (m, 8H), 3.40 (t, 3H), 2.56 (t, 2H), 2.17 (s, 3H).

Step 4

A solution of 2-{1,5-dimethyl-3-[(morpholin-4-yl)carbonyl]-1H-pyrazol-4-yl}ethan-1-ol in (150 mg, 0.59 mmol) in DCM (5 mL) was treated with thionyl chloride (0.6 mL) at 0° C. The reaction mixture was heated to reflux for 20 min. The reaction mixture was cooled to RT and concentrated under reduced pressure to afford desired product 4-{[4-(2-chloroethyl)-1,5-dimethyl-1H-pyrazol-3-yl]carbonyl}morpholine (160 mg, 93%). $^1$H NMR (400 MHz, DMSO-$d_6$) 3.80-3.60 (m, 13H) 2.88 (t, 2H), 2.21 (s, 3H).

2-[1,5-dimethyl-3-(trifluoromethyl)-1H-pyrazol-4-yl]ethan-1-ol

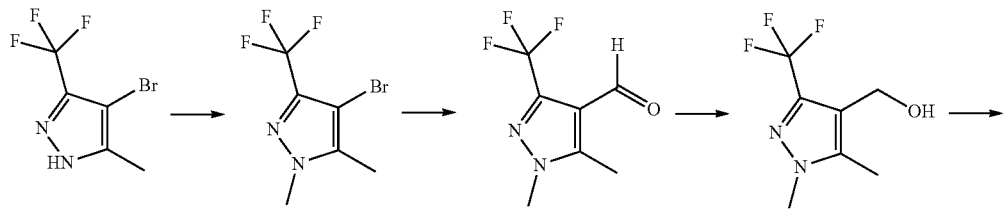

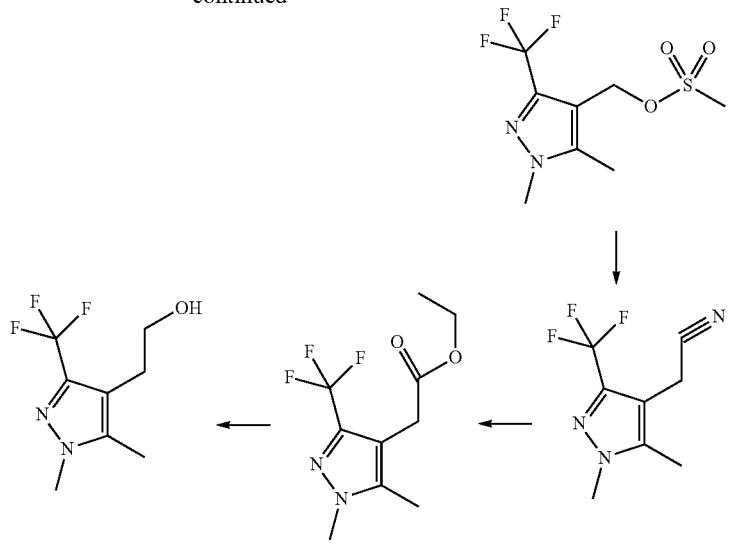

Step 1

A solution of 4-bromo-5-dimethyl-3-(trifluoromethyl)-1H-pyrazole (4.2 g, 18.3 mmol) in acetone (50 mL) was treated with $K_2CO_3$ (5.07 g, 36.7 mmol) and iodomethane (2.28 mL, 36.7 mmol) at rt and the reaction mixture was stirred at rt for 16 hr. The reaction mixture was then diluted with ethyl acetate, washed with water and brine, dried over $Na_2SO_4$ and evaporated under reduced pressure. The crude product was purified by column chromatography eluting with ethyl acetate/hexane (15:85) to give 4-bromo-1,5-dimethyl-3-(trifluoromethyl)-1H-pyrazole (2.7 g, 61%). $^1$H NMR (400 MHz, DMSO-$d_6$) δ 3.85 (s, 3H), 2.28 (s, 3H).

Step 2

A solution of 4-bromo-1,5-dimethyl-3-(trifluoromethyl)-1H-pyrazole (250 mg, 1 mmol) in THF (5 mL) was treated with n-BuLi solution (2.4M in hexane, 0.51 mL, 1.2 mmol), dropwise at −78° C. and stirred at −78° C. for 30 min. DMF (0.159 mL) was added at −78° C. and stirred at same temperature for 30 min. The reaction was then allowed to stir at 0° C. for 2 h. The reaction mixture was quenched with $NH_4Cl$ solution and extracted with EtOAc. The organic layer was washed with brine, dried over $Na_2SO_4$ and concentrated under reduced pressure to give 1,5-dimethyl-3-(trifluoromethyl)-1H-pyrazole-4-carbaldehyde (197 mg, 99%). $^1$H NMR (400 MHz, DMSO-$d_6$) δ 9.91 (s, 1H), 4.01 (s, 3H), 2.57 (s, 3H).

Step 3

A solution of 1,5-dimethyl-3-(trifluoromethyl)-1H-pyrazole-4-carbaldehyde (800 mg, 4.2 mmol) in methanol (10 mL) was cooled at 0° C. before addition of solid $NaBH_4$ (315 mg, 8.3 mmol). The reaction mixture was stirred at 0° C. for 2 hr, diluted with DCM, and washed with sat. $NaHCO_3$, water and brine, dried over $Na_2SO_4$, and concentrated to give [1,5-dimethyl-3-(trifluoromethyl)-1H-pyrazol-4-yl]methanol (700 mg, 87%). $^1$H NMR (400 MHz, DMSO-$d_6$) δ 4.86 (t, 1H), 4.33 (d, 2H), 3.78 (s, 3H), 2.27 (s, 3H).

Step 4

A solution of [1,5-dimethyl-3-(trifluoromethyl)-1H-pyrazol-4-yl]methanol (850 mg, 4.4 mmol) in DCM (15 mL) was cooled at 0° C. before dropwise addition of trimethylamine (1.28 mL, 9.2 mmol) and mesylchloride (0.712 mL, 9.2 mmol). The reaction mixture was stirred at rt for 6 hr, diluted with DCM, then washed with sat. $NaHCO_3$, water and brine, dried over $Na_2SO_4$ and evaporated to give [1,5-dimethyl-3-(trifluoromethyl)-1H-pyrazol-4-yl]methyl methanesulfonate (1.0 g, 84%). $^1$H NMR (400 MHz, DMSO-$d_6$) δ 4.70 (s, 2H), 3.60 (s, 3H), 2.31 (s, 3H).

Step 5

A solution of [1,5-dimethyl-3-(trifluoromethyl)-1H-pyrazol-4-yl]methyl methanesulfonate (1.0 g, 3.7 mmol) in DMF was treated with sodium cyanide (0.54 g, 1 mmol) and the reaction mixture was heated at 100° C. for 16 hr. The reaction mixture was diluted with ethyl acetate, washed with water and brine, dried over $Na_2SO_4$ and evaporated under reduced pressure to give 2-[1,5-dimethyl-3-(trifluoromethyl)-1H-pyrazol-4-yl]acetonitrile (740 mg, 99%). $^1$H NMR (400 MHz, DMSO-$d_6$) δ 3.87 (s, 2H), 3.80 (s, 3H), 2.31 (s, 3H).

Step 6

A solution of 2-[1,5-dimethyl-3-(trifluoromethyl)-1H-pyrazol-4-yl]acetonitrile (740 mg, 3.6 mmol) in methanol (10 mL) was treated with a solution of 4M HCl in dioxane (4M, 5 mL) at rt. The reaction mixture was heated at 80° C. for 3 hours, cooled and evaporated under reduced pressure. The crude material was dissolved in ethyl acetate, washed with $NaHCO_3$ solution, water and brine, then dried over $Na_2SO_4$ and concentrated to give methyl 2-[1,5-dimethyl-3-(trifluoromethyl)-1H-pyrazol-4-yl]acetate (856 mg, 93%). $^1$H NMR (400 MHz, DMSO-$d_6$) δ 3.98 (s, 3H), 3.59 (s, 3H), 3.56 (s, 2H), 2.19 (s, 3H).

Step 7

A solution of $LiAlH_4$ (255 mg, 6.8 mmol) in THF (5 mL) was cooled at 0° C., before dropwise addition of methyl 2-[1,5-dimethyl-3-(trifluoromethyl)-1H-pyrazol-4-yl]acetate (800 mg, 3.4 mmol) in THF (5 mL). Then the reaction mixture was stirred at 0° C. for 2 hours. The reaction mixture was cooled at 0° C. Excess of LAH was quenched with $Na_2SO_4$ solution. The mixture was stirred at rt for 30 min and was filtered through celite bed, which was washed with ethyl acetate. Then the ethyl acetate solution was taken dried over $Na_2SO_4$ and evaporated under reduced pressure. The crude product was purified by column chromatography silica eluting with EtOAc/hexane (1:1) to give the title compound as an oil (350 mg, 50%). ¹H NMR (400 MHz, DMSO-d₆) δ 4.25 (t, 2H), 3.76 (s, 3H), 3.40 (q, 2H), 2.56 (t, 2H), 2.21 (s, 3H).

4-[2-(2-bromo-5-fluorophenoxy)ethyl]-1,3,5-trimethyl-1H-pyrazole

Step 1

A solution of 2-bromo-5-fluorophenol (5.0 g, 26 mmol) in dichloromethane (100 mL) was cooled to 0° C. then treated with triethylamine (7.6 mL, 55 mmol) followed by methanesulfonyl chloride (4.25 mL, 55 mmol). The reaction mixture was allowed to warm to room temperature and was stirred for 18 hours before being quenched with sodium bicarbonate solution (2M, 20 ml). Ethyl acetate was added and the layers were separated. The organic phase was washed with water and brine, then dried (Na₂SO₄) and concentrated under reduced pressure to give the product, 2-bromo-5-fluorophenyl methanesulfonate (7 g, yield: 99%). ¹H NMR (400 MHz, DMSO-d6) δ 7.84 (dd, 1H), 7.53 (dd, 1H), 7.26 (td, 1H), 3.56 (s, 3H),
Step 2

According to the general method for mesyl transfer (method B), a solution of 2-bromo-5-fluorophenyl methanesulfonate (1.45 g, 5.4 mmol) in dry DMF (25 ml) was treated with a solution of 2-(1,3,5-trimethyl-1H-pyrazol-4-yl)ethanol (1.49 g, 9.7 mmol) in dry DMF (25 mL), followed by solid cesium carbonate (2.46 g, 7.5 mmol). The reaction mixture was heated to 90° C. overnight. The reaction mixture was partitioned between ethyl acetate (50 ml) and water (10 ml). The organic phase was washed with water, dried over Na₂SO₄, concentrated under reduced pressure and the crude product purified by flash column chromatography by elution with ethyl acetate/hexane (1:4) to provide the title compound (800 mg; 45%) ¹H NMR (400 MHz, DMSO-d6) δ 7.57 (dd, 1H), 7.02 (dd, 2H), 6.74 (td, 1H), 4.03 (t, 2H), 3.60 (s, 3H), 2.75 (t, 2H), 2.17 (s, 3H), 2.10 (s, 3H).

4-{[4-(2-chloroethyl)-1,5-dimethyl-1H-pyrazol-3-yl]carbonyl}morpholine

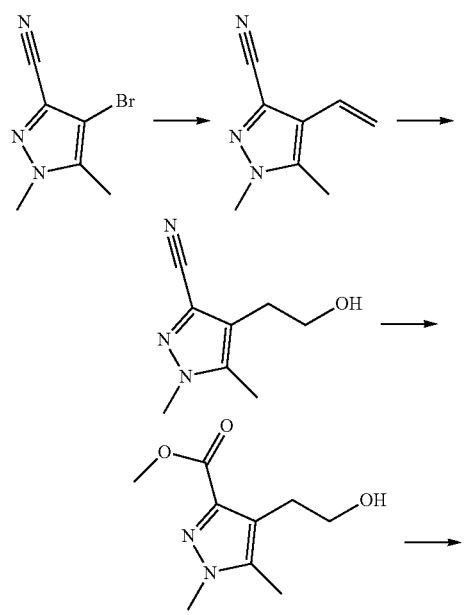

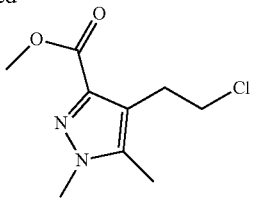

Step 1

A solution of 4-bromo-1,5-dimethyl-1H-pyrazole-carbonitrile (8.0 g, 40 mmol) in dry DMF (40 mL) was treated with tributylvinylstannane (23.4 mL, 80 mmol). The mixture was purged with argon for 15 min before addition of tetrakis(triphenylphosphine) palladium(0) (2.3 g, 2 mmol). The reaction was heated to 110° C. overnight, diluted with ethyl acetate and washed with potassium fluoride solution, water and brine, dried over Na₂SO₄, concentrated under reduced pressure. The crude product was purified by flash column chromatography by elution with ethylacetate/hexane (20:80) to provide 4-ethenyl-1,5-dimethyl-1H-pyrazole-3-carbonitrile (4.0 g, 68%). ¹H NMR (400 MHz, CDCl₃) 6.45 (dd; 1H), 5.80 (dd, 1H), 5.34 (dd, 1H), 3.82 (s, 3H), 2.29 (s, 3H).

Step 2

A solution of 4-ethenyl-1,5-dimethyl-1H-pyrazole-3-carbonitrile (1.2 g, 8.2 mmol) in dioxane (5 mL) was treated with a solution of 9-BBN (0.5M in THF, 32 ml, 16 mmol) under a nitrogen atmosphere. The reaction was heated to 100° C. overnight. The mixture was re-cooled to 0° C., and was treated with ethanol (4.8 mL), NaOH solution (6M, 2.4 mL), H₂O₂ (50% solution, 3.6 mL). The reaction mixture was heated at RT for 2 hr diluted with DCM/methanol (95:5), dried over sodium sulphate and concentrated under reduced pressure. The crude product purified by flash column chromatography by elution with DCM/methanol (98:2) to provide the title compound 4-(2-hydroxyethyl)-1,5-dimethyl-1H-pyrazole-3-carbonitrile (500 mg, 37%). 1H NMR (400 MHz, CDCl₃) 3.81 (s, 3H), 3.78 (q, 2H), 2.74 (t, 2H), 2.55 (s, 3H), 1.86 (t, 1H).

Step 3

A solution of 4-(2-hydroxyethyl)-1,5-dimethyl-1H-pyrazole-3-carbonitrile (1.0 g, 6.1 mmol) in methanol (12 mL) was treated with a solution of HCl in dioxane (4M, 12 mL). The reaction mixture was stirred at 80° C. for 5 hr and evaporated under reduced pressure. The crude product was basified with sat. NaHCO₃ solution and diluted with EtOAc, washed with water, brine, dried over sodium sulfate and evaporated under reduced pressure to give methyl 4-(2-hydroxyethyl)-1,5-dimethyl-1H-pyrazole-3-carboxylate (1.1 g, 92%). ¹H NMR (400 MHz, CDCl₃) 3.90 (s, 3H), 3.84 (s, 3H), 3.77 (q, 2H), 2.93 (t, 2H), 2.23 (s, 3H), 2.07 (t, 1H).

Step 4

A solution of methyl 4-(2-hydroxyethyl)-1,5-dimethyl-1H-pyrazole-3-carboxylate (100 mg, 0.5 mmol) in DCM (1.5 mL) was treated with thionyl chloride (0.5 mL) at 00° C. The reaction mixture was heated to reflux for 1 hr. The reaction mixture was cooled to RT and concentrated under reduced pressure to afford desired product, methyl 4-(2-chloroethyl)-1,5-dimethyl-1H-pyrazole-3-carboxylate (100 mg, 91%). ¹H NMR (400 MHz, DMSO-d₆) 3:76 (s, 3H), 3.74 (s, 3H), 3.41 (t, 2H), 2.73 (t, 2H), 2.20 (s, 3H).

Preparation of Intermediates 1-29

Intermediate 1

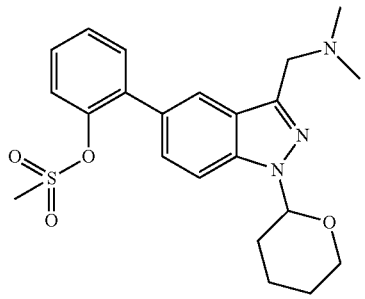 [SMILES: CN(C)Cc1nn(C2CCCCO2)c2ccc(-c3ccccc3OS(C)(=O)=O)cc12]

2-(3-((Dimethylamino)methyl)-1-(tetrahydro-2H-pyran-2-yl)-1-yl)-H-indazol-5-yl)phenyl methanesulfonate Step 1

A solution of 5-iodo-1-(tetrahydro-2H-pyran-2-yl)-1H-indazole-3-carbaldehyde (1.78 g, 5 mmol) was dissolved in dioxane (20 ml) and treated with 2-hydroxybenzene boronic acid (690 mg, 5 mmol) and tetrakis(triphenylphosphine)palladium(0) (100 mg), followed by a solution of potassium phosphate (1.59 g, 7.5 mmol) in water (5 ml). The reaction mixture was heated under reflux for 1 hr, cooled to room temperature and evaporated under reduced pressure. The residue was partitioned between ethyl acetate (20 ml) and saturated sodium bicarbonate solution (20 ml). The organic phase was dried over $Na_2SO_4$, concentrated under reduced pressure and the crude product purified by flash column chromatography by elution with DCM/EtOAc (100:0, then 95:5) to give 5-(2-hydroxyphenyl)-1-(tetrahydro-2H-pyran-2-yl)-1H-indazole-3-carbaldehyde as a pale yellow solid (1.15 g, 71%) mp 162-163° C. $^1$H NMR (400 MHz, Chloroform-d) δ 10.29 (s, 1H), 8.44 (d, J=1.9 Hz, 1H), 7.81 (d, J=8.8 Hz, 1H), 7.64 (dd, J=8.6, 1.7 Hz, 1H), 7.35-7.28 (m, 2H), 7.08-7.03 (m, 1H), 7.01 (d, J=8.0 Hz, 1H), 5.90 (dd, J=8.9, 2.7 Hz, 1H), 5.13 (s, 1H), 4.13-4.00 (m, 1H), 3.91-3.76 (m, 1H), 2.62 (m, 1H), 2.31-2.13 (m, 2H), 1.94-1.70 (m, 3H).

Step 2

A solution of 5-(2-hydroxyphenyl)-1-(tetrahydro-2H-pyran-2-yl)-1H-indazole-3-carbaldehyde (800 mg, 2.4 mmol) in THF (20 ml) was cooled to 0° C. then treated with triethylamine (370 μl. 4.8 mmol) followed by methanesulfonyl chloride (670 μl, 4.8 mmol). The reaction mixture was allowed to warm to room temperature and was stirred for 18 hours before being quenched with saturated sodium bicarbonate solution (10 ml). EtOAc (50 ml) was added and the layers were separated. The aqueous phase was further extracted with EtOAc (20 ml) and the combined organic extracts were dried ($Na_2SO_4$) and concentrated under reduced pressure. The crude product was purified by column chromatography by elution with DCM/EtOAc (97:3) to give 2-(3-formyl-1-(tetrahydro-2H-pyran-2-yl)-1H-indazol-5-yl)phenyl methanesulfonate as a colourless oil (830 mg, 92%).
$^1$H NMR (400 MHz, Chloroform-d) δ 10.30 (s, 1H), 8.46 (d, J=1.5 Hz, 1H), 7.80 (d, J=8.8 Hz, 1H), 7.75 (dd, J=8.8, 1.7 Hz, 1H), 7.60-7.51 (m, 2H), 7.50-7.43 (m, 2H), 5.91 (dd, J=9.0, 2.7 Hz, 1H), 4.13-4.05 (m, 1H), 3.85 (ddd, J=12.7, 9.6, 3.3 Hz, 1H), 2.66-2.59 (m, 4H), 2.33-2.13 (m, 2H), 1.96-1.72 (m, 3H).

Step 3

A solution of 2-(3-formyl-1-(tetrahydro-2H-pyran-2-yl)-1H-indazol-5-yl)phenyl methanesulfonate (830 mg, 2.2 mmol) in DCE (20 ml) was treated with a solution of dimethylamine in THF (2M, 3.3 ml, 6.6 mmol), followed by glacial acetic acid (750 μl, 13.2 mmol). The solution was stirred at room temperature for 10 mins before addition of solid sodium triacetoxyborohydride (1.40 g, 6.6 mmol). The reaction mixture was stirred at room temperature for 18 hours before being quenched with sodium carbonate solution (2M, 20 ml). DCM (20 ml) was added and the layers were separated. The aqueous phase was further extracted with DCM (10 ml) and the combined organic extracts were dried ($Na_2SO_4$) and concentrated under reduced pressure. The crude product was purified by column chromatography by elution with EtOAc/diethylamine (95:5) to give the title compound as a colourless oil (650 mg, 69%). $^1$H NMR (400 MHz, Chloroform-d) δ 8.03 (d, J=1.5 Hz, 1H), 7.66 (d, J=8.6 Hz, 1H), 7.58 (dd, J=8.6, 1.6 Hz, 1H), 7.52 (m, 2H), 7.42 (m 2H), 5.72 (dd, J=9.9, 2.5 Hz, 1H), 4.21-4.07 (m, 1H), 3.85 (d, J=2.4 Hz, 2H), 3.79 (td, J=11.2, 10.7, 2.5 Hz, 1H), 2.64-2.58 (m, 1H), 2.56 (s, 3H), 2.32 (s, 6H), 2.22-2.13 (m, 1H), 2.08 (m 1H), 1.85-1.75 (m, 2H), 1.73-1.64 (m, 1H).

Intermediate 2

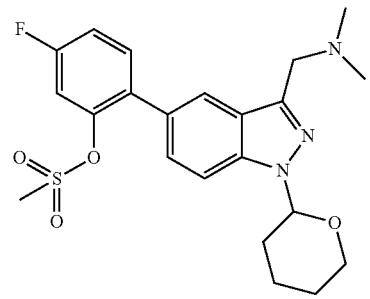 [SMILES: CN(C)Cc1nn(C2CCCCO2)c2ccc(-c3ccc(F)cc3OS(C)(=O)=O)cc12]

2-(3-((dimethylamino)methyl)-1-(tetrahydro-2H-pyran-2-yl)-1H-indazol-5-yl)-5-fluorophenyl methanesulfonate Step 1

A solution of 5-iodo-1-(tetrahydro-2H-pyran-2-yl)-1H-indazole-3-carbaldehyde (1.60 g, 4.5 mmol) was dissolved in dioxane (20 ml) and treated with 4-fluoro-2-hydroxybenzene boronic acid (697 mg, 4.5 mmol) and tetrakis(triphenylphosphine) palladium(0) (100 mg), followed by a solution of potassium phosphate (1.43 g, 6.7 mmol) in water (5 ml). The reaction mixture was heated under reflux for 2 hr, cooled to room temperature and evaporated under reduced pressure. The residue was partitioned between ethyl acetate (20 ml) and saturated sodium bicarbonate solution (20 ml). The organic phase was dried over $Na_2SO_4$, concentrated under reduced pressure and the crude product purified by flash column chromatography by elution with DCM/EtOAc (100:0, then 95:5) to give 5-(4-fluoro-2-hydroxyphenyl)-1-(tetrahydro-2H-pyran-2-yl)-1H-indazole-3-carbaldehyde as a colourless solid (1.15 g, 75%). mp 171-173° C. $^1$H NMR (400 MHz, Chloroform-d) δ 10.28 (s, 1H), 8.39 (d, J=2.1 Hz, 1H), 7.82 (d, J=8.7 Hz, 1H), 7.56 (dd, J=8.8, 1.9 Hz, 1H), 7.25 (dd, J=9.2, 6.5 Hz, 1H), 6.80-6.72 (m, 2H), 5.94-5.87 (m, 1H), 5.34 (s, 1H), 4.11-3.98 (m, 1H), 3.83 (ddd, J=1H), 2.69-2.52 (m, 1H), 2.30-2.12 (m, 2H), 1.94-1.71 (m, 3H).

Step 2

A solution of 5-(4-fluoro-2-hydroxyphenyl)-1-(tetrahydro-2H-pyran-2-yl)-1H-indazole-3-carbaldehyde (1.15 g, 3.3 mmol) in THF (20 ml) was cooled to 0° C. then treated with triethylamine (520 µl. 6.6 mmol) followed by methanesulfonyl chloride (940 µl, 6.6 mmol). The reaction mixture was allowed to warm to room temperature and was stirred for 18 hours before being quenched with saturated sodium bicarbonate solution (10 ml). EtOAc (50 ml) was added and the layers were separated. The aqueous phase was further extracted with EtOAc (20 ml) and the combined organic extracts were dried ($Na_2SO_4$) and concentrated under reduced pressure to give 5-fluoro-2-(3-formyl-1-(tetrahydro-2H-pyran-2-yl)-1H-indazol-5-yl)phenyl methanesulfonate as a colourless oil (1.20 g, ~100%). $^1$H NMR (400 MHz, Chloroform-d) δ 10.28 (s, 1H), 8.40 (d, J=1.6 Hz, 1H), 7.79 (d, J=8.7 Hz, 1H), 7.67 (dd, J=8.6, 1.6 Hz, 1H), 7.52 (dd, J=8.6, 6.2 Hz, 1H), 7.31 (dd, J=8.9, 2.6 Hz, 1H), 7.17 (td, J=8.2, 2.6 Hz, 1H), 5.89 (dd, J=9.1, 2.6 Hz, 1H), 4.07 (dd, J=8.8, 5.3 Hz, 1H), 3.83 (ddd, J=12.6, 9.6, 3.3 Hz, 1H), 2.67 (s, 3H), 2.60 (dtd, J=13.3, 9.3, 5.4 Hz, 1H), 2.31-2.11 (m, 2H), 1.93-1.69 (m, 3H).

Step 3

A solution of 5-fluoro-2-(3-formyl-1-(tetrahydro-2H-pyran-2-yl)-1H-indazol-5-yl)phenyl methanesulfonate (1.20 g, 3.3 mmol) in DCE (20 ml) was treated with a solution of dimethylamine in THF (2M, 5.0 ml, 9.9 mmol), followed by glacial acetic acid (1200 dl, 19.8 mmol). The solution was stirred at room temperature for 10 mins before addition of solid sodium triacetoxyborohydride (2.10 g, 9.9 mmol). The reaction mixture was stirred at room temperature for 18 hours before being quenched with sodium carbonate solution (2M, 20 ml). DCM (20 ml) was added and the layers were separated. The aqueous phase was further extracted with DCM (10 ml) and the combined organic extracts were dried ($Na_2SO_4$) and concentrated under reduced pressure. The crude product was purified by column chromatography by elution with EtOAc/diethylamine (95:5), then triturated with cyclohexane to give the title compound as a colourless solid (880 mg, 60%). mp 148-150° C. $^1$H NMR (400 MHz, Chloroform-d) δ 8.00 (d, J=1.3 Hz, 1H), 7.67 (d, J=8.6 Hz, 1H), 7.56-7.51 (m, 1H), 7.52-7.46 (m, 1H), 7.34-7.27 (m, 1H), 7.16 (td, J=8.2, 2.6 Hz, 1H), 5.73 (dd, J=9.9, 2.6 Hz, 1H), 4.19-4.08 (m, 1H), 3.86 (d, J=2.6 Hz, 2H), 3.80 (td, J=10.9, 2.5 Hz, 1H), 2.63 (s, 3H), 2.60-2.55 (m, 1H), 2.33 (s, 6H), 2.19 (dd, J=9.4, 4.6 Hz, 1H), 2.15-2.05 (m, 1H), 1.87-1.76 (m, 2H), 1.75-1.64 (m, 1H).

Intermediate 3

3-(3-((Dimethylamino)methyl)-1-(tetrahydro-2H-pyran-2-yl)-1H-indazol-5-yl)phenyl methanesulfonate Step 1

A solution of 5-iodo-1-(tetrahydro-2H-pyran-2-yl)-1H-indazole-3-carbaldehyde (1.60 g, 4.5 mmol) was dissolved in dioxane (20 ml) and treated with 3-hydroxybenzene boronic acid (690 mg, 5 mmol) and tetrakis(triphenylphosphine) palladium(0) (100 mg), followed by a solution of potassium phosphate (1.43 g, 6.7 mmol) in water (5 ml). The reaction mixture was heated under reflux for 2 hr, cooled to room temperature and evaporated under reduced pressure. The residue was partitioned between ethyl acetate (20 ml) and saturated sodium bicarbonate solution (20 ml). The organic phase was dried over $Na_2SO_4$, concentrated under reduced pressure and the crude product purified by flash column chromatography by elution with DCM/EtOAc (100:0, then 95:5) to give 5-(3-hydroxyphenyl)-1-(tetrahydro-2H-pyran-2-yl)-1H-indazole-3-carbaldehyde as a pale yellow solid (910 mg, 62%). $^1$H NMR (400 MHz, Chloroform-d) δ 10.29 (s, 1H), 8.51 (s, 1H), 7.74 (s, 2H), 7.35 (t, J=7.7 Hz, 1H), 7.25 (d, J=7.8 Hz, 1H), 7.16 (d, J=2.1 Hz, 1H), 6.87 (dd, J=8.1, 2.3 Hz, 1H), 5.89 (dd, J=9.1, 2.7 Hz, 1H), 5.04 (s, 1H), 4.05 (dt, J=10.9, 3.8 Hz, 1H), 3.83 (dt, J=11.7, 5.8 Hz, 1H), 2.61 (td, J=13.2, 11.8, 7.1 Hz, 1H), 2.30-2.11 (m, 2H), 1.92-1.68 (m, 3H).

Step 2

A solution of 5-(3-hydroxyphenyl)-1-(tetrahydro-2H-pyran-2-yl)-1H-indazole-3-carbaldehyde (900 mg, 2.8 mmol) in THF (20 ml) was cooled to 0° C. then treated with triethylamine (433 µl. 5.6 mmol) followed by methanesulfonyl chloride (780 µl, 5.6 mmol). The reaction mixture was allowed to warm to room temperature and was stirred for 18 hours before being quenched with saturated sodium bicarbonate solution (10 ml). EtOAc (50 ml) was added and the layers were separated. The aqueous phase was further extracted with EtOAc (20 ml) and the combined organic extracts were dried ($Na_2SO_4$) and concentrated under reduced pressure to give 3-(3-formyl-1-(tetrahydro-2H-pyran-2-yl)-1H-indazol-5-yl)phenyl methanesulfonate as a colourless oil (1.0 g, ~100%). $^1$H NMR (400 MHz, Chloroform-d) δ 10.30 (s, 1H), 8.52 (d, J=1.6 Hz, 1H), 7.78 (d, J=8.8 Hz, 1H), 7.72 (dd, J=8.9, 1.5 Hz, 1H), 7.66 (dt, J=7.8, 1.2 Hz, 1H), 7.58 (t, J=2.1 Hz, 1H), 7.53 (t, J=7.9 Hz, 1H), 7.32 (dd, J=7.9, 2.4 Hz, 1H), 5.90 (dd, J=8.9, 2.7 Hz, 1H), 4.05 (dt, J=11.4, 3.9 Hz, 1H), 3.92-3.70 (m, 1H), 3.22 (s, 3H), 2.70-2.51 (m, 1H), 2.30-2.12 (m, 2H), 1.95-1.71 (m, 3H).

Step 3

A solution of 3-(3-formyl-1-(tetrahydro-2H-pyran-2-yl)-1H-indazol-5-yl)phenyl methanesulfonate (1.0 g, 2.8 mmol) in DCE (20 ml) was treated with a solution of dimethylamine in THF (2M, 4.2 ml, 8.4 mmol), followed by glacial acetic acid (1000 µl, 16.8 mmol). The solution was stirred at room temperature for 10 mins before addition of solid sodium triacetoxyborohydride (1.78 g, 8.4 mmol). The reaction mixture was stirred at room temperature for 18 hours before being quenched with sodium carbonate solution (2M, 20 ml). DCM (20 ml) was added and the layers were separated. The aqueous phase was further extracted with DCM (10 ml) and the combined organic extracts were dried ($Na_2SO_4$) and concentrated under reduced pressure. The crude product was purified by column chromatography by elution with EtOAc/diethylamine (95:5) to give the title compound as a colourless oil (710 mg, 59%). $^1$H NMR (400 MHz, Chloroform-d) δ 8.05 (d, J=1.6 Hz, 1H), 7.66 (d, J=8.7

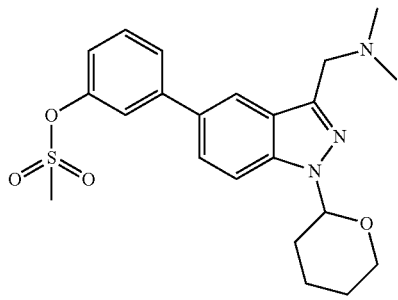 [SMILES: CN(C)Cc1nn(C2CCCCO2)c2ccc(-c3cccc(OS(C)(=O)=O)c3)cc12]

Hz, 1H), 7.67-7.58 (m, 2H), 7.57 (t, J=2.1 Hz, 1H), 7.51 (t, J=7.9 Hz, 1H), 7.29 (dd, J=8.1, 2.3 Hz, 1H), 5.73 (dd, J=9.7, 2.7 Hz, 1H), 4.16-4.05 (m, 1H), 3.90 (d, J=3.0 Hz, 2H), 3.79 (td, J=11.0, 3.0 Hz, 1H), 3.22 (s, 3H), 2.69-2.51 (m, 1H), 2.37 (s, 6H), 2.18 (td, J=6.2, 5.3, 2.4 Hz, 1H), 2.09 (dt, J=12.3, 3.3 Hz, 1H), 1.87-1.76 (m, 2H), 1.75-1.61 (m, 1H).

Intermediate 4

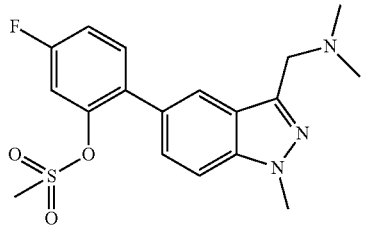 [SMILES: CN(C)Cc1nn(C)c2ccc(-c3ccc(F)cc3OS(C)(=O)=O)cc12]

2-(3-((dimethylamino)methyl)-1-methyl-1H-indazol-5-yl)-5-fluorophenyl methanesulfonate Step 1

A suspension of 5-iodo-N-methoxy-N-methyl-1H-indazole-3-carboxamide (1.0 g, 3.0 mmol) in DCM (20 ml) was treated with a catalytic quantity of tetrabutylammonium bromide and a 50% solution of potassium hydroxide in water (20 ml). The biphasic mixture was cooled to 0° C. before dropwise addition of iodomethane (204 µl, 4.4 mmol). The mixture was stirred vigorously and allowed to warm to room temperature overnight. The layers were separated and the aqueous layer re-extracted with DCM (10 ml). The organic phase was dried over $Na_2SO_4$, concentrated under reduced pressure and the crude product purified by flash column chromatography by elution with DCM/EtOAc (85:15, then 80:20) to separate the product regioisomers. The major product was eluted first and was assigned as 5-iodo-N-methoxy-N, 1dimethyl-1H-indazole-3-carboxamide by NMR (800 mg, 77%). mp 128-130° C. $^1$H NMR (400 MHz, Chloroform-d) δ 8.64 (d, J=1.7 Hz, 1H), 7.68 (dd, J=8.8, 1.5 Hz, 1H), 7.22 (d, J=8.8 Hz, 1H), 4.13 (s, 3H), 3.86 (s, 3H), 3.54 (s, 3H). Fractions containing the minor product were re-chromatographed to give a product that was assigned as 5-iodo-N-methoxy-N,2-dimethyl-2H-indazole-3-carboxamide by NMR. $δ_H$/ppm $^1$H NMR (400 MHz, Chloroform-d) δ 8.10 (d, J=1.7 Hz, 1H), 7.49 (dd, J=9.1, 1.6 Hz, 1H), 7.45 (d, J=9.0 Hz, 1H), 4.27 (s, 3H), 3.49 (s, 3H), 3.42 (s, 3H).

Step 2

A solution of 5-iodo-N-methoxy-N, 1-dimethyl-1H-indazole-3-carboxamide (800 mg, 2.3 mmol) in THF (5 ml) was cooled to 0° C. before dropwise addition of a solution of lithium aluminium hydride in THF (2M, 0.35 ml, 0.7 mmol). The reaction mixture was stirred for 30 min then quenched by addition of EtOAc (1 ml), allowed to warm to room temperature then partitioned between EtOAc (20 ml) and potassium hydrogen sulphate solution (1 M, 20 ml). The organic phase was dried over $Na_2SO_4$ and concentrated under reduced pressure to give 5-iodo-1-methyl-1H-indazole-3-carbaldehyde as a pale yellow solid (600 mg, 91%) mp 134-136° C. $^1$H NMR (400 MHz, Chloroform-d) δ 10.14 (s, 1H), 8.61 (d, J=1.5 Hz, 1H), 7.68 (dd, J=8.9, 1.7 Hz, 1H), 7.21 (d, J=8.9 Hz, 1H), 4.15 (s, 3H).

Step 3

A solution of 5-iodo-1-methyl-1H-indazole-3-carbaldehyde (500 mg, 1.7 mmol) was dissolved in dioxane (5 ml) and treated with 4-fluoro-2-hydroxybenzene boronic acid (360 mg, 2.2 mmol) and tetrakis(triphenylphosphine) palladium(0) (20 mg), followed by a solution of potassium phosphate (560 mg, 2.6 mmol) in water (1 ml). The reaction mixture was heated under reflux for 2 hr, cooled to room temperature and evaporated under reduced pressure. The residue was partitioned between ethyl acetate (20 ml) and saturated sodium bicarbonate solution (20 ml). The organic phase was dried over $Na_2SO_4$, concentrated under reduced pressure and the crude product purified by flash column chromatography by elution with DCM/EtOAc (100:0, then 95:5) to give 5-(4-fluoro-2-hydroxyphenyl)-1 methyl-1H-indazole-3-carbaldehyde as a colourless solid (450 mg, 95%). mp 212-214° C. $^1$H NMR (400 MHz, Methanol-d4) δ 10.15 (s, 1H), 8.30 (d, J=1.3 Hz, 1H), 7.73 (d, J=1.5 Hz, 1H), 7.69 (s, 1H), 7.32 (dd, J=9.2, 6.7 Hz, 1H), 6.74-6.64 (m, 2H), 4.62 (s, 1H), 4.24 (s, 3H).

Step 4

A solution of 5-(4-fluoro-2-hydroxyphenyl)-1-methyl-1H-indazole-3-carbaldehyde (440 mg, 1.6 mmol) in THF (10 ml) was cooled to 0° C. then treated with triethylamine (250 µl. 3.2 mmol) followed by methanesulfonyl chloride (450 µl, 3.2 mmol). The reaction mixture was allowed to warm to room temperature and was stirred for 18 hours before being quenched with saturated sodium bicarbonate solution (10 ml). EtOAc (50 ml) was added and the layers were separated. The aqueous phase was further extracted with EtOAc (20 ml) and the combined organic extracts were dried ($Na_2SO_4$) and concentrated under reduced pressure to give 5-fluoro-2-(3-formyl-1-methyl-1H-indazol-5-yl)phenyl methanesulfonate as a colourless solid (525 mg, 94%) mp 181-183° C. $^1$H NMR (400 MHz, Chloroform-d) δ 10.26 (s, 1H), 8.46-8.37 (m, 1H), 7.70 (dd, J=8.8, 1.5 Hz, 1H), 7.59 (d, J=8.7 Hz, 1H), 7.53 (dd, J=8.7, 6.3 Hz, 1H), 7.31 (dd, J=8.8, 2.5 Hz, 1H), 7.18 (td, J=8.2, 2.6 Hz, 1H), 4.26 (s, 3H), 2.69 (s, 3H).

Step 5

A solution of 5-fluoro-2-(3-formyl-1-methyl-1H-indazol-5-yl)phenyl methanesulfonate (520 mg, 1.6 mmol) in DCE (5 ml) was treated with a solution of dimethylamine in THF (2M, 2.4 ml, 4.8 mmol), followed by glacial acetic acid (580 µl, 9.6 mmol). The solution was stirred at room temperature for 10 mins before addition of solid sodium triacetoxyborohydride (1.10 g, 4.8 mmol). The reaction mixture was stirred at room temperature for 18 hours before being quenched with sodium carbonate solution (2M, 20 ml). DCM (20 ml) was added and the layers were separated. The aqueous phase was further extracted with DCM (10 ml) and the combined organic extracts were dried ($Na_2SO_4$) and concentrated under reduced pressure. The crude product was purified by column chromatography by elution with EtOAc/diethylamine (95:5), then triturated with cyclohexane to give the title compound as a colourless solid (350 mg, 58%). Mp 105-107° C. $^1$H NMR (400 MHz, Chloroform-d) δ 7.95 (d, J=1.4 Hz, 1H), 7.53 (dd, J=6.9, 1.9 Hz, 1H), 7.52-7.48 (m, 1H), 7.44 (d, J=8.7 Hz, 1H), 7.28 (dd, J=8.8, 2.8 Hz, 1H), 7.15 (td, J=8.1, 2.6 Hz, 1H), 4.09 (s, 3H), 3.83 (s, 2H), 2.60 (s, 3H), 2.32 (s, 6H).

Intermediate 5

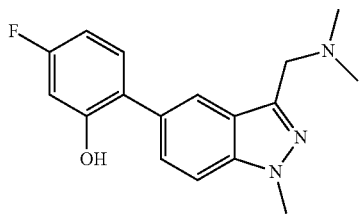 [SMILES: CN(C)Cc1nn(C)c2ccc(-c3ccc(F)cc3O)cc12]

2-(3-((dimethylamino)methyl)-1-methyl-1H-indazol-5-yl)-5-fluorophenol

A solution of 5-(4-fluoro-2-hydroxyphenyl)-1-methyl-1H-indazole-3-carbaldehyde (for preparation see Intermediate 4, step 3) (100 mg, 0.4 mmol) in THF (3 ml) was treated with a solution of dimethylamine in THF (2M, 0.6 ml, 1.2 mmol), followed by glacial acetic acid (145 μl, 2.4 mmol). The solution was stirred at room temperature for 10 mins before addition of solid sodium triacetoxyborohydride (250 mg, 1.2 mmol) and DCE (2 ml). The reaction mixture was stirred at room temperature for 18 hours before being quenched with sodium carbonate solution (2M, 20 ml). DCM (20 ml) was added and the layers were separated. The aqueous phase was further extracted with DCM (10 ml) and the combined organic extracts were dried ($Na_2SO_4$) and concentrated under reduced pressure. The crude product was purified by column chromatography by elution with EtOAc/diethylamine (95:5), to give the title compound as a colourless foam (81 mg, 68%). $^1$H NMR (400 MHz, Chloroform-d) δ 8.27 (s, 1H), 7.88 (d, J=1.5 Hz, 1H), 7.48 (dd, J=8.7, 1.5 Hz, 1H), 7.35 (d, J=8.7 Hz, 1H), 7.11. (dd, J=8.6, 6.7 Hz, 1H), 6.58 (td, J=8.4, 2.5 Hz, 1H), 6.47 (dd, J=10.5, 2.6 Hz, 1H), 4.03 (s, 3H), 3.86 (s, 2H), 2.34 (s, 6H).

Intermediate 6

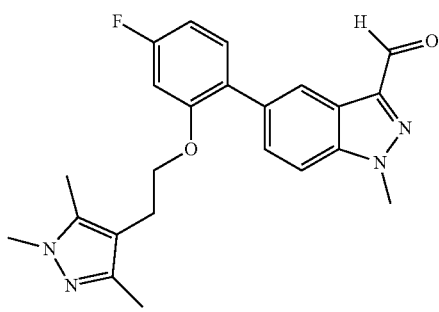 [SMILES: Cc1nn(C)c(C)c1CCOc1cc(F)ccc1-c1ccc2c(c1)c(C=O)nn2C]

5-(4-fluoro-2-(2-(1,3,5-trimethyl-1H-pyrazol-4-yl)ethoxy)phenyl)-1-methyl-1H-indazole-3-carbaldehyde A solution of 5-(4-fluoro-2-hydroxyphenyl)-1-methyl-1H-indazole-3-carbaldehyde (for preparation see Intermediate 4, step 3) (200 mg; 0.74 mmol) and triphenylphosphine (388 mg; 1.48 mmol) in THF (4 mL) was treated with a solution of 2-(1,3,5-trimethyl-1H-pyrazol-4-yl)ethanol (288 mg, 1.48 mmol) in THF (3 mL). The reaction mixture was cooled to 0° C. before being treated with di-isopropyl azodicarboxylate (29 μl, 1.48 mmol). The reaction mixture was allowed to warm to room temperature, stirred overnight and concentrated under reduced pressure. The crude product was purified by automated column chromatography by elution with hexane/IPA (gradient 95:5 to then 30:70) to give the title compound as a colourless oil (240 mg, 80%). $^1$H NMR (400 MHz, Chloroform-d) δ 10.22 (s, 1H), 8.37 (d, J=1.5 Hz, 1H), 7.57 (dd, J=8.8, 1.5 Hz, 1H), 7.46 (d, J=8.7 Hz, 1H), 7.29 (dd, J=8.4, 6.8 Hz, 1H), 6.72 (td, J=8.3, 2.5 Hz, 1H), 6.67 (dd, J=11.1, 2.4 Hz, 1H), 4.21 (s, 3H), 3.94 (t, J=7.2 Hz, 2H), 3.62 (s, 3H), 2.74 (t, J=7.1 Hz, 2H), 2.04 (s, 3H), 1.95 (s, 3H).

Intermediate 7

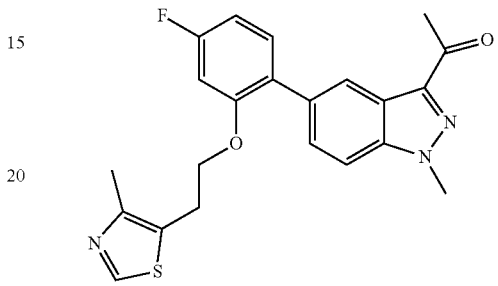

1-(5-(4-fluoro-2-(2-(4-methylthiazol-5-yl)ethoxy)phenyl)-1-methyl-1H-indazol-3-yl)ethanone Step 1

A solution of 5-iodo-N-methoxy-N, 1-dimethyl-1H-indazole-3-carboxamide [product of intermediate 4 step 1) (400 mg, 1.15 mmol) in THF (5 ml) was cooled to 0° C. before dropwise addition of a methylmagnesium bromide in THF/Toluene (1.4M, 2.5 ml, 1.8 mmol). The reaction mixture was stirred for 1 hr then quenched by addition of EtOAc (1 ml), allowed to warm to room temperature then partitioned between EtOAc (20 ml) and saturated ammonium chloride solution (10 ml). The organic phase was dried over $Na_2SO_4$ and concentrated under reduced pressure to give 1-(5-iodo-1-methyl-1H-indazole-3-yl) ethanone as a pale yellow solid (308 mg, 86%) mp 178-180° C. $^1$H NMR (400 MHz, Chloroform-d) δ 8.77 (d, J=1.5 Hz, 1H), 7.70 (dd, J=8.8, 1.5 Hz, 1H), 7.23 (d, J=8.8 Hz, 1H), 4.15 (s, 3H), 2.71 (s, 3H).

Step 2

A solution of 1-(5-iodo-1-methyl-1H-indazol-3-yl) ethanone (308 mg, 1.0 mmol) was dissolved in dioxane (5 ml) and treated with 4-fluoro-2-hydroxybenzene boronic acid (202 mg, 1.3 mmol) and tetrakis(triphenylphosphine) palladium(0) (10 mg), followed by a solution of potassium phosphate (432 mg, 2.0 mmol) in water (1 ml). The reaction mixture was heated under reflux for 2 hr, cooled to room temperature and evaporated under reduced pressure. The residue was partitioned between ethyl acetate (20 ml) and saturated sodium bicarbonate solution (20 ml). The organic phase was dried over $Na_2SO_4$, concentrated under reduced pressure and the crude product purified by flash column chromatography by elution with DCM/EtOAc (100:0, then 90:10) to give 1-(5-(4-fluoro-2-hydroxyphenyl)-1-methyl-1H-indazol-3-yl)ethanone as a colourless solid (277 mg, 97%). mp 228-229° C. $^1$H NMR (400 MHz, Methanol-d4) δ 8.33 (d, J=1.7 Hz, 1H), 7.68 (dd, J=8.8, 1.5 Hz, 1H), 7.60 (d, J=8.7 Hz, 1H), 7.35-7.23 (m, 1H), 6.71-6.62 (m, 2H), 4.18 (s, 3H), 2.68 (s, 3H).

Step 3

A solution 1-(5-(4-fluoro-2-hydroxyphenyl)-1-methyl-1H-indazol-3-yl)ethanone (155 mg, 0.5 mmol) in dichloromethane (10 ml) was cooled to 0° C. then treated with triethylamine (166 μl. 1.0 mmol) followed by methanesulfonyl chloride (84 μl, 1.0 mmol). The reaction mixture was allowed to warm to room temperature and was stirred for 18 hours before being quenched with saturated sodium bicarbonate solution (10 ml). Dichloromethane (20 ml) was added and the layers were separated. The aqueous phase was further extracted with dichloromethane (20 ml) and the combined organic extracts were dried ($Na_2SO_4$) and concentrated under reduced pressure. The crude product was purified by column chromatography by elution with dichloromethane/ethyl acetate (90:10). Fractions containing the product were combined and evaporated to give 2-(3-acetyl-1-methyl-1H-indazol-5-yl)-5-fluorophenyl methanesulfonate as a pale yellow solid (105 mg, 54%), mp 167-168° C.

$^1$H NMR (400 MHz, Chloroform-d) δ 8.47 (d, J=1.4 Hz, 1H), 7.67-7.62 (m, 1H), 7.57-7.50 (m, 2H), 7.31 (dd, J=8.9, 2.6 Hz, 1H), 7.17 (td, J=8.2, 2.6 Hz, 1H), 4.22 (s, 3H), 2.74 (s, 3H), 2.66 (s, 3H).

Step 4

According to the general method for mesyl transfer (Method A), 2-(3-acetyl-1-methyl-1H-indazol-5-yl)-5-fluorophenyl methanesulfonate (65 mg, 0.18 mmol was reacted with 2-(4-methylthiazol-5-yl)ethanol (51 mg, 0.36 mmol) and sodium t-butoxide (34 mg, 0.36 mmol) in acetonitrile (0.5 ml). Purification by column chromatography by elution with dichloromethane/ethyl acetate (80:20), followed by ethyl acetate/diethylamine (95:50 provided 1-(5-(4-fluoro-2-(2-(4-methylthiazol-5-yl)ethoxy)phenyl)-1-methyl-1H-indazol-3-yl)ethanone as a colourless oil (40 mg, 54%). $^1$H NMR (400 MHz, Chloroform-d) δ 8.53 (s, 1H), 8.47-8.40 (m, 1H), 7.46 (dd, J=8.8, 1.8 Hz, 1H), 7.40 (d, J=8.8 Hz, 1H), 7.34 (dd, J=8.5, 6.7 Hz, 1H), 6.78 (td, J=8.2, 2.4 Hz, 1H), 6.70 (dd, J=10.8, 2.4 Hz, 1H), 4.20 (s, 3H), 4.14 (t, J=6.3 Hz, 2H), 3.18 (t, J=6.3 Hz, 2H), 2.74 (s, 3H), 2.24 (s, 3H).

Intermediate 8

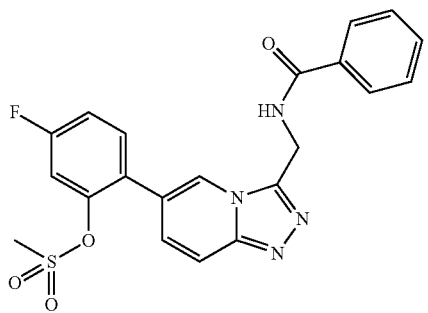 [SMILES: CS(=O)(=O)Oc1cc(F)ccc1-c1ccc2nnc(CNC(=O)c3ccccc3)n2c1]

2-(3-(benzamidomethyl)-[1,2,4]triazolo[4,3-a]pyridin-6-yl)-5-fluorophenyl methanesulfonate Step 1

A mixture of 5-bromo-2-hydrazinylpyridine (564 mg, 3.0 mmol) and hippuric acid (557 mg, 3.0 mmol) was heated to form a melt, which was maintained at 180° C. for one hour. The mixture solidified on cooling and the resulting solid was dissolved in warm methanol (10 ml). The product, N-((6-bromo-[1,2,4]triazolo[4,3-a]pyridin-3-yl)methyl)benzamide, crystallised on cooling and was collected by filtration (320 mg, 32%). mp 208-209° C. $^1$H NMR (400 MHz, DMSO-d6) δ 9.29 (t, J=5.6 Hz, 1H), 9.02-8.94 (m, 1H), 7.93-7.84 (m, 2H), 7.78 (d, J=9.6 Hz, 1H), 7.58-7.44 (m, 4H), 5.01 (d, J=5.5 Hz, 2H).

Step 2

A solution of N-((6-bromo-[1,2,4]triazolo[4,3-a]pyridin-3-yl)methyl)benzamide (260 mg, 0.78 mmol) was dissolved in dioxane (5 ml) and treated with 4-fluoro-2-hydroxybenzene boronic acid (250 mg, 1.6 mmol) and tetrakis(triphenylphosphine) palladium(0) (10 mg), followed by a solution of potassium phosphate (432 mg, 2.0 mmol) in water (1 ml). The reaction mixture was heated under reflux for 2 hr, cooled to room temperature and evaporated under reduced pressure. The residue was partitioned between ethyl acetate/methanol (10:1, 20 ml) and saturated sodium bicarbonate solution (20 ml). The organic phase was dried over $Na_2SO_4$, concentrated under reduced pressure and the crude product purified by flash column chromatography by elution with ethyl acetate/methanol (100:0, then 90:10) to give N-((6-(4-fluoro-2-hydroxyphenyl)-[1,2,4]triazolo[4,3-a]pyridin-3-yl)methyl)benzamide as a colourless solid (277 mg, 98%). mp 185-186° C. $^1$H NMR (400 MHz, Methanol-d4) δ 8.74 (d, J=1.4 Hz, 1H); 7.89-7.82 (m, 2H), 7.79-7.68 (m, 2H), 7.57-7.50 (m, 1H), 7.49-7.42 (m, 2H), 7.41-7.32 (m, 1H), 6.73-6.71 (m, 1H), 6.69 (dq, J=4.5, 2.3 Hz, 1H), 5.17 (s, 2H).

Step 3

A solution of N-((6-(4-fluoro-2-hydroxyphenyl)-[1,2,4] triazolo[4,3-a]pyridin-3-yl)methyl)benzamide (157 mg, 0.43 mmol) in dichloromethane (10 ml) was cooled to 0° C. then treated with triethylamine (120 μl, 0.86 mmol) followed by methanesulfonyl chloride (67 μl, 0.86 mmol). The reaction mixture was allowed to warm to room temperature and was stirred for 18 hours before being quenched with saturated sodium bicarbonate solution (10 ml). Dichloromethane (20 ml) was added and the layers were separated. The aqueous phase was further extracted with dichloromethane (20 ml) and the combined organic extracts were dried ($Na_2SO_4$) and concentrated under reduced pressure. The crude product was purified by column chromatography by elution with ethyl acetate/methanol/diethylamine (90:5:5). Fractions containing the product were combined and evaporated to give 2-(3-(benzamidomethyl)-[1,2,4]triazolo[4,3-a]pyridin-6-yl)-5-fluorophenyl methanesulfonate as a colourless solid (135 mg, 71%). mp 208-210° C. $^1$H NMR (400 MHz, Methanol-d4) δ 8.82 (s, 1H), 7.89-7.81 (m, 3H), 7.70-7.61 (m, 2H), 7.59-7.52 (m, 1H), 7.47 (t, J=7.6 Hz, 2H), 7.41 (dd, J=9.1, 2.5 Hz, 1H), 7.31 (td, J=8.3, 2.7 Hz, 1H), 5.17 (s, 2H), 3.07 (s, 3H).

Intermediate 9

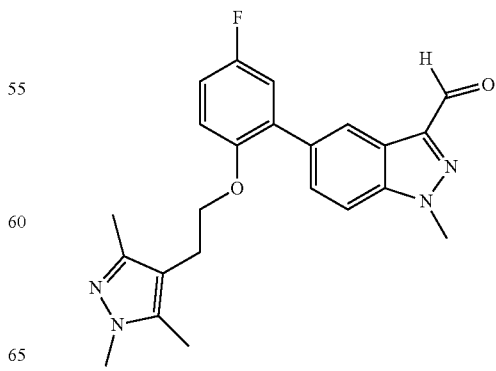

5-(5-fluoro-2-(2-(1,3,5-trimethyl-1H-pyrazol-4-yl)ethoxy)phenyl)-1-methyl-1H-indazole-3-carbaldehyde Step 1

A solution of 5-iodo-1-methyl-1H-indazole-3-carbaldehyde (prepared as in intermediate 4, step 2) (600 mg, 1.75 mmol) was dissolved in dioxane (15 mL) and treated with 5-fluoro-2-hydroxybenzene boronic acid (355 mg, 1.3 mmol) and tetrakis(triphenylphosphine) palladium(0) (50 mg), followed by a solution of potassium phosphate (744 mg, 2.0 mmol) in water (4.5 mL). The reaction mixture was heated under reflux for 2 hr, cooled to room temperature and evaporated under reduced pressure. The residue was partitioned between ethyl acetate (20 mL) and saturated sodium bicarbonate solution (20 mL). The organic phase was dried over $Na_2SO_4$, concentrated under reduced pressure and the crude product purified by flash column chromatography by elution with EtOAc/hexane (0-20% EtOAc) to give 5-(5-fluoro-2-hydroxyphenyl)-1 methyl-1H-indazole-3-carbaldehyde as a yellow solid (213 mg, 45%). $^1$H NMR (400 MHz, $CDCl_3$) δ 10.23 (s, 1H), 8.43 (d, J=1.2 Hz, 1H), 7.70-7.54 (m, 1H), 7.14-6.89 (m, 4H), 5.10 (s, 1H), 4.26 (s, 3H).

Step 2

A solution of 5-(5-fluoro-2-hydroxyphenyl)-1-methyl-1H-indazole-3-carbaldehyde (200 mg; 0.74 mmol) and triphenylphosphine (388 mg; 1.48 mmol) in THF (4 mL) was treated with a solution of 2-(1,3,5-trimethyl-1H-pyrazol-4-yl)ethanol (228 mg, 1.48 mmol) in THF (3 mL). The reaction mixture was cooled to 0° C. before being treated with di-isopropyl azodicarboxylate (291 µl, 1.48 mmol). The reaction mixture was allowed to warm to room temperature, stirred overnight and concentrated under reduced pressure. The crude product was purified by automated column chromatography by elution with hexane/IPA (gradient of 95:5 to 40:60) to give the title compound as a colourless oil (155 mg, 52%); $^1$H NMR (400 MHz, $CDCl_3$) δ 10.26 (s, 1H), 8.51-8.37 (m, 1H), 7.64 (dd, J=8.8, 1.7 Hz, 1H), 7.50 (d, J=8.8 Hz, 1H), 7.12 (dd, J=9.0, 3.1 Hz, 1H), 7.01 (td, J=8.3, 3.1 Hz, 1H), 6.90 (dd, J=9.0, 4.6 Hz, 1H), 4.25 (s, 3H), 3.92 (t, J=7.2 Hz, 2H), 3.65 (s, 3H), 2.73 (t, J=7.2 Hz, 2H), 2.06 (s, 3H), 1.98 (s, 3H).

Intermediate 10

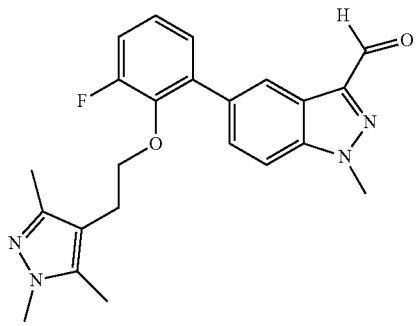 [SMILES: Cc1nn(C)c(C)c1CCOc1c(F)cccc1-c1ccc2c(c1)c(C=O)nn2C]

5-(3-fluoro-2-(2-(1,3,5-trimethyl-1H-pyrazol-4-yl)ethoxy)phenyl)-1-methyl-1H-indazole-3-carbaldehyde Step 1

A solution of 5-iodo-1-methyl-1H-indazole-3-carbaldehyde (prepared as in intermediate 4, step 2) (600 mg, 1.75 mmol) was dissolved in dioxane (15 mL) and treated with 3-fluoro-2-hydroxybenzene boronic acid (355 mg, 1.3 mmol) and tetrakis(triphenylphosphine) palladium(0) (50 mg), followed by a solution of potassium phosphate (744 mg, 2.0 mmol) in water (4.5 mL). The reaction mixture was heated under reflux for 2 hr, cooled to room temperature and evaporated under reduced pressure. The residue was partitioned between ethyl acetate (20 mL) and saturated sodium bicarbonate solution (20 mL). The organic phase was dried over $Na_2SO_4$, concentrated under reduced pressure and the crude product triturated from EtOAc/hexane to give 5-(3-fluoro-2-hydroxyphenyl)-1 methyl-1H-indazole-3-carbaldehyde as an orange solid (388 mg, 82%). $^1$H NMR (400 MHz, $CDCl_3$) δ 10.26 (s, 1H), 8.49 (d, J=2.0 Hz, 1H), 7.77 (dd, J=8.8, 1.5 Hz, 1H), 7.57 (d, J=8.8 Hz, 1H), 7.23-7.19 (m, 1H), 7.18-7.11 (m, 1H), 7.01-6.94 (m, 1H), 5.39 (d, J=5.4 Hz, 1H), 4.25 (s, 3H).

Step 2

A solution of 5-(3-fluoro-2-hydroxyphenyl)-1-methyl-1H-indazole-3-carbaldehyde (350 mg; 1.30 mmol) and triphenylphosphine (679 mg; 2.59 mmol) in THF (7 mL) was treated with a solution of 2-(1,3,5-trimethyl-1H-pyrazol-4-yl)ethanol (399 mg, 2.59 mmol) in THF (5 mL). The reaction mixture was cooled to 0° C. before being treated with di-isopropyl azodicarboxylate (510 µl, 2.59 mmol). The reaction mixture was allowed to warm to room temperature, stirred overnight and concentrated under reduced pressure. The crude product was purified by automated column chromatography by elution with hexane/IPA (gradient of 95:5 to 40:60) to give the title compound as a colourless oil (490 mg, 93%); $^1$H NMR (400 MHz, $CDCl_3$) δ 10.27 (s, 1H), 8.40 (s, 1H), 7.68-7.60 (m, 1H), 7.47 (d, J=8.8 Hz, 1H), 7.23-7.09 (m, 3H), 4.27 (s, 3H), 3.78 (t, J=7.4 Hz, 2H), 3.60 (s, 3H), 2.60 (t, J=7.4 Hz, 3H), 1.96 (s, 6H).

Intermediate 11

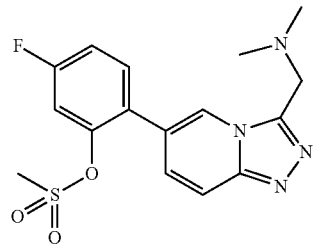 [SMILES: CN(C)Cc1nnc2ccc(-c3ccc(F)cc3OS(C)(=O)=O)cn12]

2-(3-((dimethylamino)methyl)-[1,2,4]triazolo[4,3-a]pyridin-6-yl)-5-fluorophenyl methanesulfonate Step 1

A solution of 5-bromo-2-hydrazinylpyridine (564 mg, 3.0 mmol) in DCM (10 ml) was treated with hydroxybenzotriazole (40 mg, 0.3 mmol) followed by N,N-dimethylglycine (340 mg, 3.5 mmol) and finally EDCl (632 mg, 3.5 mmol) by portionwise addition. The solution was stirred at room temperature overnight, then washed with water, dried ($Na_2SO_4$) and concentrated under reduced pressure. The crude intermediate was dissolved in THF (50 ml) and treated with triphenylphosphine (1.57 g, 6 mmol) and triethylamine (1.67 ml, 12 mmol), followed by portionwise addition of hexachloroethane (1.42 g, 6 mmol). The mixture was stirred at room temperature overnight, then filtered. The filtrate was concentrated under reduced pressure and purified by SCX chromatography by elution with methanolic ammonia (2M).

Fractions containing the product were combined and evaporated to give 1-(6-bromo-[1,2,4]triazolo[4,3-a]pyridin-3-yl)-N,N-dimethylmethanamine as an orange solid (387 mg, 51%) mp 167-169° C. ¹H NMR (400 MHz, Methanol-d4) δ 8.79 (t, J=1.5 Hz, 1H), 7.71 (d, J=9.8 Hz, 1H), 7.58 (dd, J=9.8, 1.5 Hz, 1H), 4.05 (s, 2H), 2.32 (s, 6H).

Step 2

A solution of 1-(6-bromo-[1,2,4]triazolo[4,3-a]pyridin-3-yl)-N,N-dimethylmethanamine (387 mg, 1.5 mmol) was dissolved in dioxane (5 ml) and treated with 4-fluoro-2-hydroxybenzene boronic acid (467 mg, 3.0 mmol) and tetrakis(triphenylphosphine) palladium(0) (20 mg), followed by a solution of potassium phosphate (810 mg, 3.75 mmol) in water (1 ml). The reaction mixture was heated under reflux overnight, cooled to room temperature and evaporated under reduced pressure. The residue was partitioned between ethyl acetate (20 ml) and water (20 ml). The organic phase was dried over Na₂SO₄, concentrated under reduced pressure and the crude product purified by flash column chromatography by elution with ethyl acetate/methanol/diethylamine (95:0:5, then 90:5:5) to give 2-(3-((dimethylamino)methyl)-[1,2,4]triazolo[4,3-a]pyridin-6-yl)-5-fluorophenol as a yellow solid (193 mg, 45%). ¹H NMR (400 MHz, Methanol-d4) δ δ 8.62 (d, J=1.4 Hz, 1H), 7.75-7.61 (m, 2H), 7.35 (dd, J=8.5, 6.7 Hz, 1H), 6.70 (dd, J=10.7, 2.5 Hz, 1H), 6.62 (td, J=8.3, 2.5 Hz, 1H), 4.03 (s, 2H), 2.30 (s, 6H).

Step 3

A solution of 2-(3-((dimethylamino)methyl)-[1,2,4]triazolo[4,3-a]pyridin-6-yl)-5-fluorophenol (193 mg, 0.67 mmol) in dichloromethane (5 ml) was cooled to 0° C. then treated with triethylamine (500 μl. 4.0 mmol) followed by methanesulfonyl chloride (300 μl, 4.0 mmol). The reaction mixture was allowed to warm to room temperature and was stirred for 18 hours before being quenched with saturated sodium carbonate solution (2M, 20 ml). Dichloromethane (20 ml) was added and the layers were separated. The aqueous phase was further extracted with dichloromethane (20 ml) and the combined organic extracts were dried (Na₂SO₄) and concentrated under reduced pressure. The crude product was purified by column chromatography by elution with ethyl acetate then ethyl acetate/diethylamine (95:5). Fractions containing the product were combined and evaporated to give 2-(3-((dimethylamino)methyl)-[1,2,4]triazolo[4,3-a]pyridin-6-yl)-5-fluorophenyl methanesulfonate as a orange solid (110 mg, 45%) mp 161-163° C. ¹H NMR (400 MHz, Chloroform-d) δ 8.52 (d, J=1.6 Hz, 1H), 7.81-7.73 (m, 1H), 7.48 (dd, J=8.7, 6.1 Hz, 1H), 7.37 (dd, J=9.6, 1.7 Hz, 1H), 7.30 (dd, J=8.8, 2.6 Hz, 1H), 7.22-7.12 (m, 1H), 4.00 (s, 2H), 3.02 (s, 3H), 2.26 (s, 6H).

Intermediate 12

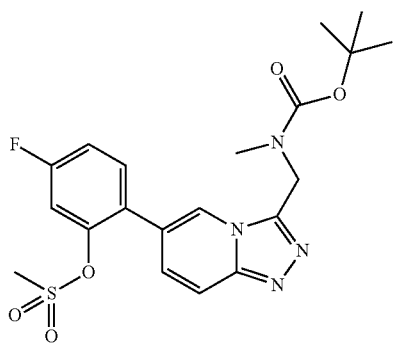 [SMILES: CN(Cc1nnc2ccc(-c3ccc(F)cc3OS(C)(=O)=O)cn12)C(=O)OC(C)(C)C]

2-(3-(((tert-butoxycarbonyl)(methyl)amino)methyl)-[1,2,4]triazolo[4,3-a]pyridin-6-yl)-5-fluorophenyl methanesulfonate Step 1

A solution of 5-bromo-2-hydrazinylpyridine (1.12 g, 6.0 mmol) in DCM (20 ml) was treated with hydroxybenzotriazole (94 mg, 0.7 mmol) followed by N-Boc-sarcosine (1.25 g, 6.6 mmol) and finally EDCl (1.34 g, 7 mmol) by portionwise addition. The solution was stirred at room temperature overnight, then washed with water, dried (Na₂SO₄) and concentrated under reduced pressure. The crude intermediate was dissolved in THF (70 ml) and treated with triphenylphosphine (3.14 g, 12 mmol) and triethylamine (3.34 ml, 24 mmol), followed by portionwise addition of hexachloroethane (2.84 g, 12 mmol). The mixture was stirred at room temperature overnight, then filtered. The filtrate was concentrated under reduced pressure and purified by SCX chromatography by elution with methanolic ammonia (2M). Fractions containing the product were combined and evaporated to give crude product, which was further purified by column chromatography by elution with dichloromethan/ethyl acetate (1:1 then 0:1). Fractions containing the major product were combined and evaporated under reduced pressure to give tert-butyl ((6-bromo-[1,2,4]triazolo[4,3-a]pyridin-3-yl)methyl)(methyl)carbamate as a yellow solid (650 mg, 31%) mp 102-104° C. ¹H NMR (400 MHz, Chloroform-d) δ 8.76 (s, 1H), 7.63 (d, J=9.7 Hz, 1H), 7.30 (d, J=9.5 Hz, 1H), 4.95 (s, 2H), 2.80 (s, 3H), 1.47 (s, 9H).

Step 2

A solution of tert-butyl ((6-bromo-[1,2,4]triazolo[4,3-a]pyridin-3-yl)methyl)(methyl)carbamate (650 mg, 1.9 mmol) was dissolved in dioxane (8 ml) and treated with 4-fluoro-2-hydroxybenzene boronic acid (592 mg, 3.8 mmol) and tetrakis(triphenylphosphine) palladium(0) (40 mg), followed by a solution of potassium phosphate (1.08 g, 4.75 mmol) in water (2 ml). The reaction mixture was heated under reflux overnight, cooled to room temperature and evaporated under reduced pressure. The residue was partitioned between ethyl acetate (20 ml) and water (20 ml). The organic phase was dried over Na₂SO₄, concentrated under reduced pressure and the crude product purified by flash column chromatography by gradient elution with ethyl acetate/hexane (1:1), then ethyl acetate and then ethylacetate/methanol (95:5, then 90:10) to give tert-butyl ((6-(4-fluoro-2-hydroxyphenyl)-[1,2,4]triazolo[4,3-a]pyridin-3-yl)methyl)(methyl)carbamate as a colourless solid (650 mg, ~100%) mp 127-129° C. ¹H NMR (400 MHz, Methanol-d4) δ 8.67 (s, 1H), 7.84-7.67 (m, 2H), 7.37 (dd, J=8.9, 5.7 Hz, 1H), 6.78-6.64 (m, 2H), 5.05 (s, 2H), 2.90 (s, 3H), 1.45 (s, 9H).

Step 3

A solution of tert-butyl ((6-(4-fluoro-2-hydroxyphenyl)-[1,2,4]triazolo[4,3-a]pyridin-3-yl)methyl)(methyl)carbamate (650 mg, 1.9 mmol) in dichloromethane (5 ml) was cooled to 0° C. then treated with triethylamine (560μ, 4.0 mmol) followed by methanesulfonyl chloride (310 μl, 4.0 mmol). The reaction mixture was allowed to warm to room temperature and was stirred for 18 hours before being quenched with sodium carbonate solution (2M, 20 ml). Dichloromethane (20 ml) was added and the layers were separated. The aqueous phase was further extracted with dichloromethane (20 ml) and the combined organic extracts were dried (Na₂SO₄) and concentrated under reduced pressure. The crude product was purified by column chromatography by elution with ethyl acetate then ethyl acetate/diethylamine (100:0 then 95:5). Fractions containing the product were combined and evaporated to give a foam which was triturated with cyclohexane to give 2-(3-(((tert-butoxycarbonyl)(methyl)amino)-methyl)-[1,2,4]triazolo[4,3-a]pyridin-6-yl)-5-fluorophenyl methanesulfonate as a colourless solid (530 mg, 62%) mp 147-149° C. $^1$H NMR (400 MHz, Chloroform-d) δ 8.69 (s, 1H), 7.84 (d, J=9.4 Hz, 1H), 7.49 (d, J=9.9 Hz, 1H), 7.45 (dd, J=8.7, 6.2 Hz, 1H), 7.31 (dd, J=8.8, 2.5 Hz, 1H), 7.22-7.09 (m, 1H), 5.03 (s, 2H), 3.00 (s, 3H), 2.89 (s, 3H), 1.45 (s, 9H).

Intermediate 13

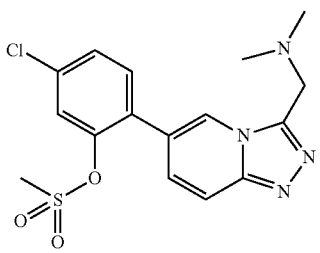 [SMILES: CN(C)Cc1nnc2ccc(-c3ccc(Cl)cc3OS(C)(=O)=O)cn12]

5-chloro-2-(3-((dimethylamino)methyl)-[1,2,4]triazolo[4,3-a]pyridin-6-yl)phenyl methanesulfonate Step 1

A solution of 1-(6-bromo-[1,2,4]triazolo[4,3-a]pyridin-3-yl)-N,N-dimethylmethanamine [product of Step 1, Intermediate 11] (387 mg, 1.5 mmol) was dissolved in dioxane (8 ml) and treated with 4-chloro-2-hydroxybenzene boronic acid (516 mg, 3.0 mmol) and tetrakis(triphenylphosphine) palladium(0) (20 mg), followed by a solution of potassium phosphate (810 mg, 3.75 mmol) in water (1 ml). The reaction mixture was heated under reflux overnight, cooled to room temperature and evaporated under reduced pressure. The residue was partitioned between ethyl acetate (20 ml) and water (20 ml). The organic phase was dried over Na$_2$SO$_4$, concentrated under reduced pressure and the crude product purified by flash column chromatography by elution with ethyl acetate/methanol/diethylamine (95:0:5, then 90:5:5) to give 5-chloro-2-(3-((dimethylamino)methyl)-[1,2,4]triazolo[4,3-a]pyridin-6-yl)phenol as a yellow solid (240 mg, 52%). $^1$H NMR (400 MHz, Methanol-d4) δ 8.68 (d, J=1.4 Hz, 1H), 7.79-7.64 (m, 2H), 7.35 (d, J=8.3 Hz, 1H), 6.96 (d, J=2.1 Hz, 1H), 6.89 (dd, J=8.1, 2.2 Hz, 1H), 4.06 (s, 2H), 2.31 (s, 6H).

Step 2

A solution of 5-chloro-2-(3-((dimethylamino)methyl)-[1,2,4]triazolo[4,3-a]pyridin-6-yl)phenol (240 mg, 0.8 mmol) in dichloromethane (5 ml) was cooled to 0° C. then treated with triethylamine (500 µl, 4.0 mmol) followed by methanesulfonyl chloride (300 µl, 4.0 mmol). The reaction mixture was allowed to warm to room temperature and was stirred for 18 hours before being quenched with saturated sodium carbonate solution (2M, 20 ml). Dichloromethane (20 ml) was added and the layers were separated. The aqueous phase was further extracted with dichloromethane (20 ml) and the combined organic extracts were dried (Na$_2$SO$_4$) and concentrated under reduced pressure. The crude product was triturated with cyclohexane to give 5-chloro-2-(3-((dimethylamino)methyl)-[1,2,4]triazolo[4,3-a]pyridin-6-yl)phenyl methanesulfonate as a orange solid (280 mg, 92%) mp 169-170° C. $^1$H NMR (400 MHz, Chloroform-d) δ 8.55 (t, J=1.4 Hz, 1H), 7.84-7.75 (m, 1H), 7.57 (d, J=1.8 Hz, 1H), 7.49-7.40 (m, 2H), 7.39 (dd, J=9.5, 1.6 Hz, 1H), 4.02 (s, 2H), 3.04 (s, 3H), 2.28 (s, 6H).

Intermediate 14

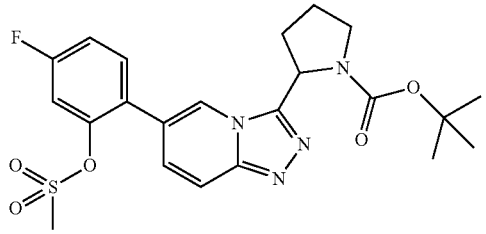 [SMILES: CC(C)(C)OC(=O)N1CCCC1c1nnc2ccc(-c3ccc(F)cc3OS(C)(=O)=O)cn12]

tert-butyl 2-{6-[4-fluoro-2-(methanesulfonyloxy)phenyl]-[1,2,4]triazolo[4,3-a]pyridin-3-yl}pyrrolidine-1-carboxylate Step 1

A solution of 5-bromo-2-hydrazinylpyridine (500 mg, 2.66 mmol) in DCM (10 ml) was treated with hydroxybenzotriazole (48 mg, 0.31 mmol) followed by N-Boc-proline (642 mg, 3.0 mmol) and finally EDCl (621 mg, 3.2 mmol) by portionwise addition. The solution was stirred at room temperature overnight, then washed with water and brine, dried (Na$_2$SO$_4$) and concentrated under reduced pressure. The crude product was purified by column chromatography by elution with dichloromethane/methanol (98:2). Fractions containing the product were combined and evaporated to give tert-butyl 2-[N'-(5-bromo-1,2-dihydropyridin-2-ylidene)hydrazinecarbonyl]pyrrolidine-1-carboxylate as a brown solid (900 mg, 88%). $^1$H NMR (400 MHz, DMSO-d6) δ 9.87 (d, J=10.2 Hz, 1H), 8.58 (d, J=6.7 Hz, 1H), 8.10 (s, 1H), 7.65 (m, 1H), 6.58 (dd. 1H) 4.15 (m, 1H), 3.37 (d, 1H), 3.30 (m, 1H), 2.17 (m, 1H), 1.80-1.86 (m, 4H), 1.40 (s, 9H), 1.23-1.38 (m, 4H).

Step 2

Tert-butyl 2-[N'-(5-bromo-1,2-dihydropyridin-2-ylidene)hydrazinecarbonyl]pyrrolidine-1-carboxylate (900 mg, 2.33 mmol was dissolved in THF (20 ml) and treated with triphenylphosphine (1.25 g, 4.67 mmol) and triethylamine (1.30 ml, 9.34 mmol), followed by portionwise addition of hexachloroethane (1.10 g, 4.67 mmol). The mixture was stirred at room temperature overnight, then filtered through Celite. The filtrate was concentrated under reduced pressure and purified by column chromatography on silica by elution with dichloromethane/methanol (98:2). Fractions containing the product were combined and evaporated to give crude product, tert-butyl 2-{6-bromo-[1,2,4]triazolo[4,3a]pyridin-3-yl}pyrrolidine-1-carboxylate (650 mg, 95.7%) as a mixture of rotamers. $^1$H NMR (400 MHz, DMSO-d6) δ 8.98 (d, 1H), 7.77 (dd, 1H), 7.64-7.54 (m, 1H), 7.47 (d, 1H), 3.42-3.33 (m, 2H), 2.32-2.10 (m, 3H), 1.95-1.90 (m, 1H), 1.34-0.80 (m, 11H).

Step 3

A solution of tert-butyl 2-{6-bromo-[1,2,4]triazolo[4,3a]pyridin-3-yl}pyrrolidine-1-carboxylate (300 mg, 0.8 mmol) was dissolved in dioxane (10 ml) and treated with 4-fluoro-2-hydroxybenzene boronic acid (206 mg, 1.6 mmol) and tetrakis(triphenylphosphine) palladium(0) (94 mg), followed by a solution of potassium phosphate (433 mg, 2.0 mmol) in water (2 ml). The reaction mixture was heated under reflux overnight, cooled to room temperature and filtered through Celite, washing with ethyl acetate and separated. The organic phase was dried over Na$_2$SO$_4$, concentrated under reduced pressure and the crude product purified by flash column chromatography by elution with dichloromethane/methanol (95:5) to give tert-butyl 2-[6-(4-fluoro-2-hydroxyphenyl)-[1,2,4]triazolo[4,3-a]pyridin-3-yl]pyrrolidine-1-carboxylate (280 mg, 86%). ¹H NMR (400 MHz, DMSO-d6) δ 10.45 (s, 1H), 8.61 (d, 1H), 7.75 (m, 1H), 7.62-7.56 (m, 2H), 7.39 (m, 1H), 6.77 (m, 2H), 5.47 (m, 1H), 3.50 (m, 2H), 2.32-1.96 (m, 4H), 1.33-0.91 (m, 11H).
Step 4

A solution of tert-butyl 2-[6-(4-fluoro-2-hydroxyphenyl)-[1,2,4]triazolo[4,3-a]pyridin-3-yl]pyrrolidine-1-carboxylate (80 mg, 0.2 mmol) in dichloromethane (5 ml) was cooled to 0° C. then treated with triethylamine (59 μL, 0.4 mmol) followed by methanesulfonyl chloride (33 μl, 0.42 mmol). The reaction mixture was allowed to warm to room temperature and was stirred for 18 hours before being quenched with sodium bicarbonate solution (2M, 20 ml). Dichloromethane (20 ml) was added and the layers were separated. The aqueous phase was further extracted with dichloromethane (20 ml) and the combined organic extracts were dried (Na₂SO₄) and concentrated under reduced pressure. The crude product was purified by column chromatography by gradient elution with dichloromethane/methanol (99:1-95:5). Fractions containing the product were combined and evaporated to give the product, tert-butyl 2-{6-[4-fluoro-2-(methanesulfonyloxy)phenyl]-[1,2,4]triazolo[4,3-a]pyridin-3-yl}pyrrolidine-1-carboxylate as a solid (75 mg, 78%). ¹H NMR (400 MHz, Chloroform-d) δ 8.73 (s, 1H), 7.78 (m, 1H), 7.68-7.62 (m, 1H), 7.45 (m, 1H), 7.37 (d, 1H) 7.30 (d, 1H), 7.16 (m, 1H), 5.35 (m, 1H), 3.69-3.54 (m, 2H), 2.72 (s, 3H), 2.61-2.58 (m, 2H), 2.30 (m, 1H), 2.05 (m, 1H), 1.56-1.02 (m, 11H).

Intermediate 15

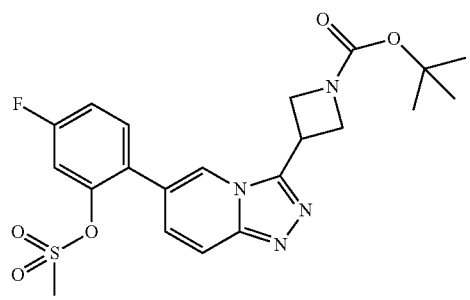 [SMILES: CC(C)(C)OC(=O)N1CC(c2nnc3ccc(-c4ccc(F)cc4OS(C)(=O)=O)cn23)C1]

Tert-butyl 3-{6-[4-fluoro-2-(methanesulfonyloxy)phenyl]-[1,2,4]triazolo[4,3-a]pyridin-3-yl}azetidine-1-carboxylate Step 1

A solution of 5-bromo-2-hydrazinylpyridine (1.0 g, 5.32 mmol) in DCM (10 ml) was treated with hydroxybenzotriazole (98 mg, 0.64 mmol) followed by N-Boc-azetidine-3-carboxylic acid (1.17 g, 5.85 mmol) and finally EDCl (1.22 g, 6.38 mmol) by portionwise addition. The solution was stirred at room temperature overnight, then washed with saturated sodium bicarbonate, water and brine, dried (Na₂SO₄) and concentrated under reduced pressure. The crude product was purified by column chromatography by elution with dichloromethane/methanol (96:4). Fractions containing the product were combined and evaporated to give tert-butyl 3-[N'-(5-bromopyridin-2-yl)hydrazinecarbonyl]azetidine-1-carboxylate as a solid (1.95 g, 99%). ¹H NMR (400 MHz, DMSO-d6) δ 9.90 (s, 1H), 8.61 (s, 1H), 8.12 (s, 1H), 7.68 (d, 1H), 6.55 (d, 1H), 5.75 (s, 1H), 3.98 (s, 2H), 3.85 (s, 2H), 1.36 (s, 9H).

Step 2

Tert-butyl 3-[N'-(5-bromopyridin-2-yl)hydrazinecarbonyl]azetidine-1-carboxylate (1.95 g, 5.25 mmol was dissolved in THF (50 ml) and treated with triphenylphosphine (2.75 g, 10.5 mmol) and triethylamine (2.93 ml, 21 mmol), followed by portionwise addition of hexachloroethane (2.48 g, 10.5 mmol). The mixture was stirred at room temperature overnight, then filtered through Celite. The filtrate was washed with ethyl acetate, dried (Na₂SO₄), concentrated under reduced pressure and purified by column chromatography on silica by elution with dichloromethane/methanol (98:2). Fractions containing the product were combined and evaporated to give crude product, tert-butyl 3-{6-bromo-[1,2,4]triazolo[4,3-a]pyridin-3-yl}azetidine-1-carboxylate (1.40 g, 75%) as a brown solid. ¹H NMR (400 MHz, Chloroform-d) δ 8.01 (s, 1H), 7.68 (d, 1H), 7.31 (d, 1H), 4.44 (m, 4H), 4.15 (m, 1H), 1.45 (s, 9H).

Step 3

A solution of tert-butyl 3-{6-bromo-[1,2,4]triazolo[4,3-a]pyridin-3-yl}azetidine-1-carboxylate (500 mg, 1.4 mmol) was dissolved in dioxane (10 ml) and treated with 4-fluoro-2-hydroxybenzene boronic acid (357 mg, 2.8 mmol) and tetrakis(triphenylphosphine) palladium(0) (163 mg), followed by a solution of potassium phosphate (751 mg, 3.5 mmol) in water (2 ml). The reaction mixture was heated under reflux overnight, cooled to room temperature and filtered through Celite, washing with ethyl acetate and separated. The organic phase was dried over Na₂SO₄, concentrated under reduced pressure and the crude product purified by flash column chromatography by gradient elution with dichloromethane/methanol (97:3-95:5) to give tert-butyl 3-[6-(4-fluoro-2-hydroxyphenyl)-[1,2,4]triazolo[4,3-a]pyridin-3-yl]azetidine-1-carboxylate (440 mg, 81%). ¹H NMR (400 MHz, Chloroform-d) δ 9.5 (br. s, 1H), 8.11 (s, 1H), 7.71 (d, 1H), 7.52 (d, 1H), 7.25 (m, 1H), 6.84 (m, 1H), 6.69 (m, 1H), 4.43 (m, 4H), 4.21 (m, 1H), 1.44 (s, 9H).

Step 4

A solution of tert-butyl 3-[6-(4-fluoro-2-hydroxyphenyl)-[1,2,4]triazolo[4,3-a]pyridin-3-yl]azetidine-1-carboxylate (250 mg, 0.65 mmol) in dichloromethane (5 ml) was cooled to 0° C. then treated with triethylamine (190 μL, 1.36 mmol) followed by methanesulfonyl chloride (106 μl, 1.36 mmol). The reaction mixture was allowed to warm to room temperature and was stirred for 18 hours before being quenched with sodium bicarbonate solution (2M, 20 ml). Dichloromethane (20 ml) was added and the layers were separated. The organic phase was washed with water and brine then dried (Na₂SO₄) and concentrated under reduced pressure. The crude product was purified by column chromatography by gradient elution with dichloromethane/methanol (99:1-98:2). Fractions containing the product were combined and evaporated to give the product, tert-butyl 3-{6-[4-fluoro-2-(methanesulfonyloxy)phenyl]-[1,2,4]triazolo[4,3-a]pyridin-3-yl}azetidine-1-carboxylate as a solid (260 mg, 86%). ¹H NMR (400 MHz, DMSO-d6) δ 8.45 (s, 1H), 7.85 (d, 1H), 7.72 (m, 1H), 7.53 (dd, 1H), 7.48 (d, 1H) 7.45 (m, 1H), 4.38-4.24 (m, 5H), 3.30 (s, 3H), 2.61-2.58 (m, 2H), 2.30 (m, 1H), 2.05 (m, 1H), 1.39 (s, 9H).

Intermediate 16

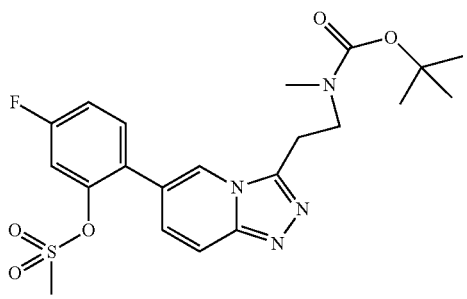 [SMILES: CN(CCc1nnc2ccc(-c3ccc(F)cc3OS(C)(=O)=O)cn12)C(=O)OC(C)(C)C]

tert-butyl N-(2-{6-[4-fluoro-2-(methanesulfonyloxy)
phenyl]-[1,2,4]triazolo[4,3-a]pyridin-3-yl}ethyl)-N-
methylcarbamate Step 1

A solution of 5-bromo-2-hydrazinylpyridine (500 mg, 2.66 mmol) in DCM (10 ml) was treated with hydroxybenztriazole (49 mg, 0.32 mmol) followed by N-Boc-β-alanine (605 mg, 2.98 mmol) and finally EDCl (611 mg, 3.19 mmol) by portionwise addition. The solution was stirred at room temperature overnight, then washed with water and brine, dried ($Na_2SO_4$) and concentrated under reduced pressure. The crude product was purified by column chromatography by gradient elution with dichloromethane/methanol (99:1-97:3). Fractions containing the product were combined and evaporated to give tert-butyl N-{2-[N'-(5-bromo-1,2-dihydropyridin-2-ylidene) hydrazinecarbonyl]ethyl}-N-methylcarbamate as a gum (850 mg; 86%). $^1$H NMR (400 MHz, DMSO-d6) δ 9.84 (s, 1H), 8.54 (s, 1H), 8.11 (s, 1H), 7.66 (d, 1H), 6.52 (d, 1H), 3.37 (t, 2H), 2.77 (s, 3H), 2.39 (t, 2H), 1.40 (s, 9H).

Step 2

Tert-butyl N-{2-[N'-(5-bromo-1,2-dihydropyridin-2-ylidene)hydrazinecarbonyl]ethyl}-N-methylcarbamate (850 mg, 2.28 mmol was dissolved in THF (20 ml) and treated with triphenylphosphine (1.19 g, 4.56 mmol) and triethylamine (1.27 ml, 9.1 mmol), followed by portionwise addition of hexachloroethane (1.08 g, 4.56 mmol). The mixture was stirred at room temperature overnight, then filtered through Celite. The filtrate was washed with ethyl acetate, dried ($Na_2SO_4$), concentrated under reduced pressure and purified by column chromatography on silica by elution with dichloromethane/methanol (97:3). Fractions containing the product were combined and evaporated to give crude product, tert-butyl N-(2-{6-bromo-[1,2,4]triazolo[4,3-a]pyridin-3-yl}ethyl)-N-methylcarbamate (600 mg, 74%) as a solid. $^1$H NMR (400 MHz, DMSO-d6) indicated a mixture of rotamers δ 8.84 (d, 1H), 7.73 (dd, 1H), 7.45 (dd, 1H), 3.58 (t, 2H), 3.16 (t, 2H), 2.80 (s, 3H) 1.16 (d, 9H).

Step 3

A solution of tert-butyl N-(2-{6-bromo-[1,2,4]triazolo[4,3-a]pyridin-3-yl}ethyl)-N-methylcarbamate (300 mg, 0.84 mmol) was dissolved in dioxane (10 ml) and treated with 4-fluoro-2-hydroxybenzene boronic acid (213 mg, 1.7 mmol) and tetrakis(triphenylphosphine) palladium(0) (98 mg), followed by a solution of potassium phosphate (448 mg, 2.1 mmol) in water (2 ml). The reaction mixture was heated under reflux overnight under an argon atmosphere, cooled to room temperature and filtered through Celite, washing with ethyl acetate and separated. The organic phase was dried over $Na_2SO_4$, concentrated under reduced pressure and the crude product purified by flash column chromatography by elution with dichloromethane/methanol (95:5) to give tert-butyl N-{2-[6-(4-fluoro-2-hydroxyphenyl)-[1,2,4]triazolo[4,3-a]pyridin-3-yl]ethyl}-N-methylcarbamate as a brown solid (250 mg, 77%). $^1$H NMR (400 MHz, DMSO-d6) indicates a mixture of rotamers δ 10.39 (s, 1H), 8.44 (s, 1H), 7.74-7.66 (m, 2H), 7.53 (d, 1H), 7.41 (m, 1H), 6.77 (m, 2H), 3.60 (m, 2H), 3.32 (m, 2H), 2.83 (s, 3H), 1.13 (d, 9H).

Step 4

A solution of tert-butyl N-{2-[6-(4-fluoro-2-hydroxyphenyl)-[1,2,4]triazolo[4,3-a]pyridin-3-yl]ethyl}-N-methylcarbamate (250 mg, 0.65 mmol) in dichloromethane (5 ml) was cooled to 0° C. then treated with triethylamine (189 μL, 1.36 mmol) followed by methanesulfonyl chloride (105 μl, 1.36 mmol). The reaction mixture was allowed to warm to room temperature and was stirred for 18 hours before being quenched with sodium bicarbonate solution (2M, 20 ml). Dichloromethane (20 ml) was added and the layers were separated. The organic phase was washed with water and brine then dried ($Na_2SO_4$) and concentrated under reduced pressure. The crude product was purified by column chromatography by gradient elution with dichloromethane/methanol (99:1-98:2). Fractions containing the product were combined and evaporated to give the product, tert-butyl N-(2-{6-[4-fluoro-2-(methanesulfonyloxy)phenyl]-[1,2,4]triazolo[4,3-a]pyridin-3-yl})ethyl)-N-methylcarbamate as a solid (220 mg, 73%). $^1$H NMR (400 MHz, DMSO-d6) indicates a mixture of rotamers δ 8.56 (d, 1H), 7.81 (dd, 1H), 7.69 (dd, 1H), 7.54 (dd, 1H), 7.45 (m, 2H), 3.60 (m, 2H), 3.35 (m, 2H), 3.25 (s, 3H), 2.80 (d, 3H), 1.13 (d, 9H).

Intermediate 17

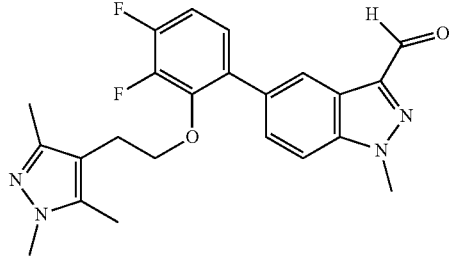 [SMILES: Cc1nn(C)c(C)c1CCOc1c(-c2ccc3c(c2)c(C=O)nn3C)ccc(F)c1F]

5-(3,4-difluoro-2-(2-(1,3,5-trimethyl-1H-pyrazol-4-
yl)ethoxy) phenyl)-1-methyl-1H-indazole-3-carbaldehyde Step 1

A solution of 5-iodo-1-methyl-1H-indazole-3-carbaldehyde (prepared as in intermediate 4, step 2) (1.0 g, 3.5 mmol) was dissolved in dioxane (10 mL) and treated with 3,4-difluoro-2-hydroxybenzene boronic acid (880 mg, 5 mmol) and tetrakis(triphenylphosphine) palladium(0) (30 mg), followed by a solution of potassium phosphate (1.06 g, 5.0 mmol) in water (2 mL).

The reaction mixture was heated under reflux for 1 hr, cooled to room temperature and evaporated under reduced pressure. The residue was partitioned between ethyl acetate/methanol (10:1, 100 mL) and brine (50 mL). The aqueous phase was re-extracted with ethyl acetate/methanol (10:1, 50 mL), and the combined organic extract was dried over $Na_2SO_4$, concentrated under reduced pressure and the crude product triturated from ethyl acetate to give 5-(3, 4-difluoro-2-hydroxyphenyl)-1-methyl-1H-indazole-3-carbaldehyde as an orange solid (483 mg, 48%) mp 216-218° C. $^1$H NMR (400 MHz, DMSO-d6) δ 10.36 (s, 1H), 10.16 (s, 1H), 8.25 (d, J=1.5 Hz, 1H), 7.88 (d, J=8.8 Hz, 1H), 7.69 (dd, J=8.8, 1.6 Hz, 1H), 7.18 (ddd, J=8.6, 6.1, 2.1 Hz, 1H), 7.05-6.91 (m, 1H), 4.25 (s, 3H).

Step 2

A solution of 5-(3,4-difluoro-2-hydroxyphenyl)-1-methyl-1H-indazole-3-carbaldehyde (374 mg; 1.30 mmol) and triphenylphosphine (679 mg; 2.59 mmol) in THF (7 mL) was treated with a solution of 2-(1,3,5-trimethyl-1H-pyrazol-4-yl)ethanol (399 mg, 2.59 mmol) in THF (5 mL). The reaction mixture was cooled to 0° C. before being treated with di-isopropyl azodicarboxylate (510 µl, 2.59 mmol). The reaction mixture was allowed to warm to room temperature, stirred overnight and concentrated under reduced pressure. The crude product was purified by column chromatography by gradient elution with hexane/IPA (80:20 to 70:30) to give the title compound as a colourless solid (320 mg, 58%) mp 173-174° C. $^1$H NMR (400 MHz, Chloroform-d) δ 10.25 (s, 1H), 8.35 (d, J=1.6 Hz, 1H), 7.59 (dd, J=8.8, 1.5 Hz, 1H), 7.46 (d, J=8.6 Hz, 1H), 7.12 (ddd, J=8.3, 5.9, 2.2 Hz, 1H), 6.99 (td, J=9.1, 7.2 Hz, 1H), 4.26 (s, 3H), 3.80 (t, J=7.5 Hz, 2H), 3.60 (s, 3H), 2.60 (t, J=7.5 Hz, 2H), 1.96 (s, 3H), 1.94 (s, 3H).

Intermediate 18

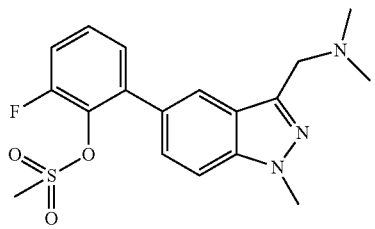 [SMILES: CN(C)Cc1nn(C)c2ccc(-c3cccc(F)c3OS(C)(=O)=O)cc12]

2-(3-((dimethylamino)methyl)-1-methyl-1H-indazol-5-yl)-6-fluorophenyl methanesulfonate Step 1

To a solution of 5-iodo-1-methyl-1H-indazole-3-carbaldehyde (prepared as in intermediate 4, step 2) (1.0 g, 3.5 mmol) (1.00 g, 3.50 mmol) in 1,4-dioxane (10 mL) was added 3-fluoro-2-hydroxyphenyl boronic acid (1.00 g, 6.41 mmol), tetrakis(triphenylphosphine)palladium(0) (30 mg, 0.026 mmol) and an aqueous solution (3 mL) of potassium phosphate (1.72 g, 8.75 mmol). The yellowish orange solution was refluxed at 107° C. for 2.5 hr to give a reddish brown mixture which was then concentrated under reduced pressure. EtOAc (40 mL) and saturated aqueous sodium carbonate solution (2×20 mL) was added to extract the product and the organic layer was dried over Na$_2$SO$_4$, concentrated in vacuo to give an orange powder. The crude product was purified by flash column chromatography by elution with 5% EtOAc in DCM to give 5-(3-fluoro-2-hydroxyphenyl)-1-methyl-1H-indazole-3-carbaldehyde as a fluffy white solid (461 mg, 49%). m.p. 211-212° C.; $^1$H NMR (DMSO-d$_6$, 400 MHz, 300 K) δ 10.16 (1H, s), 9.72 (1H, d, J=1.6 Hz), 8.29 (1H, dd, J=1.7, 0.8 Hz), 7.87 (1H, dd, J=8.8, 0.9 Hz), 7.72 (1H, dd, J=8.8, 1.6 Hz), 7.23-7.16 (2H, m), 6.93 (1H, td, J=8.0, 5.2 Hz), 4.25 (3H, s).

Step 2

To a pale yellow solution of 5-(3-fluoro-2-hydroxyphenyl)-1-methyl-1H-indazole-3-carbaldehyde (461 mg, 1.71 mmol) in anhydrous THF (10 mL) at 0° C. was added triethylamine (0.48 mL, 3.4 mmol), methanesulfonyl chloride (0.26 mL, 3.4 mmol). The resulting cloudy white mixture was stirred for 18 hr to give a pale yellow mixture. Saturated aqueous sodium bicarbonate solution (10 mL) was added to quench the reaction. EtOAc (2×30 mL) was added to extract the product. The combined organic layers were dried over Na$_2$SO$_4$, concentrated in vacuo to give 2-fluoro-6-(3-formyl-1-methyl-1H-indazol-5-yl)phenyl methanesulfonate as a pale yellow solid (584 mg, 98%). $^1$H NMR (CDCl$_3$, 400 MHz, 300 K) δ 10.23 (1H, s), 8.43 (1H, s), 7.70 (1H, dd, J=8.7, 1.6 Hz), 7.57 (1H, dd, J=8.8, 0.9 Hz), 7.39-7.22 (3H, m), 4.23 (3H, s), 2.88 (3H, s).

Step 3

To 2-fluoro-6-(3-formyl-1-methyl-1H-indazol-5-yl)phenyl methanesulfonate (584 mg, 1.68 mmol) in 1,2-dichloroethane (DCE) was added dimethylamine (2M in THF, 2.6 mL, 5.1 mmol) and glacial acetic acid (0.59 mL, 10 mmol) to give a yellow mixture which was stirred at room temperature for 10 min. Sodium triacetoxyborohydride (95%, 1.14 g, 5.1 mmol) was then added and the yellow mixture was stirred at room temperature for 16 hr. Sodium carbonate solution (2M, 40 mL) was added to quench the reaction. DCM (2×25 mL) was added to extract the product and the combined organic layer was dried over Na$_2$SO$_4$, concentrated in vacuo to give a yellow oil. The crude product was purified by flash column chromatography by elution with 5% diethylamine in EtOAc to give 2-(3-((dimethylamino)methyl)-1-methyl-1H-indazol-5-yl)-6-fluorophenyl methanesulfonate as a viscous yellow oil (542 mg, 86%). $^1$H NMR (CDCl$_3$, 400 MHz, 300 K) δ 7.98 (1H, dd, J=1.6, 0.8 Hz), 7.55 (1H, dd, J=8.7, 1.6 Hz), 7.44 (1H, dd, J=8.7, 0.7 Hz), 7.37-7.19 (3H, m), 4.07 (3H, s), 3.82 (2H, s), 2.73 (3H, s), 2.31 (6H, s).

Intermediate 19

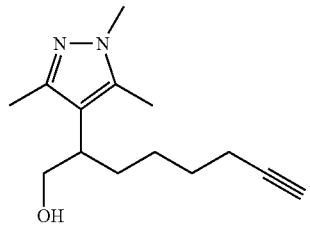 [SMILES: C#CCCCCC(CO)c1c(C)nn(C)c1C]

2-(1,3,5-trimethyl-1H-pyrazol-4-yl)oct-7-yn-1-ol

Step 1

To sodium hydride (60% in mineral oil, 1.69 g, 42.3 mmol) in anhydrous tetrahydrofuran (THF) (120 mL) at 0° C. was added acetylacetone (4.1 mL, 40 mmol) to give a cloudy white mixture which was stirred for 1 hr. Ethyl bromoacetate (5.3 mL, 48 mmol) was then added and the mixture was stirred for 18 hr. The cloudy yellow reaction mixture was washed with saturated aqueous ammonium chloride solution (100 mL). The aqueous layer was back extracted with ethyl acetate (2×100 mL). The combined organic layers were washed with brine (100 mL), dried over magnesium sulfate (MgSO$_4$) and concentrated in vacuo to give Ethyl 3-acetyl-4-oxopentanoate as a yellow oil (7.18 g, 96%). Diketone $^1$H NMR (CDCl$_3$, 400 MHz, 300 K) δ 4.18-4.01 (3H, m), 2.80 (2H, d, J=7.3 Hz), 2.19 (6H, s), 1.24-1.15 (3H, m); Enol $\delta_H$/ppm $^1$H NMR (CDCl$_3$, 400 MHz, 300 K) δ 4.18-4.01 (2H, m), 3.18 (2H), 2.08 (6H, s), 1.24-1.15 (3H, m).

Step 2

Methylhydrazine (2.6 mL, 42 mmol) was added dropwise to Ethyl 3-acetyl-4-oxopentanoate (7.18 g, 38.6 mmol) in acetic acid (60 mL) at 0° C. and the yellow solution was stirred at room temperature for 20 hr. The majority of acetic acid was removed in vacuo and the residue was neutralised by saturated aqueous sodium carbonate solution (100 mL). Ethyl acetate (100 mL) was added to extract the product and the yellow organic layer was washed with brine (100 mL), dried over MgSO$_4$ and concentrated in vacuo. The crude product was purified by flash column chromatography by elution with 2% methanol in dichloromethane to give the Ethyl 2-(1,3,5-trimethyl-1H-pyrazol-4-yl)acetate as a yellow oil (3.99 g, 53%). $^1$H NMR (CDCl$_3$, 400 MHz, 300 K) δ 4.06 (3H, q, J=7.1 Hz), 3.65 (3H, s), 3.27 (2H, s), 2.13 (6H, s), 1.19 (3H, t).

Step 3

To a solution of diisopropylamine (0.86 mL, 6.1 mmol) in anhydrous THF (10 mL) at 0° C. was added n-butyllithium (2.5M in hexane) under nitrogen to give a light yellow solution which was stirred at room temperature for 10 min. Ethyl 2-(1,3,5-trimethyl-1H-pyrazol-4-yl)acetate (1.00 g, 5.10 mmol) was added at −78° C. and the yellowish orange mixture was stirred at −78° C. for 1 hr. 6-iodo-1-hexyne (0.78 mL, 5.9 mmol) was added to give orange mixture which was stirred at −78° C. for another 1 hr before the addition of 1,3-Dimethyl-3,4,5,6-tetrahydro-2(1H)-pyrimidinone (DMPU). The mixture was slowly warmed to 0° C. in 1 hr and water (5 mL) was added to quench the reaction. Ethyl acetate (3×200 mL) was used to extract the product and the organic layer was washed with saturated aqueous ammonium chloride solution (20 mL), hydrochloric acid (1M, 20 mL), saturated aqueous sodium carbonate solution (20 mL), brine (20 mL), dried over MgSO$_4$ and concentrated in vacuo to give an orange liquid. The crude product was purified by flash column chromatography by elution with 50% ethyl acetate in hexane to give Ethyl 2-(1,3,5-trimethyl-1H-pyrazol-4-yl)oct-7-ynoate as a pale yellow oil (233 mg, 17%). ESI HRMS, found 277.1919 (C$_{16}$H$_{25}$N$_2$O$_2$), MH$^+$, requires 277.1916. $^1$H NMR (CDCl$_3$, 400 MHz, 300 K) δ 4.12-4.01 (2H, m), 3.66 (3H, s), 3.37 (1H, dd, J=8.4, 7.1 Hz), 2.17 (6H, d, J=3.8 Hz), 2.13 (2H, td, J=7.1, 2.5 Hz), 2.07-1.97 (1H, m), 1.89 (1H, t, J=2.6 Hz), 1.73-1.64 (1H, m), 1.54-1.46 (2H, m), 1.35-1.27 (2H, m), 1.18 (3H, t, J=7.1 Hz, H$_k$).

Step 4

Lithium aluminium hydride (2M in THF, 0.46 mL, 0.93 mmol) was added to Ethyl 2-(1,3,5-trimethyl-1H-pyrazol-4-yl)oct-7-ynoate (233 mg, 0.843 mmol) in anhydrous THF (10 mL) at 0° C. under nitrogen to give a colourless solution which was stirred at room temperature for 45 min. Water (50 μL), 15% sodium hydroxide (50 μL), followed by water (150 μL) were added at 0° C. to give a cloudy white mixture which was stirred at room temperature for 20 min. MgSO$_4$ was added and the mixture was stirred for another 20 min. The mixture was filtered and the filtrate was concentrated in vacuo to give 2-(1,3,5-trimethyl-1H-pyrazol-4-yl)oct-7-yn-1-ol as a pale yellow oil (197 mg, ~100%). ESI HRMS, found 235.1817 (C$_{14}$H$_{23}$N$_2$O), MH$^+$, requires 235.1810. $^1$H NMR (CDCl$_3$, 400 MHz, 300 K) δ 3.76-3.61 (2H, m), 3.69 (3H, s), 2.76-2.68 (1H, m), 2.18 (6H, d, J=6.6 Hz), 2.14 (2H, ddd, J=9.7, 4.9, 2.4 Hz), 1.91 (1H, t, J=2.7 Hz), 1.70-1.51 (2H, m), 1.52-1.43 (2H, m), 1.35-1.27 (2H, m).

Intermediate 20

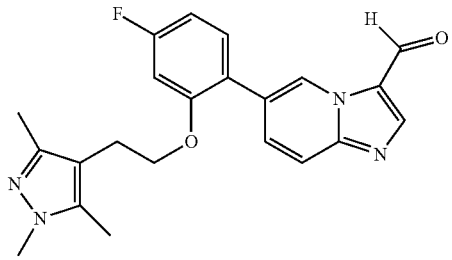 [SMILES: Cc1nn(C)c(C)c1CCOc1cc(F)ccc1-c1ccc2ncc(C=O)n2c1]

6-{4-fluoro-2-[2-(1,3,5-trimethyl-1H-pyrazol-4-yl)ethoxy]phenyl}imidazo[1,2-a]pyridine-3-carbaldehyde Step 1

A solution of 6-bromoimidazo[1,2-a]pyridine-3-carbaldehyde (250 mg, 1.1 mmol) was dissolved in dioxane (15 mL) and treated with 4-fluoro-2-hydroxybenzene boronic acid (280 mg, 2.2 mmol) and tetrakis(triphenylphosphine) palladium(0) (128 mg), followed by a solution of potassium phosphate (590 mg, 2.7 mmol) in water (2 mL). The reaction mixture was purged with argon then heated to 100° C. overnight, cooled to room temperature and evaporated filtered through a bed of Celite and washed with ethylacetate. The ethylacetate layer taken dried over Na$_2$SO$_4$, and evaporated under reduced pressure. The crude product was purified by column chromatography eluting with 2-3% MeOH in DCM to give 6-(4-fluoro-2-hydroxyphenyl)imidazo[1,2-a]pyridine-3-carbaldehyde (251 mg, 88%). $^1$H NMR (400 MHz, DMSO-d$_6$) δ 10.52 (s, 1H), 9.95 (s, 1H), 9.62 (s, 1H), 8.55 (s, 1H), 7.89 (d, 2H), 7.47 (td, 1H), 7.45 (m, 2H).

Step 2

A solution of 6-(4-fluoro-2-hydroxyphenyl)imidazo[1,2-a]pyridine-3-carbaldehyde (710 mg, 2.8 mmol) in dichloromethane (25 ml) was cooled to 0° C. then treated with triethylamine (811 μL, 5.8 mmol) followed by methanesulfonyl chloride (450 μL, 5.8 mmol). The reaction mixture was allowed to warm to room temperature and was stirred for 18 hours before being quenched with sodium bicarbonate solution (2M, 20 ml). Dichloromethane (20 ml) was added and the layers were separated. The organic phase was washed with water and brine then dried (Na$_2$SO$_4$) and concentrated under reduced pressure to give the product 5-fluoro-2-{3-formylimidazo[1,2-a]pyridin-6-yl}phenyl methanesulfonate (650 mg, 70%). $^1$H NMR (400 MHz, DMSO-d$_6$) δ 9.98 (s, 1H), 9.49 (s, 1H), 8.60 (s, 1H), 7.98 (d, 1H), 7.80 (d, 1H), 7.78 (td, 1H), 7.60 (dd, 1H), 7.45 (td, 1H), 2.50 (s, 3H).

Step 3

According to the general method for mesyl transfer (Method B), 5-fluoro-2-{3-formylimidazo[1,2-a]pyridin-6-yl}phenyl methanesulfonate (650 mg, 1.9 mmol) was reacted with 4-(2-hydroxyethyl)-N,N,1,5-tetramethyl-1H-pyrazole-3-carboxamide (539 mg, 3.5 mmol) and cesium carbonate (823 mg, 2.5 mmol) in DMF (18.0 mL) at 110° C. for 12 hr. The reaction mixture was extracted with EtOAc and washed with water and brine. The combined organic parts were evaporated under reduced pressure to get the title intermediate. (200 mg, 26%). $^1$H NMR (400 MHz, DMSO-d$_6$) δ 9.96 (s, 1H), 9.56 (s, 1H), 8.57 (s, 1H), 7.90 (d, 1H), 7.76 (d, 1H), 7.49 (td, 1H), 7.09 (dd, 1H), 6.91 (td, 1H), 4.05 (t, 2H), 3.50 (s, 3H), 2.70 (t, 2H), 2.10 (s, 3H), 2.04 (s, 3H).

Intermediate 21
tert-butyl N-[2-(5-{4-fluoro-2-[2-(1,3,5-trimethyl-1H-pyrazol-4-yl)ethoxy]phenyl}-2H-indazol-3-yl)ethyl]carbamate
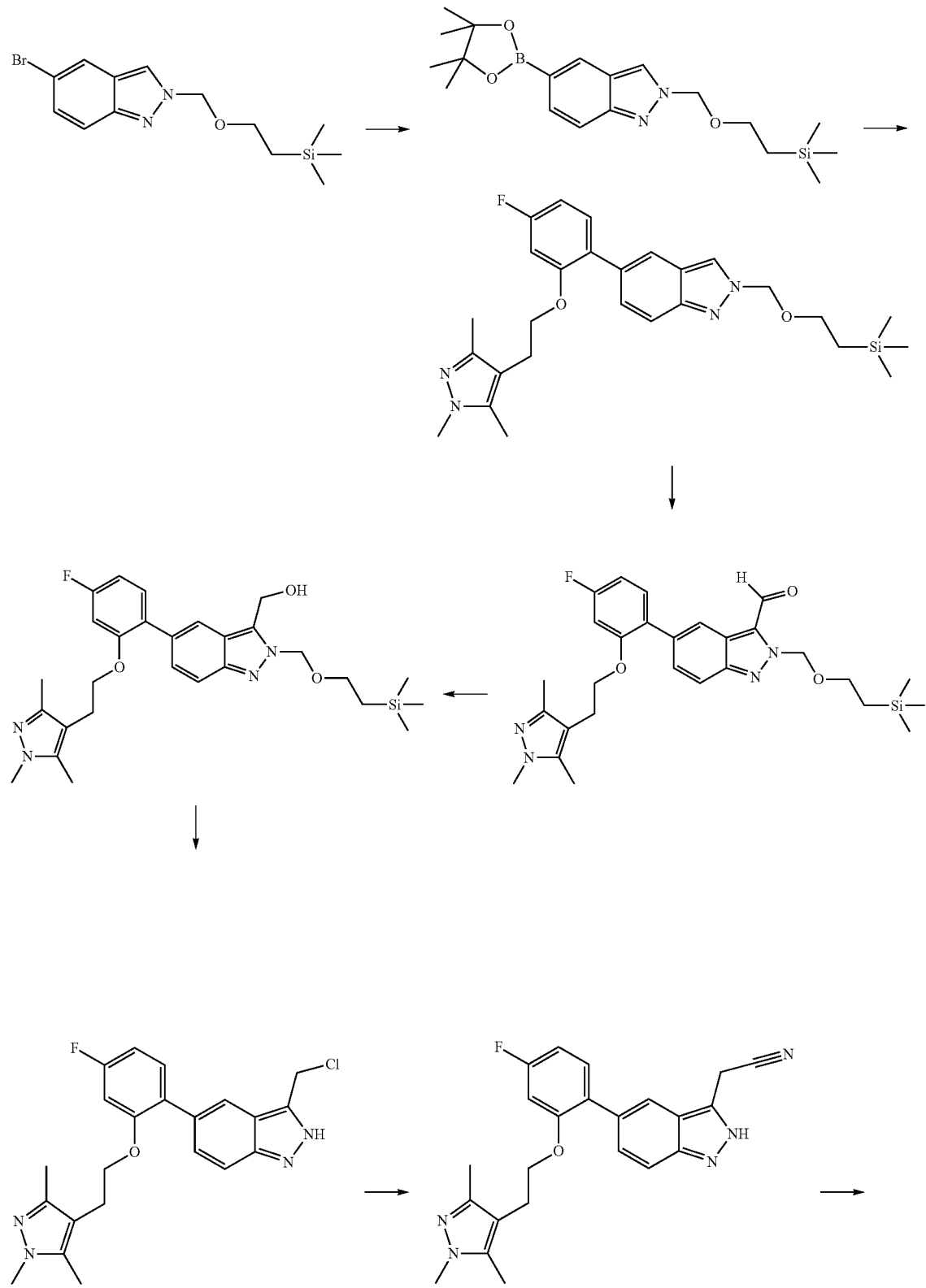

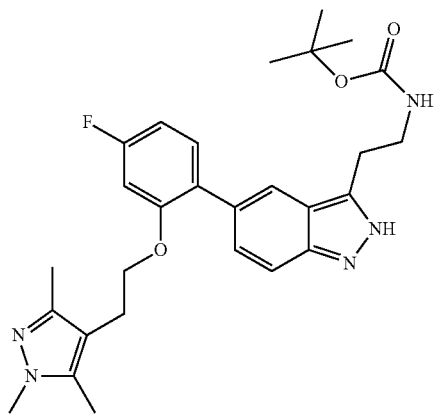

Step 1

A solution of 5-bromo-2-{[2-(trimethylsilyl)ethoxy]methyl}-2H-indazole (1.5 g, 4.6 mmol) was dissolved in dioxane (40 mL) and treated with bis(pinacolato)diboron (1.75 g, 6.9 mmol), potassium acetate (1.35 g, 13.5 mmol) and Pd(dppf)Cl$_2$.DCM (374 mg). The reaction mixture was purged with argon then heated to 100° C. overnight, cooled to room temperature and evaporated filtered through a bed of Celite and washed with ethyl acetate. The ethyl acetate layer was dried over Na$_2$SO$_4$, and evaporated under reduced pressure to give 5-(4,4,5,5-tetramethyl-1,3,2-dioxaborolan-2-yl)-2-{[2-(trimethylsilyl)ethoxy]methyl}-2H-indazole. (1.7 g, 99%). $^1$H NMR (400 MHz, DMSO-d$_6$) δ 8.58 (s, 1H), 8.19 (s, 1H), 7.59 (d, 1H), 7.47 (d, 1H), 5.73 (s, 2H), 3.60 (t, 2H), 1.30 (s, 12H), 0.85 (t, 2H), −0.07 (s, 9H).

Step 2

A solution of 5-(4,4,5,5-tetramethyl-1,3,2-dioxaborolan-2-yl)-2-{[2-(trimethylsilyl)ethoxy]methyl}-2H-indazole (1.0 g, 2.67 mmol) and 4-[2-(2-bromo-5-fluorophenoxy)ethyl]-1,3,5-trimethyl-1H-pyrazole (0.87 g, 2.67 mmol) in dioxane (20 mL) was treated with potassium carbonate (1.1 g, 8.0 mmol) dissolved in water (5 mL. The mixture was degassed with argon for 15 min before addition of Pd(dppf)Cl$_2$.DCM (218 mg) The reaction mixture was heated at 100° C. for 16 hr, cooled to RT, filtered through Celite and the filtrate was diluted with EtOAc. The organic layer was washed with water, brine, dried over Na$_2$SO$_4$ and concentrated under reduced pressure. The crude product was purified by Combiflash (40 g silica column, 50% EtOAc-Hexane) to afford the product 5-{4-fluoro-2-[2-(1,3,5-trimethyl-1H-pyrazol-4-yl)ethoxy]phenyl}-2-{[2-(trimethylsilyl)ethoxy]methyl}-2H-indazole (750 mg, 57%). $^1$H NMR (400 MHz, DMSO-d$_6$) δ 8.51 (s, 1H), 7.68 (s, 1H), 7.60 (d, 1H), 7.34-7.27 (m, 2H), 6.99 (dd, 1H), 6.83 (td, 1H), 5.76 (s, 2H), 4.00 (t, 2H), 3.61 (t, 2H), 3.52 (s, 3H), 2.66 (t, 2H), 1.88 (s, 6H), 0.87 (t, 2H), −0.04 (s, 9H).

Step 3

A stirred solution of 5-{4-fluoro-2-[2-(1,3,5-trimethyl-1H-pyrazol-4-yl)ethoxy]phenyl}-2-{[2-(trimethylsilyl)ethoxy]methyl}-2H-indazole (750 mg, 1.5 mmol) in THF (14 mL) was treated with n-BuLi solution (2.4M in hexane, 1.26 mL, 3 mmol) dropwise at −78° C. The reaction mixture was stirred at −78° C. for 30 min. Then DMF (0.468 mL, 6.0 mmol) was added at −78° C. The reaction mixture was allowed to warm up to 0° C. and stirred for 2 hr. The reaction mixture was quenched with NH$_4$Cl solution and extracted with EtOAc. The organic layer was washed with brine, dried over Na$_2$SO$_4$ and concentrated under reduced pressure to give 5-{4-fluoro-2-[2-(1,3,5-trimethyl-1H-pyrazol-4-yl)ethoxy]phenyl}-2-{[2-(trimethylsilyl)ethoxy]methyl}-2H-indazole-3-carbaldehyde (750 mg, 95%). $^1$H NMR (400 MHz, DMSO-d$_6$) δ 10.40 (s, 1H), 8.17 (s, 1H), 7.86 (d, 1H), 7.48 (d, 1H), 7.40 (dd, 2H), 7.04 (dd, 1H), 6.86 (td, 1H), 6.16 (s, 2H), 4.02 (t, 2H), 3.63 (t, 2H), 3.60 (s, 3H), 2.66 (t, 2H), 1.98 (s, 3H), 1.84 (s, 3H), 0:85 (t, 2H), −0.07 (s, 9H).

Step 4

A solution of 5-{4-fluoro-2-[2-(1,3,5-trimethyl-1H-pyrazol-4-yl)ethoxy]phenyl}-2-{[2-(trimethylsilyl)ethoxy]methyl}-2H-indazole-3-carbaldehyde (750 mg, 1.43 mmol) in methanol (11 mL) was treated with sodium borohydride (109 mg, 2.9 mmol) at 0° C. and stirred at 0° C. for 1.5 h. The reaction mixture was quenched with NaHCO$_3$ solution and extracted with DCM. The organic layer was dried over Na$_2$SO$_4$ and concentrated under reduced pressure to give 5-{4-fluoro-2-[2-(1,3,5-trimethyl-1H-pyrazol-4-yl)ethoxy]phenyl}-2-{[2-(trimethylsilyl)-ethoxy]methyl}-2H-indazol-3-yl)methanol (750 mg, 99%). $^1$H NMR (400 MHz, DMSO-d$_6$) δ 7.73 (s, 1H), 7.56 (d, 1H), 7.30-7.26 (m, 2H), 6.98 (dd, 1H), 6.84 (td, 1H), 5.80 (s, 2H), 5.55 (t, 1H), 4.95 (d, 2H), 4.02 (t, 2H), 3.59 (t, 2H), 3.51 (s, 3H), 2.66 (t, 2H), 1.96 (s, 3H), 1.89 (s, 3H), 0.86 (t, 2H), −0.06 (s, 9H).

Step 5

A solution of 5-{4-fluoro-2-[2-(1,3,5-trimethyl-1H-pyrazol-4-yl)ethoxy]phenyl}-2-{[2-(trimethylsilyl)-ethoxy]methyl}-2H-indazol-3-yl)methanol (50 mg, 0.095 mmol) in thionyl chloride (2 mL) was heated to 80° C. for 3 h. The reaction was concentrated under reduced pressure. The crude product was neutralized with NaHCO$_3$ solution and extracted with EtOAc. The organic layer was dried over Na$_2$SO$_4$ and concentrated under reduced pressure to give 3-(chloromethyl)-5-{4-fluoro-2-[2-(1,3,5-trimethyl-1H-pyrazol-4-yl)ethoxy]phenyl}-2H-indazole (39 mg, 99%). $^1$H NMR (400 MHz, DMSO-d$_6$) δ 7.87 (s, 1H), 7.72 (d, 1H), 7.48 (d, 1H), 7.33 (d, 1H), 7.00 (dd, 1H), 6.87 (td, 1H), 5.73 (s, 2H), 5.15 (s, 2H), 4.01 (t, 2H), 3.57 (s, 3H), 2.67 (t, 2H), 1.92 (s, 3H), 1.87 (s, 3H).

Step 6

A solution of 3-(chloromethyl)-5-{4-fluoro-2-[2-(1,3,5-trimethyl-1H-pyrazol-4-yl)ethoxy]phenyl}-2H-indazole (354 mg, 0.86 mmol) in DMF (5 mL) was treated with sodium cyanide (126 mg, 2.6 mmol) and the reaction mixture was heated to 100° C. for 3 h. The reaction mixture was cooled to rt, diluted with EtOAc and washed with water. The organic layer was dried over Na$_2$SO$_4$ and concentrated under reduced pressure. The crude product was purified through column chromatography on silica by elution with MeOH-DCM (4:96) to afford a fraction containing 2-(5-{4-fluoro-2-[2-(1,3,5-trimethyl-1H-pyrazol-4-yl)ethoxy]phenyl}-2H-indazol-3-yl)acetonitrile, which was taken onto the next step without purification.

Step 7

A solution of 2-(5-{4-fluoro-2-[2-(1,3,5-trimethyl-1H-pyrazol-4-yl)ethoxy]phenyl}-2H-indazol-3-yl)acetonitrile (100 mg, 0.25 mmol) in methanol (2.5 mL) was treated with Boc$_2$O (0.114 mL, 0.50 mmol) and NiCl$_2$.6H$_2$O (5.9 mg, 0.025 mmol) followed by portionwise addition of NaBH$_4$ (65 mg, 1.73 mmol) at 0° C. The reaction mixture was allowed to stirred at RT for 16 h. The reaction mixture was quenched with NaHCO$_3$ solution and extracted with DCM. The organic layer was dried over Na$_2$SO$_4$ and concentrated under reduced pressure. The crude was purified over prep TLC (3% MeOH in DCM) to give tert-butyl N-[2-(5-{4-fluoro-2-[2-(1,3,5-trimethyl-1H-pyrazol-4-yl)ethoxy]phenyl}-2H-indazol-3-yl)ethyl]carbamate (27 mg, 21%). LC-MS rt 3.33 min, MH$^+$ 508.

Intermediate 22 tert-butyl N-[(tert-butoxy)carbonyl]-N-{2-[6-(4-fluoro-2-hydroxyphenyl)imidazo[1,2-a]pyridin-3-yl]ethyl}carbamate

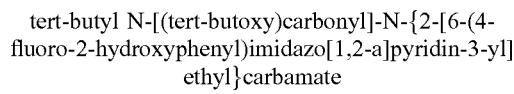

Step 1

A solution of 2-{6-bromoimidazo[1,2-a]pyridin-3-yl}ethylamine (1.4 g, 5.8 mmol) in DCM (20 ml) was cooled at 0° C. and treated with triethylamine (2.4 mL, 17.5 mmol) and (Boc)$_2$O (3.35 mL, 14.6 mmol). The reaction mixture was stirred at rt for 16 hr, diluted with DCM, and washed with sat. NaHCO$_3$, water and brine, dried over sodium sulphate and evaporated under reduced pressure. The crude product was separated by column chromatography on silica eluting with 4% MeOH in DCM to give tert-butyl N-(2-{6-bromoimidazo[1,2-a]pyridin-3-yl}ethyl)carbamate (1.0 g, 50%)$^1$H NMR (400 MHz, DMSO-d$_6$) δ 8.64 (s, 1H), 7.51 (d, 1H), 7.41 (s, 1H), 7.30 (d, 1H), 6.95 (t, 1H), 3.26 (t, 2H), 3.00 (t, 2H), 1.43 (s, 9H) and tert-butyl N-[(tert-butoxy)carbonyl]-N-{2-[6-bromo-imidazo[1,2-a]pyridin-3-yl]ethyl}carbamate (900 mg, 35%). $^1$H NMR (400 MHz, DMSO-d$_6$) 6.8.63 (s, 1H), 7.53 (d, 1H), 7.35-7.30 (m, 2H), 3.78 (t, 2H), 3.18 (t, 2H), 1.31 (s, 18H).

Step 2

A solution of tert-butyl N-[(tert-butoxy)carbonyl]-N-{2-[6-bromo-imidazo[1,2-a]pyridin-3-yl]ethyl}carbamate (900 mg, 2.0 mmol) was dissolved in dioxane (20 mL) and treated with 4-fluoro-2-hydroxybenzene boronic acid (637 mg, 4.1 mmol) followed by a solution of potassium phosphate (1.08 g, 5.1 mmol) in water (5 mL). The reaction mixture was purged with argon before addition of tetrakis(triphenylphosphine) palladium(0) (236 mg) and the mixture was then heated to 100° C. for 16 hr, cooled to room temperature and filtered through a bed of Celite and washed with ethyl acetate. The ethyl acetate layer taken dried over Na$_2$SO$_4$, and evaporated under reduced pressure. The crude product was purified by column chromatography eluting with 5% MeOH in DCM to give tert-butyl N-[(tert-butoxy)carbonyl]-N-{2-[6-(4-fluoro-2-hydroxyphenyl)imidazo[1,2-a]pyridin-3-yl]ethyl}carbamate (250 mg, 26%). $^1$H NMR (400 MHz, DMSO-d$_6$) δ 10.27 (s, 1H), 8.35 (s, 1H), 7.65 (d, 1H), 7.53 (d, 1H), 7.41-7.30 (m, 2H), 6.75 (td, 1H), 3.80 (t, 2H), 3.25 (t, 3H), 1.28 (s, 18H).

Intermediate 23 tert-butyl N-(2-{6-[4-fluoro-2-(methanesulfonyloxy)phenyl]imidazo[1,2-a]pyridin-3-yl}ethyl)carbamate

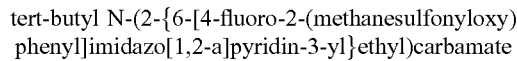

Step 1

A solution of 2-{6-bromoimidazo[1,2-a]pyridin-3-yl}ethylamine (350 mg, 1.46 mmol) in DCM (10 ml) was cooled at 0° C. and treated with triethylamine (0.61 mL, 4.4 mmol) and (Boc)$_2$O (0.84 mL, 3.6 mmol). The reaction mixture was stirred at rt for 16 hr, diluted with DCM, and washed with sat. NaHCO$_3$, water and brine, dried over sodium sulphate and in 100-200 silica eluting with 4% MeOH in DCM to give tert-butyl N-(2-{6-bromoimidazo[1,2-a]pyridin-3-yl}ethyl)carbamate (490 mg, 99%). $^1$H NMR (400 MHz, DMSO-d$_6$) δ 8.64 (s, 1H), 7.51 (d, 1H), 7.41 (s, 1H), 7.30 (d, 1H), 6.95 (t, 1H), 3.26 (t, 2H), 3.00 (t, 2H), 1.43 (s, 9H).

Step 2

A solution of tert-butyl N-(2-{6-bromoimidazo[1,2-a]pyridin-3-yl}ethyl)carbamate (1.4 g, 4.2 mmol) was dissolved in dioxane/water (5:1, 15 mL) and treated with 4-fluoro-2-hydroxybenzene boronic acid (1.3 g, 8.2 mmol) and tetrakis(triphenylphosphine) palladium(0) (476 mg, 0.4 mmol), followed by a solution of potassium phosphate (2.1 g, 10.3 mmol) in water (2 mL). The reaction mixture was purged with argon then heated to 100° C. for 16 hr, cooled to room temperature and filtered through a bed of Celite and washed with ethyl acetate. The ethyl acetate layer taken dried over Na$_2$SO$_4$, and evaporated under reduced pressure. The crude product was purified by column chromatography eluting with 5% MeOH in DCM to give tert-butyl N-{2-[6-(4-fluoro-2-hydroxyphenyl)imidazo[1,2-a]pyridin-3-yl]ethyl}carbamate (250 mg, 57%), which was taken onto the next step without further purification.

Step 3

A solution of tert-butyl N-{2-[6-(4-fluoro-2-hydroxyphenyl)imidazo[1,2-a]pyridin-3-yl]ethyl}carbamate (250 mg, 0.67 mmol) in dichloromethane (10 mL) was cooled to 0° C. then treated with triethylamine (235 µL, 1.7 mmol) followed by methanesulfonyl chloride (63 µL, 0.68 mmol). The reaction mixture was allowed to warm to room temperature and was stirred for 4 hr. The reaction mixture was then diluted with DCM, and washed with sat. NaHCO$_3$, water and brine, dried over Na$_2$SO$_4$ and concentrated under reduced pressure. The crude was then purified by column chromatography eluting with 3% MeOH in DCM to give tert-butyl N-(2-{6-[4-fluoro-2-(methanesulfonyloxy)phenyl]imidazo[1,2-a]pyridin-3-yl}ethyl)carbamate (170 mg, 56%). $^1$H NMR (400 MHz, DMSO-d$_6$) δ 8.44 (s, 1H), 7.72 (td, 1H), 7.61 (d, 1H), 7.51 (dd, 1H), 7.45-7.39 (m, 2H), 7.32 (d, 1H), 6.97 (td, 1H), 4.10 (t, 1H), 3.30-3.20 (m, 5H), 3.03 (t, 2H), 1.30 (s, 9H).

Intermediate 24 tert-butyl N-{([6-(4-fluoro-2-hydroxyphenyl)imidazo[1,2-a]pyridin-3-yl]methyl}-N-methylcarbamate

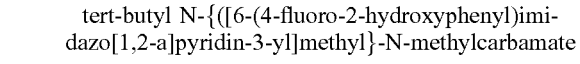

Step 1

A solution of 2-{6-bromoimidazo[1,2-a]pyridin-3-yl}-N-methyl-methylamine (1.4 g, 5.8 mmol) in DCM (20 ml) was cooled at 0° C. and treated with triethylamine (1.62 mL, 8.8 mmol) and (Boc)$_2$O (2.0 mL, 8.8 mmol). The reaction mixture was stirred at rt for 16 hr, diluted with DCM, and washed with sat. NaHCO$_3$, water and brine, dried over sodium sulphate and evaporated under reduced pressure. The crude product was purified by column chromatography on silica eluting with 3% MeOH in DCM to give tert-butyl N-({6-bromoimidazo[1,2-a]pyridin-3-yl}methyl)-N-methylcarbamate (1.30 g, 65%). $^1$H NMR (400 MHz, DMSO-d$_6$) δ 8.70 (br.s, 1H), 7.62 (s, 1H), 7.59 (d, 1H), 7.38 (d, 1H), 4.77 (s, 2H), 2.67 (s, 3H), 1.41 (s, 9H).
Step 2

A solution of tert-butyl N-({6-bromoimidazo[1,2-a]pyridin-3-yl}methyl)-N-methylcarbamate (1.1 g, 3.2 mmol) was dissolved in dioxane (8 mL) and treated with 4-fluoro-2-hydroxybenzene boronic acid (1.0 g, 6.5 mmol) and potassium phosphate (1.7 g, 3.3 mmol) in water (2 mL). The reaction mixture was purged with argon for 5 min, before addition of tetrakis (triphenylphosphine) palladium(0) (374 mg). The reaction mixture was heated to 100° C. under nitrogen overnight, cooled to room temperature and filtered through a bed of Celite, which was washed with ethyl acetate. The ethyl acetate layer was dried over Na$_2$SO$_4$, and evaporated under reduced pressure. The crude product was purified by column chromatography eluting with 5% MeOH in DCM to give tert-butyl N-{[6-(4-fluoro-2-hydroxyphenyl)imidazo[1,2-a]pyridin-3-yl]methyl}-N-methylcarbamate (1.0 g, 83%). $^1$H NMR (400 MHz, CDCl$_3$) δ 8.50 (s, 1H), 7.59 (d, 1H), 7.55 (s, 1H), 7.37 (d, 1H), 7.20 (td, 1H), 6.73 (dd, 1H), 6.67 (td, 1H), 4.74 (s, 2H), 2.73 (s, 3H), 1.42 (s, 9H).

Intermediate 25 tert-butyl N-{[6-(4-fluoro-2-hydroxyphenyl)imidazo [1,2-a]pyridin-3-yl]ethyl}-N-methylcarbamate Step 1

A solution of tert-butyl (2-(6-bromoimidazo[1,2-a]pyridin-3-yl)ethyl)carbamate (1.4 g, 4.1 mmol) in THF (15 mL) was cooled at 0° C. and treated with sodium hydride (50% dispersion, 119 mg, 4.9 mmol. The reaction mixture was stirred at 0° C. for 30 min before dropwise addition of iodomethane (0.31 mL, 4.9 mmol). The reaction mixture was warmed to rt and stirred for a further 16 hr, then diluted with ethyl acetate, washed with water and brine, dried over sodium sulphate and concentrated under reduced pressure. The crude product was purified by column chromatography on silica eluting with 3% MeOH in DCM to give tert-butyl N-({6-bromoimidazo[1,2-a]pyridin-3-yl}ethyl)-N-methylcarbamate (1.2 g, 82%). $^1$H NMR (400 MHz, DMSO-de) δ 8.72 (br.s, 1H), 7.57 (s, 1H), 7.39 (d, 1H), 7.31 (d, 1H), 3.47 (t, 2H), 3.16 (t, 2H), 2.78 (s, 3H), 0.99 (s, 9H).
Step 2

A solution of tert-butyl N-({6-bromoimidazo[1,2-a]pyridin-3-yl}ethyl)-N-methylcarbamate (1.2 g, 3.4 mmol) was dissolved in dioxane (13 mL) and treated with 4-fluoro-2-hydroxybenzene boronic acid (1.05 g, 6.8 mmol) followed by a solution of potassium phosphate (1.8 g, 8.5 mmol) in water (2 mL). The reaction mixture was purged with argon before addition of tetrakis(triphenylphosphine) palladium(0) (392 mg), then heated to 100° C. overnight, cooled to room temperature and evaporated filtered through a bed of Celite and washed with ethyl acetate. The ethyl acetate layer taken dried over Na$_2$SO$_4$, and evaporated under reduced pressure. The crude product was purified by column chromatography eluting with 5% MeOH in DCM to give tert-butyl N-{[6-(4-fluoro-2-hydroxyphenyl)imidazo[1,2-a]pyridin-3-yl]ethyl}-N-methylcarbamate (1.0 g, 76%). $^1$H NMR (400 MHz, DMSO-d$_6$) δ 10.29 (s, 1H), 8.42 (s, 1H), 7.80-7.55 (m, 2H), 7.50-7.40 (m, 3H), 6.80-6.70 (m, 2H), 3.49 (t, 2H), 3.15 (t, 2H), 2.80 (s, 3H), 1.04 (s, 9H).

Intermediate 26

6-(3-Fluoro-2-(2-(1,3,5-trimethyl-1H-pyrazol-4-yl) ethoxy)phenyl)imidazo[1,2-a]pyridine-3-carbaldehyde Step 1

To a stirred solution of 6-bromoimidazo[1,2-a]pyridine-3-carbaldehyde (1.2 g, 5.30 mmol) in dioxane:water (4:1, 20 mL), (3-fluoro-2-hydroxyphenyl)boronic acid (1.25 g, 8.0 mmol,) and K$_3$PO$_4$ (2.83 g, 13.33 mmol) was added, and the reaction mixture was purged with argon for 15 min. Tetrakis (triphenyl phosphine)palladium(0) (0.617 g, 0.53 mmol) was added and the reaction mixture was stirred at 100° C. for 5 h. The reaction mixture was filtered through a pad of Celite and washed the filtration cake with 10% MeOH/DCM (2×15 mL). The combined filtrate was evaporated to dryness under reduced pressure. The crude product was purified column chromatography to afford 6-(3-fluoro-2-hydroxyphenyl)imidazo[1, 2-a]pyridine-3-carbaldehyde (720 mg, 51%) as a light yellow solid.

$^1$H NMR (400 MHz, CDCl$_3$) δ 9.98 (s, 1H), 9.77 (s, 1H), 8.36 (s, 1H), 7.86 (s, 1H), 7.71-7.50 (m, 2H), 7.20-7.12 (m, 2H), 7.02-6.97 (m, 1H).
Step 2

To a stirred solution of 6-(3-fluoro-2-hydroxyphenyl) imidazo[1, 2-a]pyridine-3-carbaldehyde (0.6 g, 2.34 mmol) and triphenylphosphine (1.23 g, 4.68 mmol) in THF (15 mL) was added dropwise a solution of 2-(1,3,5-trimethyl-1H-pyrazol-4-yl)ethanol (720 mg, 4.68 mmol) in THF (10 mL). The reaction mixture was cooled to 0° C. and was added di-isopropyl azodicarboxylate (0.92 mL, 4.68 mmol). The reaction mixture was allowed to warm to room temperature, stirred overnight and concentrated under reduced pressure. The crude was purified by column chromatography to afford 6-(3-fluoro-2-(2-(1,3,5-trimethyl-1H-pyrazol-4-yl)ethoxy) phenyl)imidazo [1,2-a]pyridine-3-carbaldehyde (440 mg, 48%) as an off-white solid. $^1$H NMR (400 MHz, CDCl$_3$) δ 9.97 (s, 1H), 9.61 (s, 1H), 8.36 (s, 1H), 7.79-7.64 (m, 2H), 7.23-7.08 (m, 3H), 3.93 (t, J=7.4 Hz, 2H), 3.60 (s, 3H), 2.65 (t, J=7.5 Hz, 2H), 2.01 (s, 3H), 1.94 (s, 3H).

Intermediate 27 tert-butyl (2-(6-(3-fluoro-2-hydroxyphenyl) imidazo [1, 2-a]pyridin-3-yl) ethyl) carbamate To a stirred solution of tert-butyl (2-(6-bromoimidazo[1, 2-a]pyridin-3-yl)ethyl)carbamate (750 mg, 2.20 mmol) in dioxane/water (3:1, 14 mL), (3-fluoro-2-hydroxyphenyl) boronic acid (510 mg, 3.30 mmol) and K$_3$PO$_4$ (1.17 g, 5.50 mmol) was added and degassed with argon for 15 min. Pd(PPh$_3$)$_4$ (250 mg, 0.22 mmol) was added to the reaction mixture and stirred at 90° C. for 5 h. The progress of the reaction was monitored by TLC. After completion of the reaction, the reaction mixture was filtered through Celite and washed with 10% MeOH in DCM. The reaction mixture was concentrated under reduced pressure and purified by column chromatography to afford tert-butyl (2-(6-(3-fluoro-2-hydroxyphenyl) imidazo [1, 2-a]pyridin-3-yl) ethyl) carbamate (600 mg, 76%). $^1$H NMR (400 MHz, DMSO-d6) δ 9.80 (s, 1H), 8.42 (s, 1H), 7.69-7.48 (m, 1H), 7.42 (t, J=4.8 Hz, 2H), 7.27-7.21 (m, 2H), 7.02-6.87 (m, 2H), 3.27 (t, J=6.7 Hz, 2H), 3.03 (q, J=7.6, 7.2 Hz, 2H), 1.31 (s, 9H).

97

Intermediate 28 tert-butyl (2-(6-(3-fluoro-2-hydroxyphenyl)imidazo[1,2-a]pyridin-3-yl)ethyl) (N-methyl) carbamate A solution of tert-butyl (2-(6-bromoimidazo[1,2-a]pyridin-3-yl)ethyl)(N-methyl)carbamate (Intermediate 23 Step 1, 180 mg, 0.50 mmol) in dioxane and water (4:2, 10 mL), (3-fluoro-2-hydroxyphenyl)boronic acid (110 mg, 0.76 mmol) and K$_3$PO$_4$ (265 mg, 1.25 mmol) was degassed with argon for 15 min. Pd (PPh$_3$)$_4$ (57 mg, 0.05 mmol) was added to the reaction mixture and stirred at 90° C. for 5 hr. The progress of the reaction was monitored by TLC. After completion of the reaction, the reaction mixture was filtered through celite and washed with EtOAc followed by water. The reaction mixture was extracted with EtOAc. The combined organic layer were washed with brine, dried over anhydrous Na$_2$SO$_4$ and concentrated under reduced pressure. The residue was purified by column chromatography to afford the title intermediate (140 mg, 72%) as an off white solid.

Intermediate 29 tert-butyl (2-(6-(3, 4-difluoro-2-hydroxyphenyl) imidazo [1, 2-a]pyridin-3-yl) ethyl) carbamate A solution of tert-butyl (2-(6-bromoimidazo[1,2-a]pyridin-3-yl)ethyl)carbamate (90 mg, 0.23 mmol) in dioxane/water (3:1, 14 mL) was treated with 2,3-difluoro-6-(4,4,5,5-tetramethyl-1,3,2-dioxaborolan-2-yl)phenol (71 mg, 0.46 mmol) and K$_3$PO$_4$ (1.17 g, 5.50 mmol). The mixture was degassed with argon for 15 min before addition of Pd(PPh$_3$)$_4$ (250 mg, 0.22 mmol) and the reaction mixture was then heated to 90° C. for 5 hr. The reaction mixture was filtered through Celite and washed with 10% MeOH in DCM. The reaction mixture was concentrated under reduced pressure and purified by column chromatography to afford tert-butyl (2-(6-(3, 4-difluoro-2-hydroxyphenyl) imidazo [1, 2-a]pyridin-3-yl) ethyl) carbamate (38 mg, 31%). $^1$H NMR (400 MHz, CDCl$_3$) δ 8.06 (s, 1H), 7.63 (d, J=9.3 Hz, 1H), 7.51 (s, 1H), 7.25 (s, 1H), 7.12-7.05 (m, 1H), 7.05-6.94 (m, 1H), 5.31 (s, 2H), 3.96 (t, J=7.1 Hz, 1H), 3.69 (d, J=9.6 Hz, 1H), 3.52 (d, J=6.0 Hz, 3H), 3.11-3.03 (m, 2H

98

Preparation of Examples 1-108

Example 1

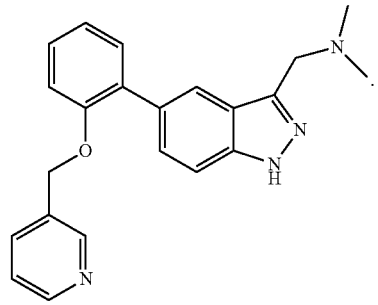 [SMILES: CN(C)Cc1n[nH]c2ccc(-c3ccccc3OCc3cccnc3)cc12]

N,N-dimethyl-1-(5-(2-(pyridin-3-ylmethoxy)phenyl)-1H-indazol-3-yl)methanamine

Step 1

According to the general method for mesyl transfer (Method A), intermediate 1 (43 mg, 0.1 mmol was reacted with 3-pyridinemethanol (9.7 μL, 0.1 mmol) and sodium t-butoxide (9.6 mg, 0.1 mmol) in acetonitrile (0.5 ml). Partial purification by column chromatography provided the THP protected indazole. δ$_H$/ppm $^1$H NMR (400 MHz, Chloroform-d) δ 8.61 (d, J=2.2 Hz, 1H), 8.53 (dd, J=4.9, 1.6 Hz, 1H), 8.01 (d, J=1.5 Hz, 1H), 7.65-7.59 (m, 2H), 7.58 (s, 1H), 7.42 (dd, J=7.5, 1.8 Hz, 1H), 7.32 (td, J=7.9, 1.9 Hz, 1H), 7.23 (dd, J=7.9, 4.8 Hz, 1H), 7.11 (d, J=7.5 Hz, 1H), 7.07 (d, J=8.4 Hz, 1H), 5.71 (dd, J=9.8, 2.6 Hz, 1H), 5.09 (s, 2H), 4.09 (s, 1H), 3.81 (s, 2H), 3.77 (td, J=11.6, 3.1 Hz, 1H), 2.67-2.51 (m, 1H), 2.29 (s, 6H), 2.16 (ddd, J=8.8, 4.5, 2.3 Hz, 1H), 2.11-2.07 (m, 1H), 1.84-1.71 (m, 2H), 1.65 (dt, J=9.3, 3.1 Hz, 1H).

Step 2

According to the general method for THP deprotection (Method A), the product from Step 1 was used to prepare the title compound as a colourless oil (14.2 mg, yield over 2 steps: 40%) LC-MS rt 10.1 min MH$^+$ 359.

δ$_H$/ppm $^1$H NMR (400 MHz, Chloroform-d) δ 8.64 (d, J=2.1 Hz, 1H), 8.56 (dd, J=5.0, 1.5 Hz, 1H), 8.00 (d, J=1.2 Hz, 1H), 7.64 (ddd, J=8.6, 5.6, 1.8 Hz, 2H), 7.49-7.42 (m, 2H), 7.36 (td, J=7.8, 1.8 Hz, 1H), 7.25 (dd, J=7.8, 4.8 Hz, 1H), 7.14 (t, J=7.7 Hz, 1H), 7.10 (d, J=8.3 Hz, 1H), 5.11 (s, 2H), 3.88 (s, 2H), 2.36 (s, 6H).

The following compounds were made by analogous methods:

| Ex No | Structure | SM Intermediate N° | Mesyl method | THP method | Reductive amination | Boc Deprotection | Yield | Characterisation |
|---|---|---|---|---|---|---|---|---|
| | | | | General Procedure | | | | |
| 2 | N,N-dimethyl-1-(5-(2-phenethoxyphenyl)-1H-indazol-3-yl)methanamine | 1 | A | A | | | 11.8 mg, yield over 2 steps: 32% | LC-MS rt: 12.8 min MH+ 372 $^1$H NMR (400 MHz, Chloroform-d) δ 7.99 (d, J = 1.2 Hz, 1H), 7.53 (dd, J = 8.5, 1.6 Hz, 1H), 7.46-7.39 (m, 2H), 7.33 (td, J = 7.9, 1.9 Hz, 1H), 7.24 (td, J = 5.1, 4.7, 2.2 Hz, 3H), 7.17 (dd, J = 7.3, 2.1 Hz, 2H), 7.07 (t, J = 7.4 Hz, 1H), 7.01 (d, J = 8.2 Hz, 1H), 4.22 (t, J = 6.8 Hz, 2H), 3.90 (s, 2H), 3.04 (t, J = 6.8 Hz, 2H), 2.37 (s, 6H). |
| 3 | N,N-dimethyl-1-(5-(2-(quinolin-4-ylmethoxy)phenyl)-1H-indazol-3-yl)methanamine | 1 | A | A | | | 15.9 mg, yield over 2 steps: 37% | LC-MS rt: 10.9 min MH+ 409 $^1$H NMR (400 MHz, Chloroform-d) δ 8.84 (d, J = 4.5 Hz, 1H), 8.17 (d, J = 8.4 Hz, 1H), 8.04 (d, J = 1.3 Hz, 1H), 7.91 (d, J = 8.2 Hz, 1H), 7.74 (dd, J = 8.3, 6.9 Hz, 1H), 7.66 (dd, J = 8.7, 1.6 Hz, 1H), 7.54 (t, J = 7.6 Hz, 1H), 7.51-7.44 (m, 3H), 7.38 (td, J = 7.8, 1.8 Hz, 1H), 7.20-7.12 (m, 2H), 5.58 (s, 2H), 3.85 (s, 2H), 2.32 (s, 6H). |

-continued

| Ex No | Structure | SM Intermediate N° | Mesyl method | THP method | Reductive amination | Boc Deprotection | Yield | Characterisation |
|---|---|---|---|---|---|---|---|---|
| 4 | N,N-dimethyl-1-(5-(2-(2-(pyridin-3-yl)ethoxy)phenyl)-1H-indazol-3-yl)methanamine | 1 | A | A | | | 3.3 mg, yield over 2 steps: 7.7% | LC-MS rt 8.8 min MH$^+$ 373 $^1$H NMR (400 MHz, Chloroform-d) δ 8.47 (dd, J = 4.9, 1.7 Hz, 1H), 8.46 (d, J = 2.3 Hz, 1H), 7.92 (d, J = 1.1 Hz, 1H), 7.50 (d, J = 8.7 Hz, 1H), 7.46-7.38 (m, 3H), 7.33 (td, J = 7.9, 1.9 Hz, 1H), 7.13-7.04 (m, 2H), 6.99 (d, J = 8.1 Hz, 1H), 4.22 (t, J = 6.2 Hz, 2H), 3.93 (s, 2H), 3.02 (t, J = 6.2 Hz, 2H), 2.40 (s, 6H). |
| 5 | 1-(5-(2-(1H-imidazol-1-yl)ethoxy)phenyl)-1H-indazol-3-yl)-N,N-dimethylmethanamine | 1 | A | A | | | 10.9 mg, yield over 2 steps: 30% | LC-MS rt 7.7 min MH$^+$ 362 $^1$H NMR (400 MHz, Methanol-d4) δ 7.87 (d, J = 1.2 Hz, 1H), 7.52 (d, J = 8.6 Hz, 1H), 7.45-7.35 (m, 3H), 7.41-7.31 (m, 1H), 7.10-7.00 (m, 2H), 6.95 (s, 1H), 6.84 (s, 1H), 4.32 (s, 2H), 4.24 (s, 2H), 3.92 (s, 2H), 2.35 (s, 6H). |

| Ex No | Structure | SM Intermediate N° | Mesyl method | THP method | Reductive amination | Boc Deprotection | Yield | Characterisation |
|---|---|---|---|---|---|---|---|---|
| 6 | N,N-dimethyl-1-(5-(2-benzyloxyphenyl)-1H-indazol-3-yl)methanamine | 1 | C | A | | | 17.2 mg, yield over 2 steps: 10% | LC-MS rt 2.2 min (50-98) MH+ 358 ¹H NMR (400 MHz, Chloroform-d) δ 8.07 (d, J = 1.3 Hz, 1H), 7.67 (dd, J = 8.8, 1.8 Hz, 1H), 7.47 (d, J = 8.6 Hz, 1H), 7.44 (dd, J = 7.8, 1.8 Hz, 1H), 7.40-7.27 (m, 7H), 7.10 (t, J = 7.5 Hz, 3H), 5.12 (s, 2H), 3.91 (s, 2H), 2.36 (s, 6H). |
| 7 | 1-(5-(4-fluoro-2-(2-(1,3,5-trimethyl-1H-pyrazol-4-yl)ethoxy)phenyl)-1H-indazol-3-yl)-N,N-dimethylmethanamine | 2 | A | A | | | 5.9 mg, yield over 2 steps: 14% | LC-MS rt 11.1 min MH+ 422 ¹H NMR (400 MHz, Chloroform-d) δ 7.92 (s, 1H), 7.46 (d, J = 1.3 Hz, 2H), 7.31 (dd, J = 8.5, 6.9 Hz, 1H), 6.75 (td, J = 8.1, 2.4 Hz, 1H), 6.69 (dd, J = 11.0, 2.5 Hz, 1H), 3.95 (t, J = 7.1 Hz, 2H), 3.90 (s, 2H), 3.64 (s, 3H), 2.75 (t, J = 7.1 Hz, 2H), 2.36 (s, 6H), 2.07 (s, 3H), 1.92 (s, 3H). |
| | | 2 | B | B | | | 31 mg, 42% | "data as above" |

-continued

| Ex No | Structure | SM Intermediate N° | General Procedure | | | | Yield | Characterisation |
|---|---|---|---|---|---|---|---|---|
| | | | Mesyl method | THP method | Reductive amination | Boc Deprotection | | |
| 8 | N,N-dimethyl-1-(5-(4-fluoro-2-(2-(pyridin-3-yl)ethoxy)phenyl)-1H-indazol-3-yl)methanamine | 2 | A | A | | | 10.0 mg, yield over 2 steps: 25% | LC-MS rt 8.9 min MH+ 391 1H NMR (400 MHz, Chloroform-d) δ 8.48 (dd, J = 4.9, 1.7 Hz, 1H), 8.44 (d, J = 2.2 Hz, 1H), 7.84 (d, J = 2.1 Hz, 1H), 7.48 (d, J = 8.7 Hz, 1H), 7.41 (dt, J = 7.8, 2.0 Hz, 1H), 7.35-7.28 (m, 2H), 7.08 (dd, J = 7.8, 4.7 Hz, 1H), 6.75 (td, J = 8.3, 2.5 Hz, 1H), 6.69 (dd, J = 10.8, 2.5 Hz, 1H), 4.18 (t, J = 6.1 Hz, 2H), 3.91 (d, J = 2.4 Hz, 2H), 3.01 (t, J = 6.1 Hz, 2H), 2.38 (s, 6H). |
| 9 | N,N-dimethyl-1-(5-(4-fluoro-2-(pyridin-3-ylmethoxy)phenyl)-1H-indazol-3-yl)methanamine | 2 | A | A | | | 14.2 mg, yield over 2 steps: 40% | LC-MS rt 9.5 min MH+ 377 1H NMR (400 MHz, Chloroform-d) δ 8.63 (d, J = 2.0 Hz, 1H), 8.56 (dd, J = 4.8, 1.7 Hz, 1H), 7.93 (d, J = 1.6 Hz, 1H), 7.62 (dt, J = 7.9, 2.1 Hz, 1H), 7.54 (dd, J = 8.8, 1.5 Hz, 1H), 7.41 (d, J = 8.6 Hz, 1H), 7.37 (dd, J = 9.2, 6.7 Hz, 1H), 7.24 (dd, J = 7.9, 4.9 Hz, 1H), 6.82 (ddd, J = 10.7, 5.1, 2.5 Hz, 2H), 5.08 (s, 2H), 3.86 (s, 2H), 2.34 (s, 6H). |

| Ex No | Structure | SM Intermediate N° | Mesyl method | THP method | Reductive amination | Boc Deprotection | Yield | Characterisation |
|---|---|---|---|---|---|---|---|---|
| 10 | 1-(5-(2-(4-fluoro-2-(1H-imidazol-1-yl)ethoxy)phenyl)-1H-indazol-3-yl)-N,N-dimethylmethanamine | 2 | A | A | | | 15.1 mg, yield over 2 steps: 40% | LC-MS rt 4.0 min MH⁺ 380. ¹H NMR (400 MHz, Methanol-d4) δ 7.88-7.79 (m, 1H), 7.53 (d, J = 8.6 Hz, 1H), 7.42 (d, J = 1.5 Hz, 1H), 7.35 (dd, J = 7.4, 1.5 Hz, 2H), 6.95 (s, 1H), 6.87 (d, J = 11.0 Hz, 1H), 6.84 (s, 1H), 6.80 (td, J = 8.3, 2.5 Hz, 1H), 4.34 (dd, J = 5.3, 3.9 Hz, 2H), 4.30-4.23 (m, 2H), 3.91 (s, 2H), 2.33 (s, 6H). |
| 11 | 1-(5-(2-(2-(1H-benzo[d]imidazol-1-yl)ethoxy)-4-fluorophenyl)-1H-indazol-3-yl)-N,N-dimethylmethanamine | 2 | A | A | | | 11.9 mg, yield over 2 steps: 28% | LC-MS rt 9.4 min MH⁺ 430. ¹H NMR (400 MHz, Chloroform-d) δ 7.81 (d, J = 1.2 Hz, 1H), 7.72 (s, 1H), 7.60 (d, 1H), 7.36-7.17 (m, 5H), 6.77 (d, J = 2.4 Hz, 1H), 6.64 (dd, J = 10.6, 2.5 Hz, 1H), 4.50 (t, 1H), 4.28 (t, 2H), 4.04 (s, 2H), 2.48 (s, 6H). |

| Ex No | Structure | SM Intermediate N° | Mesyl method | THP method | Reductive amination | Boc Deprotection | Yield | Characterisation |
|---|---|---|---|---|---|---|---|---|
| 12 | 1-(5-(2-(1H-1,2,4-triazol-1-yl)ethoxy)-4-fluorophenyl)-1H-indazol-3-yl)-N,N-dimethylmethanamine | 2 | A | A | | | 3.7 mg, yield over 2 steps: 10% | LC-MS rt 9.9 min MH+ 381. $^1$H NMR (400 MHz, Chloroform-d) δ 7.99 (s, 1H), 7.83 (d, J = 2.7 Hz, 2H), 7.51 (d, J = 8.4 Hz, 2H), 7.34-7.29 (m, 1H), 7.13 (dd, J = 8.5, 1.7 Hz, 1H), 6.79 (d, J = 2.4 Hz, 1H), 6.72-6.62 (m, 1H), 4.49 (t, J = 4.7 Hz, 2H), 4.32 (t, J = 4.7 Hz, 2H), 3.94 (s, 2H), 2.40 (s, 6H). |
| 13 | 1-(5-(2-(2,4-dimethyl-1H-imidazol-1-yl)ethoxy)-4-fluorophenyl)-1H-indazol-3-yl)-N,N-dimethylmethanamine | 2 | A | A | | | 9.7 mg, yield over 2 steps: 24% | LC-MS rt 8.5 min MH+ 408. $^1$H NMR (400 MHz, Chloroform-d) δ 7.80 (d, J = 1.2 Hz, 1H), 7.55 (d, J = 8.6 Hz, 1H), 7.32 (dd, J = 8.4, 6.8 Hz, 1H), 7.20 (dd, J = 8.7, 1.6 Hz, 1H), 6.79 (td, J = 8.3, 2.4 Hz, 1H), 6.67 (dd, J = 10.7, 2.4 Hz, 1H), 6.41 (s, 1H), 4.16 (t, J = 5.6 Hz, 2H), 4.07 (t, J = 5.0 Hz, 2H), 3.93 (s, 2H), 2.40 (s, 6H), 2.11 (s, 3H), 2.03 (s, 3H). |

| Ex No | Structure | SM Intermediate N° | Mesyl method | THP method | Reductive amination | Boc Deprotection | Yield | Characterisation |
|---|---|---|---|---|---|---|---|---|
| 14 | N,N-dimethyl-1-(5-(3-(pyridin-3-ylmethoxy)phenyl)-1H-indazol-3-yl)methanamine | 3 | A | A | | | 5.4 mg, yield over 2 steps: 15% | LC-MS rt 9.4 min MH⁺ 359 ¹H NMR (400 MHz, Chloroform-d) δ 8.76 (d, J = 2.2 Hz, 1H), 8.63 (dd, J = 5.0, 1.6 Hz, 1H), 8.05 (d, J = 1.7 Hz, 1H), 7.85 (dt, J = 7.8, 1.9 Hz, 1H), 7.64 (dd, J = 8.7, 1.8 Hz, 1H), 7.53 (d, J = 8.8 Hz, 1H), 7.46-7.34 (m, 2H), 7.31-7.29 (m, 1H), 7.28 (s, 1H), 7.01-6.95 (m, 1H), 5.19 (s, 2H), 3.91 (s, 2H), 2.38 (s, 6H). |
| 15 | N,N-dimethyl-1-(5-(3-(pyridin-4-ylmethoxy)phenyl)-1H-indazol-3-yl)methanamine | 3 | A | A | | | 6.1 mg, yield over 2 steps: 17% | LC-MS rt 8.8 min MH⁺ 359. ¹H NMR (400 MHz, Chloroform-d) δ 8.69-8.63 (m, 2H), 8.05 (d, J = 1.5 Hz, 1H), 7.64 (dd, J = 8.7, 1.6 Hz, 1H), 7.53 (d, J = 8.7 Hz, 1H), 7.46-7.41 (m, 2H), 7.40 (d, 1H), 7.32-7.27 (m, 2H), 6.95 (dd, J = 8.2, 2.5 Hz, 1H), 5.21 (s, 2H), 3.95 (s, 2H), 2.40 (s, 6H). |

| Ex No | Structure | SM Intermediate N° | Mesyl method | THP method | Reductive amination | Boc Deprotection | Yield | Characterisation |
|---|---|---|---|---|---|---|---|---|
| 16 | 1-(5-(2-(3-(1H-imidazol-1-yl)ethoxy)phenyl)-1H-indazol-3-yl)-N,N-dimethylmethanamine | 3 | A | A | | | 6.1 mg, yield over 2 steps: 17% | LC-MS rt 7.7 min MH+ 362 1H NMR (400 MHz, Chloroform-d) δ 8.02 (d, J = 1.4 Hz, 1H), 7.68 (s, 1H), 7.60 (dd, J = 8.6, 1.7 Hz, 1H), 7.50 (d, J = 8.7 Hz, 1H), 7.37 (t, J = 8.0 Hz, 1H), 7.27 (td, 1H), 7.14 (t, J = 2.1 Hz, 1H), 7.13-7.10 (m, 2H), 6.86 (dd, J = 8.1, 2.4 Hz, 1H), 4.40 (t, 2H), 4.33 (t, 2H), 3.94 (s, 2H), 2.39 (s, 6H). |
| 17 | 1-(5-(4-fluoro-2-(2-(1,3,5-trimethyl-1H-pyrazol-4-yl)ethoxy)phenyl)-1-methyl-1H-indazol-3-yl)-N,N-dimethylmethanamine | 6 | | | A | | 13.5 mg, 31% | LC-MS rt 11.6 min MH+ 436 1H NMR (400 MHz, Chloroform-d) δ 7.88 (d, J = 1.8 Hz, 1H), 7.48 (dd, J = 8.7, 1.5 Hz, 1H), 7.35 (d, J = 8.7 Hz, 1H), 7.33-7.26 (m, 1H), 6.73 (td, J = 8.3, 2.5 Hz, 1H), 6.67 (dd, J = 10.8, 2.4 Hz, 1H), 4.08 (s, 3H), 3.93 (t, J = 7.2 Hz, 2H), 3.83 (s, 2H), 3.63 (s, 3H), 2.75 (t, J = 7.3 Hz, 2H), 2.33 (s, 6H), 2.08 (s, 3H), 1.92 (s, 3H). |

-continued

| Ex No | Structure | SM Intermediate N° | Mesyl method | THP method | Reductive amination | Boc Deprotection | Yield | Characterisation |
|---|---|---|---|---|---|---|---|---|
| 18 | 1-(5-(4-fluoro-2-(2-(1,3,5-trimethyl-1H-pyrazol-4-yl)ethoxy)phenyl)-1-methyl-1H-indazol-3-yl)-N-methylmethanamine | 6 | | | A | | 40.6 mg, 91% | LC-MS rt 11.8 min MH⁺ 422 ¹H NMR (400 MHz, Methanol-d4) δ 7.77 (d, J = 1.4 Hz, 1H), 7.45 (d, J = 8.9 Hz, 1H), 7.40 (dd, J = 8.8, 1.5 Hz, 1H), 7.29 (dd, J = 8.5, 6.8 Hz, 1H), 6.83 (dd, J = 11.2, 2.5 Hz, 1H), 6.73 (td, J = 8.3, 2.5 Hz, 1H), 4.07 (s, 3H), 4.07 (s, 3H), 4.01 (t, J = 6.4 Hz, 2H), 3.55 (s, 2H), 2.71 (t, J = 6.5 Hz, 2H), 2.44 (s, 3H), 1.91 (s, 3H), 1.86 (s, 3H). |
| 19 | 1-(5-(2-(2-(1H-1,2,4-triazol-1-yl)ethoxy)-4-fluorophenyl)-1-methyl-1H-indazol-3-yl)-N,N-dimethylmethanamine | 5 | | | General method for alkylation using alkyltosylates | | 19.9 mg, 56% | LC-MS rt 10.4 min MH⁺ 395 ¹H NMR (400 MHz, Chloroform-d) δ 7.93 (s, 1H), 7.85-7.77 (m, 2H), 7.39 (d, J = 8.7 Hz, 1H), 7.32 (dd, J = 8.4, 6.8 Hz, 1H), 7.23 (dd, J = 8.7, 1.6 Hz, 1H), 6.79 (td, J = 8.1, 2.4 Hz, 1H), 6.66 (dd, J = 10.6, 2.4 Hz, 1H), 4.48 (t, J = 4.9 Hz, 2H), 4.30 (t, J = 4.8 Hz, 2H), 4.10 (s, 3H), 3.84 (s, 2H), 2.33 (s, 6H). |

| Ex No | Structure | SM Intermediate N° | Mesyl method | THP method | Reductive amination | Boc Deprotection | Yield | Characterisation |
|---|---|---|---|---|---|---|---|---|
| 20 | 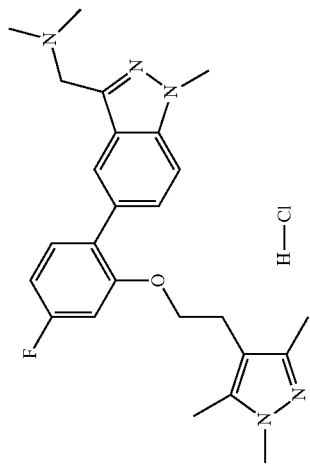<br>1-(5-(4-fluoro-2-(2-(1,3,5-trimethyl-1H-pyrazol-4-yl)ethoxy)phenyl)-1-methyl-1H-indazol-3-yl)-N,N-dimethylmethanamine HCl salt | 4 | B | | | | 90 mg, 38% | LC-MS rt 7.05 min (prep) MH⁺ 436 ¹H NMR (400 MHz, Methanol-d4) δ 8.54 (s, 1H), 7.84-7.77 (m, 1H), 7.53 (d, J = 8.7 Hz, 1H), 7.44 (dd, J = 8.8, 1.6 Hz, 1H), 7.30 (dd, J = 8.3, 6.8 Hz, 1H), 6.86 (dd, J = 11.2, 2.5 Hz, 1H), 6.76 (td, J = 8.3, 2.5 Hz, 1H), 4.25 (s, 2H), 4.13 (s, 3H), 4.03 (t, J = 6.5 Hz, 2H), 3.57 (s, 3H), 2.73 (t, J = 6.4 Hz, 2H), 2.62 (s, 6H), 1.90 (s, 3H), 1.89 (s, 3H). |
| 21 | 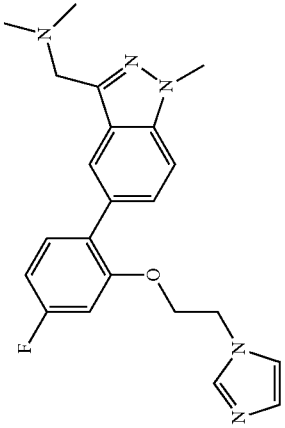<br>1-(5-(2-(2-(1H-imidaozl-1-yl)ethoxy)-4-fluorophenyl)-1-methyl-1H-indazol-3-yl)-N,N-dimethylmethanamine | 5 | A | | | | 11.7 mg, 44% | LC-MS rt 6.7 min (20-98%) MH⁺ 394 ¹H NMR (400 MHz, Methanol-d4) δ 8.35 (s, 2H), 7.71 (d, J = 1.0 Hz, 1H), 7.66 (d, J = 8.6 Hz, 1H), 7.42 (dd, J = 8.7, 1.5 Hz, 1H), 7.34-7.27 (m, 2H), 7.08 (s, 1H), 6.97 (s, 1H), 6.90 (dd, J = 11.0, 2.4 Hz, 1H), 6.81 (td, J = 8.3, 2.2 Hz, 1H), 4.66 (s, 2H), 4.35 (t, J = 4.7 Hz, 2H), 4.30-4.23 (m, 2H), 4.20 (s, 3H), 2.99 (s, 6H). |

-continued

| Ex No | Structure | Name | SM Intermediate N° | Mesyl method | THP method | Reductive amination | Boc Deprotection | Yield | Characterisation |
|---|---|---|---|---|---|---|---|---|---|
| 22 | 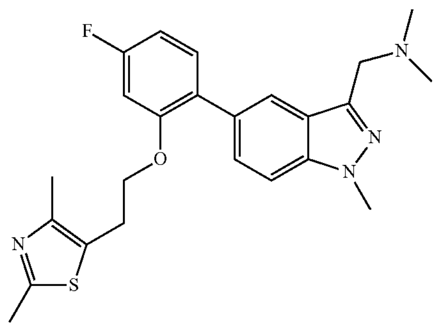 | 1-(5-(2-(2-(2,4-dimethylthiazol-5-yl)ethoxy)-4-fluorophenyl)-1-methyl-1H-indazol-3-yl)-N,N-dimethylmethanamine | 5 | A | | | | 4.5 mg, 15% | LC-MS rt 11.1 min (20-98%) MH+ 439 $^1$H NMR (400 MHz, Methanol-d4) δ 8.93 (s, 1H), 8.24 (s, 1H), 7.97 (d, J = 8.8 Hz, 1H), 7.86 (dd, J = 8.8, 1.6 Hz, 1H), 7.77 (dd, J = 8.5, 6.7 Hz, 1H), 7.33 (dd, J = 11.2, 2.5 Hz, 1H), 7.22 (td, J = 8.3, 2.5 Hz, 1H), 4.87 (s, 2H), 4.66-4.53 (m, 5H), 3.51 (t, J = 6.8 Hz, 2H), 3.19 (s, 6H), 2.89 (s, 3H), 2.44 (s, 3H). |
| 23 | 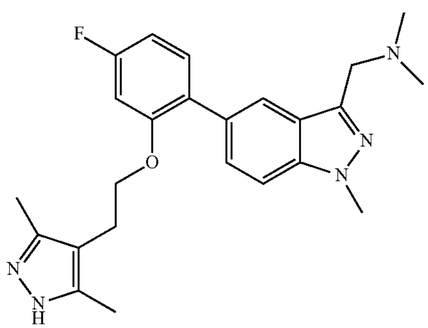 | 1-(5-(2-(2-(3,5-dimethyl-1H-pyrazol-4-yl)ethoxy)-4-fluorophenyl)-1-methyl-1H-indazol-3-yl)-N,N-dimethylmethanamine | 5 | A | | | | 2.8 mg, 44% | LC-MS rt 10.3 min (20-98%) MH+ 422 $^1$H NMR (400 MHz, Methanol-d4) δ 8.50 (s, 1H), 7.97 (d, J = 1.4 Hz, 1H), 7.70 (dd, J = 8.8, 1.5 Hz, 1H), 7.63 (d, J = 8.6 Hz, 1H), 7.57 (d, J = 8.7 Hz, 1H), 7.45 (dd, J = 8.8, 1.6 Hz, 1H), 7.32 (td, J = 9.1, 8.7, 6.8 Hz, 1H), 6.90 (dd, J = 11.2, 2.5 Hz, 1H), 6.77 (td, J = 8.3, 2.5 Hz, 1H), 6.71-6.65 (m, 1H), 4.56 (s, 1H), 4.51 (s, 1H), 4.17 (s, 2H), 4.16 (s, 2H), 4.08 (t, J = 6.4 Hz, 2H), 2.85 (s, 3H), 2.83 (s, 3H), 2.76 (t, J = 6.4 Hz, 2H), 1.91 (s, 6H). |

| Ex No | Structure | SM Intermediate N° | Mesyl method | THP method | Reductive amination | Boc Deprotection | Yield | Characterisation |
|---|---|---|---|---|---|---|---|---|
| 24 | 1-(5-(2-(4-methylthiazol-5-yl)ethoxy)-4-fluorophenyl)-1-methyl-1H-indazol-3-yl)-N,N-dimethylmethanamine | 5 | A | | | | 14.5 mg, 57% | LC-MS rt 11.6 min (20-98%) MH+ 424 (400 MHz, Methanol-d4) δ 8.67 (s, 1H), 8.54 (s, 1H), 7.81 (d, J = 1.2 Hz, 1H), 7.52 (d, J = 8.7 Hz, 1H), 7.41 (dd, J = 8.9, 1.4 Hz, 1H), 7.34 (dd, J = 8.4, 6.7 Hz, 1H), 6.91 (dd, J = 11.1, 2.5 Hz, 1H), 6.80 (td, J = 8.3, 2.4 Hz, 1H), 4.40 (s, 2H), 4.22 (t, J = 5.8 Hz, 2H), 4.15 (s, 3H), 3.19 (t, J = 5.8 Hz, 2H), 2.73 (s, 6H), 2.11 (s, 3H). |
| 25 | 1-(5-(4-fluoro-2-(2-(4-methylthiazol-5-yl)ethoxy)phenyl)-1-methyl-1H-indazol-3-yl)ethanamine | 7 | | | C | | 22 mg, 55% | LC-MS rt 12.6 min (5-98%) MH+ 411. 1H NMR (400 MHz, Chloroform-d) δ 8.69 (s, 1H), 7.67 (d, J = 1.1 Hz, 1H), 7.39 (dd, J = 8.9, 1.7 Hz, 1H), 7.34-7.30 (m, 1H), 7.30-7.27 (m, 1H), 6.73 (td, J = 8.3, 2.5 Hz, 1H), 6.68 (dd, J = 10.8, 2.4 Hz, 1H), 5.32 (s, 2H), 4.80 (q, J = 6.8 Hz, 1H), 4.20-4.07 (m, 2H), 4.04 (s, 3H), 3.21-3.06 (m, 2H), 2.07 (s, 3H), 1.81 (d, J = 6.8 Hz, 3H). |

| Ex No | Structure | SM Intermediate N° | Mesyl method | THP method | Reductive amination | Boc Deprotection | Yield | Characterisation |
|---|---|---|---|---|---|---|---|---|
| 26 | 1-(5-(4-fluoro-2-(2-(4-methylthiazol-5-yl)ethoxy)phenyl)-1-methyl-1H-indazol-3-yl)-N,N-dimethylethanamine | Product from example 25 | | | D | | 3.1 mg, 26% | LC-MS rt 12.8 min (5-98%) MH+ 439. 1H NMR (400 MHz, Methanol-d4) δ 8.67 (s, 1H), 8.50 (s, 1H), 7.82 (d, J = 0.9 Hz, 1H), 7.55 (d, J = 8.7 Hz, 1H), 7.42 (dd, J = 8.8, 1.4 Hz, 1H), 7.34 (dd, J = 8.5, 6.7 Hz, 1H), 6.92 (dd, J = 11.1, 2.5 Hz, 1H), 6.81 (td, J = 8.3, 2.4 Hz, 1H), 4.23 (t, J = 5.7 Hz, 2H), 4.17 (s, 3H), 3.20 (t, J = 5.8 Hz, 2H), 2.80 (s, 6H), 2.11 (s, 3H), 1.84 (d, J = 6.9 Hz, 3H). |
| 27 | (6-(4-fluoro-2-(2-(4-methylthiazol-5-yl)ethoxy)phenyl)-[1,2,4]triazolo[4,3-a]pyridin-3-yl)methanamine | 8 | D | | general method for benzamide deprotection | | 15 mg, 64% | LC-MS rt 10.9 min (5-98%) MH+ 384. 1H NMR (400 MHz, Methanol-d4) δ 8.66 (s, 1H), 8.46 (d, J = 1.5 Hz, 1H), 7.73-7.65 (m, 1H), 7.51-7.44 (m, 3H), 6.99 (dd, J = 11.1, 2.4 Hz, 1H), 6.85 (td, J = 8.3, 2.4 Hz, 1H), 4.51 (s, 2H), 4.29 (t, J = 5.8 Hz, 2H), 3.26 (t, J = 5.8 Hz, 2H), 2.20 (s, 3H). |

| Ex No | Structure | SM Intermediate N° | Mesyl method | THP method | Reductive amination | Boc Deprotection | Yield | Characterisation |
|---|---|---|---|---|---|---|---|---|
| 28 | (6-(4-fluoro-2-(2-(1,3,5-trimethyl-1H-pyrazol-4-yl)ethoxy)phenyl)-[1,2,4]triazolo[4,3-a]pyridin-3-yl)methanamine | 8 | D | | general method for benzamide | deprotection | 20 mg, 86% | LC-MS rt 11.0 min (5-98%) MH+ 395. ¹H NMR (400 MHz, Chloroform-d) δ 8.32 (d, J = 1.4 Hz, 1H), 7.73 (d, J = 9.8 Hz, 1H), 7.37 (dd, J = 9.5, 1.6 Hz, 1H), 7.31 (dd, J = 8.4, 6.5 Hz, 1H), 6.78 (td, J = 8.1, 2.4 Hz, 1H), 6.72 (dd, J = 10.8, 2.5 Hz, 1H), 4.45 (s, 2H), 4.00 (t, J = 7.2 Hz, 2H), 3.66 (s, 3H), 2.79 (t, J = 7.2 Hz, 2H), 2.11 (s, 3H), 1.99 (s, 3H), 1.81 (s, 2H). |
| 29 | 1-(5-(5-fluoro-2-(2-(1,3,5-trimethyl-1H-pyrazol-4-yl)ethoxy)phenyl)-1-methyl-1H-indazol-3-yl)-N,N-dimethylmethanamine | 9 | | | E | | 24 mg, 40% | LC-MS rt 12.2 min (5-98%) MH+ 436 ¹H NMR (400 MHz, CDCl₃) δ 8.38 (s, 1H), 7.87 (s, 1H), 7.64-7.47 (m, 2H), 7.15-6.97 (m, 3H), 4.64 (s, 2H), 4.17 (s, 3H), 3.97 (t, J = 6.5 Hz, 2H), 3.55 (s, 3H), 2.91 (s, 6H), 2.69 (t, J = 6.5 Hz, 2H), 1.92 (s, 3H), 1.87 (s, 3H). |

| Ex No | Structure | SM Intermediate N° | Mesyl method | THP method | Reductive amination | Boc Deprotection | Yield | Characterisation |
|---|---|---|---|---|---|---|---|---|
| 30 | 1-(5-(3-fluoro-2-(2-(1,3,5-trimethyl-1H-pyrazol-4-yl)ethoxy)phenyl)-1-methyl-1H-indazol-3-yl)-N,N-dimethylmethanamine | 10 | | | E | | 40 mg, 33% | LC-MS rt 12.3 min (5-98%) MH+ 436 1H NMR (400 MHz, MeOD) δ 8.39 (s, 1H), 7.89 (d, J = 4.0 Hz, 1H), 7.62-7.51 (m, 2H), 7.19 (h, J = 5.1 Hz, 3H), 4.64 (s, 2H), 4.20 (s, 3H), 3.76 (t, J = 6.9 Hz, 2H), 3.49 (s, 3H), 2.93 (s, 6H), 2.59 (t, J = 6.8 Hz, 2H), 1.90 (s, 3H), 1.88 (s, 3H). |
| 36 | 1-(5-(4-fluoro-2-(2-(4-methylthiazol-5-yl)ethoxy)phenyl)-1H-indazol-3-yl)-N,N-dimethylmethanamine | 2 | E | B | | | 23.8 mg, 43% | LC-MS rt 11.6 min MH+ 411. 1H NMR (400 MHz, MeOD) 8.66 (s, 1H), 8.50 (s, 1H), 7.85-7.80 (m, 1H), 7.53 (d, J = 8.7 Hz, 1H), 7.39 (dd, J = 8.7, 1.4 Hz, 1H), 7.34 (dd, J = 8.5, 6.7 Hz, 1H), 6.90 (dd, J = 11.2, 2.5 Hz, 1H), 6.79 (td, J = 8.4, 2.5 Hz, 1H), 4.61 (s, 2H), 4.21 (t, J = 5.8 Hz, 2H), 3.18 (t, J = 5.7 Hz, 2H), 2.87 (s, 6H), 2.09 (s, 3H). |

-continued

| Ex No | Structure | SM Intermediate N° | Mesyl method | THP method | Reductive amination | Boc Deprotection | Yield | Characterisation |
|---|---|---|---|---|---|---|---|---|
| 37 | 1-(6-(4-fluoro-2-(2-(1,3,5-trimethyl-1H-pyrazol-4-yl)ethoxy)phenyl)-[1,2,4]triazolo[4,3-a]pyridin-3-yl)-N,N-dimethylmethanamine | 11 | B | | | | 40 mg; 28% | LC-MS rt 10.5 min MH+ 423 $^1$H NMR (400 MHz, Methanol-d4) 8.54 (d, J = 1.4 Hz, 1H), 8.20 (s, 1H), 7.72 (d, J = 9.4 Hz, 1H), 7.52 (dd, J = 9.3, 1.4 Hz, 1H), 7.43 (dd, J = 8.5, 6.6 Hz, 1H), 6.94 (dd, J = 10.9, 2.4 Hz, 1H), 6.82 (td, J = 8.3, 2.4 Hz, 1H), 4.30 (s, 2H), 4.12 (t, J = 6.6 Hz, 2H), 3.60 (s, 3H), 2.81 (t, J = 6.6 Hz, 2H), 2.51 (s, 6H), 1.99 (s, 3H), 1.98 (s, 3H). |
| 38 | 1-(6-(4-fluoro-2-(2-(4-methylthiazol-5-yl)ethoxy)phenyl)-[1,2,4]triazolo[4,3-a]pyridin-3-yl)-N-methylmethanamine | 12 | B | | | A | 46 mg; 56% | LC-MS rt 10.3 min MH+ 398. $^1$H NMR (400 MHz, Methanol-d4) δ 8.66 (s, 1H), 8.50 (d, J = 1.4 Hz, 1H), 8.41 (s, 1H), 7.72 (d, J = 9.5 Hz, 1H), 7.51 (dd, J = 9.5, 1.5 Hz, 1H), 7.46 (dd, J = 8.5, 6.6 Hz, 1H), 7.00 (dd, J = 11.1, 2.5 Hz, 1H), 6.86 (td, J = 8.3, 2.4 Hz, 1H), 4.63 (s, 2H), 4.30 (t, J = 5.9 Hz, 2H), 3.26 (t, J = 5.8 Hz, 2H), 2.73 (s, 3H), 2.21 (s, 3H). |

| Ex No | Structure | SM Intermediate N° | Mesyl method | THP method | Reductive amination | Boc Deprotection | Yield | Characterisation |
|---|---|---|---|---|---|---|---|---|
| 39 | 1-(6-(4-fluoro-2-(2-(1,3,5-trimethyl-1H-pyrazol-4-yl)ethoxy)phenyl)-[1,2,4]triazolo[4,3-a]pyridin-3-yl)-N-methylmethanamine | 13 | B | | | A | 53 mg; 61% | LC-MS rt 10.6 min MH+ 409. 1H NMR (400 MHz, Methanol-d4) 8.51-8.45 (m, 1H), 8.33 (s, 1H), 7.74 (d, J = 9.7 Hz, 1H), 7.54 (dd, J = 9.3, 1.5 Hz, 1H), 7.44 (dd, J = 8.5, 6.5 Hz, 1H), 6.97 (dd, J = 11.2, 2.4 Hz, 1H), 6.84 (td, J = 8.3, 2.5 Hz, 1H), 4.69 (s, 2H), 4.13 (t, J = 6.5 Hz, 2H), 3.60 (s, 3H), 2.85-2.77 (m, 5H), 2.02 (s, 3H), 1.95 (s, 3H). |
| 40 | 1-(6-(4-chloro-2-(2-(4-methylthiazol-5-yl)ethoxy)phenyl)-[1,2,4]triazolo[4,3-a]pyridin-3-yl)-N,N-dimethylmethanamine | 13 | B | | | | 28 mg; 24% | LC-MS rt 11.2 min MH+ 428 1H NMR (400 MHz, Chloroform-d) δ 8.49 (s, 1H), 8.45-8.39 (m, 1H), 7.72 (d, J = 9.4 Hz, 1H), 7.36-7.26 (m, 2H), 7.08 (dd, J = 8.1, 2.0 Hz, 1H), 6.98 (d, J = 2.0 Hz, 1H), 4.19 (t, J = 6.3 Hz, 2H), 4.00 (s, 2H), 3.21 (t, J = 6.3 Hz, 2H), 2.31 (s, 6H), 2.26 (s, 5H). |

-continued

| Ex No | Structure | SM Intermediate N° | Mesyl method | THP method | Reductive amination | Boc Deprotection | Yield | Characterisation |
|---|---|---|---|---|---|---|---|---|
| 41 | 1-(6-(4-chloro-2-(2-(1,3,5-trimethyl-1H-pyrazol-4-yl)ethoxy)phenyl)-[1,2,4]triazolo[4,3-a]pyridin-3-yl)-N,N-dimethylmethanamine | 4 | B | | | | 42 mg; 31% | LC-MS rt 10.5 min MH+ 423 ¹H NMR (400 MHz, Methanol-d4) δ 8.58-8.51 (m, 1H), 8.26 (s, 1H), 7.72 (d, J = 9.3 Hz, 1H), 7.52 (dd, J = 9.8, 1.8 Hz, 1H), 7.40 (d, J = 8.2 Hz, 1H), 7.16 (d, J = 2.0 Hz, 1H), 7.09 (dd, J = 8.0, 1.9 Hz, 1H), 4.15 (s, 2H), 4.12 (t, J = 6.7 Hz, 2H), 3.60 (s, 3H), 2.81 (t, J = 6.5 Hz, 2H), 2.39 (s, 6H), 1.98 (s, 6H). |
| 42 | 1-(6-(4-fluoro-2-(2-(3-isobutyl-1,5-dimethyl-1H-pyrazol-4-yl)ethoxy)phenyl)-[1,2,4]triazolo[4,3-a]pyridin-3-yl)-N,N-dimethylmethanamine | 11 | B | | | | 42 mg; 25% | LC-MS rt 12.0 min, MH+ 465. ¹H NMR (400 MHz, Methanol-d4) δ 8.51 (d, J = 6.3 Hz, 1H), 8.26 (s, 1H), 7.79-7.65 (m, 1H), 7.53 (dd, J = 9.6, 1.6 Hz, 1H), 7.44 (dd, J = 8.5, 6.6 Hz, 1H), 6.94 (ddd, J = 11.1, 5.2, 2.5 Hz, 1H), 6.83 (td, J = 8.3, 2.5 Hz, 1H), 4.22-4.03 (m, 4H), 3.63 (s, 3H), 2.83 (t, J = 6.6 Hz, 2H), 2.37 (s, 6H), 2.22 (d, J = 7.4 Hz, 2H), 2.02 (s, 3H), 1.90-1.71 (m, 1H), 0.88-0.72 (m, 6H). |

-continued

| Ex No | Structure | SM Intermediate N° | Mesyl method | THP method | Reductive amination | Boc Deprotection | Yield | Characterisation |
|---|---|---|---|---|---|---|---|---|
| 43 | 1-(6-(4-fluoro-2-(2-(5-isobutyl-1,3-dimethyl-1H-pyrazol-4-yl)ethoxy)phenyl)-[1,2,4]triazolo[4,3-a]pyridin-3-yl)-N,N-dimethylmethanamine | 11 | B | | | | 51 mg; 30% | LC-MS rt 12.2 min, MH+ 465. $^1$H NMR (400 MHz, Methanol-d4) 8.53 (d, J = 1.5 Hz, 1H), 8.21 (s, 1H), 7.72 (d, J = 9.5 Hz, 1H), 7.51 (dd, J = 9.6, 1.5 Hz, 1H), 7.43 (dd, J = 8.5, 6.6 Hz, 1H), 6.98-6.90 (m, 1H), 6.82 (td, J = 8.3, 2.4 Hz, 1H), 4.28 (s, 2H), 4.14 (t, J = 6.6 Hz, 2H), 3.63 (s, 3H), 2.82 (t, J = 6.6 Hz, 2H), 2.49 (s, 6H), 2.26 (d, J = 7.5 Hz, 2H), 2.02 (s, 3H), 1.81-1.67 (m, 1H), 0.82 (d, J = 6.5 Hz, 6H). |
| 45 | 4-(2-{2-[3-(azetidin-3-yl)-[1,2,4]triazolo[4,3-a]pyridin-6-yl]-5-fluorophenoxy}ethyl)-1,3,5-trimethyl-1H-pyrazole | 15 | B | | | B | 71 mg, ~100% | LC-MS rt 10.8 min MH+ 421. $^1$H NMR (400 MHz, DMSO-d6) δ 8.40 (s, 1H), 7.78 (d, 1H), 7.56 (d, 1H), 7.40 (dd, 1H), 7.02 (dd, 1H), 6.88 (td, 1H), 4.68 (m, 1H), 4.43 (m, 4H), 4.03 (t, 2H), 3.58 (s, 3H), 2.71 (t, 2H), 1.97 (s, 3H), 1.90 (s, 3H). |

| Ex No | Structure | | SM Intermediate N° | General Procedure | | | | Yield | Characterisation |
|---|---|---|---|---|---|---|---|---|---|
| | | | | Mesyl method | THP method | Reductive amination | Boc Deprotection | | |
| 48 | 4-[2-(5-fluoro-2-{3-[(methylamino)methyl]-[1,2,4]triazolo[4,3-a]pyridin-6-yl}phenoxy)ethyl]-N,N,1,5-tetramethyl-1H-pyrazole-3-carboxamide | | 13 | B | | | B | 15 mg, ~100% | LC-MS rt 10.3 min MH+ 466. 1H NMR (400 MHz, DMSO-d6) δ 9.37 (br.s, 2H), 8.71 (s, 1H), 7.78 (d, 1H), 7.52 (d, 1H), 7.49 (dd, 1H), 7.11 (dd, 1H), 6.91 (td, 1H), 4.78 (s, 2H), 4.09 (t, 2H), 3.65 (s, 3H), 3.04 (s, 3H), 2.88 (s, 3H), 2.81 (t, 2H), 2.67 (t, 3H), 1.99 (s, 3H). |
| 49 | 1-(5-(3,4-difluoro-2-(2-(1,3,5-trimethyl-1H-pyrazol-4-yl)ethoxy)phenyl)-1-methyl-1H-indazol-3-yl)-N,N-dimethylmethanamine | | 17 | | | E | | 170 mg, 99% | LC-MS rt 12.2 min (5-98%) MH+ 454 1H NMR (400 MHz, Chloroform-d) δ 7.85 (s, 1H), 7.45 (d, J = 8.5 Hz, 1H), 7.31 (d, J = 8.8 Hz, 1H), 7.07 (ddd, J = 8.3, 5.7, 2.1 Hz, 1H), 6.91 (q, J = 8.6 Hz, 1H), 4.04 (s, 3H), 3.81 (s, 3H), 3.70 (t, J = 7.5 Hz, 2H), 3.53 (s, 3H), 2.55 (t, J = 7.6 Hz, 2H), 2.29 (s, 6H), 1.89 (s, 3H), 1.85 (s, 3H). |

-continued

| Ex No | Structure | SM Intermediate N° | Mesyl method | THP method | Reductive amination | Boc Deprotection | Yield | Characterisation |
|---|---|---|---|---|---|---|---|---|
| 53 | [(6-{4-fluoro-2-[2-(1,3,5-trimethyl-1H-pyrazol-4-yl)ethoxy]phenyl}imidazo[1,2-a]pyridin-3-yl)methyl](methyl)amine | 24 | B | | | B | 44 mg, 99% | hplc rt 3.9 min LC-MS MH+ 408; 1H NMR (400 MHz, DMSO-d6) δ 9.70 (s, 1H), 9.18 (s, 1H), 8.40 (s, 1H), 8.07 (d, 1H), 7.99 (d, 1H), 7.72 (td, 1H), 7.14 (dd, 1H), 6.99 (td, 1H), 4.73 (s, 2H), 4.07 (t, 2H), 3.63 (s, 3H), 2.74 (t, 2H), 2.67 (s, 3H), 2.03 (s, 3H), 1.97 (s, 3H). |
| 54 | {[6-(2-{2-[1-(difluoromethyl)-3,5-dimethyl-1H-pyrazol-4-yl]ethoxy}-4-fluorophenyl)-[1,2,4]triazolo[4,3-a]pyridin-3-yl]methyl}(methyl)amine | 12 | B | | | B | 25 mg, 94% | hplc rt 4.7 min LC-MS MH+ 445; 1H NMR (400 MHz, DMSO-d6) δ 8.96 (s, 1H), 8.24 (s, 1H), 7.95 (d, 1H), 7.89 (d, 1H), 7.51 (dd, 1H), 7.05 (d, 1H), 6.93 (d, 1H), 4.66 (s, 2H), 3.97 (t, 2H), 3.58 (s, 3H), 2.70 (t, 2H), 2.63 (s, 3H), 1.94 (s, 3H), 1.84 (s, 3H). |

| Ex No | Structure | SM Intermediate N° | Mesyl method | THP method | Reductive amination | Boc Deprotection | Yield | Characterisation |
|---|---|---|---|---|---|---|---|---|
| 55 | {[6-(2-{2-[1,5-dimethyl-3-(trifluoromethyl)-1H-pyrazol-4-yl]ethoxy}-4-fluorophenyl)-[1,2,4]triazolo[4,3-a]pyridin-3-yl]methyl}(methyl)amine | 12 | B | | | B | 80 mg, 97% | LC-MS MH+ 463; 1H NMR (400 MHz, DMSO-d6) δ 9.30 (s, 2H), 8.71 (s, 1H), 7.79 (d, 1H), 7.49 (td, 1H), 7.47 (d, 1H), 7.12 (dd, 1H), 6.96 (td, 1H), 4.81 (t, 2H), 4.10 (t, 2H), 3.72 (s, 3H), 2.87 (t, 2H), 2.71 (t, 2H), 2.01 (s, 3H) |
| 66 | 4-(2-{2-[3-(azetidin-3-yl)-[1,2,4]triazolo[4,3-a]pyridin-6-yl]-5-fluorophenoxy}ethyl)-N,N,1,5-tetramethyl-1H-pyrazole-3-carboxamide | 18 | B | | | C | 18 mg, 97% | LC-MS MH+ 478; 1H NMR (400 MHz, DMSO-d6) δ 9.05 (br.s 1H), 8.97 (br.s, 1H), 8.44 (s, 1H), 7.76 (d, 1H), 7.47 (d, 1H), 7.40 (td, 1H), 7.11 (dd, 1H), 6.92 (td, 1H), 4.72 (m, 2H), 4.45 (m, 4H), 4.10 (t, 2H), 3.67 (s, 3H), 3.06 (s, 3H), 2.88 (s, 3H), 2.84 (t, 2H), 2.01 (s, 3H). |

| Ex No | Structure | | SM Intermediate N° | General Procedure | | | | Yield | Characterisation |
|---|---|---|---|---|---|---|---|---|---|
| | | | | Mesyl method | THP method | Reductive amination | Boc Deprotection | | |
| 67 | 4-[2-(5-fluoro-2-{3-[2-(methylamino)ethyl]-[1,2,4]triazolo[4,3-a]pyridin-6-yl}phenoxy)ethyl]-N,N,1,5-tetramethyl-1H-pyrazole-3-carboxamide | | 16 | B | | | B | 4 mg, 60% | LC-MS MH+ 480; 1H NMR (400 MHz, CD3OD) δ 8.88 (s, 1H), 8.23 (d, 1H), 8.04 (d, 1H), 7.54 (td, 1H), 7.05 (dd, 1H), 6.91 (td, 1H), 4.20 (t, 2H), 3.77 (s, 3H), 3.75-3.70 (m, 4H), 3.07 (s, 3H), 2.97-2.90 (m, 5H), 2.87 (s, 3H), 2.19 (s, 3H). |
| 69 | 2-(6-{4-fluoro-2-[2-(1,3,5-trimethyl-1H-pyrazol-4-yl)ethoxy]phenyl}imidazo[1,2-a]pyridin-3-yl)ethan-1-amine | | 22 | B | | | B | 10 mg, 83% | LC-MS MH+ 406; 1H NMR (400 MHz, DMSO-d6) δ 8.92 (s, 1H), 8.14 (s, 1H), 8.10 (br.s, 2H), 8.00 (dd, 1H), 7.55 (td, 1H), 7.15 (dd, 1H), 6.97 (td, 1H), 4.05 (t, 2H), 3.59 (s, 3H), 3.42 (t, 2H), 3.20 (m, 2H), 2.71 (t, 2H), 2.02 (s, 3H), 1.92 (s, 3H). |

Example 31

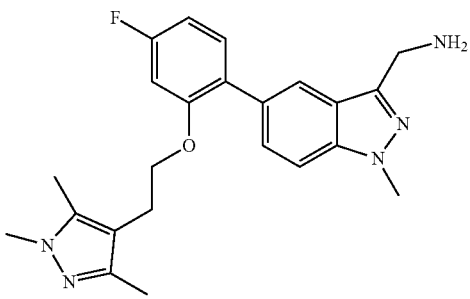 [SMILES: Cc1nn(C)c(C)c1CCOc1cc(F)ccc1-c1ccc2c(c1)c(CN)nn2C]

(5-(4-fluoro-2-(2-(1,3,5-trimethyl-1H-pyrazol-4-yl)ethoxy)phenyl)-1-methyl-1H-indazol-3-yl)methanamine Intermediate 6 (240 mg; 0.59 mmol) in ethanol (10 mL) was treated with hydroxylamine hydrochloride (74 mg; 1.06 mmol) and sodium acetate (97 mg; 1.18 mmol) and the reaction was stirred for 15 hours at room temperature. Water (50 mL) was added and the resulting solid oxime isolated by filtration (197 mg colourless solid, MH$^+$ 422). mp 230-233° C. The solid (100 mg) in methanol (6 mL) was treated with zinc dust (155 mg, 2.4 mmol) and ammonium formate (150 mg, 2.4 mmol). The suspension was heated under reflux for 4 hours before being cooled to room temperature and filtered through celite. Methanol was removed under reduced pressure and the residue purified by LC-MS by gradient elution with methanol/water/formic acid (50:50:0.1 to 98:2:0.1). Fractions containing the desired product were combined and evaporated under reduced pressure to give the title compound as a colourless solid formate salt (30 mg, 28%). LC-MS rt 11.9 min (5-98%) MH$^+$ 408. $^1$H NMR (400 MHz, MeOD) δ 8.56 (s, 1H), 7.70 (s, 1H), 7.54 (d, J=8.8 Hz, 1H), 7.45 (dd, J=8.7, 1.4 Hz, 1H), 7.30 (dd, J=8.4, 6.7 Hz, 1H), 6.89 (dd, J=11.1, 2.4 Hz, 1H), 6.77 (td, J=8.3, 2.4 Hz, 1H), 4.45 (s, 2H), 4.14 (s, 3H), 4.06 (t, J=6.3 Hz, 2H), 3.56 (s, 3H), 2.74 (t, J=6.3 Hz, 2H), 1.92 (s, 3H), 1.85 (s, 3H).

Example 32

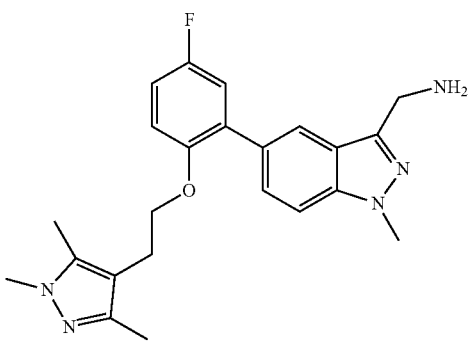 [SMILES: Cc1nn(C)c(C)c1CCOc1ccc(F)cc1-c1ccc2c(c1)c(CN)nn2C]

1-(5-(5-fluoro-2-(2-(1,3,5-trimethyl-1H-pyrazol-4-yl)ethoxy)phenyl)-1-methyl-1H-indazol-3-yl)methanamine Intermediate 9 (50 mg; 0.123 mmol) in ethanol (3 mL) was treated with hydroxylamine hydrochloride (15 mg; 0.22 mmol) and sodium acetate (20 mg; 0.25 mmol) and the reaction was stirred for 15 hours at room temperature. Water (20 mL) was added and the resulting solid oxime isolated by filtration (31 mg colourless solid, MH$^+$ 422). The solid (31 mg) in methanol (2 mL) was treated with zinc dust (48 mg, 0.70 mmol) and ammonium formate (46 mg, 0.70 mmol). The suspension was heated under reflux for 3 hours before being cooled to room temperature and filtered through celite. Methanol was removed under reduced pressure and the residue purified by LC-MS by gradient elution with methanol/water/formic acid (50:50:0.1 to 98:2:0.1). Fractions containing the desired product were combined and evaporated under reduced pressure to give the title compound as a colourless solid formate salt (7.7 mg, 23%). LC-MS rt 2.91 min (50-98%) MH$^+$ 408. $^1$H NMR (400 MHz, MeOD) δ 8.54 (s, 1H), 7.76 (s, 1H), 7.60-7.48 (m, 2H), 7.12-7.00 (m, 3H), 4.49 (s, 2H), 4.15 (s, 3H), 3.99 (t, J=6.4 Hz, 2H), 3.54 (s, 3H), 2.71 (t, J=6.4 Hz, 2H), 1.92 (s, 3H), 1.87 (s, 3H).

Example 33

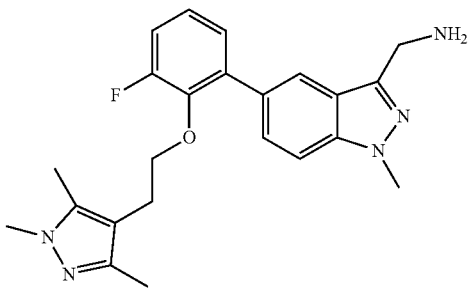 [SMILES: Cc1nn(C)c(C)c1CCOc1c(F)cccc1-c1ccc2c(c1)c(CN)nn2C]

1-(5-(3-fluoro-2-(2-(1,3,5-trimethyl-1H-pyrazol-4-yl)ethoxy)phenyl)-1-methyl-1H-indazol-3-yl)methanamine Intermediate 10 (100 mg; 0.25 mmol) in ethanol (6 mL) was treated with hydroxylamine hydrochloride (31 mg; 0.44 mmol) and sodium acetate (40 mg; 0.49 mmol) and the reaction was stirred for 15 hours at room temperature. Water (20 mL) was added and the resulting solid oxime-isolated by filtration (68 mg colourless solid, MH$^+$ 422). The solid (68 mg) in methanol (4 mL) was treated with zinc dust (105 mg, 1.61 mmol) and ammonium formate (101 mg, 0.61 mmol). The suspension was heated under reflux for 3 hours before being cooled to room temperature and filtered through celite. Methanol was removed under reduced pressure and the residue purified by LC-MS by gradient elution with methanol/water/formic acid (50:50:0.1 to 98:2:0.1). Fractions containing the desired product were combined and evaporated under reduced pressure to give the title compound as a colourless solid formate salt (10.1 mg, 14%). LC-MS rt 3.11 min (50-98%) MH$^+$ 408; $^1$H NMR (400 MHz, MeOD) δ 8.38 (s, 1H), 7.78-7.74 (m, 1H), 7.57-7.50 (m, 2H), 7.20-7.13 (m, 3H), 4.50 (s, 2H), 4.16 (s, 3H), 3.76 (t, J=6.6 Hz, 2H), 3.43 (s, 3H), 2.59 (t, J=6.6 Hz, 2H), 1.92 (s, 3H), 1.85 (s, 3H).

Example 34

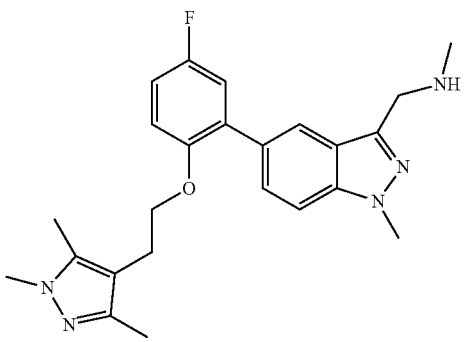

1-(5-(5-fluoro-2-(2-(1,3,5-trimethyl-1H-pyrazol-4-yl)ethoxy)phenyl)-1-methyl-1H-indazol-3-yl)-N-methylmethanamine Intermediate 9 (40 mg; 0.1 mmol) in THF (5 mL) was treated with a solution of methylamine in ethanol (2M, 2 ml, 40 mmol) then stirred at room temperature overnight. The mixture was evaporated under reduced pressure and the residue redissolved in ethanol (5 ml) then treated with sodium borohydride (19 mg; 0.49 mmol) and stirred at room temperature for 4 h. Excess borohydride was quenched by addition of hydrochloric acid (1M, 2 ml) and the mixture was evaporated under reduced pressure. The residue was partitioned between ethyl acetate and saturated sodium carbonate solution (10 ml each). The organic phase was dried (MgSO$_4$) and evaporated under reduced pressure. The crude product was purified by LC-MS by gradient elution with methanol/water/formic acid (20:80:0.1 to 98:2:0.1). Fractions containing the desired product were combined and evaporated under reduced pressure to give the title compound as a colourless solid formate salt (5.6 mg, 12%). LC-MS rt 11.9 min (5-98%) MH$^+$ 422; $^1$H NMR (400 MHz, MeOD) δ 8.38 (s, 1H), 7.78-7.74 (m, 1H), 7.57-7.50 (m, 2H), 7.20-7.13 (m, 3H), 4.50 (s, 2H), 4.16 (s, 3H), 3.76 (t, J=6.6 Hz, 2H), 3.43 (s, 3H), 2.59 (t, J=6.6 Hz, 2H), 1.92 (s, 3H), 1.85 (s, 3H).

Example 35

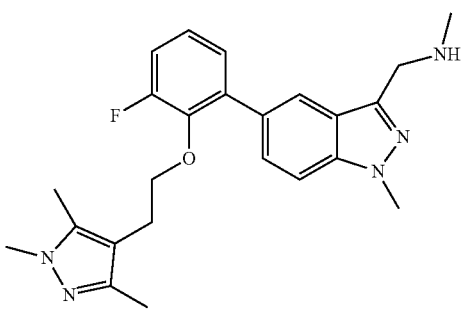

1-(5-(3-fluoro-2-(2-(1,3,5-trimethyl-1H-pyrazol-4-yl)ethoxy)phenyl)-1-methyl-1H-indazol-3-yl)-N-methylmethanamine Intermediate 10 (40 mg; 0.1 mmol) in THF (5 mL) was treated with a solution of methylamine in ethanol (2M, 2 ml, 40 mmol) then stirred at room temperature overnight. The mixture was evaporated under reduced pressure and the residue redissolved in ethanol (5 ml) then treated with sodium borohydride (19 mg; 0.49 mmol) and stirred at room temperature for 4 h. Excess borohydride was quenched by addition of hydrochloric acid (1M, 2 ml) and the mixture was evaporated under reduced pressure. The residue was partitioned between ethyl acetate and saturated sodium carbonate solution (10 ml each). The organic phase was dried (MgSO$_4$) and evaporated under reduced pressure. The crude product was purified by LC-MS by gradient elution with methanol/water/formic acid (20:80:0.1 to 98:2:0.1). Fractions containing the desired product were combined and evaporated under reduced pressure to give the title compound as a colourless solid formate salt (6.6 mg, 14%). LC-MS rt 12.1 min (5-98%) MH$^+$ 422; $^1$H NMR (400 MHz, MeOD) δ 7.81 (s, 1H), 7.63-7.46 (m, 2H), 7.14-6.99 (m, 3H), 4.59 (s, 2H), 4.17 (s, 3H), 4.00 (t, J=6.5 Hz, 2H), 3.56 (s, 3H), 2.85 (s, 3H), 2.72 (t, J=6.4 Hz, 2H), 1.93 (s, 3H), 1.89 (s, 3H).

Example 44

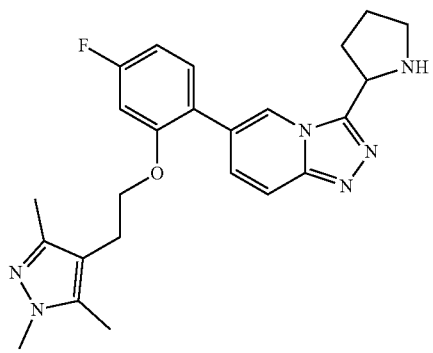 [SMILES: Cc1nn(C)c(C)c1CCOc1cc(F)ccc1-c1ccc2nnc(C3CCCN3)n2c1]

4-(2-{5-fluoro-2-[3-(pyrrolidin-2-yl)-[1,2,4]triazolo[4,3-a]pyridin-6-yl]phenoxy}ethyl)-1,3,5-trimethyl-1H-pyrazole Step 1

According to the general method for mesyl transfer (Method B), intermediate 14 (205 mg, 0.43 mmol was reacted with 2-(1,3,5-trimethyl-1H-pyrazol-4-yl)ethanol (120 mg, 0.78 mmol) and cesium carbonate (190 mg, 0.58 mmol) in DMF (5.0 ml). Purification by hplc by elution with acetonitrile/water/ammonium carbonate followed by freeze-drying of the appropriate fractions provided tert-butyl 2-(6-{4-fluoro-2-[2-(1,3,5-trimethyl-1H-pyrazol-4-yl)ethoxy]phenyl}-[1,2,4]triazolo[4,3-a]pyridin-3-yl)pyrrolidine-1-carboxylate as a solid (72 mg; 31%). $^1$H NMR (400 MHz, DMSO-d6) as a mixture of rotamers δ 8.51 (d, 1H), 7.71 (m, 1H), 7.39 (m, 2H), 7.07 (d, 1H), 6.91 (dd, 1H), 5.44 (m, 1H), 4.03 (t, 2H), 3.54-3.48 (m, 5H), 2.49 (m, 2H), 2.32 (m, 2H), 2.13 (m, 2H), 1.97 (s, 3H), 1.92 (s, 3H), 1.33+0.92 (s, 9H).

Step 2

According to the general method for Boc deprotection, the product from Step 1 (70 mg) was dissolved in dioxane (2 ml) and treated with a solution of HCl in dioxane (4M, 3 ml). The solution was stirred at room temperature for 3 hr. The solvent was removed under reduced pressure and the residue triturated with diethyl ether. The crude product was dissolved in water and freeze-dried to provide the title compound as a hydrochloride salt (45 mg, 79%) LC-MS rt 10.8 min MH+ 435. $^1$H NMR (400 MHz, DMSO-d6) δ 8.55 (s, 1H), 7.77 (d, 1H), 7.50 (d, 1H), 7.43 (dd, 1H), 7.04 (dd, 1H), 6.90 (td, 1H), 5.32 (t, 1H), 4.06 (t, 2H), 3.58 (s, 3H), 3.39 (t, 2H), 2.73 (m, 2H), 2.21 (m, 1H), 2.10 (m, 1H), 1.97 (s, 3H), 1.90 (s, 3H).

Example 46

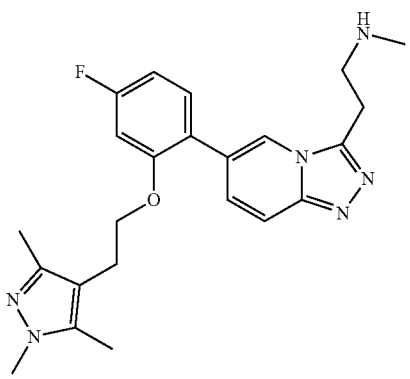 [SMILES: CNCCc1nnc2ccc(-c3ccc(F)cc3OCCc3c(C)nn(C)c3C)cn12]

[2-(6-{4-fluoro-2-[2-(1,3,5-trimethyl-1H-pyrazol-4-yl)ethoxy]phenyl}-[1,2,4]triazolo[4,3-a]pyridin-3-yl)ethyl](methyl)amine Step 1

According to the general method for mesyl transfer (Method B), intermediate 16 (220 mg, 0.47 mmol was reacted with 2-(1,3,5-trimethyl-1H-pyrazol-4-yl)ethanol (132 mg, 0.86 mmol) and cesium carbonate (209 mg, 0.64 mmol) in DMF (5.0 ml). The crude product was partially purified by column chromatography by elution with dichloromethane/acetone (80:20). Further purification by hplc by elution with acetonitrile/water/ammonium carbonate followed by freeze-drying of the appropriate fractions provided tert-butyl N-[2-(6-{4-fluoro-2-[2-(1,3,5-trimethyl-1H-pyrazol-4-yl)ethoxy]phenyl}-[1,2,4]triazolo[4,3-a]pyridin-3-yl)ethyl]-N-methylcarbamate as a solid (80 mg; 32%). $^1$H NMR (400 MHz, DMSO-d6) as a mixture of rotamers δ 8.51 (d, 1H), 7.71 (m, 1H), 7.39 (m, 2H), 7.07 (d, 1H), 6.91 (dd, 1H), 5.44 (m, 1H), 4.03 (t, 2H), 3.54-3.48 (m, 5H), 2.49 (m, 2H), 2.32 (m, 2H), 2.13 (m, 2H), 1.97 (s, 3H), 1.92 (s, 3H), 1.33+0.92 (s, 9H).

Step 2

According to the general method for Boc deprotection, the product from Step 1 (80 mg) was dissolved in dioxane (2 ml) and treated with a solution of HCl in dioxane (4M, 3 ml). The solution was stirred at room temperature for 3 hr. The solvent was removed under reduced pressure and the residue triturated with diethyl ether. The crude product was dissolved in water and freeze-dried to provide the title compound as a light yellow hydrochloride salt (50 mg, 77%) LC-MS rt 10.9 min MH+ 423. $^1$H NMR (400 MHz, DMSO-d6) δ 9.08 (br.s, 2H), 8.75 (s, 1H), 7.90 (d, 1H), 7.75 (d, 1H), 7.51 (t, 1H), 7.12 (dd, 1H), 6.96 (td, 1H), 4.08 (t, 2H), 3.64 (s, 3H), 3.60 (t, 2H), 3.44 (t, 2H), 2.76 (m, 2H), 2.62 (t, 2H), 2.04 (s, 3H), 1.99 (s, 3H).

Example 47

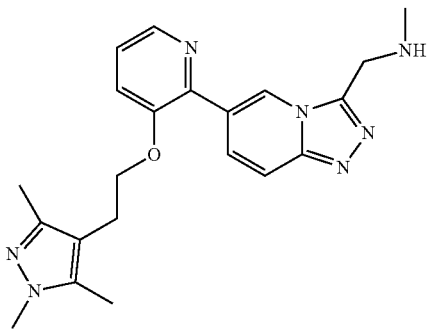 [SMILES: CNCc1nnc2ccc(-c3ncccc3OCCc3c(C)nn(C)c3C)cn12]

N-methyl[(6-{3-[2-(1,3,5-trimethyl-1H-pyrazol-4-yl)ethoxy]pyridin-2-yl}-[1,2,4]triazolo[4,3-a]pyridin-3-yl)methyl]amine Step 1

A solution of tert-butyl ((6-bromo-[1,2,4]triazolo[4,3-a]pyridin-3-yl)methyl)(methyl)carbamate (Intermediate 12, Step 2, 550 mg, 1.61 mmol), bis(pinacolato)diboron (491 mg, 1.9 mmol) and potassium acetate (474 mg, 4.8 mmol) in dioxane (10 ml) was degassed with argon for 15 min, before addition of dichloro[1,1'-bis(diphenylphosphino)ferrocene] palladium(II) dichloromethane adduct (131 mg, 0.61 mmol). The reaction mixture was heated under reflux overnight under an argon atmosphere, cooled to room temperature and filtered through Celite, washing with ethyl acetate. The organic phase was dried over Na$_2$SO$_4$, concentrated under reduced pressure and the crude product purified by flash column chromatography by elution with dichloromethane/methanol (95:5) to give tert-butyl N-methyl-N-{[6-(4,4,5,5-tetramethyl-1,3,2-dioxaborolan-2-yl)-[1,2,4]triazolo[4,3-a]pyridin-3-yl]methyl}carbamate as a dark solid contaminated with starting borane.

Step 2

A portion of the crude tert-butyl N-methyl-N-{[6-(4,4,5,5-tetramethyl-1,3,2-dioxaborolan-2-yl)-[1,2,4]triazolo[4,3-a]pyridin-3-yl]methyl}carbamate (100 mg, 0.84 mmol) was dissolved in dioxane (10 ml) and treated with 2-bromo-3-[2-(1,3,5-trimethyl-1H-pyrazol-4-yl)ethoxy]pyridine (213 mg, 1.7 mmol) and a solution of potassium carbonate (173 mg, 1.26 mmol) in water (2 ml). The mixture was purged with argon for 15 min before addition of dichloro[1,1'-bis(diphenylphosphino)ferrocene]palladium(II) dichloromethane adduct (34 mg, 0.04 mmol) and the reaction mixture was heated under reflux overnight under an argon atmosphere. After being cooled to room temperature, the mixture was diluted with ethyl acetate, washed with saturated sodium bicarbonate solution, water and brine. The organic phase was dried over Na$_2$SO$_4$, concentrated under reduced pressure and the crude product purified by flash column chromatography by elution with dichloromethane/methanol (96:4) to give tert-butyl N-methyl-N-[(6-{3-[2-(1,3,5-trimethyl-1H-pyrazol-4-yl)ethoxy]pyridin-2-yl}-[1,2,4]triazolo[4,3-a]pyridin-3-yl)methyl]carbamate as a solid (80 mg, 39%). $^1$H NMR (400 MHz, DMSO-d6) δ 9.01 (br.s, 1H), 8.25 (d, 1H), 7.93 (br.s, 1H), 7.80 (d, 1H), 7.83 (d, 1H), 7.40 (br.s, 1H), 5.00 (s, 2H), 4.11 (t, 2H) 3.53 (s, 3H), 2.95-2.75 (m, 5H), 2.02 (s, 3H), 1.97 (s, 3H), 1.35 (d, 9H).

Step 3

According to the general method for Boc deprotection, tert-butyl N-methyl-N-[(6-{3-[2-(1,3,5-trimethyl-1H-pyrazol-4-yl)ethoxy]pyridin-2-yl}-[1,2,4]triazolo[4,3-a]pyridin-3-yl)methyl]carbamate (80 mg) was dissolved in dioxane (5 ml) and treated with a solution of HCl in dioxane (4M, 5 ml). The solution was stirred at room temperature for 3 hr. The solvent was removed under reduced pressure and the residue triturated with diethyl ether. The crude product was dissolved in water and freeze-dried to provide the title compound as a light yellow hydrochloride salt (75 mg, 77%) LC-MS rt 9.2 min MH$^+$ 392. $^1$H NMR (400 MHz, DMSO-d6) δ 9.84 (br.s, 2H), 9.23 (s, 1H), 8.36 (d, 1H), 8.01 (d, 1H), 7.94 (d, 1H), 7.76 (d, 1H), 7.54 (m, 1H), 4.84 (s, 2H), 4.21 (t, 2H), 3.75 (s, 3H), 2.95 (t, 2H), 2.70 (s, 3H), 2.15 (s, 3H), 2.13 (s, 3H).

Example 50

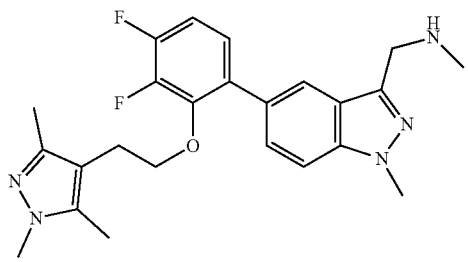 [SMILES: CNCc1nn(C)c2ccc(-c3ccc(F)c(F)c3OCCc3c(C)nn(C)c3C)cc12]

1-(5-(3, 4-difluoro-2-(2-(1,3,5-trimethyl-1H-pyrazol-4-yl)ethoxy)phenyl)-1-methyl-1H-indazol-3-yl)-N-methylmethanamine Intermediate 17 (140 mg, 0.42 mmol) was dissolved in a solution of methylamine in ethanol (33%, 10 ml) then stirred at room temperature for 2 days. The mixture was evaporated under reduced pressure and the residue redissolved in ethanol (10 ml) then treated with sodium borohydride (37 mg, mmol) and stirred at room temperature for 1 h. Excess borohydride was quenched by addition of hydrochloric acid (1M, 4 ml) and the mixture was evaporated under reduced pressure. The residue was basified with sodium hydroxide solution (10N) and extracted with DCM (2×20 ml). The organic phase was dried (Na$_2$SO$_4$) and evaporated under reduced pressure. The crude product was purified by column chromatography on silica by gradient elution with DCM/methanol/ammonia (95:5:0-95:5:1-90:10:2). Fractions containing the desired product were combined and evaporated under reduced pressure to give crude product, which was further purified by SCX chromatography by elution with 2M NH$_3$ in methanol. The basic eluent was evaporated to give the title compound as a colourless oil (110 mg, 60%). LC-MS rt 12.2 min (5-98%) MH$^+$ 440; $^1$H NMR (400 MHz, Chloroform-d) δ 7.81 (d, J=1.2 Hz, 1H), 7.46 (dd, J=8.6, 1.7 Hz, 1H), 7.33 (d, J=8.5 Hz, 1H), 7.07 (ddd, J=8.3, 5.9, 2.2 Hz, 1H), 6.93 (td, J=9.1, 7.2 Hz, 1H), 4.10 (s, 2H), 4.05 (s, 3H), 3.72 (t, J=7.6 Hz, 2H), 3.55 (s, 3H), 2.57 (t, J=7.6 Hz, 2H), 2.53 (s, 1H), 2.50 (s, 3H), 1.92 (s, 3H), 1.88 (s, 3H)

Example 51

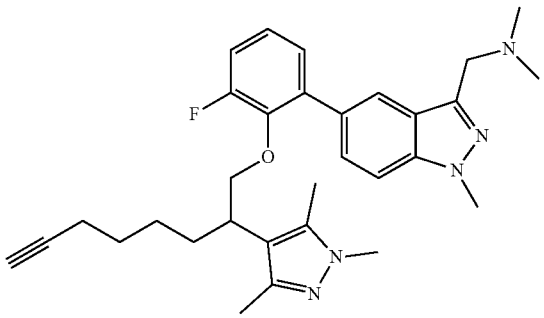 [SMILES: C#CCCCCC(COc1c(F)cccc1-c1ccc2c(c1)c(CN(C)C)nn2C)c1c(C)nn(C)c1C]

1-(5-(3-fluoro-2-((2-(1,3,5-trimethyl-1H-pyrazol-4-yl)oct-7-yn-1-yl)oxy)phenyl)-1-methyl-1H-indazol-3-yl)-N,N-dimethylmethanamine Intermediate 18 (48 mg, 0.13 mmol) and Intermediate 19 (52 mg, 0.22 mmol) were dissolved in dimethylformamide (DMF). Cesium carbonate (62 mg, 0.19 mmol) was added and the pale yellow mixture was stirred at 100° C. for 18 hr. The dark purple mixture obtained was diluted with EtOAc (40 mL), washed with water (2×50 mL), dried over Na$_2$SO$_4$, and concentrated in vacuo to give a brown oil. The crude product was purified by reversed-phase high-performance liquid chromatography by elution with 20-98% methanol in water (0.1% formic acid) over 18 min to give 1-(5-(3-fluoro-2-((2-(1,3,5-trimethyl-1H-pyrazol-4-yl)oct-7-yn-1-yl)oxy)phenyl)-1-methyl-1H-indazol-3-yl)-N,N-dimethylmethanamine as a brownish orange solid (5.1 mg, 8%). LC-MS rt 8.5 min (5-98%) MH$^+$ 516; ESI HRMS, found 516.3141 (C$_{31}$H$_{39}$N$_5$OF), MH$^+$ requires 516.3139. $^1$H NMR (CDCl$_3$, 400 MHz, 300 K) δ 7.91 (1H, s), 7.60 (1H, dd, J=8.7, 1.4 Hz), 7.38 (1H, d, J=8.7 Hz), 7.19-7.08 (3H, m), 4.16 (2H, s), 4.11 (3H, s), 3.87 (1H, m), 3.62 (3H, s), 2.53 (6H, s), 2.19 (1H, dd, J=14.3, 9.1 Hz), 1.96 (2H, td, J=6.9, 2.4 Hz), 1.94 (3H, s), 1.90 (3H, s), 1.89 (1H, t, J=2.6 Hz), 1.41-1.12 (6H, m).

Example 56

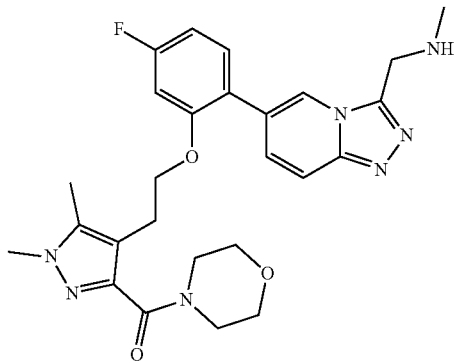

{[6-(2-{2-[1,5-dimethyl-3-(morpholine-4-carbonyl)-1H-pyrazol-4-yl]ethoxy}-4-fluorophenyl)-[1,2,4]triazolo[4,3-a]pyridin-3-yl]methyl}(methyl)amine Step 1

A solution of 2-(3-(((tert-butoxycarbonyl)(methyl)amino)methyl)-[1,2,4]triazolo[4,3-a]pyridin-6-yl)-5-fluorophenyl methanesulfonate (Intermediate 12, 140 mg, 0.37 mmol) in DMF (3 mL) was reacted 4-{[4-(2-chloroethyl)-1,5-dimethyl-1H-pyrazol-3-yl]carbonyl}morpholine (153 mg, 0.056 mmol) and cesium carbonate (428 mg, 1.31 mmol) at 90° C. for 16 hr. The reaction mixture was then diluted with ethyl acetate, and washed with water and brine, dried over sodium sulphate and concentrated. The crude product was purified by preparative HPLC (NH$_4$HCO$_3$:CH$_3$CN) to give tert-butyl N-({6-[2-(2-{1,5-dimethyl-3-[(morpholin-4-yl)carbonyl]-1H-pyrazol-4-yl}ethoxy)-4-fluorophenyl]-[1,2,4]triazolo[4,3-a]pyridin-3-yl}methyl)-N-methylcarbamate (27 mg, 12%). $^1$H NMR (400 MHz, DMSO-d$_6$) δ 8.44 (s, 1H), 7.75 (d, 1H), 7.50-7.30 (m, 2H), 7.11 (dd, 1H), 6.88 (td, 1H), 4.94 (s, 2H), 4.12 (t, 2H), 3.70-3.40 (m, 9H), 2.87 (t, 2H), 2.79 (s, 3H), 1.98 (s, 3H), 1.34 (s, 9H).

Step 2

According to the general method for Boc deprotection (method B), tert-butyl N-({6-[2-(2-{1,5-dimethyl-3-[(morpholin-4-yl)carbonyl]-1H-pyrazol-4-yl}ethoxy)-4-fluorophenyl]-[1,2,4]triazolo[4,3-a]pyridin-3-yl}methyl)-N-methylcarbamate (27 mg, 0.046 mmol) was dissolved a solution of HCl in dioxane (4M, 2 ml). The solution stirred at room temperature for 3 hr and was evaporated under reduced pressure. The crude product was triturated with ether then dissolved in water and freeze-dried to give the title compound (24 mg, 97%). hplc rt 7.5 min LC-MS MH$^+$ 508; $^1$H NMR (400 MHz, DMSO-d$_6$) δ 9.46 (s, 2H), 8.76 (s, 1H), 7.80 (d, 1H), 7.60-7.50 (m, 2H), 7.13 (dd, 1H), 6.95 (td, 1H), 4.82 (t, 2H), 4.14 (t, 2H), 3.70-3.60 (m, 5H), 3.55-3.45 (m, 6H), 2.87 (t, 2H), 2.70 (t, 2H), 2.03 (s, 3H)

Example 57

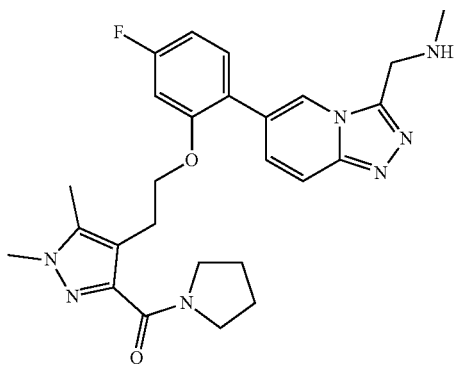

{[6-(2-{2-[1,5-dimethyl-3-(pyrrolidine-1-carbonyl)-1H-pyrazol-4-yl]ethoxy}-4-fluorophenyl)-[1,2,4]triazolo[4,3-a]pyridin-3-yl]methyl}(methyl)amine Step 1

2-(3-(((tert-butoxycarbonyl)(methyl)amino)methyl)-[1,2,4]triazolo[4,3-a]pyridin-6-yl)-5-fluorophenyl methanesulfonate (Intermediate 12, 20 mg, 0.05 mmol) was reacted with 2-{1,5-dimethyl-3-[(pyrrolidin-1-yl)carbonyl]-1H-pyrazol-4-yl}ethan-1-ol (20 mg, 0.08 mmol) and cesium carbonate (43 mg, 0.13 mmol) in DMF (0.5 ml) at 90° C. for 16 hr. The reaction mixture was cooled to RT, diluted with EtOAc and washed with water, brine, dried over Na$_2$SO$_4$ and concentrated under reduced pressure. The crude was purified by preparative TLC (3% MeOH-EtOAc) to afford tert-butyl N-({6-[2-(2-{1,5-dimethyl-3-[(pyrrolidin-1-yl)carbonyl]-1H-pyrazol-4-yl}ethoxy)-4-fluorophenyl]-[1,2,4]triazolo[4,3-a]pyridin-3-yl}methyl)-N-methylcarbamate (5 mg, 15%). $^1$H NMR (400 MHz, DMSO-d$_6$) δ 7.76 (d, 1H), 7.60 (m, 1H), 7.41 (d, 1H), 7.35 (m, 1H), 7.14 (dd, 1H), 6.90 (td, 1H), 4.95 (s, 2H), 4.13 (t, 2H), 3.7-3.6 (m, 5H), 3.40 (t, 2H), 2.93 (m, 2H), 2.79 (s, 3H), 1.93 (s, 3H), 1.77 (s, 3H), 1.33 (s, 9H).

Step 2

According to the general method for Boc deprotection (method B), tert-butyl N-({6-[2-(2-{1,5-dimethyl-3-[(pyrrolidin-1-yl)carbonyl]-1H-pyrazol-4-yl}ethoxy)-4-fluorophenyl]-[1,2,4]triazolo[4,3-a]pyridin-3-yl}methyl)-N-methylcarbamate (10 mg, 0.18 mmol) was treated with a solution of HCl in dioxane (4M, 1 mL). The solution stirred at room temperature for 2 hr and was evaporated under reduced pressure. The crude product was triturated with ether, then dissolved in water and freeze dried to give the title compound (8 mg, 96%). hplc rt 8.2 min LC-MS MH$^+$ 492; $^1$H NMR (400 MHz, DMSO-d$_6$) δ 9.29 (s, 2H), 8.73 (s, 1H), 7.80 (d, 1H), 7.55-7.40 (m, 2H), 7.16 (dd, 1H), 6.93 (td, 1H), 4.82 (s, 2H), 4.15 (t, 2H), 3.70 (s, 3H), 3.39 (t, 2H), 2.95 (t, 2H), 2.71 (s, 3H), 2.03 (s, 3H), 1.79 (s, 3H).

Example 58

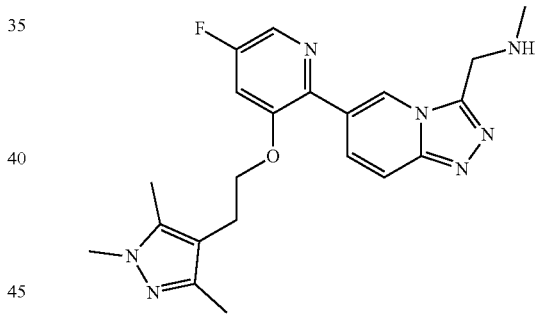

[(6-{5-fluoro-3-[2-(1,3,5-trimethyl-1H-pyrazol-4-yl)ethoxy]pyridin-2-yl}-[1,2,4]triazolo[4,3-a]pyridin-3-yl)methyl](methyl)amine Step 1

To a solution of tert-butyl N-methyl-N-{[6-(4,4,5,5-tetramethyl-1,3,2-dioxaborolan-2-yl)-[1,2,4]triazolo[4,3-a]pyridin-3-yl]methyl}carbamate (Example 47 Step 1, 240 mg, 0.85 mmol) in dioxane (20 mL) and water (4 mL) were added 2-chloro-5-fluoro-3-[2-(1,3,5-trimethyl-H-pyrazol-4-yl)ethoxy]pyridine (577 mg, 1.7 mmol) and potassium carbonate (350 mg, 2.5 mmol). The reaction mixture was purged with argon for 10 min. Pd(dppf)Cl$_2$.DCM (69 mg, 0.08 mmol) was added and the reaction mixture was heated at 100° C. overnight. The reaction mixture was then diluted with ethyl acetate and washed with sat. NaHCO$^3$, water and brine, dried over sodium sulphate and concentrated. The crude was then purified by column chromatography on silica eluting with 4% MeOH in DCM. Prep HPLC purification (CH3CN:NH4HCO3) afforded the product [tert-butyl N-[(6-{(6-{5-fluoro-3-[2-(1,3,5-trimethyl-1H-pyrazol-4-yl)

ethoxy]pyridin-2-yl)-[1,2,4]triazolo[4,3-a]pyridin-3-yl)methyl]-N-methylcarbamate (243 mg; 56%). $^1$H NMR (400 MHz, DMSO-d$_6$) δ 9.6 (br.s, 1H), 9.0 (br. s, 1H), 8.27 (s, 1H), 7:82-7.80 (m, 2H), 7.71 (d, 1H), 5.76 (s, 1H), 4.96 (s, 2H), 4.16 (t, 2H), 3.53 (s, 3H), 2.89 (t, 2H), 2.76 (s, 3H), 2.02 (s, 3H), 1.97 (s, 3H), 1.35 (s, 9H).

Step 2

According to the general method for Boc deprotection (method B), tert-butyl N-[(6-{5-fluoro-3-[2-(1,3,5-trimethyl-1H-pyrazol-4-yl)ethoxy]pyridin-2-yl}-[1,2,4]triazolo[4,3-a]pyridin-3-yl)methyl]-N-methylcarbamate (40 mg, 0.08 mmol) was dissolved in a solution of HCl in dioxane (4M, 2 ml). The solution stirred at room temperature for 2 hr and was evaporated under reduced pressure. The crude product was triturated with ether to give the crude product as a hydrochloride salt. Further purification was carried out by SCX chromatography, the sample was loaded in a methanolic solution, followed by elution with NH$_3$-MeOH to afford desired product as free base. The fraction was then treated with 2M HCl in ether at RT for 30 min. The mixture was concentrated under reduced pressure to afford desired product as hydrochloride salt. (30 mg, 93%). hplc rt 4.6 min LC-MS MH$^+$ 410; $^1$H NMR (400 MHz, DMSO-d$_6$) δ 9.38 (s, 1H), 9.01 (s, 1H), 8.34 (s, 1H), 7.88 (s, 2H), 7.63 (m, 1H), 4.81 (s, 2H), 4.15 (t, 2H), 3.60 (s, 3H), 2.85 (t, 2H), 2.73 (t, 2H), 2.06 (s, 3H), 2.00 (s, 3H).

Example 60

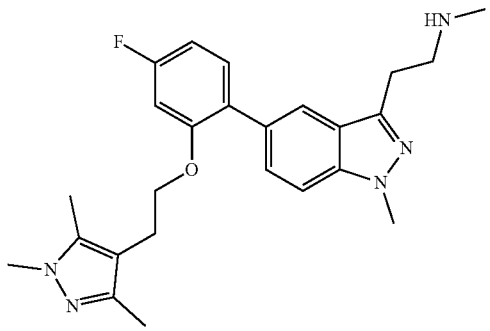

[2-(5-{4-fluoro-2-[2-(1,3,5-trimethyl-1H-pyrazol-4-yl)ethoxy]phenyl}-1-methyl-1H-indazol-3-yl)ethyl](methyl)amine Step 1

A solution of tert-butyl N-[2-(5-{4-fluoro-2-[2-(1,3,5-trimethyl-1H-pyrazol-4-yl)ethoxy]phenyl}-2H-indazol-3-yl)ethyl]carbamate (Intermediate 21, 27 mg, 0.05 mmol) in THF (0.7 mL) was treated with sodium hydride (50% dispersion in oil, 11 mg, 0.215 mmol) portionwise at 0° C. and warmed to RT over 30 min. The mixture was recooled to at 0° C. before addition of iodomethane (0.013 mL, 0.213 mmol). Conversion was incomplete hence a further charges of sodium hydride (50% dispersion in oil, 11 mg, 0.215 mmol) and iodomethane (0.013 mL, 0.213 mmol). were added and the reaction was stirred at rt for another 16 h. The reaction mixture was quenched with ice-water and extracted with EtOAc. The organic layer was washed with water, brine, dried over Na$_2$SO$_4$ and concentrated under reduced pressure. Crude was purified over prep TLC (3% MeOH-DCM) to afford desired product, tert-butyl N-[2-(5-{4-fluoro-2-[2-(1,3,5-trimethyl-1H-pyrazol-4-yl)ethoxy]phenyl}-1-methyl-1H-indazol-3-yl)ethyl]-N-methylcarbamate (12 mg; 42%), $^1$H NMR (400 MHz, DMSO-d$_6$) δ 7.70 (s, 1H), 7.54 (d, 1H), 7.41 (d, 1H), 7.33 (td, 1H), 6.99 (dd, 1H), 6.84 (td, 1H), 3.99 (m, 5H), 3.69 (m, 5H), 3.06 (t, 2H), 2.89 (s, 3H), 2.59 (t, 2H), 1.90 (s, 6H), 1.30-1.10 (m, 9H).

Step 2

According to the general method for Boc deprotection (method B) tert-butyl N-[2-(5-{4-fluoro-2-[2-(1,3,5-trimethyl-1H-pyrazol-4-yl)ethoxy]phenyl}-1-methyl-1H-indazol-3-yl)ethyl]-N-methylcarbamate (12 mg; 0.02 mmol) was a solution of HCl in dioxane (4M, 2 mL). The solution stirred at room temperature for 2 hr and was evaporated under reduced pressure. The crude product was triturated with ether then dissolved in water and freezer dried to give the title compound as a colourless solid (8 mg, 90%). Hplc rt 6.7 min, LC-MS MH$^+$ 436; $^1$H NMR (400 MHz, DMSO-d$_6$) δ 8.53 (s, 2H), 7.76 (s, 1H), 7.59 (d, 1H), 7.45 (d, 1H), 7.33 (td, 1H), 7.01 (dd, 1H), 6.86 (td, 1H), 4.03 (t, 2H), 3.70-3.60 (m, 5H), 3.30 (t, 2H), 2.70-2.60 (m, 5H), 1.92 (s, 3H), 1.89 (s, 3H).

Example 62

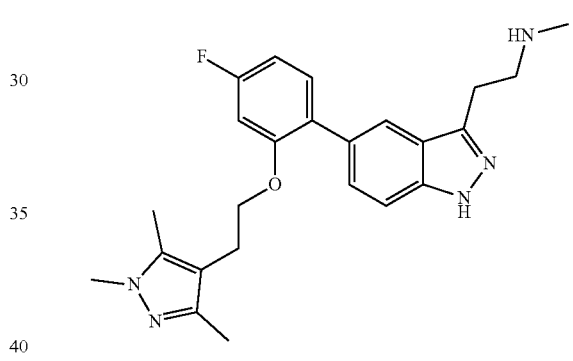

[2-(5-{4-fluoro-2-[2-(1,3,5-trimethyl-1H-pyrazol-4-yl)ethoxy]phenyl}-1H-indazol-3-yl)ethyl](methyl)amine To a stirred solution of tert-butyl N-[2-(5-{4-fluoro-2-[2-(1,3,5-trimethyl-1H-pyrazol-4-yl)ethoxy]phenyl}-2H-indazol-3-yl]carbamate (Intermediate 21, 30 mg, 0.06 mmol) in THF (1 mL) was added LiAlH$_4$ solution (2M in THF, 0.12 mL, 0.24 mmol) dropwise. The reaction mixture was heated under reflux for 2 hr. The reaction mixture was cooled to 0° C. and quenched with solid sodium sulphate decahydrate. The mixture was filtered through Celite, washed with THF and the filtrate was concentrated under reduced pressure. The crude was purified over prep TLC (6% MeOH-DCM-NH3) to afford desired product. The fraction was treated with 2M HCl in ether to afford title product as HCl salt (10 mg, 49%). LC-MS rt 1.43 min MH$^+$ 422; $^1$H NMR (400 MHz, DMSO-d$_6$) δ 7.66 (s, 1H), 7.46 (d, 1H), 7.30-7.28 (m, 2H), 6.92 (dd, 1H), 6.81 (td, 1H), 3.91 (t, 2H), 3.48 (s, 3H), 3.30 (t, 2H), 3.24 (t, 2H), 2.66 (t, 2H), 2.60 (s, 3H), 1.81 (s, 3H), 1.78 (s, 3H).

Example 63

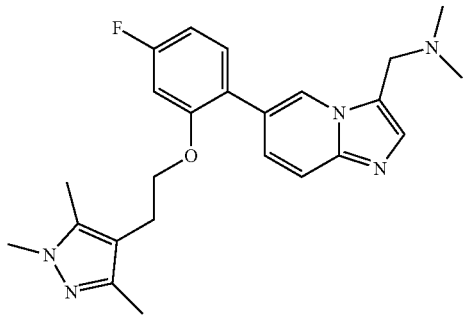

[(6-{4-fluoro-2-[2-(1,3,5-trimethyl-1H-pyrazol-4-yl)ethoxy]phenyl}imidazo[1,2-a]pyridin-3-yl)methyl]dimethylamine According to the general method for reductive amination, 6-{4-fluoro-2-[2-(1,3,5-trimethyl-1H-pyrazol-4-yl)ethoxy]phenyl}imidazo[1,2-a]pyridine-3-carbaldehyde (Intermediate 20, 45 mg, 0.11 mmol) was dissolved in methanol (1 mL) and was treated with dimethylamine solution (2M in THF, 0.11 mL, 0.22 mmol) followed by acetic acid (0.005 ml). The mixture was stirred at room temperature for 1 h before addition of solid sodium cyanoborohydride (10.9 mg, 0.17 mmol). The reaction mixture was stirred at room temperature overnight and was quenched with NaHCO₃ solution and extracted with DCM. The organic layer was dried over Na₂SO₄ and concentrated under reduced pressure. The crude product was purified by preparative TLC (3% MeOH in DCM) to afford title product (16 mg, 33%). Hplc rt 4.9 min, LC-MS MH⁺ 422; ¹H NMR (400 MHz, DMSO-de) δ 8.46 (s, 1H), 7.56 (d, 1H), 7.51 (s, 1H), 7.41 (td, 1H), 7.30 (d, 1H), 7.04 (dd, 1H), 6.89 (td, 1H), 4.00 (t, 2H), 3.73 (s, 2H), 3.51 (s, 3H), 2.68 (t, 2H), 2.14 (s, 6H), 1.89 (s, 3H), 1.88 (s, 3H).

Example 68

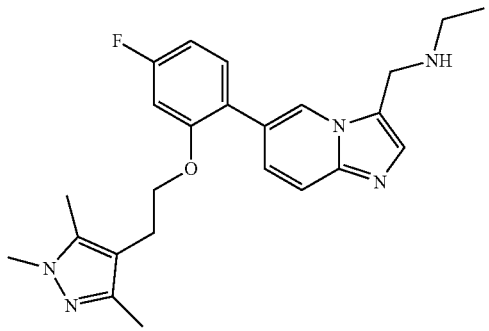 [SMILES: CCNCc1cnc2ccc(-c3ccc(F)cc3OCCc3c(C)nn(C)c3C)cn12]

Ethyl[(6-{4-fluoro-2-[2-(1,3,5-trimethyl-1H-pyrazol-4-yl)ethoxy]phenyl}imidazo[1,2-a]pyridin-3-yl)methyl]amine According to the general method for reductive amination, 6-{4-fluoro-2-[2-(1,3,5-trimethyl-1H-pyrazol-4-yl)ethoxy]phenyl}imidazo[1,2-a]pyridine-3-carbaldehyde (Intermediate 20, 45 mg, 0.11 mmol) was dissolved in methanol (1 mL) and was treated with ethylamine solution (2M in THF, 0.11 mL, 0.22 mmol) followed by acetic acid (0.005 ml). The mixture was stirred at room temperature for 1 h before addition of solid sodium cyanoborohydride (10.9 mg, 0.17 mmol). The reaction mixture was stirred at room temperature overnight and was quenched with NaHCO₃ solution and extracted with DCM. The organic layer was dried over Na₂SO₄ and concentrated under reduced pressure. The crude product was purified by preparative TLC (3% MeOH in DCM) to afford title product (16 mg, 33%). Hplc rt 4.9 min, LC-MS MH⁺ 422; ¹H NMR (400 MHz, DMSO-d₆) δ 8.52 (s, 1H), 7.55 (d, 1H), 7.54 (s, 1H), 7.43 (td, 1H), 7.30 (d, 1H), 7.04 (dd, 1H), 6.90 (td, 1H), 4.15 (s, 2H), 4.02 (t, 2H), 3.52 (s, 3H), 2.63 (m, 4H), 1.91 (s, 3H), 1.90 (s, 3H), 1.04 (t, 3H).

Example 70

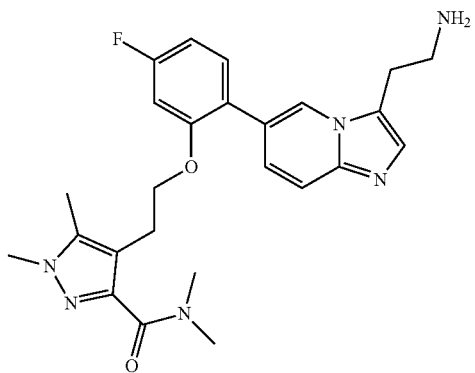 [SMILES: Cc1c(CCOc2cc(F)ccc2-c2ccc3ncc(CCN)n3c2)c(C(=O)N(C)C)nn1C]

4-(2-{2-[3-(2-aminoethyl)imidazo[1,2-a]pyridin-6-yl]-5-fluorophenoxy}ethyl)-N,N,1,5-tetramethyl-1H-pyrazole-3-carboxamide Step 1

A solution of tert-butyl N-{2-[6-(4-fluoro-2-hydroxyphenyl)imidazo[1,2-a]pyridin-3-yl]ethyl}carbamate (Intermediate 22 step 2, 65 mg, 0.14 mmol) in DMF (1 mL) was reacted with 4-(2-chloroethyl)-N,N,1,5-tetramethyl-1H-pyrazole-3-carboxamide (47.5 mg, 0.21 mmol) and cesium carbonate (157 mg, 0.48 mmol) at 80° C. for 16 hr. The reaction mixture was then diluted with DCM, and washed with sat. NaHCO₃, water and brine, dried over sodium sulphate and concentrated. This crude material was purified by prep TLC plate method to give tert-butyl N-{2-[6-(2-{2-[3-(dimethylcarbamoyl)-1,5-dimethyl-1H-pyrazol-4-yl]ethoxy}-4-fluorophenyl)imidazo[1,2-a]pyridin-3-yl]ethyl}carbamate (27 mg, 29%). ¹H NMR (400 MHz, DMSO-d₆) δ 8.34 (s, 1H), 7.50 (d, 1H), 7.45 (t, 1H), 7.41 (s, 1H), 7.22 (d, 1H), 7.06 (dd, 1H), 6.97 (dd, 1H), 6.86 (td, 1H), 4.11 (t, 2H), 3.64 (s, 3H), 3.27 (t, 2H), 3.03 (s, 3H), 3.02 (m, 2H), 2.90 (s, 3H), 2.84 (t, 2H), 1.94 (s, 3H), 1.30 (s, 9H).

Step 2

According to the general method for Boc deprotection (method B), tert-butyl N-{2-[6-(2-{2-[3-(dimethylcarbamoyl)-1,5-dimethyl-1H-pyrazol-4-yl]ethoxy}-4-fluorophenyl)imidazo[1,2-a]pyridin-3-yl]ethyl}carbamate (100 mg, 0.18 mmol) was dissolved in dioxane (2 ml) and treated with a solution of HCl in dioxane (4M, 3 ml). The solution stirred at room temperature for 2 hr and was evaporated under reduced pressure (90 mg, 99%). hplc rt 3.6 min LC-MS MH+ 465; ¹H NMR (400 MHz, DMSO-d₆) δ 14.6 (br.s, 1H), 8.93 (s, 1H), 8.13 (m, 4H), 8.04 (d, 1H), 7.99 (d, 1H), 7.55 (td, 1H), 7.17 (dd, 1H), 6.97 (td, 1H), 4.12 (t, 2H), 3.70 (s, 3H), 3.43 (t, 2H), 3.19 (m, 2H), 3.09 (s, 3H), 2.90 (s, 3H), 2.86 (t, 2H), 2.07 (s, 3H).

Example 71

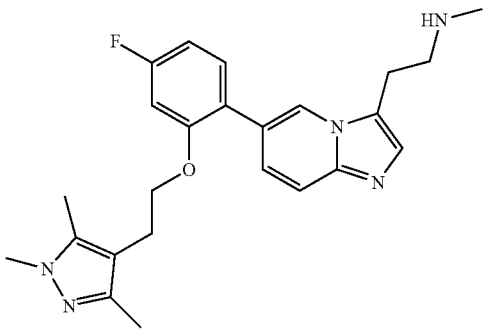

[2-(6-{4-fluoro-2-[2-(1,3,5-trimethyl-1H-pyrazol-4-yl)ethoxy]phenyl}imidazo[1,2-a]pyridin-3-yl)ethyl](methyl)amine Step 1

A solution of tert-butyl N-[2-(6-{4-fluoro-2-[2-(1,3,5-trimethyl-1H-pyrazol-4-yl)ethoxy]phenyl}imidazo[1,2-a]pyridin-3-yl)ethyl]carbamate (intermediate for Example 69) (30 mg, 0.059 mmol) in THF (1 mL) was treated with sodium hydride (50% dispersion in oil. 14.2 mg, 0.30 mmol) portionwise at 0° C. and the mixture was stirred at RT for 30 min. The mixture was re-cooled before addition of iodomethane (0.018 ml, 0.30 mmol) and was allowed to stir at RT for 3 days. The reaction mixture was quenched with ice-water and extracted with EtOAc. The organic layer was washed with water, brine, dried over Na₂SO₄ and concentrated under reduced pressure. The crude product was purified by prep TLC (3% MeOH-DCM) to afford desired product tert-butyl N-[2-(6-{4-fluoro-2-[2-(1,3,5-trimethyl-1H-pyrazol-4-yl)ethoxy]phenyl}imidazo[1,2-a]pyridin-3-yl)ethyl]-N-methylcarbamate (14 mg, 31%) ¹H NMR (400 MHz, DMSO-d₆) δ 8.35 (s, 1H), 7.52 (td, 1H), 7.41-7.36 (m, 2H), 7.25 (d, 1H), 7.04 (dd, 1H), 6.88 (td, 1H), 4.01 (t, 2H), 3.52 (s, 3H), 3.48 (t, 2H), 3.25 (m, 2H), 3.12 (t, 2H), 2.79 (t, 2H), 2.67 (s, 3H), 1.94 (s, 3H), 1.90 (s, 3H), 0.85 (s, 9H).

Step 2

According to the general method for Boc deprotection (method B) tert-butyl N-[2-(6-{4-fluoro-2-[2-(1,3,5-trimethyl-1H-pyrazol-4-yl)ethoxy]phenyl}imidazo[1,2-a]pyridin-3-yl)ethyl]-N-methylcarbamate (14 mg, 0.027 mmol) was dissolved in dioxane (2 ml) and treated with a solution of HCl in dioxane (4M, 2 ml). The solution stirred at room temperature for 2 hr and was evaporated under reduced pressure. The crude product was triturated with ether, then dissolved in water and freeze-dried to give the title compound as a colourless solid (10 mg, yield: 88%). hplc rt 7.5 min LC-MS MH+ 422; ¹H NMR (400 MHz, DMSO-d₆) δ 14.6 (br.s, 1H), 9.12 (br. s, 2H), 8.96 (s, 1H), 8.17 (s, 1H), 8.00 (dd, 2H), 7.56 (td, 1H), 7.14 (dd, 1H), 6.97 (td, 1H), 4.07 (t, 2H), 3.61 (s, 3H), 3.48 (t, 2H), 3.28 (m, 2H), 2.73 (t, 2H), 2.66 (d, 3H), 2.03 (s, 3H), 1.89 (s, 3H).

Example 72

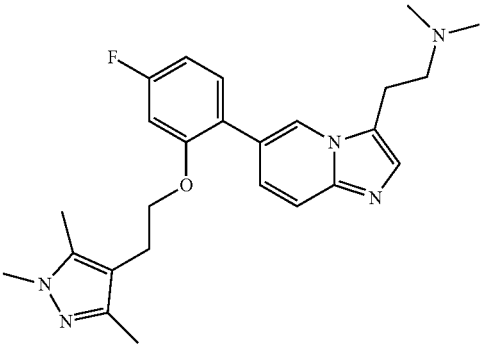

[2-(6-{4-fluoro-2-[2-(1,3,5-trimethyl-1H-pyrazol-4-yl)ethoxy]phenyl}imidazo[1,2-a]pyridin-3-yl)ethyl]dimethylamine A solution of 2-(6-{4-fluoro-2-[2-(trimethyl-1H-pyrazol-4-yl)ethoxy]phenyl}imidazo[1,2-a]pyridin-3-yl)ethan-1-amine (Example 69, 24 mg, 0.054 mmol) in methanol (2 mL) was treated with formaldehyde solution (37% in water, 8 µL, 0.27 mmol). The reaction mixture was stirred at rt for 1 hour, before being cooled to 0° C. and treated with sodium cyanoborohydride (10.2 mg, 0.16 mmol). The reaction mixture was stirred at rt for 16 hours before being diluted with DCM, washed with NaHCO₃ solution, dried over Na₂SO₄ and concentrated under reduced pressure. The crude material was purified using prep TLC to give the title compound (10 mg, 42%). hplc rt 3.7 min LC-MS MH+ 436; ¹H NMR (400 MHz, DMSO-d₆) δ 8.33 (s, 1H), 7.51 (d, 1H), 7.45-7.35 (m, 2H), 7.24 (d, 1H), 7.94 (dd, 1H), 6.88 (td, 1H), 4.01 (t, 2H), 3.52 (s, 3H), 3.02 (t, 2H), 2.68 (t, 2H), 2.64 (t, 2H), 2.22 (s, 6H), 1.91 (s, 3H), 1.89 (s, 3H).

Example 73

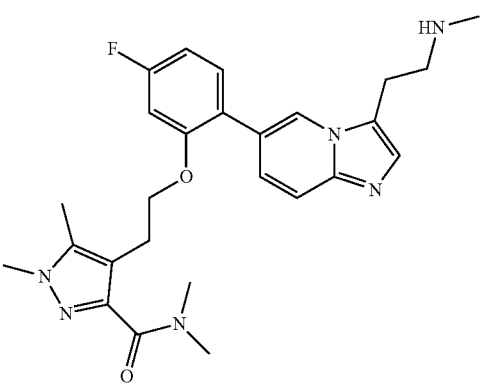

4-[2-(5-fluoro-2-{3-[2-(methylamino)ethyl]imidazo[1,2-a]pyridin-6-yl}phenoxy)ethyl]-N,N,1,5-tetramethyl-1H-pyrazole-3-carboxamide Step 1

A solution tert-butyl N-{2-[6-(2-{2-[3-(dimethylcarbamoyl)-1,5-dimethyl-1H-pyrazol-4-yl]ethoxy}-4-fluorophenyl)imidazo[1,2-a]pyridin-3-yl]ethyl}carbamate (intermediate for Example 70) (55 mg, 0.097 mmol) in THF (2 mL) was treated with sodium hydride (50% dispersion in oil. 23.4 mg, 0.49 mmol) portionwise at 0° C. and the mixture was stirred at RT for 30 min. The mixture was re-cooled before addition of iodomethane (0.03 ml, 0.49 mmol) and was allowed to stir at RT for 3 days. The reaction mixture was quenched with ice-water and extracted with EtOAc. The organic layer was washed with water, brine, dried over $Na_2SO_4$ and concentrated under reduced pressure. The crude product was purified by prep TLC (3% MeOH-DCM) to afford desired tert-butyl N-{2-[6-(2-{2-[3-(dimethylcarbamoyl)-1,5-dimethyl-1H-pyrazol-4-yl]ethoxy}-4-fluorophenyl)imidazo[1,2-a]pyridin-3-yl]ethyl}-N-methylcarbamate (30 mg, 53%) $^1$H NMR (400 MHz, DMSO-$d_6$) δ 8.42 (s, 1H), 7.58 (d, 1H), 7.45-7.30 (m, 3H), 7.08 (dd, 1H), 6.89 (td, 1H), 5.75 (s, 1H), 4.10 (t, 2H), 3.66 (s, 3H), 3.49 (t, 2H), 3.33 (m, 2H), 3.14 (t, 2H), 3.06 (s, 3H), 2.90 (s, 3H), 2.80 (t, 2H), 1.98 (s, 3H), 0.95 (s, 9H).

Step 2

According to the general method for Boc deprotection (method B), tert-butyl N-{2-[6-(2-{2-[3-(dimethylcarbamoyl)-1,5-dimethyl-1H-pyrazol-4-yl]ethoxy}-4-fluorophenyl)imidazo[1,2-a]pyridin-3-yl]ethyl}-N-methylcarbamate (30 mg, 0.05 mmol) was dissolved in a solution of HCl in dioxane (4M, 5 ml). The solution stirred at room temperature for 2 hr and was evaporated under reduced pressure. The crude product was triturated with ether then dissolved in water and freeze dried to give the title compound (22 mg, 88%). hplc rt 3.7 min LC-MS MH+ 479; $^1$H NMR (400 MHz, DMSO-$d_6$) δ 14.7 (br.s, 1H), 9.01 (s, 2H), 8.95 (s, 1H), 8.15 (s, 1H), 8.04 (d, 1H), 7.98 (d, 1H), 7.57 (dd, 1H), 7.17 (dd, 1H), 6.97 (td, 1H), 4.15 (t, 2H), 3.70 (s, 3H), 3.50 (t, 2H), 3.29 (m, 2H), 3.09 (s, 3H), 2.91 (s, 3H), 2.88 (t, 2H), 2.66 (t, 3H), 2.07 (s, 3H).

Example 74

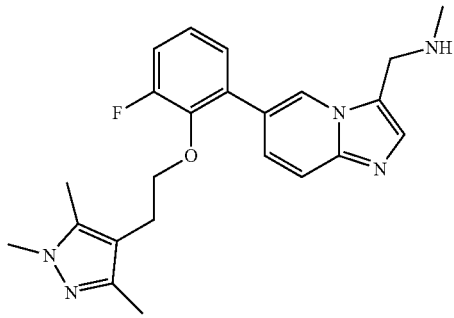

[(6-{3-fluoro-2-[2-(1,3,5-trimethyl-1H-pyrazol-4-yl)ethoxy]phenyl}imidazo[1,2-a]pyridin-3-yl)methyl](methyl)amine 6-(3-fluoro-2-(2-(1,3,5-trimethyl-1H-pyrazol-4-yl)ethoxy)phenyl)imidazo[1,2-a]pyridine-3-carbaldehyde (Intermediate 26, 0.22 g, 0.56 mmol) was dissolved in a solution of methylamine in ethanol (33%, 10 mL) then stirred at room temperature for 18 h. The mixture was evaporated under reduced pressure and the residue-redissolved in ethanol (10 mL) then was added with sodium borohydride (0.043 g, 1.12 mmol) and stirred at room temperature for 4 h. Excess borohydride was quenched by addition of hydrochloric acid (1M, 5 mL) and the mixture was evaporated under reduced pressure. The residue was basified with sodium hydroxide solution (10 N) and extracted with DCM (3×30 mL). The organic phase was dried over $Na_2SO_4$ and evaporated under reduced pressure. The crude was purified by column chromatography to afford the product which was further purified by SFC chromatography by elution with 0.1 to 1.0% $NH_3$ in methanol. The basic eluent was evaporated to obtain product as viscous oil. The product was dissolved in 4 M HCl in dioxane (5 mL) and stirred at room temperature for 15 min. The reaction mixture was then concentrated under reduced pressure. The residue was purified by trituration with diethylether (2×5 mL) followed n-pentane (2×5 mL) to afford the title compound as an off-white solid (70 mg, 52%). LC-MS MH+ 408; $^1$H NMR (400 MHz, DMSO-$d_6$) δ 9.87 (brs, 2H), 9.21 (s, 1H), 8.42 (s, 1H), 8.01-7.87 (m, 2H), 7.54 (d, J=7.7 Hz, 1H), 7.44 (t, J=10.0 Hz, 1H), 7.29 (q, J=7.1 Hz, 1H), 4.72 (d, J=5.5 Hz, 2H), 3.92 (t, J=6.8 Hz, 2H), 3.63 (s, 3H), 2.60 (m, 5H), 2.01 (s, 3H), 1.93 (s, 3H).

Example 75

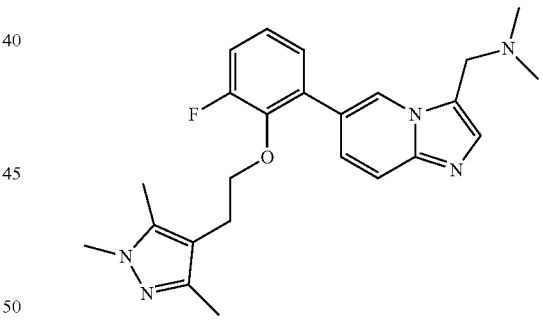

[(6-{3-fluoro-2-[2-(1,3,5-trimethyl-1H-pyrazol-4-yl)ethoxy]phenyl}imidazo[1,2-a]pyridin-3-yl)methyl]dimethylamine A solution of 6-(3-fluoro-2-(2-(1,3,5-trimethyl-1H-pyrazol-4-yl)ethoxy)phenyl)imidazo[1,2-a]pyridine-3-carbaldehyde (Intermediate 26, 0.22 g, 0.56 mmol) in THF (8 mL) was treated with dimethylamine (1.4 mL of 2M solution in THF, 2.8 mmol) and acetic acid-(0.19 mL, 3.36 mmol) was stirred at room temperature for 30 min. Sodium triacetoxyborohydride (0.48 g, 2.24 mmol) and DCE (5 mL) was added to the reaction mixture, and stirred at room temperature for 18 h. After completion of the reaction, the reaction mixture was quenched with the addition of saturated Na₂CO₃ solution (10 mL) and extracted with DCM (3×20 mL). The combined organic layer was dried over Na₂SO₄ and concentrated under reduced pressure. The crude product was purified by column chromatography to afford the product which was further purified by SFC chromatography by elution with 0.1 to 1.0% NH₃ in methanol. The product was dissolved in 4 M HCl in dioxane (5 mL) and stirred at room temperature for 15 min. The reaction mixture was then concentrated under reduced pressure. The residue was purified by trituration with diethyl ether. (2×5 mL) followed n-pentane (2×5 mL) to afford the title compound (60m g, 24%). LC-MS MH⁺ 408; ¹H NMR (400 MHz, DMSO-d₆) δ 11.70 (brs, 1H), 9.24 (s, 1H), 8.49 (s, 1H), 7.93 (q, J=9.3 Hz, 2H), 7.55 (d, J=7.7 Hz, 1H), 7.43 (t, J=9.9 Hz, 1H), 7.33-7.23 (m, 1H), 4.87 (s, 2H), 3.89 (t, J=6.9 Hz, 2H), 3.60 (s, 3H), 2.82 (s, 6H), 2.57 (t, J=6.9 Hz, 2H), 1.99 (s, 3H), 1.89 (s, 3H).

Example 76

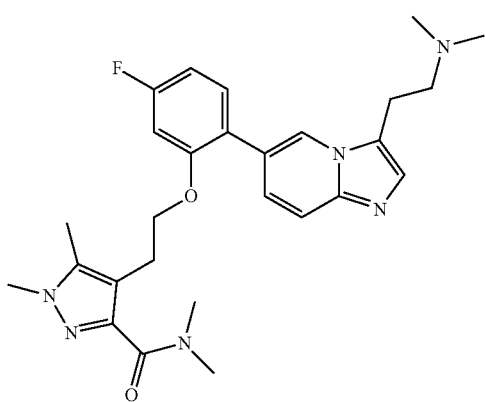

4-[2-(2-{3-[2-(dimethylamino)ethyl]imidazo[1,2-a]pyridin-6-yl}-5-fluorophenoxy)ethyl]-N,N,1,5-tetramethyl-1H-pyrazole-3-carboxamide The product from Example 70 (4-(2-{2-[3-(2-aminoethyl)imidazo[1,2-a]pyridin-6-yl]-5-fluorophenoxy}ethyl)-N,N,1,5-tetramethyl-1H-pyrazole-3-carboxamide hydrochloride salt, 90 mg, 0.18 mmol) was dissolved in methanol (2.0 mL) and treated with formaldehyde solution (37% in water, 0.8 mL, 0.9 mmol). The reaction mixture was stirred at rt for 1 hour, before being cooled to 0° C. and treated with sodium cyanoborohydride (33.9 mg, 0.54 mmol). After being stirred at rt for 16 hours, the reaction mixture was diluted with DCM and washed with NaHCO₃ solution. The organic phase was dried over Na₂SO₄ and concentrated under reduced pressure. The crude material was purified using prep TLC to give the title compound (50 mg, 56%). hplc rt 4.5 min LC-MS MH⁺ 493; ¹H NMR (400 MHz, DMSO-d₆) δ 8.32 (s, 1H), 7.50 (s, 1H), 7.45 (d, 1H), 7.42 (s, 1H), 7.22 (dd, 1H), 7.07 (dd, 1H), 6.87 (td, 1H), 4.11 (t, 2H), 3.64 (s, 3H), 3.04 (s, 3H), 3.01 (s, 2H), 2.90 (s, 3H), 2.84 (t, 2H), 2.67 (t, 2H), 1.94 (s, 3H).

Example 77

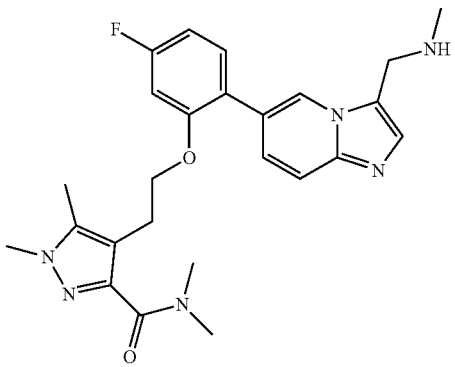

4-[2-(5-fluoro-2-{3-[(methylamino)methyl]imidazo[1,2-a]pyridin-6-yl}phenoxy)ethyl]-N,N,1,5-tetramethyl-1H-pyrazole-3-carboxamide Step 1

A solution of tert-butyl N-{[6-(4-fluoro-2-hydroxyphenyl)imidazo[1,2-a]pyridin-3-yl]methyl}-N-methylcarbamate (intermediate 24, 400 mg, 1.08 mmol) in DMF (10 mL) was reacted with 4-(2-chloroethyl)-N,N, 1,5-tetramethyl-1H-pyrazole-3-carboxamide (47.5 mg, 0.21 mmol) and cesium carbonate (1.23 g, 3.77 mmol) at 80° C. for 16 hr. The reaction mixture was then diluted with DCM, and washed with sat. NaHCO₃, water and brine, dried over sodium sulphate and concentrated. This crude material was purified by prep hplc by elution with NH₄HCO₃ buffer and CH³CN/water. to give tert-butyl N-{[6-(2-{2-[3-(dimethylcarbamoyl)-1,5-dimethyl-1H-pyrazol-4-yl]ethoxy}-4-fluorophenyl)imidazo[1,2-a]pyridin-3-yl]methyl}-N-methylcarbamate (120 mg, 20%). ¹H NMR (400 MHz, DMSO-d₆) δ 8.50-8.30 (m, 2H), 7.63 (s, 1H), 7.57 (d, 1H), 7.30-7.20 (m, 2H), 7.06 (dd, 1H), 6.84 (td, 1H), 4.78 (s, 2H), 4.09 (t, 2H), 3.63 (s, 3H), 3.03 (s, 3H), 2.89 (s, 3H), 2.68 (m, 2H), 1.89 (s, 3H), 1.36 (s, 9H).

Step 2

According to the general method for Boc deprotection (method B), tert-butyl N-{[6-(2-{2-[3-(dimethylcarbamoyl)-1,5-dimethyl-1H-pyrazol-4-yl]ethoxy}-4-fluorophenyl)imidazo[1,2-a]pyridin-3-yl]methyl}-N-methylcarbamate (90 mg, 0.16 mmol) was dissolved in dioxane (2 ml) and treated with a solution of HCl in dioxane (4M, 3 ml). The solution stirred at room temperature for 3 hr and was evaporated under reduced pressure to give the title compound as a yellow solid (74 mg, 100%). hplc rt 3.8 min LC-MS MH⁺ 465; ¹H NMR (400 MHz, DMSO-d₆) δ9.41 (br.s, 2H), 9.11 (s, 1H), 8.31 (s, 1H), 8.02 (d, 1H), 7.94 (d, 1H), 7.66 (td, 1H), 7.17 (dd, 1H), 6.99 (td, 1H), 4.72 (s, 2H), 4.13 (t, 2H), 3.67 (s, 3H), 3.55 (s, 3H), 3.09 (s, 3H), 2.91 (s, 3H), 2.85 (t, 2H), 2.62 (d, 3H), 2.05 (s, 3H).

Example 78

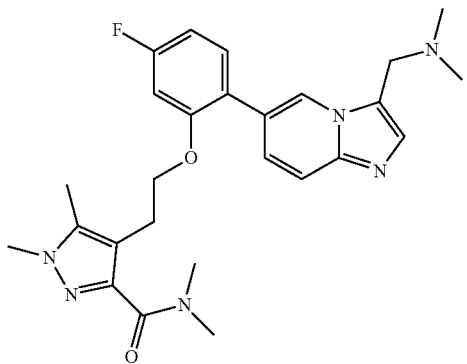

4-[2-(2-{3-[(dimethylamino)methyl]imidazo[1,2-a]pyridin-6-yl}-5-fluorophenoxy)ethyl]-N,N,1,5-tetramethyl-1H-pyrazole-3-carboxamide The product from Example 77 4-[2-(5-fluoro-2-{3-[(methylamino)methyl]imidazo [,2-a]pyridin-6-yl}phenoxy)ethyl]-N,N, 1,5-tetramethyl-1H-pyrazole-3-carboxamide (50 mg, 0.05 mmol) was dissolved in methanol (1.0 mL) and treated with formaldehyde solution (37% in water, 0.04 mL, 0.50 mmol). The reaction mixture was stirred at rt for 1 hour, before being cooled to 0° C. and treated with sodium cyanoborohydride (18.7 mg, 0.30 mmol). After being stirred at rt for 16 hours, the reaction mixture was diluted with DCM and washed with NaHCO$_3$ solution. The organic phase was dried over Na$_2$SO$_4$ and concentrated under reduced pressure. The crude material was purified using prep TLC by elution with DCM: methanol (94:6) to give the title compound (25 mg, 48%). hplc rt 5.0 min LC-MS MH$^+$ 479; $^1$H NMR (400 MHz, DMSO-d$_6$) δ δ 8.46 (s, 1H), 8.27 (s, 1H), 7.5-7.2 (m, 2H), 7.41 (t, 1H), 7.27 (dd, 1H), 7.07 (dd, 1H), 6.88 (td, 1H), 4.10 (t, 2H), 3.73 (s, 1H), 3.64 (s, 3H), 3.04 (s, 2H), 2.90 (s, 2H), 2.65 (d, 3H), 2.85 (t, 2H), 2.14 (s, 6H), 1.91 (s, 3H).

Example 79

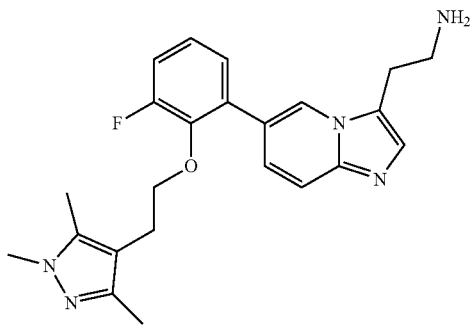 [SMILES: Cc1nn(C)c(C)c1CCOc1c(F)cccc1-c1ccc2ncc(CCN)n2c1]

2-(6-{3-fluoro-2-[2-(1,3,5-trimethyl-1H-pyrazol-4-yl)ethoxy]phenyl}imidazo[1,2-a]pyridin-3-yl)ethan-1-amine Step 1

A solution of tert-butyl (2-(6-(3-fluoro-2-hydroxyphenyl)imidazo [1, 2-a]pyridin-3-yl) ethyl) carbamate (Intermediate 27, 0.5 g, 1.3 mmol) in THF (25 mL), PPh$_3$ (0.68 mg, 2.60 mmol) and 2-(1,3,5-trimethyl-1H-pyrazol-4-yl)ethan-1-ol (0.41 g, 2.60 mmol) in THF (4 mL) was treated dropwise with di-isopropyl azodicarboxylate (0.51 mL, 2.60 mmol) at 0° C. The mixture was warmed to room temperature for 16 hr, then concentrated under reduced pressure. The crude product was purified by column chromatography to afford tert-butyl (2-(6-(3-fluoro-2-(2-(1,3,5-trimethyl-1H-pyrazol-4-yl)ethoxy)phenyl)imidazo [1,2-a]pyridin-3-yl)ethyl)carbamate (350 mg, 51%). $^1$H NMR (400 MHz, DMSO-d$_6$) δ 8.41 (s, 1H), 7.55 (dd, J=14.2, 9.2 Hz, 1H), 7.43 (s, 1H), 7.38-7.16 (m, 4H), 7.01-6.97 (m, 1H), 3.82 (t, J=7.3 Hz, 2H), 3.46 (d, J=5.9 Hz, 3H), 3.32 (s, 2H), 3.04-3.00 (m, 2H), 2.60-2.46 (m, 2H), 1.84 (d, J=6.1 Hz, 6H), 1.30 (s, 9H).

Step 2

According to the general method for Boc deprotection (method B), a solution of tert-butyl (2-(6-(3-fluoro-2-(2-(1, 3,5-trimethyl-1H-pyrazol-4-yl)ethoxy) phenyl)imidazo [1,2-a]pyridin-3-yl)ethyl)carbamate (0.1 g, 0.19 mmol) in DCM (10 mL), was treated with HCl in dioxane (4M, 0.5 mL) and stirred at room temperature for 2 hr. The reaction mixture was concentrated under reduced pressure and the residue was purified by trituration with ether and n-pentane, then again purified by SFC chromatography to afford the title compound (40 mg, 50%). LC-MS MH$^+$408; $^1$H NMR (400 MHz, DMSO-d$_6$) δ 8.82 (s, 1H), 8.07 (s, 1H), 7.90 (d, J=15.6 Hz, 3H), 7.45-7.40 (m, 1H), 7.37-7.23 (m, 2H), 3.90 (t, J=6.9 Hz, 3H), 3.48 (s, 3H), 3.34 (t, J=7.1 Hz, 2H), 3.22-3.08 (m, 2H), 2.55 (t, J=6.9 Hz, 2H), 1.94 (s, 3H), 1.82 (s, 3H)

Example 80

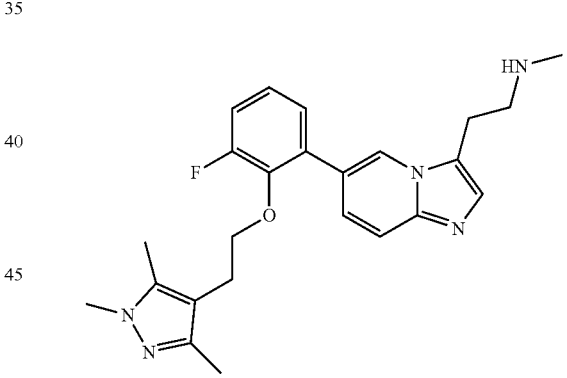

[2-(6-{3-fluoro-2-[2-(1,3,5-trimethyl-1H-pyrazol-4-yl)ethoxy]phenyl}imidazo[1,2-a]pyridin-3-yl)ethyl](methyl)amine Step 1

A solution of tert-butyl (2-(6-bromoimidazo[1,2-a]pyridin-3-yl)ethyl)(methyl)carbamate (Intermediate 28, 140 mg, 0.36 mmol) and 2-(1,3,5-trimethyl-1H-pyrazol-4-yl)ethan-1-ol (110 mg, 0.72 mmol) in toluene (10 mL), was treated with cyanomethylene tributylphosphorane, 130 mg, 0.54 mmol) and the reaction mixture was refluxed for 5 hr. After completion of the reaction, the reaction mixture was concentrated under reduced pressure and the residue was purified by column chromatography using to afford tert-butyl (2-(6-(3-fluoro-2-(2-(1,3,5-trimethyl-1H-pyrazol-4-yl)

ethoxy)phenyl)imidazo[1,2-a]pyridin-3-yl)ethyl)(methyl)-carbamate (90 mg, 48%). ¹H NMR (400 MHz, DMSO-d₆) δ 8.41 (d, J=10.7 Hz, 1H), 7.55 (d, J=9.9 Hz, 1H), 7.44-7.16 (m, 4H), 4.09 (q, J=5.3 Hz, 1H), 3.81 (t, J=7.4 Hz, 2H), 3.48 (s, 3H), 3.19-3.08 (m, 4H), 2.79 (s, 3H), 2.73 (s, 2H), 1.85 (d, J=9.4 Hz, 6H), 1.28 (s, 3H), 0.99 (s, 6H).

Step 2

According to the general method for Boc deprotection (method B), tert-butyl (2-(6-(3-fluoro-2-(2-(1,3,5-trimethyl-1H-pyrazol-4-yl)ethoxy)phenyl)imidazo[1,2-a]pyridin-3-yl)ethyl)(methyl) carbamate (90 mg, 0.17 mmol) was dissolved in DCM (10 mL), and treated with HCl in dioxane (4M, 0.2 mL) was added and stirred at room temperature for 1 hr. After completion of the reaction, the reaction mixture was concentrated under reduced pressure and the residue was purified by trituration with ether to give the title compound (74 mg, 94%) as a brown solid. LC-MS rt 2.0 min, MH⁺ 422. ¹H NMR (400 MHz, DMSO-de) δ 9.23 (s, 2H), 8.98 (s, 1H), 8.21 (s, 1H), 7.95 (s, 2H), 7.50-7.35 (m, 2H), 7.28 (td, J=8.0, 5.0 Hz, 1H), 3.94 (t, J=6.7 Hz, 2H), 3.62-3.43 (m, 6H), 3.28 (p, J=7.2 Hz, 2H), 2.58 (dt, J=16.4, 6.1 Hz, 6H), 1.91 (s, 3H).

Example 81

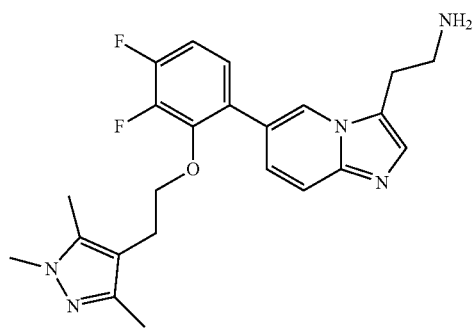 [SMILES: Cc1nn(C)c(C)c1CCOc1c(-c2ccc3ncc(CCN)n3c2)ccc(F)c1F]

2-(6-{3,4-difluoro-2-[2-(1,3,5-trimethyl-1H-pyrazol-4-yl)ethoxy]phenyl}imidazo[1,2-a]pyridin-3-yl)ethan-1-amine Step 1

A solution of tert-butyl (2-(6-(3,4-difluoro-2-hydroxyphenyl)imidazo[1,2-a]pyridin-3-yl)ethyl)carbamate (Intermediate 29, 90 mg, 0.23 mmol) and 2-(1,3,5-trimethyl-1H-pyrazol-4-yl)ethan-1-ol (71 mg, 0.46 mmol) in toluene (10 mL) was treated with cyanomethylene tributylphosphorane (83 mg, 0.34 mmol) and the reaction mixture was refluxed for 5 hr. The reaction mixture was concentrated under reduced pressure. The residue was purified by column chromatography to afford tert-butyl (2-(6-(3,4-difluoro-2-(2-(1,3,5-trimethyl-1H-pyrazol-4-yl)ethoxy)phenyl) imidazo[1,2-a]pyridin-3-yl) ethyl)carbamate (38 mg, 31%). ¹H NMR (400 MHz, CDCl₃) δ 8.06 (s, 1H), 7.63 (d, J=9.3 Hz, 1H), 7.51 (s, 1H), 7.25 (s, 1H), 7.12-7.05 (m, 1H), 7.05-6.94 (m, 1H), 5.31 (s, 2H), 3.96 (t, J=7.1 Hz, 1H), 3.69 (d, J=9.6 Hz, 1H), 3.52 (d, J=6.0 Hz, 3H), 3.11-3.03 (m, 2H), 2.64-2.60 (m, 2H), 2.03 (s, 3H), 1.91 (s, 3H), 1.43 (s, 9H).

Step 2

According to the general method for Boc deprotection (method B), a solution of tert-butyl (2-(6-(3,4-difluoro-2-(2-(1,3,5-trimethyl-1H-pyrazol-4-yl)ethoxy)phenyl)imidazo [1,2-a]pyridin-3-yl)ethyl)carbamate (38 mg, 0.07 mmol) in DCM (3 mL), was treated with HCl in dioxane (4M, 1 mL) and stirred at room temperature for 1 hr. The reaction mixture was concentrated under reduced pressure and the residue was triturated with diethyl ether followed by n-pentane to give the title compound (11 mg, 37%) as a brown solid. LC-MS rt 1.6 min, MH⁺ 426. ¹H NMR (400 MHz, DMSO-d₆) δ 8.96 (s, 1H), 8.26 (brs, 2H), 8.18 (s, 1H), 8.00-7.89 (m, 2H), 7.39 (dd, J=8.7, 6.2 Hz, 2H), 4.01 (t, J=6.8 Hz, 2H), 3.54 (s, 3H), 3.43 (t, J=7.1 Hz, 2H), 3.19 (q, J=6.4 Hz, 2H), 2.61 (t, J=6.8 Hz, 2H), 1.99 (s, 3H), 1.90 (s, 3H).

Example 82

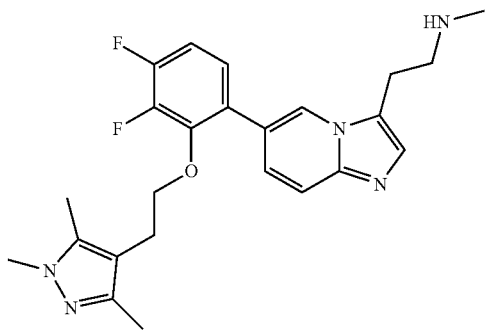

[2-(6-{3,4-difluoro-2-[2-(1,3,5-trimethyl-1H-pyrazol-4-yl)ethoxy]phenyl}imidazo[1,2-a]pyridin-3-yl)ethyl](methyl)amine Step 1

A solution of tert-butyl (2-(6-(3,4-difluoro-2-hydroxyphenyl)imidazo[1,2-a]pyridin-3-yl)ethyl)(methyl)carbamate (Intermediate 28, 80 mg, 0.19 mmol) and 2-(1,3,5-trimethyl-1H-pyrazol-4-yl)ethan-1-ol (61 mg, 0.39 mmol) in toluene (10 mL) was treated with cyanomethylene tributylphosphorane (68 mg, 0.28 mmol) and the reaction mixture was refluxed for 5 hr. The reaction mixture was concentrated under reduced pressure. The residue was purified by column chromatography to afford tert-butyl (2-(6-(3,4-difluoro-2-(2-(1,3,5-trimethyl-1H-pyrazol-4-yl)ethoxy)phenyl) imidazo[1,2-a]pyridin-3-yl) ethyl) (methyl) carbamate (60 mg, 56%). ¹H NMR (400 MHz, CDCl₃) δ 8.24 (s, 1H), 7.99 (s, 1H), 7.60 (s, 1H), 7.48 (s, 1H), 7.13 (s, 1H), 6.98 (q, J=9.0 Hz, 1H), 3.91 (t, J=7.5 Hz, 2H), 3.56 (d, J=12.5 Hz, 2H), 3.10 (s, 2H), 2.85 (d, J=17.6 Hz, 3H), 2.65 (t, J=7.5 Hz, 2H), 2.02 (s, 3H), 1.90 (s, 3H), 1.40 (s, 3H), 1.26 (s, 9H).

Step 2

According to the general method for Boc deprotection (method B), a solution of tert-butyl (2-(6-(3,4-difluoro-2-(2-(1,3,5-trimethyl-1H-pyrazol-4-yl)ethoxy)phenyl)imidazo [1,2-a]pyridin-3-yl)ethyl) (methyl) carbamate (60 mg, 0.11 mmol) in DCM (10 mL), was treated with HCl in dioxane (4M, 2 mL) and stirred at room temperature for 1 hr. The reaction mixture was concentrated under reduced pressure and the residue was triturated with diethyl ether to give the title compound (41 mg, 85%) as a brown solid. LC-MS rt 1.6 min, MH⁺ 440. 1H NMR (400 MHz, DMSO-d6) δ 9.25-9.18 (m, 2H), 8.98 (s, 1H), 8.20 (s, 1H), 7.99-7.89 (m, 2H), 7.46-7.32 (m, 2H), 4.01 (t, J=6.8 Hz, 1H), 3.75-3.43 (m, 5H), 3.29-3.24 (m, 2H), 2.60-2.57 (m, 5H), 1.99 (s, 3H), 1.89 (s, 3H).

Example 83

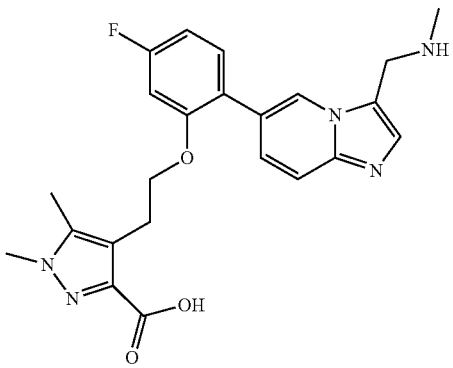

4-[2-(5-fluoro-2-{3-[(methylamino)methyl]imidazo[1,2-a]pyridin-6-yl}phenoxy)ethyl]-1,5-dimethyl-1H-pyrazole-3-carboxylic acid Step 1

A solution of tert-butyl N-{[6-(4-fluoro-2-hydroxyphenyl)imidazo[1,2-a]pyridin-3-yl]methyl}-N-methylcarbamate (intermediate 24, 180 mg, 0.48 mmol) in DMF (1.5 mL) was reacted with methyl 4-(2-chloroethyl)-1,5-dimethyl-1H-pyrazole-3-carboxylate (188 mg, 0.87 mmol) and cesium carbonate (550 mg, 1.7 mmol) at 90° C. for 16 hr. The reaction mixture was then diluted with ethyl acetate, and washed with sat. $NaHCO_3$, water and brine, dried over sodium sulphate and concentrated. This crude material was purified by prep TLC by elution with DCM: methanol (95:5) to give methyl 4-(2-{2-[3-({[(tert-butoxy)carbonyl]-(methyl)amino}methyl)imidazo[1,2-a]pyridin-6-yl]-5-fluorophenoxy}ethyl)-1,5-dimethyl-1H-pyrazole-3-carboxylate (75 mg, 28%). $^1$H NMR (400 MHz, DMSO-$d_6$) δ 8.5 (br.s, 1H), 7.62 (s, 1H), 7.56 (d, 1H), 7.32 (dd, 1H), 7.24 (d, 1H), 7.08 (dd, 1H), 6.83 (td, 1H), 5.76 (s, 2H), 4.70 (t, 2H), 4.10 (t, 2H), 3.71 (s, 3H), 3.66 (s, 3H), 3.00 (t, 2H), 2.67 (s, 3H), 2.00 (s, 3H), 1.33 (s, 9H).

Alternative Step 1

A solution of tert-butyl N-{[6-(4-fluoro-2-hydroxyphenyl)imidazo[1,2-a]pyridin-3-yl]methyl}-N-methylcarbamate (intermediate 24, 1.0 g, 2.7 mmol) and methyl 4-(2-hydroxyethyl)-1,5-dimethyl-1H-pyrazole-3-carboxylate (1.06 g, 5.4 mmol) in toluene (10 mL) was treated with cyanomethylene tributylphosphorane (1.4 mL, 5.4 mmol) at 100° C. for 16 hr. The reaction mixture was then diluted with ethyl acetate, and washed with water and brine, dried over sodium sulphate and concentrated. This crude material was purified by column chromatography by elution with DCM: methanol (95:5) to give methyl 4-(2-{2-[3-({[(tert-butoxy)carbonyl]-(methyl)amino}methyl)imidazo[1,2-a]pyridin-6-yl]-5-fluorophenoxy} ethyl)-1,5-dimethyl-1H-pyrazole-3-carboxylate (1.2 g, 81%). $^1$H NMR (400 MHz, $CDCl_3$) δ 8.44 (br.s, 1H), 7.57 (s, 1H), 7.51 (d, 1H), 7.20-7.15 (m, 2H), 6.74 (dd, 1H), 6.60 (td, 1H), 4.77 (t, 2H), 4.14 (t, 2H), 3.89 (s, 3H), 3.73 (s, 3H), 3.07 (t, 2H), 2.73 (s, 3H), 1.92 (s, 3H), 1.31 (s, 9H).

Step 2

A solution of methyl 4-(2-{2-[3-({[(tert-butoxy)carbonyl]-(methyl)amino}methyl)imidazo-[1,2-a]pyridin-6-yl]-5-fluorophenoxy}ethyl)-1,5-dimethyl-1H-pyrazole-3-carboxylate (40 mg, 0.07 mmol) in THF-water (4:1, 1.5 mL) was cooled at 0° C. and treated with a solution of lithium hydroxide (6.1 mg, 0.14 mmol) in ethanol (0.02 mL) at 0° C. The resulting mixture was stirred at rt for 16 hr. The reaction mixture was evaporated under reduced pressure, the crude reaction mixture was acidified with sat citric acid solution and extracted with DCM. The final organic layer was dried over sodium sulphate and concentrated to afford desired product 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid as an off-white solid (35 mg, 90%). $^1$H NMR (400 MHz, DMSO-$d_6$) δ 12.3 (br.s, 1H), 8.50 (s, 1H), 7.62 (s, 1H), 7.57 (d, 1H), 7.33 (dd, 1H), 7.26 (dd, 1H), 7.11 (d, 1H), 6.84 (td, 1H), 4.76 (s, 2H), 4.10 (t, 2H), 3.66 (s, 3H), 3.00 (t, 2H), 2.68 (s, 3H), 1.87 (s, 3H), 1.31 (s, 9H).

Step 3

According to the general method for Boc deprotection (method B) 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid (35 mg, 0.06 mmol) was dissolved in a solution of HCl in dioxane (4M, 1 mL). The solution stirred at room temperature for 3 hr and was evaporated under reduced pressure. The crude product was dissolved in water and freeze dried to give the title compound as a light brown solid (24 mg, 84%). hplc rt 6.8 min LC-MS MH$^+$ 438; $^1$H NMR (400 MHz, DMSO-$d_6$) δ 9.26 (br.s, 2H), 9.02 (s, 1H), 8.25 (s, 1H), 7.89 (dd, 2H), 7.62 (dd, 1H), 7.20 (dd, 1H), 6.98 (td, 1H), 4.70 (t, 2H), 4.14 (t, 2H), 3.72 (s, 3H), 3.01 (t, 2H), 2.62 (t, 3H), 2.04 (s, 3H).

Example 84

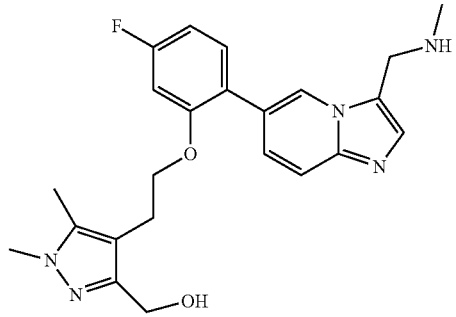

{4-[2-(5-fluoro-2-{3-[(methylamino)methyl]imidazo[1,2-a]pyridin-6-yl}phenoxy)ethyl]-1,5-dimethyl-1H-pyrazol-3-yl}methanol Step 1

A solution of methyl 4-(2-{2-[3-({[(tert-butoxy)carbonyl]-(methyl)amino}methyl)imidazo-[1,2-a]pyridin-6-yl]-5-fluorophenoxy}ethyl)-1,5-dimethyl-1H-pyrazole-3-carboxylate (Example 83 step 1 intermediate, 50 mg, 0.09 mmol) in THF (2 mL) was cooled at 0° C. and treated with a solution of LiAlH$_4$ (2M in THF, 0.09 ml, 0.045 mmol). The resulting mixture was stirred at 0° C. for 2 hr. the reaction mixture was quenched with sodium sulfate decahydrate. The reaction mixture was filtered through Celite bed, which was washed with ethyl acetate. The filtrate was dried over Na$_2$SO$_4$ and evaporated under reduced pressure. The crude product was purified by prep TLC (5% MeOH/DCM) to give tert-butyl N-{[6-(4-fluoro-2-{2-[3-(hydroxymethyl)-1,5-dimethyl-1H-pyrazol-4-yl]ethoxy}-phenyl)imidazo[1,2-a]pyridin-3-yl]methyl}-N-methylcarbamate as an off-white solid (22 mg, 47%). ¹H NMR (400 MHz, DMSO-de) 7.61 (s, 1H), 7.56 (d, 1H), 7.32 (m, 2H), 7.03 (d, 1H), 6.85 (td, 1H), 4.77 (s, 2H), 4.25 (d, 2H), 4.07 (t, 2H), 3.62 (s, 3H), 2.76 (t, 2H), 2.67 (s, 3H), 1.88 (s, 3H), 1.33 (s, 9H).

Step 2

According to the general method for Boc deprotection (method B), tert-butyl N-{[6-(4-fluoro-2-{2-[3-(hydroxymethyl)-1,5-dimethyl-1H-pyrazol-4-yl]ethoxy}-phenyl)imidazo[1,2-a]pyridin-3-yl]methyl}-N-methylcarbamate (20 mg, 0.04 mmol) was dissolved in a solution of HCl in dioxane (4M, 1 ml). The solution stirred at room temperature for 3 hr and was evaporated under reduced pressure. The crude product was dissolved in water and freeze-dried to give the title compound as a light brown solid (10 mg, 62%). hplc rt 5.3 min LC-MS MH⁺ 424; ¹H NMR (400 MHz, DMSO-d₆) δ 9.75 (br.s, 2H), 9.19 (s, 1H), 8.41 (s, 1H), 8.02 (d, 1H), 7.99 (d, 2H), 7.74 (dd, 1H), 7.30 (dd, 1H), 7.13 (s, 1H), 6.97 (td, 1H), 4.73 (t, 2H), 4.27 (s, 2H), 4.14 (t, 2H), 3.64 (s, 3H), 2.81 (t, 2H), 2.62 (t, 3H), 2.03 (s, 3H).

Example 85

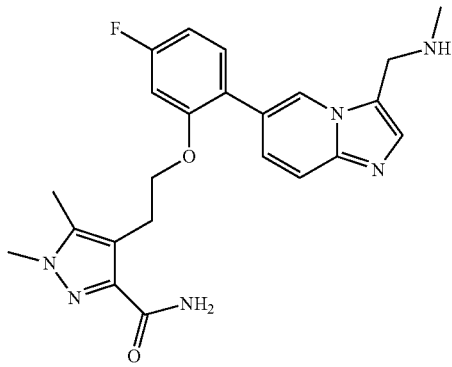

0.4-[2-(5-fluoro-2-{3-[(methylamino)methyl]imidazo[1,2-a]pyridin-6-yl}phenoxy)ethyl]-1,5-dimethyl-1H-pyrazole-3-carboxamide Step 1

A solution of 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid (Example 83 step 2, 55 mg, 0.10 mmol) in DMF (2 mL) was treated with triethylamine (0.04 mL, 0.3 mmol), ammonium chloride (6.6 mg, 0.12 mmol), hydroxybenztriazole 17.6 mg, 0.13 mmol) and EDCl (24.9 mg, 0.13 mmol). The reaction mixture was stirred at rt for 16 hrs, diluted with DCM and washed with sat. NaHCO₃, water and brine, dried over sodium sulphate and concentrated. The crude product was purified over prep TLC (5% MeOH/DCM) to give tert-butyl N-[(6-{2-[2-(3-carbamoyl-1,5-dimethyl-1H-pyrazol-4-yl)ethoxy]-4-fluorophenyl}imidazo[1,2-a]pyridin-3-yl)methyl]-N-methylcarbamate as an off-white solid (22 mg, 47%). ¹H NMR (400 MHz, DMSO-d₆) δ 8.60-8.40 (br, 2H), 7.61 (s, 1H), 7.57 (d, 1H), 7.32-7.23 (m, 4H), 7.10 (d, 1H), 6.82 (td, 1H), 5.76 (s, 1H), 4.77 (s, 2H), 4.12 (t, 2H), 3.65 (s, 3H), 3.00 (m, 2H), 2.67 (s, 3H), 1.89 (s, 3H), 1.32 (s, 9H).

Step 2

According to the general method for Boc deprotection (method B tert-butyl N-[(6-{2-[2-(3-carbamoyl-1,5-dimethyl-1H-pyrazol-4-yl)ethoxy]-4-fluorophenyl}imidazo[1,2-a]pyridin-3-yl)methyl]-N-methylcarbamate (20 mg, 0.037 mmol) was dissolved in dioxane (2 ml) and treated with a solution of HCl in ether (2M, 3 ml). The solution stirred at room temperature for 3 hr and was evaporated under reduced pressure. The crude product was dissolved in water and freeze dried to give the title compound as a light brown solid (15 mg, 92%). hplc rt 8.9 min LC-MS MH⁺ 437; ¹H NMR (400 MHz, DMSO-d₆) δ 9.32 (br.s, 2H), 9.08 (s, 1H), 8.27 (s, 1H), 7.96 (dd, 2H), 7.63 (dd, 1H), 7.30 (dd, 1H), 7.10 (s, 1H), 6.98 (td, 1H), 4.72 (s, 2H), 4.15 (t, 2H), 3.72 (s, 3H), 3.03 (t, 2H), 2.64 (t, 3H), 2.06 (s, 3H).

Example 86

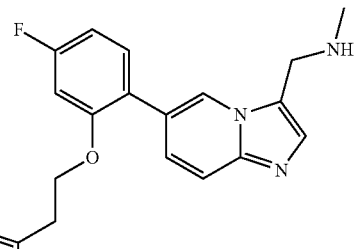

4-[2-(5-fluoro-2-{3-[(methylamino)methyl]imidazo[1,2-a]pyridin-6-yl}phenoxy)ethyl]-N,1,5-trimethyl-1H-pyrazole-3-carboxamide Step 1

A solution of 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid (Example 83 step 2, 55 mg, 0.10 mmol) in DMF (2 mL) was treated with triethylamine (0.04 mL, 0.3 mmol), methylamine solution (2M in THF, 0.20 mL, 0.20 mmol), hydroxybenztriazole 17.6 mg, 0.13 mmol) and EDCl (24.9 mg, 0.13 mmol). The reaction mixture was stirred at rt for 16 hrs, diluted with DCM and washed with sat. NaHCO₃, water and brine, dried over sodium sulphate and concentrated. The crude product was purified by prep TLC (5% MeOH/DCM) to give tert-butyl N-{[6-(2-{2-[1,5-dimethyl-3-(methylcarbamoyl)-1H-pyrazol-4-yl]ethoxy}-4-fluorophenyl)imidazo[1,2-a]pyridin-3-yl]methyl}-N-methylcarbamate as an off-white solid (40 mg, 71%). ¹H NMR (400 MHz, DMSO-de) 8.47 (br s, 2H), 7.97 (d, 1H), 7.62 (s, 1H), 7.56 (d, 1H), 7.33 (m, 1H), 7.25 (d, 1H), 7.14 (d, 1H), 6.82 (td, 1H), 4.77 (s, 2H), 4.12 (t, 2H), 3.73 (s, 3H), 3.00 (m, 2H), 2.70-2.65 (m, 5H), 1.86 (s, 3H), 1.32 (s, 9H).

Step 2

According to the general method for Boc deprotection (method B), tert-butyl N-{[6-(2-{2-[1,5-dimethyl-3-(methylcarbamoyl)-1H-pyrazol-4-yl]ethoxy}-4-fluorophenyl)imidazo[1,2-a]pyridin-3-yl]methyl}-N-methylcarbamate (40 mg, 0.073 mmol) was dissolved in dioxane (2 ml) and treated with a solution of HCl in ether (2M, 4 ml). The solution stirred at room temperature for 3 hr and was evaporated under reduced pressure. The crude product was dissolved in water and freeze-dried to give the title compound as a colourless solid (25 mg, 76%). hplc rt 9.2 min LC-MS MH+ 451; $^1$H NMR (400 MHz, DMSO-d6) δ 9.37 (br.s, 2H), 9.09 (s, 1H), 8.27 (s, 1H), 7.9-8.0 (m, 3H), 7.65 (dd, 1H), 7.24 (dd, 1H), 6.98 (td, 1H), 4.72 (s, 2H), 4.16 (t, 2H), 3.72 (s, 3H), 3.03 (t, 2H), 2.65 (d, 3H), 2.50 (t, 2H), 2.06 (s, 3H).

Example 87

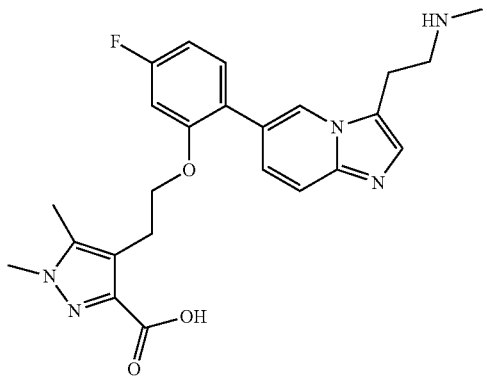

4-[2-(5-fluoro-2-{3-[2-(methylamino)ethyl]imidazo[1,2-a]pyridin-6-yl}phenoxy)ethyl]-1,5-dimethyl-1H-pyrazole-3-carboxylic acid Step 1

A solution of tert-butyl N-{[6-(4-fluoro-2-hydroxyphenyl)imidazo[1,2-a]pyridin-3-yl]ethyl}-N-methylcarbamate (intermediate 25, 600 mg, 1.3 mmol) in toluene (6.0 mL) was reacted with methyl 4-(2-hydroxyethyl)-1,5-dimethyl-1H-pyrazole-3-carboxylate (514 mg, 2.6 mmol) and cyanomethylene tributylphosphorane (0.68 mL, 2.6 mmol) at 100° C. for 16 hr. The reaction mixture was then diluted with ethyl acetate, and washed with water and brine, dried over sodium sulphate and concentrated. This crude material was purified by prep TLC by elution with DCM: methanol (95:5) to give {[(tert-butoxy)carbonyl](methyl)amino} ethyl)imidazo[1,2-a]pyridin-6-yl]-5-fluorophenoxy}ethyl)-1,5-dimethyl-1H-pyrazole-3-carboxylate (400 mg, 54%). $^1$H NMR (400 MHz, DMSO-d6) δ 8.34 (br.d, 1H), 7.63 (s, 1H), 7.53 (d, 1H), 7.50-7.40 (m, 2H), 7.21 (d, 1H), 7.07 (dd, 1H), 6.87 (td, 1H), 4.11 (t, 2H), 3.72 (s, 3H), 3.68 (s, 3H), 3.47 (t, 2H), 3.32 (s, 3H), 3.11 (t, 2H), 3.00 (t, 2H), 2.73 (s, 3H), 1.92 (s, 3H), 1.33 (s, 9H).

Step 2

A solution of {[(tert-butoxy)carbonyl](methyl)amino} ethyl)imidazo[1,2-a]pyridin-6-yl]-5-fluorophenoxy}ethyl)-1,5-dimethyl-1H-pyrazole-3-carboxylate (250 mg, 0.44 mmol) in THF-water (4:1, 3.0 mL) was cooled at 0° C. and treated with a solution of lithium hydroxide (37 mg, 0.88 mmol) in ethanol (0.02 mL) at 0° C. The resulting mixture was stirred at rt for 16 hr. The reaction mixture was evaporated under reduced pressure, the crude reaction mixture was acidified with saturated citric acid solution and extracted with DCM. The final organic layer was dried over sodium sulphate and concentrated to afford desired product 4-(2-{2-[3-(2-{[(tert-butoxy)carbonyl](methyl)amino}ethyl)imidazo[1,2-a]pyridin-6-yl]-5-fluorophenoxy}ethyl)-1,5-dimethyl-1H-pyrazole-3-carboxylic acid (200 mg, 82%). $^1$H NMR (400 MHz, DMSO-d6) δ 12.4 (br.s, 1H), 8.34 (br.d, 1H), 7.66 (s, 1H), 7.54 (d, 1H), 7.45-7.35 (m, 2H), 7.24 (d, 1H), 7.13 (dd, 1H), 6.87 (td, 1H), 4.11 (t, 2H), 3.67 (s, 3H), 3.47 (t, 2H), 3.32 (s, 3H), 3.11 (t, 2H), 2.99 (t, 2H), 2.77 (s, 3H), 1.94 (s, 3H), 1.33 (s, 9H).

Step 3

According to the general method for Boc deprotection (method B) 4-(2-{2-[3-(2-{[(tert-butoxy)carbonyl](methyl)amino}ethyl)imidazo[1,2-a]pyridin-6-yl]-5-fluorophenoxy}ethyl)-1,5-dimethyl-1H-pyrazole-3-carboxylic acid (35 mg, 0.06 mmol) was dissolved in dioxane (4 mL) and treated with a solution of HCl in ether (2M, 4 mL). The solution stirred at room temperature for 3 hr and was evaporated under reduced pressure. The crude product was dissolved in water and freeze dried to give the title compound as a light brown solid (27 mg, 87%). hplc rt 3.7 min LC-MS MH+ 452; $^1$H NMR (400 MHz, DMSO-d6) δ 14.6 (br.s, 1H), 8.97 (br. s, 2H), 8.92 (s, 1H), 8.15 (s, 1H), 8.00 (dd, 2H), 7.56 (dd, 1H), 7.21 (dd, 1H), 6.97 (td, 1H), 4.14 (t, 2H), 3.73 (s, 3H), 3.49 (t, 2H), 3.29 (q, 2H), 3.03 (t, 2H), 2.57 (d, 3H), 2.06 (s, 3H).

Example 88

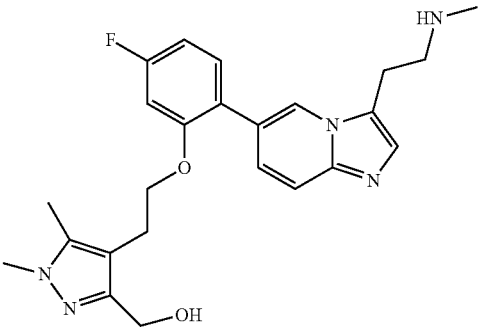

{4-[2-(5-fluoro-2-{3-[2-(methylamino)ethyl]imidazo[1,2-a]pyridin-6-yl}phenoxy)ethyl]-1,5-dimethyl-1H-pyrazol-3-yl}methanol Step 1

A solution of {[(tert-butoxy)carbonyl](methyl)amino} ethyl)imidazo[1,2-a]pyridin-6-yl]-5-fluorophenoxy}ethyl)-1,5-dimethyl-1H-pyrazole-3-carboxylate (Example 87 step 1 intermediate, 100 mg, 0.18 mmol) in THF (3 mL) was cooled at 0° C. and treated with a solution of lithium aluminium hydride (2M in THF, 0.18 ml, 0.09 mmol). The resulting mixture was stirred at 0° C. for 2 hr. the reaction mixture was quenched with sodium sulfate decahydrate. The reaction mixture was then filtered through Celite bed, which was washed with ethyl acetate. The filtrate was dried over Na2SO4 and evaporated under reduced pressure. The crude product was purified by prep TLC (5% MeOH/DCM) to tert-butyl N-{2-[6-(4-fluoro-2-{2-[3-(hydroxymethyl)-1,5-dimethyl-1H-pyrazol-4-yl]ethoxy}-phenyl)imidazo[1,2-a]pyridin-3-yl]ethyl}-N-methylcarbamate as an off-white solid (50 mg, 53%). $^1$H NMR (400 MHz, DMSO-d6) 8.35 (br.d, 1H), 7.50-7.40 (m, 3H), 7.26 (d, 1H), 7.03 (dd, 1H), 6.88 (td, 1H), 4.79 (t, 1H), 4.28 (d, 2H), 4.09 (t, 2H), 3.62 (s, 3H), 3.49 (t, 2H), 3.14 (t, 2H), 2.79 (s, 3H), 1.94 (s, 3H), 0.98 (s, 9H).

Step 2

According to the general method for Boc deprotection (method B), tert-butyl N-{2-[6-(4-fluoro-2-{2-[3-(hydroxymethyl)-1,5-dimethyl-1H-pyrazol-4-yl]ethoxy}-phenyl)imidazo[1,2-a]pyridin-3-yl]ethyl}-N-methylcarbamate (50 mg, 0.04 mmol) was dissolved in dioxane (4 mL) and treated with a solution of HCl in ether (2M, 4 mL). The solution stirred at room temperature for 3 hr and was evaporated under reduced pressure. The crude product was dissolved in water and freeze-dried to give the title compound as a light brown solid (35 mg, 86%). hplc rt 3.6 min LC-MS MH+ 436; ¹H NMR (400 MHz, DMSO-d₆) δ 14.5. (br.s, 1H), 8.91 (m, 3H), 8.13 (s, 1H), 7.97 (dd, 2H), 7.52 (dd, 1H), 7.11 (dd, 1H), 6.95 (td, 1H), 4.31 (s, 2H), 4.10 (t, 2H), 3.63 (s, 3H), 3.46 (t, 2H), 3.35 (q, 2H), 2.78 (t, 2H), 2.54 (d, 3H), 2.00 (s, 3H).

Example 89

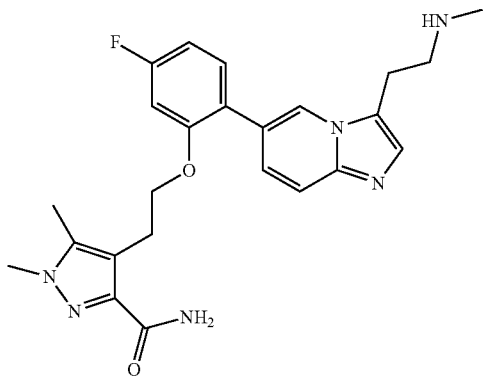

4-[2-(5-fluoro-2-{3-[2-(methylamino)ethyl]imidazo[1,2-a]pyridin-6-yl}phenoxy)ethyl]-1,5-dimethyl-1H-pyrazole-3-carboxamide Step 1

A solution of 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid (Example 87 step 2, 120 mg, 0.22 mmol) in DMF (3 mL) was treated with triethylamine (0.09 mL, 0.65 mmol), ammonium chloride (14.0 mg, 0.26 mmol), hydroxybenztriazole (37.4 mg, 0.28 mmol) and EDCl (53.0 mg, 0.28 mmol). The reaction mixture was stirred at rt for 16 hrs, diluted with DCM and washed with sat. NaHCO₃, water and brine, dried over sodium sulphate and concentrated. The crude product was purified over prep TLC (5% MeOH/DCM) to give tert-butyl N-[2-(6-{2-[2-(3-carbamoyl-1,5-dimethyl-1H-pyrazol-4-yl)ethoxy]-4-fluorophenyl}imidazo[1,2-a]pyridin-3-yl)ethyl]-N-methylcarbamate as an off-white solid (70 mg, 58%). ¹H NMR (400 MHz, DMSO-d₆) δ 8.34 (br.d, 1H), 7.52 (d, 1H), 7.45-7.30 (m, 2H), 7.26 (d, 1H), 7.20 (dd, 1H), 7.10 (s, 1H), 6.86 (td, 1H), 4.14 (t, 2H), 3.68 (s, 3H), 3.49 (t, 2H), 3.12 (t, 2H), 3.00 (t, 2H), 2.79 (s, 3H), 1.95 (s, 3H), 0.97 (s, 9H).
Step 2

According to the general method for Boc deprotection (method B), tert-butyl N-[2-(6-{2-[2-(3-carbamoyl-1,5-dimethyl-1H-pyrazol-4-yl)ethoxy]-4-fluorophenyl}imidazo[1,2-a]pyridin-3-yl)ethyl]-N-methylcarbamate (35 mg, 0.11 mmol) was dissolved in dioxane (2 ml) and treated with a solution of HCl in ether (2M, 4 ml). The solution stirred at room temperature for 3 hr and was evaporated under reduced pressure. The crude product dissolved in water and freeze dried to give the title compound as a light brown solid (25 mg, 87%). hplc rt 4.4 min LC-MS MH+ 451; ¹H NMR (400 MHz, DMSO-d₆) δ 14.7 (br.s, 1H), 9.02 (br. s, 2H), 8.94 (s, 1H), 8.15 (s, 1H), 8.03 (dd, 2H), 7.56 (dd, 1H), 7.31-7.28 (m, 2H), 7.10 (s, 1H), 6.97 (td, 1H), 4.16 (t, 2H), 3.72 (s, 3H), 3.57 (t, 2H), 3.29 (q, 2H), 3.04 (t, 2H), 2.67 (d, 3H), 2.08 (s, 3H).

Example 90

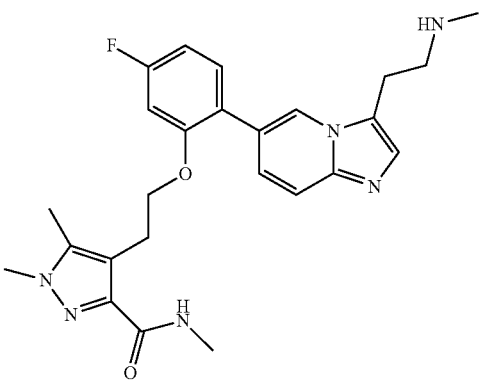

4-[2-(5-fluoro-2-{3-[2-(methylamino)ethyl]imidazo[1,2-a]pyridin-6-yl}phenoxy)ethyl]-N,1,5-trimethyl-1H-pyrazole-3-carboxamide Step 1

A solution of 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid (Example 87 step 2, 120 mg, 0.22 mmol) in DMF (3 mL) was treated with triethylamine (0.09 mL, 0.65 mmol), methylamine solution (2M in THF, 14.0 mg, 0.26 mmol), hydroxybenztriazole (37.4 mg, 0.28 mmol) and EDCl (53.0 mg, 0.28 mmol). The reaction mixture was stirred at rt for 16 hrs, diluted with DCM and washed with sat. NaHCO₃, water and brine, dried over sodium sulphate and concentrated. The crude product was purified over prep TLC (5% MeOH/DCM) to give tert-butyl N-[2-(6-{2-[2-(3-carbamoyl-1,5-dimethyl-1H-pyrazol-4-yl)ethoxy]-4-fluorophenyl}imidazo[1,2-a]pyridin-3-yl)ethyl]-N-methylcarbamate as an off-white solid (70 mg, 58%). ¹H NMR (400 MHz, DMSO-d₆) δ 8.34 (br.d, 1H), 7.52 (d, 1H), 7.45-7.30 (m, 2H), 7.26 (d, 1H), 7.20 (dd, 1H), 7.10 (s, 1H), 6.86 (td, 1H), 4.14 (t, 2H), 3.68 (s, 3H), 3.49 (t, 2H), 3.12 (t, 2H), 3.00 (t, 2H), 2.79 (s, 3H), 1.95 (s, 3H), 0.97 (s, 9H).
Step 2

According to the general method for Boc deprotection (method B), tert-butyl N-[2-(6-{2-[2-(3-cyano-1,5-dimethyl-1H-pyrazol-4-yl)ethoxy]-4-fluorophenyl}imidazo[1,2-a]pyridin-3-yl)ethyl]-N-methylcarbamate (35 mg, 0.11 mmol) was dissolved in dioxane (2 ml) and treated with a solution of HCl in dioxane (4M, 4 ml). The solution stirred at room temperature for 3 hr and was evaporated under reduced pressure. The crude product was dissolved in water and freeze dried to give the title compound as a light brown solid (15 mg, 52%). hplc rt 5.7 min LC-MS MH+ 465; $^1$H NMR (400 MHz, DMSO-d) δ 14.5 (br.s, 1H), 8.88 (s, 1H), 8.80 (br. s, 2H), 8.08 (s, 1H), 7.99-7.92 (m, 3H), 7.55 (dd, 1H), 7.24 (dd, 1H), 6.97 (td, 1H), 4.15 (t, 2H), 3.73 (s, 3H), 3.47 (t, 2H), 3.30 (q, 2H), 3.04 (t, 2H), 2.67 (d, 3H), 2.59 (t, 3H), 2.07 (s, 3H).

Example 91

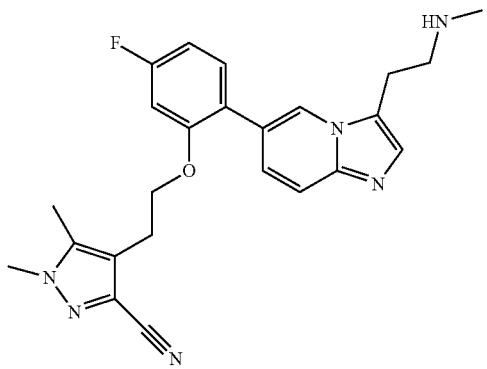

4-[2-(5-fluoro-2-{3-[2-(methylamino)ethyl]imidazo[1,2-a]pyridin-6-yl}phenoxy)ethyl]-1,5-dimethyl-1H-pyrazole-3-carbonitrile Step 1

A solution of tert-butyl N-[2-(6-{2-[2-(3-carbamoyl-1,5-dimethyl-1H-pyrazol-4-yl)ethoxy]-4-fluorophenyl}imidazo[1,2-a]pyridin-3-yl)ethyl]-N-methylcarbamate (Example 89 step 1, 40 mg, 0.072 mmol) in THF (1 mL) was treated with triethylamine (0.048 mL, 0.36 mmol). The reaction mixture was cooled to 0° C. before addition of trifluoroacetic anhydride (0.026 mL, 0.17 mmol) and the mixture was then allowed to warm to RT and stirred for 2 hr. The reaction mixture was quenched with sat NaHCO$_3$ solution and extracted with EtOAc, washed with water, brine, dried over sodium sulfate and evaporated under reduced pressure. The crude product was purified over prep TLC (5% MeOH/DCM) to give tert-butyl N-[2-(6-{2-[2-(3-cyano-1,5-dimethyl-1H-pyrazol-4-yl)ethoxy]-4-fluorophenyl}imidazo[1,2-a]pyridin-3-yl)ethyl]-N-methylcarbamate (17 mg. 44%). δ 8.31 (br.d, 1H), 7.50-7.35 (m, 3H), 7.16 (d, 1H), 7.09 (dd, 1H), 6.90 (td, 1H), 4.17 (t, 2H), 3.71 (s, 3H), 3.47 (t, 2H), 3.10 (t, 2H), 2.88 (t, 2H), 2.79 (s, 3H), 1.99 (s, 3H), 0.97 (s, 9H)

Step 2

According to the general method for Boc deprotection (method B), tert-butyl N-[2-(6-{2-[2-(3-cyano-1,5-dimethyl-1H-pyrazol-4-yl)ethoxy]-4-fluorophenyl}imidazo[1,2-a]pyridin-3-yl)ethyl]-N-methylcarbamate (17 mg, 0.11 mmol) was dissolved in dioxane (2 ml) and treated with a solution of HCl in ether (2M, 4 ml). The solution stirred at room temperature for 3 hr and was evaporated under reduced pressure. The crude product was dissolved in water and freeze dried to give the title compound as a light brown solid (12 mg, 87%). hplc rt 6.2 min LC-MS MH+ 433; $^1$H NMR (400 MHz, DMSO-d$_6$) δ 14.5 (br.s, 1H) 8.91 (br.s, 2H), 8.86 (s, 1H), 8.09 (s, 1H), 7.90 (dd, 2H), 7.51 (dd, 1H), 7.16 (dd, 1H), 6.98 (td, 1H), 4.18 (t, 2H), 3.76 (s, 3H), 3.43 (t, 2H), 3.27 (t, 2H), 2.88 (q, 2H), 2.67 (t, 3H), 2.14 (s, 3H).

Example 92

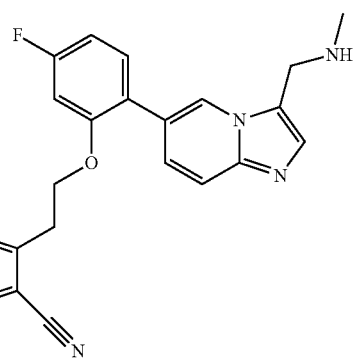

4-[2-(5-fluoro-2-{3-[(methylamino)methyl]imidazo[1,2-a]pyridin-6-yl}phenoxy)ethyl]-1,5-dimethyl-1H-pyrazole-3-carbonitrile Step 1

A solution of tert-butyl N-[(6-{2-[2-(3-carbamoyl-1,5-dimethyl-1H-pyrazol-4-yl)ethoxy]-4-fluorophenyl}imidazo[1,2-a]pyridin-3-yl)methyl]-N-methylcarbamate (Example 85 step 1, 80 mg, 0.15 mmol) in THF (1.5 mL) was treated with triethylamine (0.10 mL, 0.75 mmol). The reaction mixture was cooled to 0° C. before addition of trifluoroacetic anhydride (0.053 mL, 0.37 mmol) and the mixture was then allowed to warm to RT and stirred for 2 hr. The reaction mixture was quenched with sat NaHCO$_3$ solution and extracted with EtOAc, washed with water, brine, dried over sodium sulfate and evaporated under reduced pressure. The crude product was purified over prep TLC (5% MeOH/DCM) to give tert-butyl N-[(6-{2-[2-(3-cyano-1,5-dimethyl-1H-pyrazol-4-yl)ethoxy]-4-fluorophenyl}imidazo[1,2-a]pyridin-3-yl)methyl]-N-methylcarbamate (27 mg. 35%). $^1$H NMR (400 MHz, DMSO-d$_6$) δ 8.44 (br.d, 1H), 7.61 (s, 1H), 7.52 (d, 1H), 7.33 (dd, 1H), 7.20 (dd, 1H), 7.09 (d, 1H), 6.86 (td, 1H), 4.75 (s, 2H), 4.15 (t, 2H), 3.69 (s, 3H), 2.89 (t, 2H), 2.66 (s, 2H), 2.79 (s, 3H), 1.93 (s, 3H), 1.32 (s, 9H).

Step 2

According to the general method for Boc deprotection (method B), tert-butyl N-[(6-{2-[2-(3-cyano-1,5-dimethyl-1H-pyrazol-4-yl)ethoxy]-4-fluorophenyl}imidazo[1,2-a]pyridin-3-yl)methyl]-N-methylcarbamate (27 mg, 0.11 mmol) was dissolved in dioxane (2 ml) and treated with a solution of HCl in ether (2M, 4 ml). The solution stirred at room temperature for 3 hr and was evaporated under reduced pressure. The crude product was dissolved in water and freeze dried to give the title compound as an off white solid (7 mg, 32%) hplc rt 5.2 min LC-MS MH+ 419; $^1$H NMR (400 MHz, DMSO-d$_6$) δ 9.40 (br.s, 2H), 9.06 (s, 1H), 8.29 (s, 1H), 7.89 (dd, 2H), 7.61 (dd, 1H), 7.16 (dd, 1H), 6.98 (td, 1H), 4.69 (br.s, 2H), 4.18 (t, 2H), 3.74 (s, 3H), 2.88 (t, 2H), 2.61 (t, 2H), 2:13 (s, 3H).

Example 93

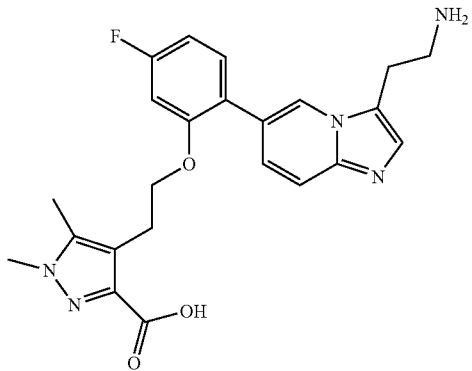 [SMILES: Cc1c(CCOc2cc(F)ccc2-c2ccc3ncc(CCN)n3c2)c(C(=O)O)nn1C]

4-(2-{2-[3-(2-aminoethyl)imidazo[1,2-a]pyridin-6-yl]-5-fluorophenoxy}ethyl)-1,5-dimethyl-1H-pyrazole-3-carboxylic acid Step 1

A solution of tert-butyl N-{[6-(4-fluoro-2-hydroxyphenyl)imidazo[1,2-a]pyridin-3-yl]ethyl}-carbamate (intermediate 23, 600 mg, 1.6 mmol) in toluene (10 mL) was reacted with methyl 4-(2-hydroxyethyl)-1,5-dimethyl-1H-pyrazole-3-carboxylate (640 mg, 3.2 mmol) and cyanomethylene tributylphosphorane (0.85 mL, 3.2 mmol) at 100° C. for 16 hr. The reaction mixture was then diluted with ethyl acetate, and washed with water and brine, dried over sodium sulphate and concentrated. This crude material was purified by column chromatography by elution with DCM: methanol (95:5) to give {[2-(tert-butoxy)carbonyl]amino}ethyl)imidazo[1,2-a]pyridin-6-yl]-5-fluorophenoxy}ethyl)-1,5-dimethyl-1H-pyrazole-3-carboxylate (500 mg, 56%). $^1$H NMR (400 MHz, CDCl$_3$) δ 8.06 (s, 1H), 7.58 (d, 1H), 7.50 (s, 1H), 7.27 (td, 1H), 7.20 (d, 1H), 6.78 (dd, 1H), 6.73 (td, 1H), 4.88 (s, 1H), 4.18 (t, 2H), 3.90 (s, 3H), 3.73 (s, 3H), 3.52 (t, 2H), 3.09 (t, 2H), 1.84 (s, 3H), 1.34 (s, 9H).

Step 2

A solution of (2-{(tert-butoxy)carbonyl]amino}ethyl)imidazo[1,2-a]pyridin-6-yl]-5-fluorophenoxy}ethyl)-1,5-dimethyl-1H-pyrazole-3-carboxylate (300 mg, 0.54 mmol) in THF-water (4:1, 3.0 mL) was cooled at 0° C. and treated with a solution of lithium hydroxide (46 mg, 1.09 mmol) in ethanol (0.02 mL) at 0° C. The resulting mixture was stirred at rt for 16 hr. The reaction mixture was evaporated under reduced pressure, the crude reaction mixture was acidified with saturated citric acid solution and extracted with DCM. The final organic layer was dried over sodium sulphate and concentrated to afford desired product 4-(2-{2-[3-(2-{(tert-butoxy)carbonyl]amino}ethyl)imidazo[1,2-a]pyridin-6-yl]-5-fluorophenoxy}ethyl)-1,5-dimethyl-1H-pyrazole-3-carboxylic acid (280 mg, 96%) as a brown solid. $^1$H NMR (400 MHz, CDCl$_3$) δ 8.07 (s, 1H), 7.73 (d, 1H), 7.48 (s, 1H), 7.29 (m, 1H), 6.80-6.70 (m, 1H), 4.73 (s, 1H), 4.14 (t, 2H), 3.71 (s, 3H), 3.49 (t, 2H), 3.09 (s, 3H), 1.96 (s, 3H), 1.40 (d, 9H).

Step 3

According to the general method for Boc deprotection (method B) 4-(2-{2-[3-(2-{2-[(tert-butoxy)carbonyl]amino}ethyl)imidazo[1,2-a]pyridin-6-yl]-5-fluorophenoxy}ethyl)-1,5-dimethyl-1H-pyrazole-3-carboxylic acid (40 mg, 0.06 mmol) was dissolved in dioxane (4 mL) and treated with a solution of HCl in ether (2M, 4 mL). The solution stirred at room temperature for 3 hr and was evaporated under reduced pressure. The crude product was dissolved in water and freeze dried to give the title compound as a light brown solid (30 mg, 92%). hplc rt 3.7 min LC-MS MH$^+$ 452; $^1$H NMR (400 MHz, DMSO-d$_6$) δ 14.6 (br.s, 1H), 12.4 (br.s, 1H), 8.90 (s, 1H), 8.14 (s, 3H), 8.00 (dd, 2H), 7.55 (dd, 1H), 7.21 (dd, 1H), 6.97 (td, 1H), 4.14 (t, 2H), 3.74 (s, 3H), 3.43 (t, 2H), 3.20 (q, 2H), 3.03 (t, 2H), 2.06 (s, 3H).

Example 94

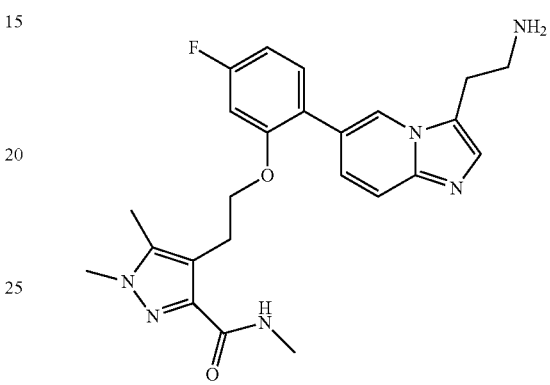

4-(2-{2-[3-(2-aminoethyl)imidazo[1,2-a]pyridin-6-yl]-5-fluorophenoxy}ethyl)-N,1,5-trimethyl-1H-pyrazole-3-carboxamide Step 1

A solution of 4-(2-{2-[3-({[(tert-butoxy)carbonyl](methyl)amino}methyl)imidazo[1,2-a]pyridin-6-yl]-5-fluorophenoxy}ethyl)-1,5-dimethyl-1H-pyrazole-3-carboxylic acid (Example 93 step 2, 100 mg, 0.19 mmol) in THF (2 mL) was treated with triethylamine (0.078 mL, 0.56 mmol), methylamine solution (2M in THF, 1.8 mL, 0.26 mmol), hydroxybenztriazole (31.9 mg, 0.24 mmol) and EDCl (45.3 mg, 0.24 mmol). The reaction mixture was stirred at rt for 16 hrs, diluted with DCM and washed with sat. NaHCO$_3$, water and brine, dried over sodium sulphate and concentrated. The crude product was purified by prep TLC (5% MeOH/DCM) to give tert-butyl N-[2-(6-{2-[2-(3-(methyl) carbamoyl-1,5-dimethyl-1H-pyrazol-4-yl)ethoxy]-4-fluorophenyl}imidazo[1,2-a]pyridin-3-yl)ethyl]-carbamate as an off-white solid (60 mg, 58%). $^1$H NMR (400 MHz, CDCl$_3$) δ 8.07 (s, 1H), 7.54 (d, 1H), 7.46 (s, 1H), 7.19 (m, 1H), 6.85 (td, 1H), 6.77 (dd, 1H), 6.70 (td, 1H), 5.03 (s, 1H), 4.22 (t, 2H), 3.62 (s, 3H), 3.48 (t, 2H), 3.09 (s, 3H), 2.92 (s, 3H), 1.80 (s, 3H), 1.39 (d, 9H).

Step 2

According to the general method for Boc deprotection (method B) tert-butyl N-[2-(6-{2-[2-(3-(methyl) carbamoyl-1,5-dimethyl-1H-pyrazol-4-yl)ethoxy]-4-fluorophenyl} imidazo[1,2-a]pyridin-3-yl)ethyl]-carbamate (40 mg, 0.073 mmol) was dissolved in dioxane (2 ml) and treated with a solution of HCl in ether (2M, 5 ml). The solution stirred at room temperature for 3 hr and was evaporated under reduced pressure. The crude product dissolved in water and freeze dried to give the title compound as a light brown solid (30 mg, 92%) hplc rt 7.6 min LC-MS MH$^+$ 451; $^1$H NMR (400 MHz, DMSO-d$_6$) δ 14.7 (br.s, 1H), 8.95 (s, 1H), 8.19

(br. s, 3H), 8.15 (s, 1H), 8.02 (dd, 2H), 7.91 (q, 1H), 7.56 (dd, 1H), 7.24 (dd, 1H), 6.97 (td, 1H), 4.16 (t, 2H), 3.73 (s, 3H), 3.45 (t, 2H), 3.20 (q, 2H), 3.04 (t, 2H), 2.67 (d, 3H), 2.07 (s, 3H).

Example 95

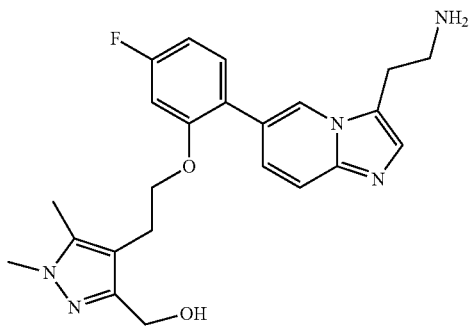 [SMILES: Cc1c(CCOc2cc(F)ccc2-c2ccc3ncc(CCN)n3c2)c(CO)nn1C]

[4-(2-{2-[3-(2-aminoethyl)imidazo[1,2-a]pyridin-6-yl]-5-fluorophenoxy)ethyl)-1,5-dimethyl-1H-pyrazol-3-yl]methanol Step 1

A solution of {[(tert-butoxy)carbonyl]amino}ethyl)imidazo[1,2-a]pyridin-6-yl]-5-fluorophenoxy}ethyl)-1,5-dimethyl-1H-pyrazole-3-carboxylate (Example 93 step 1 intermediate, 100 mg, 0.18 mmol) in THF (3 mL) was cooled at 0° C. and treated with a solution of lithium aluminium hydride (2M in THF, 0.18 ml, 0.09 mmol). The resulting mixture was stirred at 0° C. for 2 hr. the reaction mixture was quenched with sodium sulfate decahydrate. The reaction mixture was then filtered through Celite bed, which was washed with ethyl acetate. The filtrate was dried over $Na_2SO_4$ and evaporated under reduced pressure. The crude product was purified by prep TLC (5% MeOH/DCM) to tert-butyl N-{2-[6-(4-fluoro-2-{2-[3-(hydroxymethyl)-1,5-dimethyl-1H-pyrazol-4-yl]ethoxy}-phenyl)-imidazo[1,2-a]pyridin-3-yl]ethyl}-carbamate (60 mg, 63%). $^1$H NMR (400 MHz, $CDCl_3$) δ 8.05 (s, 1H), 7.58 (d, 1H), 7.46 (s, 1H), 7.20 (m, 1H), 6.75-6.70 (m, 2H), 4.99 (s, 1H), 4.47 (s, 2H), 4.05 (t, 2H), 3.60 (s, 3H), 3.48 (t, 2H), 3.06 (t, 3H), 2.84 (t, 2H), 1.92 (s, 3H), 1.36 (d, 9H).

Step 2

According to the general method for. Boc deprotection (method B), tert-butyl N-{2-[6-(4-fluoro-2-{2-[3-(hydroxymethyl)-1,5-dimethyl-1H-pyrazol-4-yl]ethoxy}-phenyl)imidazo[1,2-a]pyridin-3-yl]ethyl}-carbamate (60 mg, 0.0115 mmol) was dissolved in dioxane (4 mL) and treated with a solution of HCl in ether (2M, 3 mL). The solution stirred at room temperature for 3 hr and was evaporated under reduced pressure. The crude product was dissolved in water and freeze-dried to give the title compound as a light brown solid (40 mg, 82%). hplc rt 7.2 min LC-MS MH⁺ 424; $^1$H NMR (400 MHz, DMSO-$d_6$) δ 14.6 (br.s, 1H), 8.94 (s, 1H), 8.14 (br. s, 3H), 8.03 (dd, 2H), 7.56 (dd, 1H), 7.13 (dd, 1H), 6.97 (td, 1H), 4.26 (s, 2H), 4.14 (t, 2H), 3.62 (s, 3H), 3.43 (t, 2H), 3.20 (q, 2H), 2.80 (t, 2H), 2.03 (s, 3H).

Example 96

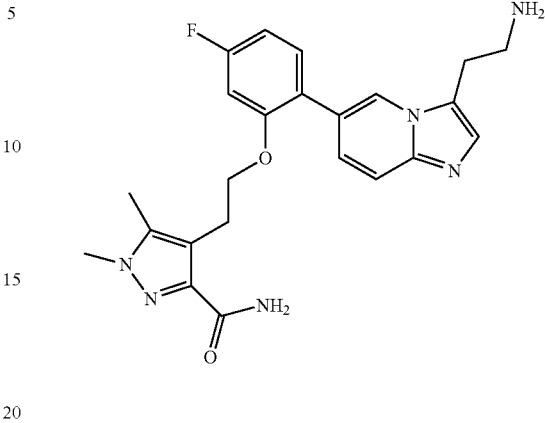

4-(2-{2-[3-(2-aminoethyl)imidazo[1,2-a]pyridin-6-yl]-5-fluorophenoxy}ethyl)-1,5-dimethyl-1H-pyrazole-3-carboxamide Step 1

A solution of 4-(2-{2-[3-(2-{[(tert-butoxy)carbonyl]amino}ethyl)imidazo[1,2-a]pyridin-6-yl]-5-fluorophenoxy}ethyl)-1,5-dimethyl-1H-pyrazole-3-carboxylic acid (Example 93 step 2, 180 mg, 0.34 mmol) in DMF (3 mL) was treated with triethylamine (0.14 mL, 1.0 mmol), ammonium chloride (21.5 mg, 0.40 mmol), hydroxybenztriazole (57.3 mg, 0.43 mmol) and EDCl (81.5 mg, 0.43 mmol). The reaction mixture was stirred at rt for 16 hrs, diluted with DCM and washed with sat. $NaHCO_3$, water and brine, dried over sodium sulphate and concentrated. The crude product was purified by prep TLC (5% MeOH/DCM) to give tert-butyl N-[2-(6-{2-[2-(3-carbamoyl-1,5-dimethyl-1H-pyrazol-4-yl)ethoxy]-4-fluorophenyl}imidazo[1,2-a]pyridin-3-yl)ethyl]carbamate as a light brown solid (120 mg, 67%). $^1$H NMR (400 MHz, $CDCl_3$) δ 8.10 (s, 1H), 7.55 (d, 1H), 7.46 (s, 1H), 7.20 (m, 1H), 6.79 (dd, 1H), 6.75-6.70 (m, 2H), 5.28 (s, 1H), 5.25 (s, 1H), 4.17 (t, 2H), 3.65 (s, 3H), 3.48 (t, 2H), 3.08 (t, 3H), 1.87 (s, 3H), 1.40 (d, 9H).

Step 2

According to the general method for Boc deprotection (method B), tert-butyl N-[2-(6-{2-[2-(3-carbamoyl-1,5-dimethyl-1H-pyrazol-4-yl)ethoxy]-4-fluorophenyl}imidazo[1,2-a]pyridin-3-yl)ethyl]carbamate (50 mg, 0.093 mmol) was dissolved in dioxane (2 ml) and treated with a solution of HCl in ether (2M, 4 ml). The solution stirred at room temperature for 3 hr and was evaporated under reduced pressure. The crude product dissolved in water and freeze dried to give the title compound as a light brown solid (30 mg, 74%). hplc rt 4.8 min LC-MS MH⁺ 437; $^1$H NMR (400 MHz, DMSO-$d_6$) δ 14.8 (br.s, 1H), 8.94 (s, 1H), 8.23 (br. s, 3H), 8.15 (s, 1H), 8.03 (dd, 2H), 7.56 (dd, 1H), 7.30 (dd, 2H), 7.10 (s, 1H), 6.97 (td, 1H), 4.16 (t, 2H), 3.71 (s, 3H), 3.46 (t, 2H), 3.20 (q, 2H), 3.04 (t, 2H), 2.07 (s, 3H).

Example 97

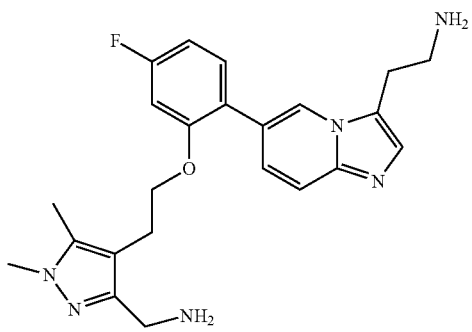 [SMILES: Cc1c(CCOc2cc(F)ccc2-c2ccc3ncc(CCN)n3c2)c(CN)nn1C]

2-[6-(2-{2-[3-(aminomethyl)-1,5-dimethyl-1H-pyrazol-4-yl]ethoxy}-4-fluorophenyl)imidazo[1,2-a]pyridin-3-yl]ethan-1-amine Step 1

A solution of tert-butyl N-{2-[6-(4-fluoro-2-{2-[3-(hydroxymethyl)-1,5-dimethyl-1H-pyrazol-4-yl]ethoxy}-phenyl)imidazo[1,2-a]pyridin-3-yl]ethyl}-carbamate (Example 95 Step 1 70 mg, 0.13 mmol) in DCM (3 mL) was cooled at 0° C. and treated with trimethylamine (0.056 mL, 0.20 mmol) and mesylchloride (0.016 mL, 0.20 mmol), both added drop wise. The reaction mixture was stirred at rt for 2 hr, diluted with DCM washed with sat. NaHCO₃ solution and brine, dried over sodium sulphate and concentrated. The crude tert-butyl N-(2-{6-[4-fluoro-2-(2-{3-[(methanesulfonyloxy)methyl]-1,5-dimethyl-1H-pyrazol-4-yl}ethoxy)phenyl]-imidazo[1,2-a]pyridin-3-yl}ethyl)carbamate (70 mg, 87%) was taken onto the next step with any purification.

Step 2

A solution of tert-butyl N-(2-{6-[4-fluoro-2-(2-{3-[(methanesulfonyloxy)methyl]-1,5-dimethyl-1H-pyrazol-4-yl}ethoxy)phenyl]-imidazo[1,2-a]pyridin-3-yl}ethyl)carbamate (70 mg, 0.116 mmol) in DMF (2 mL) was treated with sodium azide (13.7 mg, 0.23 mmol). The reaction mixture was heated at 90° C. for 16 hrs, diluted with DCM, washed with sat. NaHCO₃ solution and brine, dried over sodium sulphate and concentrated. The crude product, tert-butyl N-{2-[6-(2-{2-[3-(azidomethyl)-1,5-dimethyl-1H-pyrazol-4-yl]ethoxy}-4-fluorophenyl)imidazo[1,2-a]pyridin-3-yl]ethyl}carbamate (50 mg, 80%) was taken onto the next step without further purification.

Step 3

A solution of tert-butyl N-{2-[6-(2-{2-[3-(azidomethyl)-1,5-dimethyl-1H-pyrazol-4-yl]ethoxy}-4-fluorophenyl)imidazo[1,2-a]pyridin-3-yl]ethyl}carbamate in MeOH (1.5 mL) was degassed with argon for about 10 min followed by the addition of Pd/C (15 mg) and the resultant mixture was stirred under $H_2$ (balloon pressure) for 2 h at ambient temperature. Reaction mixture was filtered through Celite bed, washed with MeOH and the filtrate was evaporated. The crude product was purified over prep TLC (5% MeOH/DCM) to give tert-butyl N-{2-[6-(2-{2-[3-(aminomethyl)-1,5-dimethyl-1H-pyrazol-4-yl]ethoxy}-4-fluorophenyl)imidazo[1,2-a]pyridin-3-yl]ethyl}carbamate (17 mg, 36%) as an off-white solid. $^1$H NMR (400 MHz, DMSO-$d_6$) δ 8.37 (br. s, 4H), 7.52 (td, 1H), 7.45-7.40 (m, 2H), 7.26 (d, 1H), 7.06 (d, 1H), 7.00 (dd, 2H), 6.89 (td, 1H), 4.08 (t, 2H), 3.56 (s, 3H), 3.52 (s, 2H), 3.29 (t, 2H), 3.02 (t, 2H), 2.77 (t, 2H), 1.92 (s, 3H), 1.33 (s, 9H).

Step 4

According to the general method for Boc deprotection (method B), tert-butyl N-{2-[6-(2-{2-[3-(aminomethyl)-1,5-dimethyl-1H-pyrazol-4-yl]ethoxy}-4-fluorophenyl)imidazo[1,2-a]pyridin-3-yl]ethyl}carbamate (17 mg, 0.033 mmol) was dissolved in dioxane (2 ml), cooled at 0° C., and treated with a solution of HCl in ether (2M, 3 ml). The solution stirred at room temperature for 3 hr and was evaporated under reduced pressure. The crude product dissolved in water and freeze dried to give the title compound as a light brown solid (8 mg, 58%). hplc rt 4.5 min LC-MS MH⁺ 423; $^1$H NMR (400 MHz, DMSO-$d_6$) δ 14.7 (br.s, 1H), 9.00 (s, 1H), 8.24 (br. s, 4H), 8.15 (s, 1H), 8.11 (d, 1H), 8.01 (d, 2H), 7.57 (td, 1H), 7.13 (dd, 2H), 6.98 (td, 1H), 4.10 (t, 2H), 3.67 (s, 3H), 3.46 (t, 2H), 3.20 (t, 2H), 2.82 (t, 2H), 2.05 (s, 3H).

Example 98

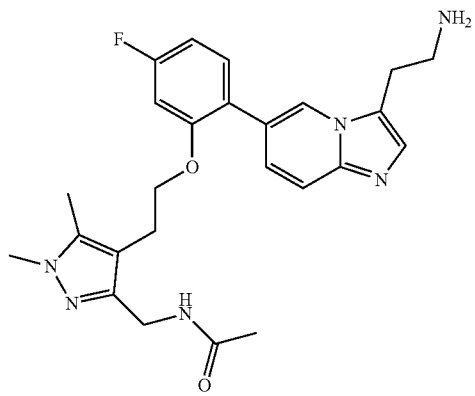 [SMILES: CC(=O)NCc1nn(C)c(C)c1CCOc1cc(F)ccc1-c1ccc2ncc(CCN)n2c1]

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}acetamide Step 1

A solution of tert-butyl N-{2-[6-(2-{2-[3-(aminomethyl)-1,5-dimethyl-1H-pyrazol-4-yl]ethoxy}-4-fluorophenyl)imidazo[1,2-a]pyridin-3-yl]ethyl}carbamate (Example 97 Step 3, 90 mg, 0.17 mmol) in DCM (3 mL) was cooled at 0° C. before dropwise addition of triethylamine (0.048 mL, 0.344 mmol) followed by acetyl chloride (0.018 mL, 0.258 mmol). The reaction mixture was warmed to rt for 2 hr, diluted with DCM washed with sat.NaHCO₃ solution and brine, dried over sodium sulphate and concentrated under reduced pressure. The crude product was purified by prep TLC (5% MeOH/DCM) to give tert-butyl N-{2-[6-(2-{2-[3-(acetamidomethyl)-1,5-dimethyl-1H-pyrazol-4-yl]ethoxy}-4-fluorophenyl)imidazo[1,2-a]pyridin-3-yl]ethyl}carbamate (40 mg, 41%). $^1$H NMR (400 MHz, DMSO-$d_6$) δ 8.38 (s, 1H), 8.04 (t, 1H), 7.52 (d, 1H), 7.50-7.40 (m, 2H), 7.30 (d, 1H), 7.05-6.95 (m, 2H), 6.88 (td, 1H), 4.07 (d, 2H), 4.01 (t, 2H), 3.57 (s, 3H), 3.09 (m, 2H), 3.04 (t, 2H), 2.75 (t, 2H), 1.91 (s, 3H), 1.74 (s, 3H), 1.33 (s, 9H).

Step 2

According to the general method for Boc deprotection (method B), tert-butyl N-{2-[6-(2-{2-[3-(acetamidomethyl)-1,5-dimethyl-1H-pyrazol-4-yl]ethoxy}-4-fluorophenyl)imidazo[1,2-a]pyridin-3-yl]ethyl}carbamate (40 mg, 0.07 mmol) was dissolved in dioxane (2 mL), cooled to 0° C. and treated with a solution of HCl in ether (2M, 5 mL). The solution stirred at room temperature for 3 hr and was evaporated under reduced pressure. The crude product dissolved in water and freeze dried to give the title compound as a light brown solid (30 mg, 91%). hplc rt 5.3 min LC-MS MH+ 465; $^1$H NMR (400 MHz, DMSO-d$_6$) δ 14.6 (br.s, 1H), 8.95 (s, 1H), 8.17-8.08 (m, 5H), 7.99 (d, 1H), 7.55 (td, 1H), 7.09 (dd, 1H), 6.96 (td, 1H), 4.05 (t, 2H), 3.95 (d, 2H), 3.62 (s, 3H), 3.45 (t, 2H), 3.20 (q, 2H), 2.76 (t, 2H), 2.05 (s, 3H), 1.72 (s, 3H).

Example 99

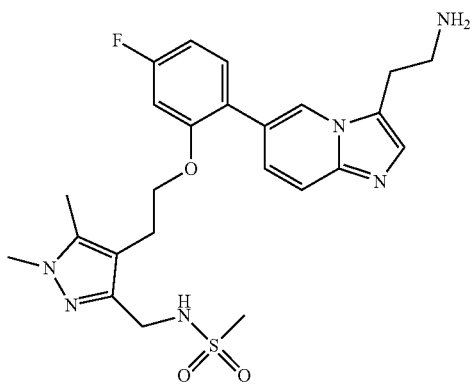 [SMILES: Cc1c(CCOc2cc(F)ccc2-c2ccc3ncc(CCN)n3c2)c(CNS(C)(=O)=O)nn1C]

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}methanesulfonamide Step 1
A solution of tert-butyl N-{2-[6-(2-{2-[3-(aminomethyl)-1,5-dimethyl-1H-pyrazol-4-yl]ethoxy}-4-fluorophenyl)imidazo[1,2-a]pyridin-3-yl]ethyl}carbamate (Example 97 Step 3, 90 mg, 0.17 mmol) in DCM (3 mL) was cooled at 0° C. before dropwise addition of triethylamine (0.048 mL, 0.344 mmol) followed by mesyl chloride (0.02 mL, 0.258 mmol). The reaction mixture was warmed to rt for 2 hr, diluted with DCM washed with sat.NaHCO$_3$ solution and brine, dried over sodium sulphate and concentrated under reduced pressure. The crude product was purified by prep TLC (5% MeOH/DCM) to give tert-butyl N-{2-[6-(4-fluoro-2-{2-[3-(methanesulfonamidomethyl)-1,5-dimethyl-1H-pyrazol-4-yl]ethoxy}phenyl)imidazo[1,2-a]pyridin-3-yl]ethyl}carbamate (30 mg, 29%). $^1$H NMR (400 MHz, DMSO-d$_6$) δ 8.36 (s, 1H), 7.51 (d, 1H), 7.50-7.40 (m, 2H), 7.29 (d, 1H), 7.20 (t, 1H), 7.05-6.95 (m, 2H), 6.89 (td, 1H), 4.08 (t, 2H), 3.95 (d, 2H), 3.58 (s, 3H), 3.28 (m, 2H), 3.09 (t, 2H), 3.04 (t, 2H), 2.81 (m, 5H), 1.91 (s, 3H), 1.33 (s, 9H).

Step 2
According to the general method for Boc deprotection (method B tert-butyl N-{2-[6-(4-fluoro-2-{2-[3-(methanesulfonamidomethyl)-1,5-dimethyl-1H-pyrazol-4-yl]ethoxy}phenyl)imidazo[1,2-a]pyridin-3-yl]ethyl}carbamate (30 mg, 0.05 mmol) was dissolved in dioxane (2 ml) cooled at 0° C. and treated with a solution of HCl in ether (2M, 4 ml). The solution stirred at room temperature for 3 hr and was evaporated under reduced pressure. The crude product dissolved in water and freeze dried to give the title compound as a light brown solid (19 mg, 76%). hplc rt 5.5 min LC-MS MH+ 501; $^1$H NMR (400 MHz, DMSO-d$_6$) δ 14.6 (br.s, 1H), 8.90 (s, 1H), 8.05 (br. s, 4H), 8.04 (d, 1H), 7.95 (d, 1H), 7.56 (dd, 1H), 7.19 (t, 1H), 7.07 (dd, 1H), 6.94 (td, 1H), 4.08 (t, 2H), 3.90 (d, 2H), 3.60 (s, 3H), 3.41 (t, 2H), 3.17 (q, 2H), 2.81 (s, 3H), 2.78 (t, 2H), 2.01 (s, 3H).

Example 100

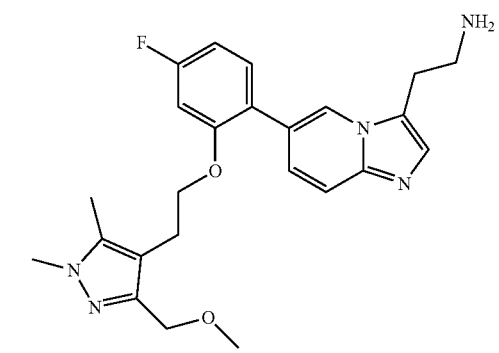 [SMILES: COCc1nn(C)c(C)c1CCOc1cc(F)ccc1-c1ccc2ncc(CCN)n2c1]

2-[6-(4-fluoro-2-{2-[3-(methoxymethyl)-1,5-dimethyl-1H-pyrazol-4-yl]ethoxy}phenyl)imidazo[1,2-a]pyridin-3-yl]ethan-1-amine Step 1
A solution of tert-butyl N-{2-[6-(4-fluoro-2-{2-[3-(hydroxymethyl)-1,5-dimethyl-1H-pyrazol-4-yl]ethoxy}-phenyl)imidazo[1,2-a]pyridin-3-yl]ethyl}-carbamate (Example 95 Step 1, 200 mg, 0.36 mmol) in DCM (5 mL) was cooled at 0° C. and treated with triethylamine (0.152 mL, 1.09 mmol) followed by dropwise addition of mesyl chloride (0.042 mL, 0.544 mmol). The reaction mixture was stirred at rt for 2 hr, diluted with DCM, washed with sat.NaHCO$_3$ solution and brine, dried over sodium sulphate and concentrated under reduced pressure. Crude LCMS showed formation of corresponding —Cl derivative tert-butyl N-{2-[6-(4-fluoro-2-{2-[3-chloro-1,5-dimethyl-1H-pyrazol-4-yl]ethoxy}phenyl)imidazo[1,2-a]pyridin-3-yl]ethyl}carbamate (196 mg, 100%. The crude was forwarded to next step without any purification.

Step 2
A solution of tert-butyl N-{2-[6-(4-fluoro-2-{2-[3-chloro-1,5-dimethyl-1H-pyrazol-4-yl]ethoxy}phenyl)imidazo[1,2-a]pyridin-3-yl]ethyl}carbamate (100 mg, 0.18 mmol) in methanol (1.0 mL) was treated with sodium methoxide (54 mg, 0.92 mmol) The reaction mixture was stirred at rt for 16 hrs, diluted with EtOAc, washed with water and brine, dried over sodium sulphate and concentrated under reduced pressure. The crude product was purified by prep TLC to give tert-butyl N-{2-[6-(4-fluoro-2-{2-[3-(methoxymethyl)-1,5-dimethyl-1H-pyrazol-4-yl]ethoxy}phenyl)imidazo[1,2-a]pyridin-3-yl]ethyl}carbamate (20 mg, 20%). The product was taken onto the next step without full characterisation Step 3
According to the general method for Boc deprotection (method B), tert-butyl N-{2-[6-(4-fluoro-2-{2-[3-(methoxymethyl)-1,5-dimethyl-1H-pyrazol-4-yl]ethoxy}phenyl)imidazo[1,2-a]pyridin-3-yl]ethyl}carbamate (20 mg, 0.1037 mmol) was dissolved in dioxane (2 ml) and treated with a solution of HCl in ether (2M, 2 ml). The solution stirred at room temperature for 3 hr and was evaporated under reduced pressure. The crude product dissolved in water and freeze dried to give the title compound as a light brown solid (14 mg, 86%). hplc rt 8.3 min LC-MS MH+ 438; $^1$H NMR (400 MHz, DMSO-d$_6$) δ 14.6 (br.s, 1H), 8.93 (s, 1H), 8.23 (br. s, 3H), 8.20-8.10 (m, 4H), 8.00 (dd, 2H), 7.56 (dd, 1H), 7.11 (dd, 2H), 6.97 (td, 1H), 4.16 (s, 2H), 4.10 (t, 2H), 3.63 (s, 3H), 3.43 (t, 2H), 3.19 (q, 2H), 3.13 (s, 3H), 2.77 (t, 2H), 2.03 (s, 3H).

Example 101

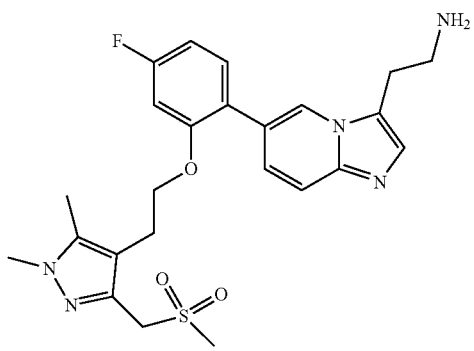 [SMILES: Cc1c(CCOc2cc(F)ccc2-c2ccc3ncc(CCN)n3c2)c(CS(C)(=O)=O)nn1C]

2-[6-(4-fluoro-2-{2-[3-(methanesulfonylmethyl)-1,5-dimethyl-1H-pyrazol-4-yl]ethoxy}phenyl)imidazo[1,2-a]pyridin-3-yl]ethan-1-amine Step 1

A solution of tert-butyl N-{2-[6-(4-fluoro-2-{2-[3-chloro-1,5-dimethyl-1H-pyrazol-4-yl]ethoxy}phenyl)imidazo[1,2-a]pyridin-3-yl]ethyl}carbamate (Example 100 Step 1, 100 mg, 0.18 mmol) in DMF (1.5 mL) was treated with NaSO$_2$Me (37.7 mg, 0.37 mmol) and the reaction mixture was stirred at RT for 6 h. The reaction mixture was diluted with EtOAc and washed with water. Organic layer was dried over Na$_2$SO$^4$ and concentrated under reduced pressure. The crude product was purified by prep TLC (5% MeOH in DCM) to afford desired product tert-butyl N-{2-[6-(4-fluoro-2-{2-[3-(methanesulfonylmethyl)-1,5-dimethyl-1H-pyrazol-4-yl]ethoxy}phenyl)imidazo[1,2-a]pyridin-3-yl]ethyl}carbamate (17 mg, 16%), which was taken onto the next step without full characterisation.

Step 2

According to the general method for Boc deprotection (method B), tert-butyl N-{2-[6-(4-fluoro-2-{2-[3-(methanesulfonylmethyl)-1,5-dimethyl-1H-pyrazol-4-yl]ethoxy}phenyl)imidazo[1,2-a]pyridin-3-yl]ethyl}carbamate (17 mg, 0.029 mmol) treated with a solution of HCl in ether (2M, 2 ml). The solution stirred at room temperature for 4 hr and was evaporated under reduced pressure. The crude product was triturates with ether to give a yellow solid, which was dissolved in water and freeze dried to give the title compound (15 mg, 93%). hplc rt 7.6 min LC-MS MH$^+$ 486; $^1$H NMR (400 MHz, DMSO-d$_6$) δ 14.6 (br.s, 1H), 8.96 (s, 1H), 8.14 (br. s, 4H), 8.09 (d, H), 7.99 (d, 2H), 7.55 (dd, 1H), 7.09 (dd, 2H), 6.97 (td, 1H), 4.27 (s, 2H), 4.12 (t, 2H), 3.67 (s, 3H), 3.44 (t, 2H), 3.19 (q, 2H), 2.91 (s, 2H), 2.84 (t, 2H), 2.07 (s, 3H).

Example 102

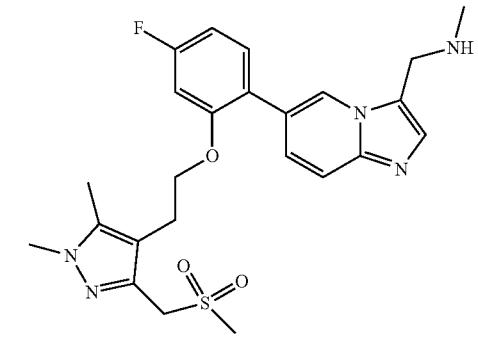

{[6-(4-fluoro-2-{2-[3-(methanesulfonylmethyl)-1,5-dimethyl-1H-pyrazol-4-yl]ethoxy}phenyl)imidazo[1,2-a]pyridin-3-yl]methyl}(methyl)amine Step 1

A solution of tert-butyl N-{[6-(4-fluoro-2-{2-[3-(hydroxymethyl)-1,5-dimethyl-1H-pyrazol-4-yl]ethoxy}-phenyl)imidazo[1,2-a]pyridin-3-yl]methyl}-N-methylcarbamate (Example 84 Step 1, 750 mg, 1.4 mmol) in DCM (1 mL) was cooled at 0° C. and treated with triethylamine (0.4 mL, 2.8 mmol) followed by dropwise addition of mesyl chloride (0.17 mL, 2.15 mmol). The reaction mixture was stirred at rt for 2 hr, diluted with DCM, washed with sat. NaHCO$_3$ solution and brine, dried over sodium sulphate and concentrated under reduced pressure to give tert-butyl N-({6-[4-fluoro-2-(2-{3-[(methanesulfonyloxy)methyl]-1,5-dimethyl-1H-pyrazol-4-yl}ethoxy)phenyl]imidazo[1,2-a]pyridin-3-yl}methyl)-N-methylcarbamate (700 mg, 81%) $^1$H NMR (400 MHz, CDCl$_3$) δ 8.96 (s, 1H), 8.33 (d, 1H), 7.93 (d, 1H), 7.81 (s, 1H) 7.29 (td, 1H), 6.74 (m, 2H), 4.80 (s, 2H), 4.51 (s, 2H), 4.11 (t, 2H), 3.78 (s, 3H), 2.93 (t, 2H), 2.87 (s, 3H), 2.82 (s, 3H), 2.10 (s, 3H), 1.41 (s, 9H).

Step 2

A solution of tert-butyl N-({6-[4-fluoro-2-(2-{3-[(methanesulfonyloxy)methyl]-1,5-dimethyl-1H-pyrazol-4-yl}ethoxy)phenyl]imidazo[1,2-a]pyridin-3-yl}methyl)-N-methylcarbamate (150 mg, 0.28 mmol) in DMF (1.5 mL) was treated with NaSO2Me (56.5 mg, 0.55 mmol) and the reaction mixture was stirred at RT for 16 h, then at 80° C. for 3 hr. The reaction mixture was diluted with EtOAc and washed with water. The organic layer was dried over Na$_2$SO$_4$ and concentrated under reduced pressure. The crude product was purified by prep TLC (5% MeOH in EtOAc) to afford desired product tert-butyl N-{[6-(4-fluoro-2-{2-[3-(methanesulfonylmethyl)-1,5-dimethyl-1H-pyrazol-4-yl]ethoxy}phenyl)imidazo[1,2-a]pyridin-3-yl]methyl}-N-methylcarbamate (23 mg, 14%), which was taken onto the next step without full characterisation.

Step 3

According to the general method for Boc deprotection (method B), tert-butyl N-{[6-(4-fluoro-2-{2-[3-(methanesulfonylmethyl)-1,5-dimethyl-1H-pyrazol-4-yl]ethoxy}phenyl)imidazo[1,2-a]pyridin-3-yl]methyl}-N-methylcarbamate (23 mg, 0.039 mmol) treated with a solution of HCl in ether (2M, 3 mL). The solution stirred at room temperature for 4 hr and was evaporated under reduced pressure. The crude product was triturated with ether to give a yellow solid, which was dissolved in water and freeze dried to give the title compound (18 mg, 94%). hplc rt 4.7 min LC-MS MH+ 486; ¹H NMR (400 MHz, DMSO-d₆) δ 9.71 (s, 2H), 9.20 (s, 1H), 8.40 (s, 1H), 8.15 (d, 1H), 7.99 (d, 1H), 7.73 (td, 1H), 7.10 (dd, 2H), 6.99 (td, 1H), 4.74 (s, 2H), 4.25 (s, 2H), 4.13 (t, 2H), 3.67 (s, 3H), 2.91 (s, 3H), 2.84 (t, 2H), 2.64 (s, 3H), 2.06 (s, 3H).

Example 103

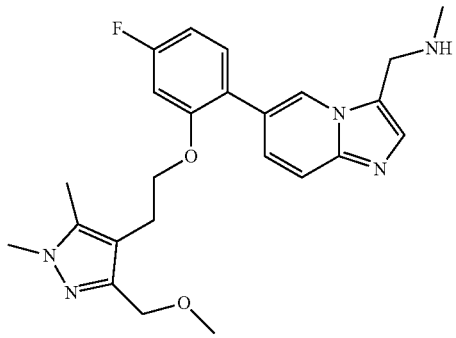

{[6-(4-fluoro-2-{2-[3-(methoxymethyl)-1,5-dimethyl-1H-pyrazol-4-yl]ethoxy}phenyl)imidazo[1,2-a]pyridin-3-yl]methyl}(methyl)amine Step 1

A solution tert-butyl N-({6-[4-fluoro-2-(2-{3-[(methanesulfonyloxy)methyl]-1,5-dimethyl-1H-pyrazol-4-yl}ethoxy)phenyl]imidazo[1,2-a]pyridin-3-yl}methyl)-N-methylcarbamate (Example 102, Step 1, 150 mg, 0.28 mmol) in methanol (1.0 mL) was treated with sodium methoxide (5M, 0.3 mL, 1.34 mmol) The reaction mixture was stirred at rt for 16 hrs, diluted with EtOAc, washed with water and brine, dried over sodium sulphate and concentrated under reduced pressure. The crude product was purified by prep TLC to give tert-butyl N-{[6-(4-fluoro-2-{2-[3-(methoxymethyl)-1,5-dimethyl-1H-pyrazol-4-yl]ethoxy}phenyl)imidazo[1,2-a]pyridin-3-yl]methyl}-N-methylcarbamate (40 mg, 27%). The product was taken onto the next step without full characterisation Step 2

According to the general method for Boc deprotection (method B), give tert-butyl N-{[6-(4-fluoro-2-{2-[3-(methoxymethyl)-1,5-dimethyl-1H-pyrazol-4-yl]ethoxy}phenyl)imidazo[1,2-a]pyridin-3-yl]methyl}-N-methylcarbamate (40 mg, 0.074 mmol) was dissolved in dioxane (2 mL) and treated with a solution of HCl in ether (2M, 2 mL). The solution stirred at room temperature for 3 hr and was evaporated under reduced pressure. The crude product dissolved in water and freeze dried to give the title compound as a light brown solid (20.1 mg, 62%). hplc rt 5.1 min LC-MS MH+ 438; ¹H NMR (400 MHz, DMSO-d₆) δ 9.84 (s, 2H), 9.20 (s, 1H), 8.43 (s, 1H), 8.03 (dd, 2H), 7.76 (dd, 1H), 7.12 (dd, 2H), 6.98 (td, 1H), 4.91 (s, 2H), 4.18 (s, 2H), 4.10 (t, 2H), 3.64 (s, 3H), (t, 2H), 3.15 (s, 3H), 2.78 (t, 2H), 2.61 (s, 3H), 2.03 (s, 3H).

Example 104

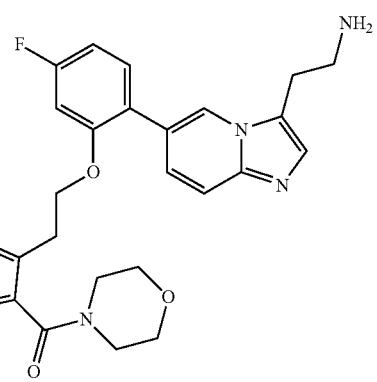

2-[6-(2-{2-[1,5-dimethyl-3-(morpholine-4-carbonyl)-1H-pyrazol-4-yl]ethoxy}-4-fluorophenyl) imidazo[1,2-a]pyridin-3-yl]ethan-1-amine Step 1

A solution of 4-(2-{2-[3-(2-{[(tert-butoxy)carbonyl]amino}ethyl)imidazo[1,2-a]pyridin-6-yl]-5-fluorophenoxy}ethyl)-1,5-dimethyl-1H-pyrazole-3-carboxylic acid (Example 93 step 2, 80 mg, 0.15 mmol) in THF (2 mL) was treated with triethylamine (0.04 mL, 0.30 mmol), morpholine (0.02 mL, 0.22 mmol), hydroxybenztriazole (25.5 mg, 0.19 mmol) and EDCl (36 mg, 0.19 mmol), The reaction mixture was stirred at rt for 16 hrs with partial conversion. Further charges of each reagent were added and the mixture stirred again overnight, diluted with ethyl acetate and washed with sat. NaHCO₃, water and brine, dried over sodium sulphate and concentrated. The crude product was purified by prep TLC (3% MeOH/DCM) to give tert-butyl N-(2-{6-[2-(2-{1,5-dimethyl-3-[(morpholin-4-yl)carbonyl]-1H-pyrazol-4-yl}ethoxy)-4-fluorophenyl]imidazo[1,2-a]pyridin-3-yl}ethyl)carbamate as a light brown solid (40 mg, 44%). ¹H NMR (400 MHz, CDCl₃) δ 8.10 (s, 1H), 7.55 (d, 1H), 7.46 (s, 1H), 7.20 (m, 1H), 6.79 (dd, 1H), 6.75-6.70 (m, 2H), 5.28 (s, 1H), 5.25 (s, 1H), 4.17 (t, 2H), 3.65 (s, 3H), 3.48 (t, 2H), 3.08 (t, 3H), 1.87 (s, 3H), 1.40 (d, 9H).

Step 2

According to the general method for Boc deprotection (method B tert-butyl N-(2-{6-[2-(2-{1,5-dimethyl-3-[(morpholin-4-yl)carbonyl]-1H-pyrazol-4-yl}ethoxy)-4-fluorophenyl]imidazo[1,2-a]pyridin-3-yl}ethyl)carbamate (40 mg, 0.066 mmol) was dissolved in a solution of HCl in ether (2M, 5 ml). The solution stirred at room temperature for 4 hr and was evaporated under reduced pressure. The crude product dissolved in water and freeze dried to give the title compound as a light brown solid (20 mg, 61%). hplc rt 4.6 min LC-MS MH+ 507; ¹H NMR (400 MHz, DMSO-d₆) δ 8.95 (s, 1H), 8.20 (br. s, 2H), 8.15 (s, 1H), 8.01 (dd, 2H), 7.57 (dd, 1H), 7.17 (dd, 1H), 6.97 (td, 1H), 4.14 (t, 2H), 3.71 (s, 3H), 3.54 (m, 8H), 3.19 (q, 2H), 2.88 (t, 2H), 2.07 (s, 3H).

Example 105

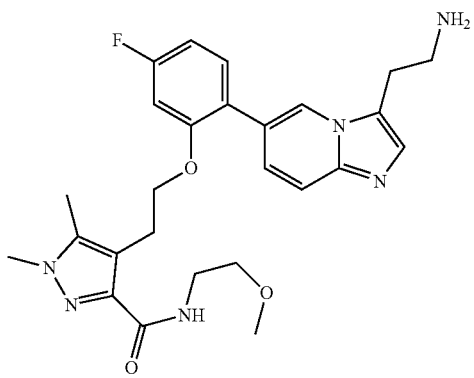 [SMILES: COCCNC(=O)c1nn(C)c(C)c1CCOc1cc(F)ccc1-c1ccc2ncc(CCN)n2c1]

4-(2-{2-[3-(2-aminoethyl)imidazo[1,2-a]pyridin-6-yl]-5-fluorophenoxy}ethyl)-N-(2-methoxyethyl)-1,5-dimethyl-1H-pyrazole-3-carboxamide Step 1

A solution of 4-(2-{2-[3-(2-{[(tert-butoxy)carbonyl]amino}ethyl)imidazo[1,2-a]pyridin-6-yl]-5-fluorophenoxy}ethyl)-1,5-dimethyl-1H-pyrazole-3-carboxylic acid (Example 93 step 2, 80 mg, 0.15 mmol) in THF (2 mL) was treated with triethylamine (0.04 mL, 0.30 mmol), 2-methoxyethylamine (0.019 mL, 0.22 mmol), hydroxybenztriazole (25 mg, 0.19 mmol) and EDCl (36 mg, 0.19 mmol). The reaction mixture was stirred at rt for 16 hrs, with partial conversion. Another charge of each reagent was added and the mixture stirred again at rt for 20 hr. The reaction was quenched with sat. NaHCO$_3$, and extracted with EtOAc. The organic layer was washed with water and brine, dried over sodium sulphate and concentrated. The crude product was purified by prep TLC (3% MeOH/DCM) to give tert-butyl N-(2-{6-[4-fluoro-2-(2-{3-[(2-methoxyethyl)carbamoyl]-1,5-dimethyl-1H-pyrazol-4-yl}ethoxy)phenyl]imidazo[1,2-a]pyridin-3-yl}ethyl)carbamate as a light brown solid (35 mg, 40%). $^1$H NMR (400 MHz, DMSO-d$_6$) δ 8.34 (s, 1H), 7.78 (t, 1H), 7.50 (d, 1H), 7.45 (m, 2H), 7.22 (d, 1H), 7.13 (d, 1H), 6.98 (t, 1H), 6.86 (dd, 1H), 4.14 (t, 2H), 3.75 (s, 3H), 3.39 (t, 2H), 3.25-3.20 (m, 5H), 3.02 (m, 4H), 1.90 (s, 3H), 1.30 (d, 9H).

Step 2

According to the general method for Boc deprotection (method B), tert-butyl N-(2-{6-[4-fluoro-2-(2-{3-[(2-methoxyethyl)carbamoyl]-1,5-dimethyl-1H-pyrazol-4-yl}ethoxy)phenyl]imidazo[1,2-a]pyridin-3-yl}ethyl)carbamate (35 mg, 0.059 mmol) was dissolved in a solution of HCl in ether (2M, 5 mL). The solution stirred at room temperature for 4 hr and was evaporated under reduced pressure. The crude product dissolved in water and freeze dried to give the title compound as a light brown solid (30 mg, 90%). hplc rt 4.8 min LC-MS MH$^+$ 495; $^1$H NMR (400 MHz, DMSO-d$_6$) δ 14.8 (br.s, 1H), 8.95 (s, 1H), 8.20-8.15 (m, 4H), 8.02 (dd, 2H), 7.78 (d, 1H), 7.56 (td, 1H), 7.22 (dd, 2H), 6.96 (td, 1H), 4.15 (t, 2H), 3.71 (s, 3H), 3.46 (t, 2H), 3.39 (m, 2H), 3.33 (t, 2H), 3.25 (m, 5H), 3.04 (t, 2H), 2.06 (s, 3H).

Example 106

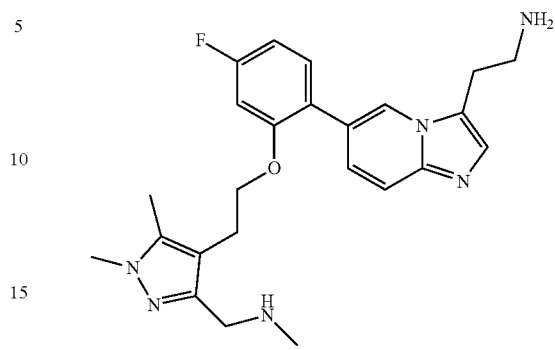

2-{6-[2-(2-{1,5-dimethyl-3-[(methylamino)methyl]-1H-pyrazol-4-yl}ethoxy)-4-fluorophenyl]imidazo[1,2-a]pyridin-3-yl}ethan-1-amine Step 1

A solution of tert-butyl N-{2-[6-(4-fluoro-2-{2-[3-chloro-1,5-dimethyl-1H-pyrazol-4-yl]ethoxy}phenyl)imidazo[1,2-a]pyridin-3-yl]ethyl}carbamate (Example 100 Step 1, 340 mg, 0.63 mmol)) in acetonitrile (7 mL) was treated potassium carbonate (173 mg, 1.23 mmol) followed by methylamine solution (2M in THF, 0.078 mmol, 2.5 mmol). The reaction mixture was stirred at rt for 16 hr, diluted with EtOAc, washed with sat. NaHCO$_3$ solution and brine, dried over sodium sulphate and concentrated. The crude product was purified by prep TLC using 5% MeOH/DCM to give tert-butyl N-(2-{6-[2-(2-{1,5-dimethyl-3-[(methylamino)methyl]-1H-pyrazol-4-yl}ethoxy)-4-fluorophenyl]imidazo[1,2-a]pyridin-3-yl}ethyl)carbamate (300 mg, 89%). $^1$H NMR (400 MHz, DMSO-d$_6$) δ 8.36 (s, 1H), 7.52 (d, 1H), 7.44 (t, 1H), 7.41 (s, 1H), 7.26 (d, 2H), 7.07 (td, 1H), 7.01 (dd, 1H), 6.88 (td, 1H), 4.08 (m, 3H), 3.58 (s, 3H), 3.52 (t, 2H), 3.32 (t, 2H), 3.17 (s, 3H), 3.04 (t, 2H), 2.79 (t, 2H), 2.25 (s, 3H), 1.95 (s, 3H), 1.30 (s, 9H).

Step 2

According to the general method for Boc deprotection (method B), tert-butyl N-(2-{6-[2-(2-{1,5-dimethyl-3-[(methylamino)methyl]-1H-pyrazol-4-yl}ethoxy)-4-fluorophenyl]imidazo[1,2-a]pyridin-3-yl}ethyl)carbamate (30 mg, 0.056 mmol) was dissolved in dioxane (2 ml), cooled at 0° C., and treated with a solution of HCl in ether (2M, 4 ml). The solution stirred at room temperature for 3 hr and was evaporated under reduced pressure. The crude product dissolved in water and freeze dried to give the title compound as a light brown solid (10 mg, 41%). hplc rt 4.2 min LC-MS MH$^+$ 437; $^1$H NMR (400 MHz, DMSO-d$_6$) δ 14.7 (br.s, 1H), 9.01 (m, 2H), 8.28 (br. s, 2H), 8.15 (s, 1H), 8.09 (d, 1H), 8.02 (d, 2H), 7.57 (td, 1H), 7.13 (dd, 2H), 6.98 (td, 1H), 4.10 (t, 2H), 3.94 (t, 2H), 3.68 (s, 3H), 3.47 (t, 2H), 3.21 (t, 2H), 2.86 (t, 2H), 2.06 (s, 3H).

Example 107

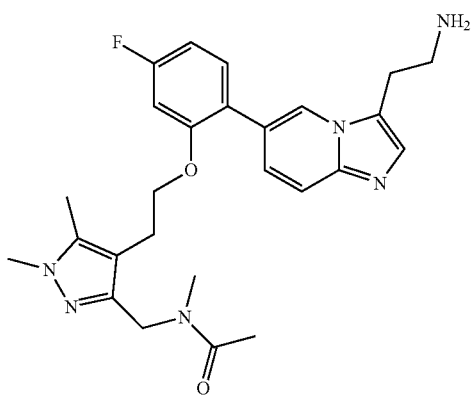 [SMILES: CC(=O)N(C)Cc1nn(C)c(C)c1CCOc1cc(F)ccc1-c1ccc2ncc(CCN)n2c1]

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}-N-methylacetamide Step 1

A solution of tert-butyl N-(2-{6-[2-(2-{1,5-dimethyl-3-[(methylamino)methyl]-1H-pyrazol-4-yl}ethoxy)-4-fluorophenyl]imidazo[1,2-a]pyridin-3-yl}ethyl)carbamate (Example 106 Step 1, 100 mg, 0.19 mmol) in DCM (3 mL) was cooled at 0° C. before dropwise addition of triethylamine (0.052 mL, 0.37 mmol) followed by acetyl chloride (0.02 mL, 0.28 mmol). The reaction mixture was warmed to rt for 2 hr, diluted with DCM washed with sat.NaHCO₃ solution and brine, dried over sodium sulphate and concentrated under reduced pressure. The crude product was purified by prep TLC (5% MeOH/DCM) to give tert-butyl N-(2-{6-[2-(2-{1,5-dimethyl-3-[(N-methylacetamido)methyl]-1H-pyrazol-4-yl}ethoxy)-4-fluorophenyl]imidazo[1,2-a]pyridin-3-yl}ethyl)carbamate (17 mg, 16%), which was taken on without further purification.

Step 2

According to the general method for Boc deprotection (method B), tert-butyl N-(2-{6-[2-(2-{1,5-dimethyl-3-[(N-methylacetamido)methyl]-1H-pyrazol-4-yl}ethoxy)-4-fluorophenyl]imidazo[1,2-a]pyridin-3-yl}ethyl)carbamate (17 mg, 0.07 mmol) was dissolved in dioxane (2 mL), cooled to 0° C. and treated with a solution of HCl in ether (2M, 4 mL). The solution stirred at room temperature for 3 hr and was evaporated under reduced pressure. The crude product dissolved in water and freeze dried to give the title compound as a light brown solid (10 mg, 71%). hplc rt 3.7 min LC-MS MH⁺ 479; ¹H NMR (400 MHz, DMSO-de) δ 14.6 (br.s, 1H), 8.96 (s, 1H), 8.15-8.05 (m, 4H), 8.00 (d, 1H), 7.55 (td, 1H), 7.11 (dd, 1H), 6.97 (td, 1H), 4.17 (s, 2H), 3.98 (t, 2H), 3.62 (s, 3H), 3.20 (q, 2H), 2.82 (s, 3H), 2.76 (t, 2H), 2.05 (s, 3H), 1.90 (s, 3H).

Example 108

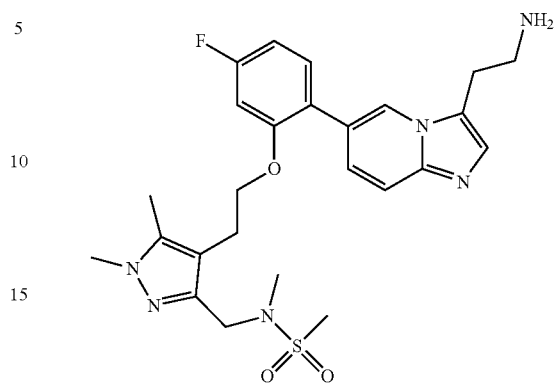

N-{[4-(2-{2-[3-(2-aminoethyl)imidazo[1,2-a]pyridin-6-yl]-5-fluorophenoxy}ethyl)-1,5-dimethyl-1H-pyrazol-3-yl]methyl}-N-methylmethanesulfonamide Step 1

A solution of tert-butyl N-(2-{6-[2-(2-{1,5-dimethyl-3-[(methylamino)methyl]-1H-pyrazol-4-yl}ethoxy)-4-fluorophenyl]imidazo[1,2-a]pyridin-3-yl}ethyl)carbamate (Example 106 Step 1, 100 mg, 0.19 mmol) in DCM (3 mL) was cooled at 0° C. before dropwise addition of triethylamine (0.052 mL, 0.37 mmol) followed by mesyl chloride (0.022 mL, 0.28 mmol). The reaction mixture was warmed to rt for 2 hr, diluted with DCM, washed with sat.NaHCO₃ solution and brine, dried over sodium sulphate and concentrated under reduced pressure. The crude product was purified by prep TLC (5% MeOH/DCM) to give tert-butyl N-(2-{6-[2-(2-{1,5-dimethyl-3-[(N-methylmethanesulfonamido)methyl]-1H-pyrazol-4-yl}ethoxy)-4-fluorophenyl]imidazo[1,2-a]pyridin-3-yl}ethyl)carbamate (10 mg, 9%) which was carried onto the next step without full characterization.

Step 2

According to the general method for Boc deprotection (method B) tert-butyl N-(2-{6-[2-(2-{1,5-dimethyl-3-[(N-methylmethanesulfonamido)methyl]-1H-pyrazol-4-yl}ethoxy)-4-fluorophenyl]imidazo[1,2-a]pyridin-3-yl}ethyl)carbamate (10 mg, 0.016 mmol) was dissolved in dioxane (2 ml) cooled at 0° C. and treated with a solution of HCl in ether (2M, 3 ml). The solution stirred at room temperature for 3 hr and was evaporated under reduced pressure. The crude product dissolved in water and freeze dried to give the title compound as a light brown solid (4 mg, 48%). hplc rt 5.1 min LC-MS MH⁺ 515; ¹H NMR (400 MHz, DMSO-de) δ 14.6 (br.s, 1H), 8.92 (s, 1H), 8.13-8.05 (m, 4H), 7.97 (d, 1H), 7.55 (dd, 1H), 7.10 (dd, 1H), 6.97 (td, 1H), 4.08 (t, 2H), 4.02 (s, 2H), 3.65 (s, 3H), 3.43 (t, 2H), 3.19 (q, 2H), 2.88 (s, 3H), 2.81 (t, 2H), 2.59 (s, 3H), 2.07 (s, 3H).

The following Example compounds are made in analogous methods to Examples 1 to 108.

195 | 196
-continued
52 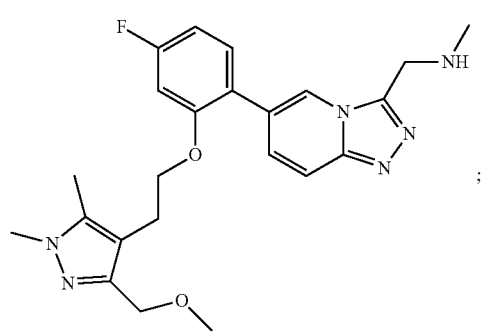
111 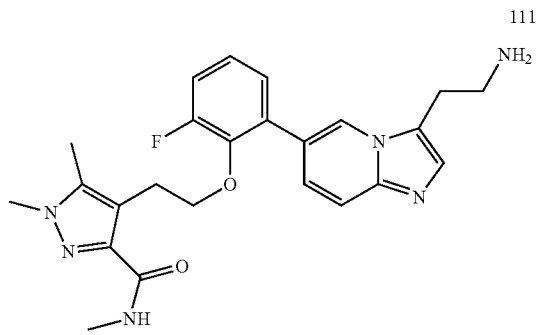
59 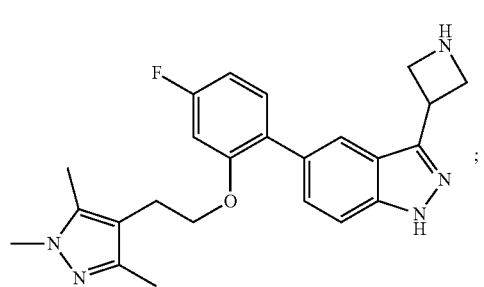
112 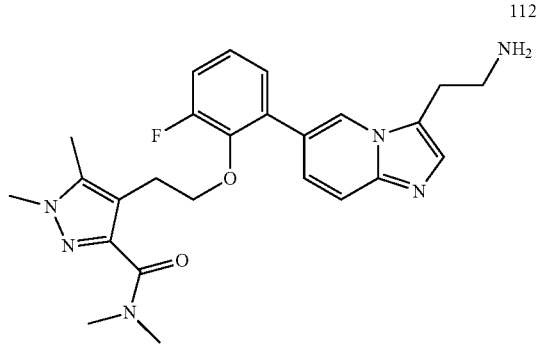
61 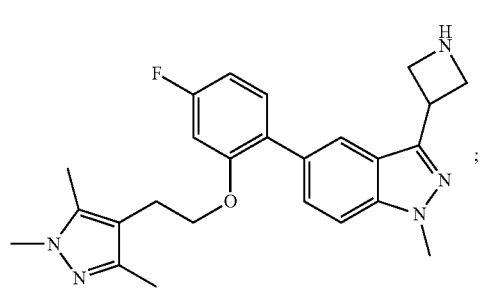
113 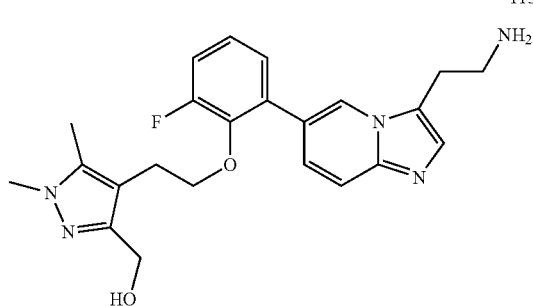
109 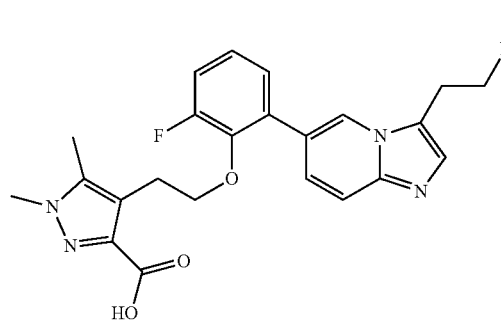
114 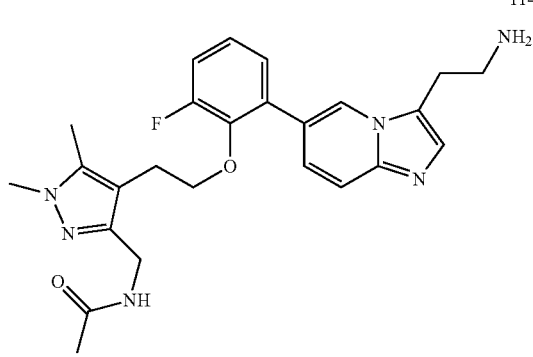
110 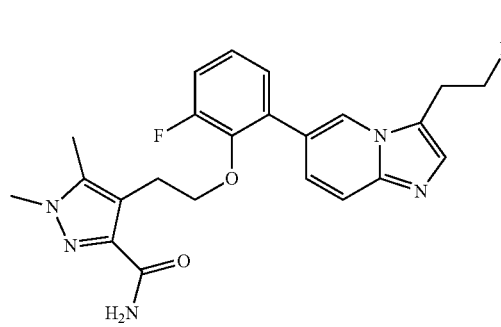
115 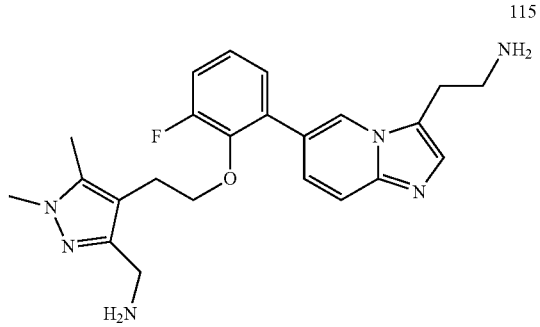

-continued
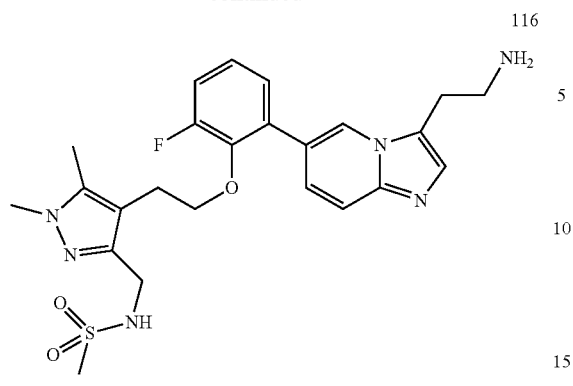
116
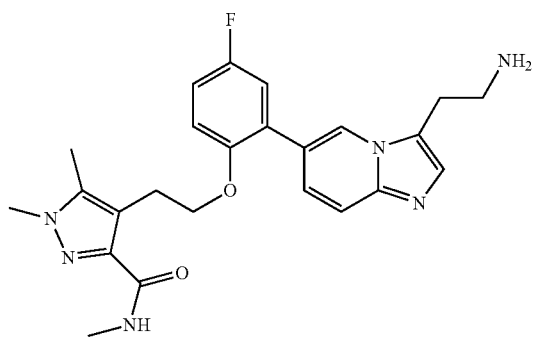
120
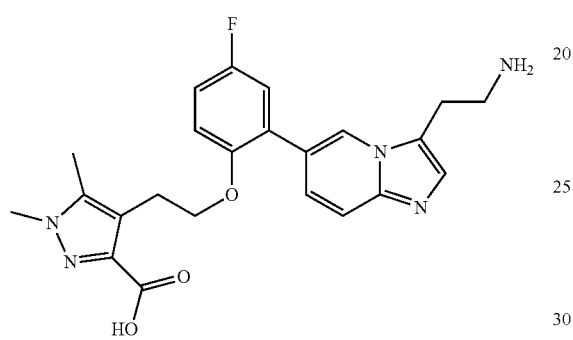
117
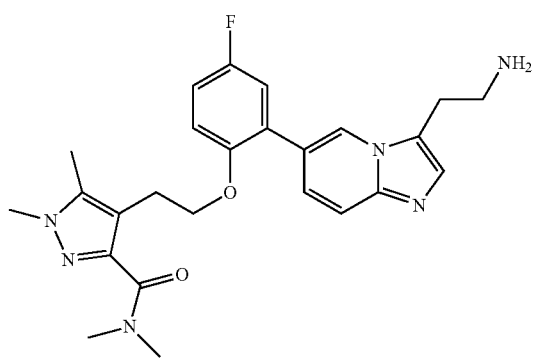
121
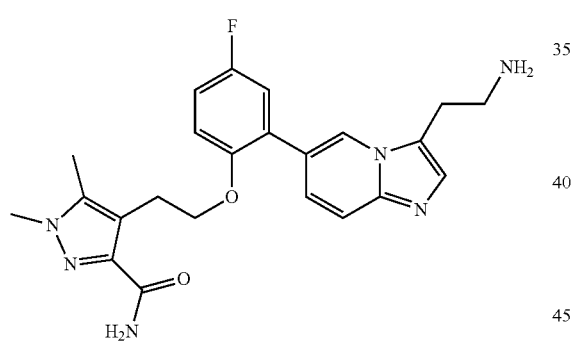
118
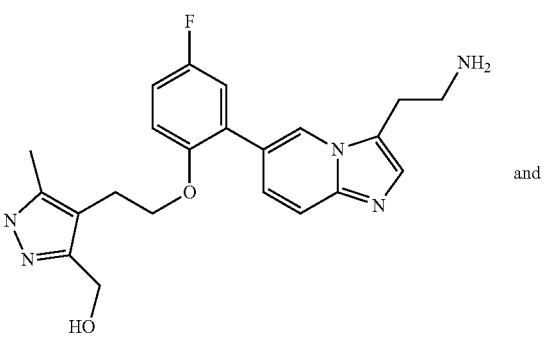
122
and
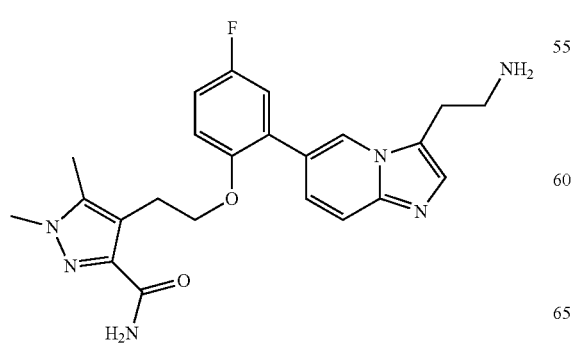
119
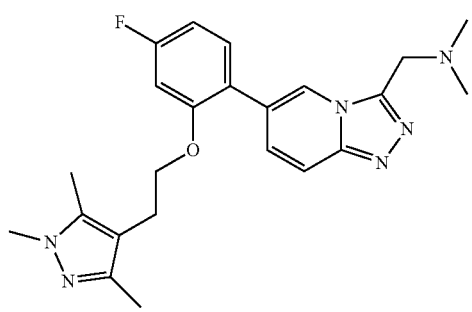

199
-continued
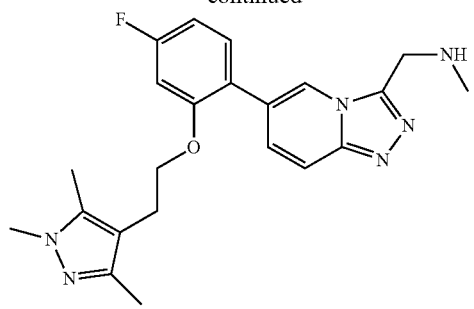
200
-continued
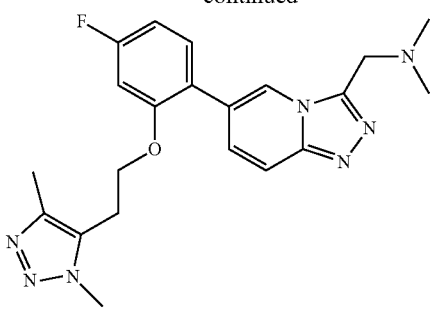

-continued

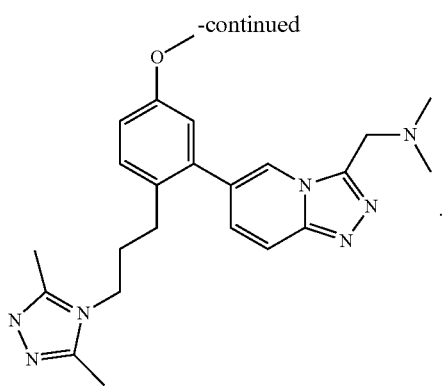

Details of Biological Assays, and Data
(a)
The $IC_{50}$ values of Example compounds of the invention for *Plasmodium vivax* (Pv) NMT, Human NMT1 and Human NMT2 were measured using a sensitive fluorescence-based assay based on detection of CoA by 7-diethylamino-3-(4-maleimido-phenyl)-4-methylcoumarin, as described in Goncalves, V., et al., Analytical Biochemistry, 2012, 421, 342-344 and Goncalves, V., et al., *J. Med. Chem*, 2012, 55, 3578. An adapted version of the assay was used to measure the $IC_{50}$ values of *Plasmodium falciparum* (PfNMT), *Plasmodium berghei* (PbNMT), *Leishmania donovani* (LdNMT), *Leishmania major* (LmNMT), and *Trypanosoma brucei* (TbNMT) for certain compounds of the invention. For PfNMT, PbNMT, LmNMT, LdNMT and TbNMT the final enzyme concentration and peptide substrates are modified, see below:
   PfNMT Final Concentration: 500 ng/mL
   PbNMT Final Concentration: 400 ng/mL
   LmNMT Final Concentration: 400 ng/mL
   LdNMT Final Concentration: 400 ng/mL
   TbNMT Final Concentration: 500 ng/mL
   PfNMT, PbNMT, LmNMT and LdNMT Peptide Substrate: *Homo sapiens* p60$^{src}$ (2-16) Amino Acids, final concentration 4.0 µM, Sequence: GSNKSKPKDASQRRR-NH$_2$, as in PvNMT.
   TbNMT Peptide Substrate: *Plasmodium falciparum* ARF (2-16) amino acids final concentration 4.0 µM Sequence: GLYVSRLFNRLFQKK-NH$_2$.
NMT $IC_{50}$ values for Example compounds of the invention are provided in the table of FIG. 1.
(b)
$EC_{50}$ values for *Plasmodium falciparum* (Pf) NMT were measured for certain compounds of the invention using an assay utilising SYBR Green dye. The assay was carried out as follows:
   Synchronous *Plasmodium falciparum* 3D7 late stage trophozoites at 33-36 h were used. Final parasitemia and haematocrit were between 0.1-0.2% and 2% respectively. Red blood cells used for the assay were centrifuged to remove the buffy coat and washed twice in Roswell Park Memorial Institute (RPMI) Media 1640 so that no white blood cells were present. The culture medium contained RPMI 1640 with 5 g/L Albumax, 0.025 g/L gentamycin and 0.292 g/L L-glutamine.
   Sterile 96 well black tissue culture plates (Costar) were used routinely for every assay. Drugs were diluted in culture medium and used in duplicate wells for each dilution ranging from 10.000, 3.333, 1.111, 0.370, 0.123, 0.041 and 0.014 µM respectively in a final volume of 100 µL per well. Chloroquine was used as a standard with ten times reduced concentrations range as above. Two sets of control were used in duplicate wells, one set with no added drugs (positive control) and one with uninfected red blood cells (negative control).
   The plates were incubated at 37° C. for 48 h in a gas chamber flushed with 5% $CO_2$, 5% $O_2$ and 90% $N_2$. After 48 h supernatants were taken out from each well and replaced with fresh drug and incubated for a further 48 h in the same manner. At the end of the 96 h incubation, 25 µL of SYBR Green I dye (SYBR Green I nucleic acid gel stain 10000×, in DMSO from Invitrogen) in lysis buffer (1 µL dye to 1 mL lysis buffer) was added to each well and stored overnight at −20° C. The lysis buffer contained Tris (20 mM, pH 8.0), EDTA (2 mM), Saponin (0.16%) and Triton X-100 (1.6% v/v).
   Plates were warmed to room temperature and fluorescence intensity was measured with a FLUOstar Omega Microplate fluorescence reader (BMG Labtech). Values were expressed in relative fluorescence units. Binding of SYBR Green is specific for parasite DNA as mature erythrocytes lack DNA and RNA. Fluorescence intensity unit was converted to percentage (%) of growth as follows:

% growth=(culture under drug)−(uninfected RBC)/
(culture with no drug)−(uninfected RBC)×100 and the $EC_{50}$ value was determined.
   The *Plasmodium falciparum* (Pf) NMT $EC_{50}$ values for certain Example compounds of the invention are provided in the table of FIG. 1.
(C)
Mouse Malaria Model Protocol
Day 0
   Blood from a donor mouse infected with *Plasmodium berghei*, GFP ANKA 507 clone 1 strain at a parasitemia of 10% is collected using a 26G 10 mm needle containing 50 µL Heparin (200 u/ml). From this suspension, 1×10$^6$ parasites in 200 µL PBS is delivered through intra-peritoneal injection using a 26G 10 mm needle and a 1 ml syringe into 3-4 naive mice per treatment group.
Day 3-6
   72, 96, 120 and 144 hours post-infection, the experimental groups are treated with the compounds (5-50 mg/kg in 200 µL PBS) twice daily for four days either by intra-peritoneal injection or oral gavage. The dosage is partly determined by a preliminary toxicity test (pre-experiment). For intra-peritoneal injection, mice are injected on the right side using a 26G 10 mm needle and a 1 ml syringe. For oral gavage, mice are dosed using a 22G 38 mm oral dosing needle and a 1 ml syringe. Simultaneous controls of PBS only (2×200 µL) and CQ (2×45 mg/kg in 200 µL PBS for intra-peritoneal injection or 2×60 mg/kg in 200 µL PBS for oral gavage) are also conducted. Other routes of application are possible. A blood smear to determine parasite load is performed daily (from day 3 onwards) by taking a drop of tail blood and staining the blood smear with Giemsa. 8-10 fields with 1000-2000 total RBCs are counted and the number of cells infected with parasites is determined. Percentage parasitemia is then determined for both control and experimental groups.
   The percentage reduction in the parasite burden for mice treated with certain Example compounds of the invention over control mice is indicated in the table of FIG. 1.
(d)
Metabolic Activity Assay (MTS Assay)
   Example NMT inhibitors of the invention were tested for activity in an in vitro metabolic activity assay using human cell lines (HeLa and BL-41). Compounds having activity in inhibiting metabolic activity in the assay are expected to be useful as agents for preventing and/or treating cancer, by virtue of being inhibitors of human NMT1 and/or NMT2.

Cell Preparation:

Hela cells were grown in DMEM media (supplemented with 10% FBS) and seeded in a 96-well plate 24 h prior to treatment. BL-41 cells were grown in RPMI-1640 media (supplemented with 10% FBS) and seeded directly before treatment. Cell suspensions were prepared by adjusting the cell density to the appropriate concentration (as stated in the table below) and 50 µL of the cell suspension was transferred to wells B-G in columns 2-11 of a 96-well plate.

Number of Cells Plated.

|  | Hela | BL-41 |
| --- | --- | --- |
| Cell suspension concentration (cells/mL) | 16,000 | 700,000 |
| cells per well | 800 | 35,000 |

Assay Procedure:

100 µL of growth media containing 0.2% DMSO was added to wells B-G in columns 2 and 11 as positive controls and 100 µL of growth media containing Puromycin (3 µg/mL; final concentration in the plate 2 µg/mL) was added to wells B-G in column 3 as a negative control. 7 concentrations of inhibitor solution were prepared using example NMT inhibitors (same final percentage of DMSO, dilution factor=3 starting from 15 µM or 150 µM) and 100 µL of inhibitor solution was added to wells B-G in columns 4-10 (final concentration of example NMT inhibitor in the plate starting from 10 µM or 100 µM; total volume of the wells=150 µL). The plate was incubated at 37° C. with 5% $CO_2$ level for HeLa cells and 10% $CO_2$ for BL-41 cells. A representation of a typical 96-well plate is shown in FIG. 2.

After 72 h, 20 µL MTS reagent (Promega, prepared according to the supplier protocol) was added to each well of the 96-well plate. The plate was incubated at 37° C. (2 hours for HeLa cells and 4 hours for BL-41 cells) and absorbance was measured at 490 nm with a Spectra Max M2/M2e microplate reader. The average absorbance value of the negative control (Puromycin-treated cells) was subtracted from each value and the metabolic activity was calculated as a percentage relative to the positive control (DMSO-treated cells). $EC_{50}$ s were calculated using Grafit 7.0 (Erithacus Software Ltd, UK).

Each of the compounds tested showed activity in the metabolic activity assay, having an $EC_{50}$ value of less than 5 µM, and indicating that the compounds are useful as anti-cancer agents. $EC_{50}$ values for example NMT inhibitors of the invention are shown in the table of FIG. 1 (for the BL-41 cell results) and FIG. 3 (for the HeLa cell results).

(e)
Rhinovirus Production Assay

Example 30 of the invention was tested for activity in an in vitro rhinovirus production assay using the human HeLa Ohio cell line. The results are shown in FIG. 4. Compounds having activity in inhibiting rhinovirus production in the assay are expected to be useful as agents for preventing and/or treating asthma or chronic obstructive pulmonary disease (COPD), by virtue of being inhibitors of human NMT1 and/or NMT2, which are thought to myristoylate rhinovirus capsid subunit VP4 and be essential for virus assembly.

Cell Preparation and Infections:

Hela Ohio cells were grown in growth media (DMEM supplemented with 10% FBS, 1% Sodium Bicarbonate and 25 mM Hepes) and seeded 24 h prior to infection in a 12-well plate at a cell density allowing to obtain 100% confluent cells ($5.95 \times 10^5$ cells per well) the next day. Confluent cells were treated with different concentrations of inhibitor, as indicated in the table below, each in triplicate. The Example 30 inhibitor solution was prepared by serial dilutions in growth media and the DMSO control contained the same percentage of DMSO as in the solution with the highest concentration of inhibitor. The cell media was replaced by 1 ml per well of the inhibitor dilution and the plate was incubated for 6 h at 37° C. with 5% $CO_2$. Cells were then infected with HRV16 at an MOI of 1 in the presence of the inhibitor. The virus stock ($2.492 \times 10^7$ PFU/ml) was diluted in growth media to obtain a virus solution at $5.95 \times 10^5$ PFU/ml. This virus dilution was used to dilute the inhibitor as previously described in order to obtain virus solutions with the inhibitor concentrations indicated in the table below. The cell media was as replaced by 1 ml per well of virus+inhibitor solution and the plate was incubated for 1 h at room temperature to allow virus adsorption onto the cells. The cells were then washed with PBS and the media was replaced with 1 ml per well of growth media+inhibitor, prepared as previously described. After 16 h of incubation at 37° C. with 5% $CO_2$, the plate was frozen at −80° C. and submitted to 2 cycles of freezing-thawing to release the virus from the cells. The media and cells form each well were then transferred to 1.5 ml tubes and centrifuged for 1 min at 16000×g to remove cell debris.

Concentrations of Inhibitor

| (nM) |
| --- |
| 2000 |
| 1000 |
| 500 |
| 200 |
| 20 |
| 2 |
| 0 (DMSO Control) |

Virus Titre Assay:

The virus titres from the cleared supernatants were determined by measuring the 50% Tissue Culture Infective Dose ($TCID_{50}$). Each sample was diluted in a series of 10-fold dilutions in $TCID_{50}$ media (DMEM supplemented with 2% FBS, 1% Sodium Bicarbonate, 25 mM Hepes and 1% Penicillin-Streptomycin) and 50 µl of each of the dilutions 1/10 to $1/10^{-8}$ were added onto a 96-well plate, in 6 replicates. HeLa Ohio cells at a cell density of $1 \times 10^5$ cells/ml in $TCID_{50}$ media were then added to each well (150 µl per well). Some wells with cells alone (without sample) were included as control. The plates were then incubated for 96 h at 37° C. with 5% $CO_2$. The appearance of characteristic cytopathic effect, compared to control cells, was then assessed by observation of the plates on an inverted microscope and the virus titres were subsequently calculated by the method of Reed and Muench.

The experiment was performed in triplicate and mean values +/−SD are shown in FIG. 4.

(f)
Rhinovirus Production Assay 2

Examples 30, 35, 49 and 50 of the invention was tested for activity in a rhinovirus replication assay in the human HeLa Ohio cell line. The results are shown in FIGS. 5a to 5c. Compounds having activity in inhibiting rhinovirus production in the assay are expected to be useful as agents for preventing and/or treating asthma or chronic obstructive pulmonary disease (COPD), by virtue of being inhibitors of human NMT1 and/or NMT2, which are thought to myristoylate rhinovirus capsid subunit VP4 and be essential for virus assembly.

Cell Preparation and Infections:

HeLa Ohio cells were grown in growth media (DMEM supplemented with 10% FBS, 1% Sodium Bicarbonate and 25 mM Hepes) and seeded 24 hours prior to infection in a 96-well plate at a cell density allowing to obtain 100% confluent cells ($5.6 \times 10^4$ cells per well) the next day.

Confluent cells were infected with HRV16 at an MOI of 0.05 in the presence of different concentrations of inhibitor, as indicated in the table below, each in duplicate. The virus stock ($5.6 \times 10^6$ PFU/ml) was diluted in growth media to obtain a virus solution at $1.4 \times 10^4$ PFU/ml. This virus dilution was used to dilute the inhibitor by serial dilutions in order to obtain virus solutions with the inhibitor concentrations indicated in the table below. The DMSO control contained the same percentage of DMSO as in the solution with the highest concentration of inhibitor. The cell media was as replaced by 200 µl per well of virus+inhibitor solution and the plate was incubated for 48 hours at 37° C. with 5% $CO_2$.

Cells with the same inhibitor dilutions but without virus were used in parallel to control for compound cytotoxicity. Concentrations of Inhibitor

| (nM) |
| --- |
| 500 |
| 250 |
| 125 |
| 50 |
| 25 |
| 10 |
| 5 |
| 2 |
| 1 |
| 0.5 |
| 0 (DMSO Control) |

Cell Viability Assay:

The number of viable cells was determined 48 hours post-infection using the CellTiter 96® AQ$_{ueous}$ One Solution Cell Proliferation Assay (Promega) according to the manufacturer's instructions. Briefly, the volume of the media was adjusted to 100 µl/well and 20 µl of CellTiter 96® AQueous One Solution Reagent was added to each well. The plates were incubated for a further 2 to 4 hours at 37° C. with 5% $CO_2$ and absorbance at 490 nm was measured using a 96-well plate reader (FLUOstar Omega). The percentage of virus-induced cytopathic effect (% CPE) was calculated with the following equation:

% CPE=100×OD$_{490\ nm}$ [(uninfected compound treated control−infected compound treated test sample)/(uninfected compound treated control−infected DMSO treated control)].

Cytotoxicity of the compounds was evaluated by determining the cell viability of the compound-treated uninfected cells, expressed as a percentage of the DMSO-treated control.

The results are shown in FIGS. 5a to 5c: FIGS. 5a and 5b show the virus-induced cytopathic effect (CPE) measured by a Metabolic Activity Assay (MTS assay) 2 days post-infection; FIG. 5c shows the cell viability of the inhibitor-treated but uninfected cells, measured in parallel by MTS 2 days post-treatment. The result show that Examples 30, 35, 49 and 50 inhibit HRV16 production in a dose-dependent manner, without affecting cell viability.

(g)

*Plasmodium* Liver Stage Assay

This assay is a slightly modified version of the assay previously described in Meister, S. *Imaging of Plasmodium liver stages to drive next-generation antimalarial drug discovery* Science, 2011, vol. 334, pages 1372-1377.

HepG2-A16-CD81EGFP cells stably transformed to express a GFP-CD81 fusion protein were cultured at 37° C. in 5% CO2 in DMEM (Invitrogen, Carlsbad, Calif., USA) supplemented with 10% FCS, 0.29 mg/mL glutamine, 100 units of penicillin, and 100 µg/mL streptomycin. The cells were seeded 24 h prior to infection into 1536-well plates at 3000 cells/well. The cells were pretreated for 12 h with the drug in a 12-point dilution series, and the cells were then infected with freshly dissected *P. berghei* sporozoites expressing luciferase (1000 sporozoites/well). After 48 h of incubation, the viability of *P. berghei* exoerythrocytic forms (EEF) was measured by bioluminescence. $EC_{50}$ values were obtained using the measured bioluminescence intensity and a nonlinear variable slope four-parameter regression curve fitting model in Prism 6 (GraphPad Software Inc.).

The *P. berghei* liver stage assay $EC_{50}$ (µM) values for certain Example compounds of the invention are provided in the table of FIG. 1.

The compounds of Examples 1-101 exhibit one or more of the following:

(i) inhibition of *Plasmodium falciparum* (Pf) N-myristoyl transferase in the range of $IC_{50}$ 0.00001 to 99.9 µM in assay (a);

(ii) inhibition of *Plasmodium vivax* (Pv) N-myristoyl transferase in the range of $IC_{50}$ 0.00001 to 99.9 µM in assay (a);

(iii) inhibition of *Plasmodium berghei* (Pb) N-myristoyl transferase in the range of $IC_{50}$ 0.00001 to 99.9 µM in assay (a);

(iv) inhibition of *Leishmania donovani* (Ld) N-myristoyl transferase in the range of $IC_{50}$ 0.001 to 99.9 µM in assay (a);

(v) inhibition of *Leishmania major* (Lm) N-myristoyl transferase in the range of $IC_{50}$ 0.001 to 99.9 µM in assay (a);

(vi) inhibition of *Trypanosoma brucei* (Tb) N-myristoyl transferase in the range of $IC_{50}$ 0.001 to 99.9 µM in assay (a);

(vii) inhibition of *Plasmodium falciparum* (Pf strains 3D7 or NF54) in the range of $EC_{50}$ 0.001 to 10 µM in assay (b) (Selected examples 1-43 were tested against the 3D7 strain while subsequent compounds were assessed against the NF54 strain).

(viii) reduction in the parasite burden in the mouse malaria model (*Plasmodium berghei*) following twice daily intraperitoneal administration at 10 mg/kg in the range 10-100%;

(ix) inhibition of metabolic activity in HeLa cells in the range of $EC_{50}$ 0.001 to 10 µM in assay (d);

(x) inhibition of metabolic activity in BL-41 cells in the range of $EC_{50}$ 0.001 to 10 µM in assay (d).

(xii) inhibition of *Plasmodium berghei* liver stage in the range of $EC_{50}$ 0.00001 to 10 µM in assay (g);

(xii) inhibition of viral replication in the range of $EC_{50}$ 0.001 to 10 µM in assay (e) or (f), and preferably inhibition of viral replication in the range of $EC_{50}$ 0.001 to 10 µM in assay (e) or (f) whilst having no effect on uninfected cells over the same timescale of the experiment.

Certain compounds of Examples 1-101 also exhibit inhibitory activity for Human N-myristoyl transferase 1 and/or Human N-myristoyl transferase 2 in the range of $IC_{50}$ 0.00001 to 99.9 µM.

Preferred Example compounds of the invention are those which exhibit inhibitory activity at lower concentrations within the $IC_{50}$ range shown above. For example, the compounds of examples 7, 8, 9, 17, 18, 20, 22, 24, 29, 30, 31, 32, 33, 35, 36, 39, and 48, exhibit $IC_{50}$ at *Plasmodium falciparum* (Pf) N-myristoyl transferase in the range of $IC_{50}$ 0.00001 to 0.1 µM in assay (a).

Preferred Example compounds of the invention are those which exhibit inhibitory activity at lower concentrations within the $IC_{50}$ range shown above. For example, the compounds of examples 2, 3, 4, 6, 7, 8, 9, 10, 11, 12, 13, 17, 18, 19, 20, 22, 23, 24, 26, 28, 29, 30 and 32, 33, 34, 35, 36, 37, 38, 39, 41, 42, 43, 45, 46, 48, 49, 50, 53, 55, 56, 57, 58, 60, 62, 63, 66, 67, 68, 69, 70, 71, 72, 74, 75, 76, 77, 78, 79, 80, 81, 82, 86, 86, 88, 89, 90, 91, 92, 93, 94, 95, 96 exhibit $IC_{50}$ at *Plasmodium vivax* (Pv) N-myristoyl transferase in the range of $IC_{50}$ 0.00001 to 0.1 µM in assay (a).

Preferred Example compounds of the invention are those which exhibit inhibitory activity at lower concentrations within the $IC_{50}$ range shown above. For example, the compounds of Examples 7 and 8 exhibit $IC_{50}$ at *Leishmania donovani* (Ld) N-myristoyl transferase in the range of $IC_{50}$ 0.001 to 0.1 µM in assay (a).

Preferred Example compounds of the invention are those which exhibit inhibitory activity at lower concentrations within the $IC_{50}$ range shown above. For example, the compound of Example 8 exhibits $IC_{50}$ at *Leishmania major* (Lm) N-myristoyl transferase in the range of $IC_{50}$ 0.001 to 0.1 µM in assay (a).

Preferred Example compounds of the invention are those which exhibit inhibitory activity at lower concentrations within the $IC_{50}$ range shown above. For example, the compound of Example 7 exhibits $IC_{50}$ at *Trypanosoma brucei* (Tb) N-myristoyl transferase in the range of $IC_{50}$ 0.001 to 0.1 µM in assay (a).

Preferred Example compounds of the invention are those which exhibit inhibitory activity at lower concentrations within the $IC_{50}$ range shown above. For example, the compounds of Examples 7, 8, 17 and 18 exhibit $IC_{50}$ at *Plasmodium berghei* (Pb) N-myristoyl transferase in the range of $IC_{50}$ 0.00001 to 0.1 µM in assay (a).

The example compounds of the invention for which $EC_{50}$ values for *Plasmodium falciparum* (Pf) were measured using assay (b) all showed $EC_{50}$ for *Plasmodium falciparum* (Pf) in the range of $EC_{50}$ 0.001 to 10 µM. Some of those examples exhibited inhibitory activity at lower concentrations within the $EC_{50}$ range shown above. Preferred example compounds of the invention are those which exhibit inhibitory activity at lower concentrations within the $EC_{50}$ range shown above. For example, examples 7, 17.53, 56, 70, 77, 78, 85, 92, 94 exhibit $EC_{50}$ at *Plasmodium falciparum* (Pf 3D7 or NF54 strains) in the range of $IC_{50}$ 0.0001 to 0.1 µM in assay (b).

The example compounds of the invention for which $EC_{50}$ values for *Plasmodium berghei* (Pb) in the liver stage of the diseases were measured using assay (g) all showed $EC_{50}$) in the range of $EC_{50}$ 0.001 to 10 µM. Some of those examples exhibited inhibitory activity at lower concentrations within the $EC_{50}$ range shown above. Preferred example compounds of the invention are those which exhibit inhibitory activity at lower concentrations within the $EC_{50}$ range shown above. For example, examples 8, 17, 18, 29, 30, 35, 37, 39, 53, 55, 56, 62, 68, 70, 72, 76 and 92 exhibit $EC_{50}$ at *Plasmodium berghei* in the range of $IC_{50}$ 0.0001 to 0.1 µM in assay (g).

The example compounds of the invention for which a reduction in parasite burden in the mouse malaria model was measured using the protocol described at (c) above all showed effects following twice-daily administration at 5 or 10 mg/kg/dose. Preferred example compounds of the invention are those which lowered the parasite burden by more than 30%. For example, the examples 7, 17, 18 and 30 lowered the parasite burden by more than 30% in the mouse malaria model.

The example compounds of the invention for which $EC_{50}$ values were measured in the metabolic activity assay (assay (d)) all showed $EC_{50}$ for HeLa and/or BL-41 cells in the range of $EC_{50}$ 0.01 to 10 µM. Some of those examples exhibited inhibitory activity at lower concentrations within the $EC_{50}$ range shown above. For example, examples 17, 18, 30, 49, 50, 62, 63, 70, 76, 77, 83, 86, 94, 97, 100 exhibit $EC_{50}$ in the range of from 0.001 to 1 µM in assay (d) for HeLa and/or BL-41 cells; and examples 30, 49 and 50 exhibit $EC_{50}$ in the range of from 0.001 to 0.1 µM in assay (d) for HeLa and/or BL-41 cells.

Examples 30, 35, 49, and 50 of the invention for which $EC_{50}$ value was measured in the rhinovirus assay (assay (e)) exhibited $EC_{50}$ in the range of from 0.01 to 0.1 µM.

The invention claimed is:
1. An inhibitor of N-myristoyl transferase (NMT) which is a compound of formula (I) or a salt thereof,

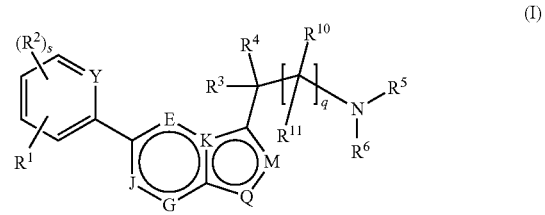

wherein:
Y is selected from the group consisting of —CH—, —C($R^2$)— and —N—;
$R^1$ is a group of formula —X-L-A;
X is selected from the group consisting of —O—, —N(H)— and —S—, or is absent;
L is selected from the group consisting of —(CHR$^{12}$)$_m$— and —(CHR$^{12}$)$_m$O—, or is absent;
m is 1, 2 or 3;
A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —OCH$_3$, —OCF$_3$, —CN, —C$_{1-6}$alkyl optionally substituted by up to 3 halogen, hydroxyl, or —OC$_{1-4}$alkyl groups, —S(O)C$_{1-4}$alkyl, —S(O)$_2$C$_{1-4}$alkyl, —C(O)N(R$^9$)$_2$, —C(O)N(R$^{13}$)C$_{1-4}$alkylOC$_{1-4}$alkyl, —C(O)N(C$_{1-4}$alkylOC$_{1-4}$alkyl)$_2$, —CH$_2$C(O)N(R$^9$)$_2$, —CH$_2$C(O)N(R$^{13}$)C$_{1-4}$alkylOC$_{1-4}$alkyl, —CH$_2$C(O)N(C$_{1-4}$alkylOC$_{1-4}$alkyl)$_2$, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —NHC(O)CF$_3$, —NHS(O)$_2$C$_{1-4}$alkyl, CH$_2$N(R$^{13}$)$_2$, CH$_2$N(R$^{13}$)C(O)C$_{1-4}$alkyl, CH$_2$N(R$^{13}$)S(O)$_2$C$_{1-4}$alkyl, —CH$_2$S(O)$_2$C$_{1-4}$alkyl, and CO$_2$H
s is 0, 1, 2, or 3;

each R² is independently selected from the group consisting of —F, —Cl, —Br, —OCH₃, —OCF₃, —CN, —C$_{1-4}$alkyl optionally substituted by up to 3 halogen or hydroxyl groups, —S(O)C$_{1-4}$alkyl, —S(O)₂C$_{1-4}$alkyl, —S(O)₂NHC$_{1-4}$alkyl, —S(O)₂N(C$_{1-4}$alkyl)₂, —NHC$_{1-4}$ alkyl, —N(C$_{1-4}$alkyl)₂, —NHC(O)C$_{1-4}$ alkyl, —NHC(O)CF₃, and —NHS(O)₂C$_{1-4}$alkyl;

E, J and G are each C(R⁷);

K is carbon;

Q is N(R⁸) and M is nitrogen;

q is 0 or 1;

R³ is hydrogen or methyl; R⁴ is hydrogen or methyl;

R⁵ is hydrogen or C$_{1-6}$alkyl optionally substituted by up to 3 —F, —Cl, —Br, —OH, —OCH₃, —OCF₃ or —CN groups; R⁶ is hydrogen or C$_{1-6}$alkyl optionally substituted by up to 3 —F, —Cl, —Br, —OH, —OCH₃, —OCF₃ or —CN groups; or the R⁵ and R⁶ groups and the N they are bonded to form a 4 to 7 membered non-aromatic heterocycle, the heterocycle optionally comprising 1 or 2 further heteroatoms selected from N, O and S, optionally substituted by up to 3 —F, —Cl, —Br, —OH, —OCH₃, —OCF₃ or —CN groups;

when present R¹⁰ is hydrogen or methyl;

when present R¹¹ is hydrogen or methyl;

or the R³ group and the R⁵ group and the intervening atoms form a 3 to 7 membered non-aromatic heterocycle composed of the intervening atoms and bond, or the intervening atoms and —(CHR$^a$)$_r$—; or the R¹⁰ group and the R⁵ group and the intervening atoms form a 3 to 7 membered non-aromatic heterocycle composed of the intervening atoms and —(CHR$^a$)$_r$—;

r is 1, 2, 3, 4 or 5; R$^a$ is hydrogen or methyl;

each R⁷ is independently selected from the group consisting of hydrogen, halogen, C$_{1-4}$alkoxy, and C$_{1-4}$alkyl optionally substituted with 1, 2 or 3 halogens; and R⁸ is selected from the group selected from hydrogen and C$_{1-4}$alkyl;

each R⁹ is independently selected from the group consisting of hydrogen and C$_{1-4}$alkyl, or two R⁹ groups and the N they are bonded to form a 4 to 7 membered non-aromatic heterocycle, the heterocycle optionally comprising 1 or 2 further heteroatoms selected from N, O and S; and each R¹² is independently selected from the group consisting of hydrogen, C$_{1-6}$alkyl optionally substituted by up to 3 —F, —Cl, —Br, I, —OH, —OCH₃, —OCF₃ or —CN groups, C$_{1-6}$alkenyl optionally substituted by up to 3 —F, —Cl, —Br, I, —OH, —OCH₃, —OCF₃ or —CN groups, and C$_{1-6}$alkynyl optionally substituted by up to 3 —F, —Cl, —Br, I, —OH, —OCH₃, —OCF₃ or —CN groups; and each R¹³ is independently selected from the group consisting of hydrogen and C$_{1-4}$alkyl.

2. An NMT inhibitor as claimed in claim 1, wherein X is selected from the group consisting of —O—, —N(H)— and —S—; and/or L is selected from the group consisting of —(CHR¹²)$_m$— and —(CHR¹²)$_m$O—.

3. An NMT inhibitor as claimed in claim 1, wherein the compound has the formula (IA)

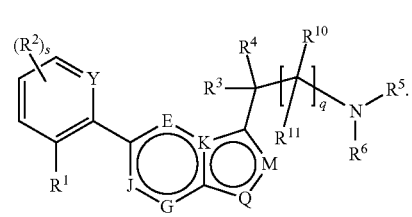

4. An NMT inhibitor as claimed in claim 1, wherein the compound has the formula (IB)

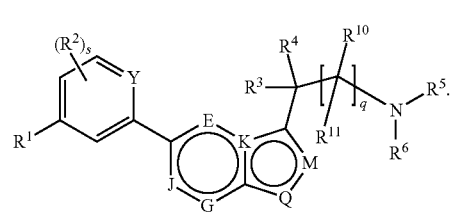

5. An NMT inhibitor as claimed in claim 1, wherein q is 1, R¹⁰ is hydrogen and R¹¹ is hydrogen.

6. An NMT inhibitor as claimed in claim 1, wherein A is an aromatic carbocycle or heterocycle selected from the group consisting of phenyl, pyridinyl, quinolinyl, imidazolyl, benzimidazolyl, pyrazolyl, thiazolyl, 1,2,3-triazolyl and 1,2,4-triazolyl, said aromatic carbocycle or heterocycle being optionally substituted with 1, 2, or 3 groups independently selected from the group consisting of —C$_{1-4}$alkyl, wherein each —C$_{1-4}$alkyl is optionally substituted by up to 3 halogen, hydroxyl or —OC$_{1-4}$alkyl groups; —C(O)N(R⁹)₂ wherein the two R⁹ groups and the N they are bonded to form a 4 to 7 membered non-aromatic heterocycle, the heterocycle optionally comprising 1 or 2 further heteroatoms selected from N, O and S; —CH₂C(O)N(R⁹)₂; —C(O)N(R¹³)C$_{1-4}$alkylOC$_{1-4}$alkyl, —CH₂N(R¹³)₂, and CH₂N(R¹³)S(O)₂C$_{1-4}$alkyl.

7. An NMT inhibitor as claimed in claim 1, wherein Y is —CH— or —C(R²).

8. An NMT inhibitor as claimed in claim 1, wherein X is —O— and L is —(CH₂)$_m$.

9. An NMT inhibitor as claimed in claim 1, wherein R⁷ is hydrogen or methyl, and/or R⁸ is hydrogen or methyl.

10. An NMT inhibitor as claimed in claim 1, wherein q is 1.

11. An NMT inhibitor as claimed in claim 1, wherein A is substituted with 1, 2, or 3 groups, and at least one of the substituents is —C(O)N(R⁹)₂, —C(O)N(R¹³)C$_{1-4}$alkylOC$_{1-4}$ alkyl, —C(O)N(C$_{1-4}$alkylOC$_{1-4}$alkyl)₂, —CH₂C(O)N(R⁹)₂, —CH₂C(O)N(R¹³)C$_{1-4}$alkylOC$_{1-4}$alkyl, —CH₂C(O)N(C$_{1-4}$alkylOC$_{1-4}$alkyl)₂, —NHC(O)C$_{1-4}$alkyl, —NHC(O)CF₃, CH₂N(R¹³)C(O)C$_{1-4}$alkyl, CH₂N(R¹³)S(O)₂C$_{1-4}$ alkyl, or CO₂H.

12. An NMT inhibitor as claimed in claim 1, wherein the compound has the formula (IA*)

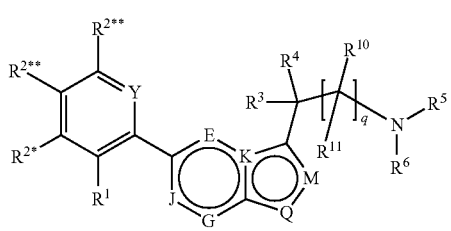

(IA*)

wherein each $R^{2*}$ is independently selected from the group consisting of —F, —Cl, —Br, —OCH$_3$, —OCF$_3$, —CN, —C$_{1-4}$alkyl optionally substituted by up to 3 halogen or hydroxyl groups, —S(O)C$_{1-4}$alkyl, —S(O)$_2$C$_{1-4}$alkyl, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —NHC(O)CF$_3$, and —NHS(O)$_2$C$_{1-4}$alkyl; and $R^{2**}$ is selected from the group consisting of —H, —F, —Cl, —Br, —OCH$_3$, —OCF$_3$, —CN, —C$_{1-4}$alkyl optionally substituted by up to 3 halogen or hydroxyl groups, —S(O)C$_{1-4}$alkyl, —S(O)$_2$C$_{1-4}$alkyl, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —NHC(O)CF$_3$, and —NHS(O)$_2$C$_{1-4}$alkyl.

13. An NMT inhibitor as claimed in claim 1, with the proviso the compound is not an NMT inhibitor where A is substituted with 1, 2, or 3 groups, and at least one of the substituents is —C(O)N(R$^9$)$_2$, —C(O)N(R$^{13}$)C$_{1-4}$alkylOC$_{1-4}$ alkyl, —C(O)N(C$_{1-4}$alkylOC$_{1-4}$alkyl)$_2$, —CH$_2$C(O)N(R$^9$)$_2$, —CH$_2$C(O)N(R$^{13}$)C$_{1-4}$alkylOC$_4$alkyl, —CH$_2$C(O)N(C$_{1-4}$alkylOC$_{1-4}$alkyl)$_2$, —NHC(O)C$_{1-4}$alkyl, —NHC(O)CF$_3$, CH$_2$N(R$^{13}$)C(O)C$_{1-4}$alkyl, CH$_2$N(R$^{13}$)S(O)$_2$C$_{1-4}$alkyl, or CO$_2$H.

14. An NMT inhibitor as claimed in claim 1, wherein s is 0, 1, 2 or 3, and, where present, each R$^2$ is independently selected from the group consisting of —F, —Cl, —Br, —OCH$_3$, —OCF$_3$, —CN, and —C$_{1-4}$alkyl optionally substituted by up to 3 halogen or hydroxyl groups.

15. An NMT inhibitor as claimed in claim 6, wherein A is selected from the group consisting of phenyl; 3-pyridinyl; 4-quinolinyl; 1-imidazolyl, said imidazolyl being optionally substituted by 1 or 2 methyl groups; 1-benzimidazolyl; optionally substituted 5-thiazolyl; optionally substituted 1,2,4-triazol-1-yl, optionally substituted 1,2,4-triazol-4-yl, optionally substituted 1,2,4-triazol-3-yl and optionally substituted 1,2,3-triazol-4-yl.

16. An NMT inhibitor as claimed in claim 1, wherein said compound is N,N-dimethyl-1-(5-(2-(pyridin-3-ylmethoxy)phenyl)-1H-indazol-3-yl)methanamine;
N,N-dimethyl-1-(5-(2-phenethoxyphenyl)-1H-indazol-3-yl)methanamine;
N,N-dimethyl-1-(5-(2-(quinolin-4-ylmethoxy)phenyl)-1H-indazol-3-yl)methanamine;
N,N-dimethyl-1-(5-(2-(2-(pyridin-3-yl)ethoxy)phenyl)-1H-indazol-3-yl)methanamine;
1-(5-(2-(1H-imidazol-1-yl)ethoxy)phenyl)-1H-indazol-3-yl)-N,N-dimethylmethanamine;
N,N-dimethyl-1-(5-(2-benzyloxyphenyl)-1H-indazol-3-yl)methanamine;
1-(5-(4-fluoro-2-(2-(1,3,5-trimethyl-1H-pyrazol-4-yl)ethoxy)phenyl)-1H-indazol-3-yl)-N,N-dimethylmethanamine;
N,N-dimethyl-1-(5-(4-fluoro-2-(2-(pyridin-3-yl)ethoxy)phenyl)-1H-indazol-3-yl)methanamine;
N,N-dimethyl-1-(5-(4-fluoro-2-(pyridin-3-ylmethoxy)phenyl)-1H-indazol-3-yl)methanamine;
1-(5-(2-(4-fluoro-2-(1H-imidazol-1-yl)ethoxy)phenyl)-1H-indazol-3-yl)-N,N-dimethylmethanamine;
1-(5-(2-(2-(1H-benzo[d]imidazol-1-yl)ethoxy)-4-fluorophenyl)-1H-indazol-3-yl)-N,N-dimethylmethanamine;
1-(5-(2-(2-(1H-1,2,4-triazol-1-yl)ethoxy)-4-fluorophenyl)-1H-indazol-3-yl)-N,N-dimethylmethanamine;
1-(5-(2-(2-(2,4-dimethyl-1H-imidazol-1-yl)ethoxy)-4-fluorophenyl)-1H-indazol-3-yl)-N,N-dimethylmethanamine;
N,N-dimethyl-1-(5-(3-(pyridin-3-ylmethoxy)phenyl)-1H-indazol-3-yl)methanamine;
N,N-dimethyl-1-(5-(3-(pyridin-4-ylmethoxy)phenyl)-1H-indazol-3-yl)methanamine;
1-(5-(2-(3-(1H-imidazol-1-yl)ethoxy)phenyl)-1H-indazol-3-yl)-N,N-dimethylmethanamine;
1-(5-(4-fluoro-2-(2-(1,3,5-trimethyl-1H-pyrazol-4-yl)ethoxy)phenyl)-1-methyl-1H-indazol-3-yl)-N,N-dimethylmethanamine;
1-(5-(4-fluoro-2-(2-(1,3,5-trimethyl-1H-pyrazol-4-yl)ethoxy)phenyl)-1-methyl-1H-indazol-3-yl)-N-methylmethanamine;
1-(5-(2-(2-(1H-1,2,4-triazol-1-yl)ethoxy)-4-fluorophenyl)-1-methyl-1H-indazol-3-yl)-N,N-dimethylmethanamine;
1-(5-(4-fluoro-2-(2-(1,3,5-trimethyl-1H-pyrazol-4-yl)ethoxy)phenyl)-1-methyl-1H-indazol-3-yl)-N,N-dimethylmethanamine HCl salt;
1-(5-(2-(2-(1H-imidazol-1-yl)ethoxy)-4-fluorophenyl)-1-methyl-1H-indazol-3-yl)-N,N-dimethylmethanamine;
1-(5-(2-(2-(2,4-dimethylthiazol-5-yl)ethoxy)-4-fluorophenyl)-1-methyl-1-indazol-3-yl)-N,N-dimethylmethanamine;
1-(5-(2-(2-(3,5-dimethyl-1H-pyrazol-4-yl)ethoxy)-4-fluorophenyl)-1-methyl-1H-indazol-3-yl)-N,N-dimethylmethanamine;
1-(5-(2-(2-(4-methylthiazol-5-yl)ethoxy)-4-fluorophenyl)-1-methyl-1H-indazol-3-yl)-N,N-dimethylmethanamine;
1-(5-(4-fluoro-2-(2-(4-methylthiazol-5-yl)ethoxy)phenyl)-1-methyl-1H-indazol-3-yl)ethanamine;
1-(5-(4-fluoro-2-(2-(4-methylthiazol-5-yl)ethoxy)phenyl)-1-methyl-1H-indazol-3-yl)-N,N-dimethylethanamine;
1-(5-(5-fluoro-2-(2-(1,3,5-trimethyl-1H-pyrazol-4-yl)ethoxy)phenyl)-1-methyl-1H-indazol-3-yl)-N,N-dimethylmethanamine;
1-(5-(3-fluoro-2-(2-(1,3,5-trimethyl-1H-pyrazol-4-yl)ethoxy)phenyl)-1-methyl-1H-indazol-3-yl)-N,N-dimethylmethanamine;
(5-(4-fluoro-2-(2-(1,3,5-trimethyl-1H-pyrazol-4-yl)ethoxy)phenyl)-1-methyl-1H-indazol-3-yl)methanamine;
1-(5-(5-fluoro-2-(2-(1,3,5-trimethyl-1H-pyrazol-4-yl)ethoxy)phenyl)-1-methyl-1H-indazol-3-yl)methanamine;
1-(5-(3-fluoro-2-(2-(1,3,5-trimethyl-1H-pyrazol-4-yl)ethoxy)phenyl)-1-methyl-1H-indazol-3-yl)methanamine;
1-(5-(5-fluoro-2-(2-(1,3,5-trimethyl-1H-pyrazol-4-yl)ethoxy)phenyl)-1-methyl-1H-indazol-3-yl)-N-methylmethanamine;

1-(5-(3-fluoro-2-(2-(1,3,5-trimethyl-1H-pyrazol-4-yl)
  ethoxy)phenyl)-1-methyl-1H-indazol-3-yl)-N-methyl-
  methanamine;
1-(5-(4-fluoro-2-(2-(4-methylthiazol-5-yl)ethoxy)phe-
  nyl)-1H-indazol-3-yl)-N,N-dimethylmethanamine;
1-(5-(3, 4-difluoro-2-(2-(1,3,5-trimethyl-1H-pyrazol-4-
  yl)ethoxy)phenyl)-1-methyl-1H-indazol-3-yl)-N,N-di-
  methylmethanamine;
1-(5-(3, 4-difluoro-2-(2-(1,3,5-trimethyl-1H-pyrazol-4-
  yl)ethoxy)phenyl)-1-methyl-1H-indazol-3-yl)-N-meth-
  ylmethanamine;
1-(5-(3-fluoro-2-((2-(1,3,5-trimethyl-1H-pyrazol-4-yl)
  oct-7-yn-1-yl)oxy)phenyl)-1-methyl-1H-indazol-3-yl)-
  N,N-dimethylmethanamine;
[2-(5-{4-fluoro-2-[2-(1,3,5-trimethyl-1H-pyrazol-4-yl)
  ethoxy]phenyl}-1-methyl-1H-indazol-3-yl)ethyl]
  (methyl)amine;
[2-(5-{4-fluoro-2-[2-(1,3,5-trimethyl-1H-pyrazol-4-yl)
  ethoxy]phenyl}-1H-indazol-3-yl)ethyl](methyl)amine;

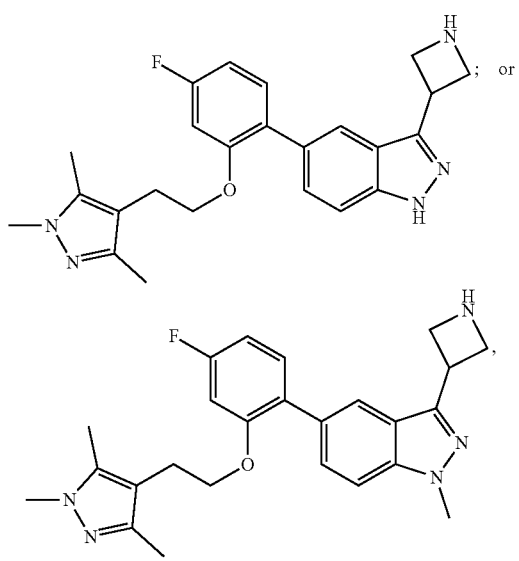

or a salt of any one thereof.

17. A pharmaceutical composition which comprises an NMT inhibitor as claimed in claim 1 and a pharmaceutically acceptable carrier.

18. An NMT inhibitor as defined in claim 1, wherein A is a 6-10-membered aromatic carbocycle or a 5-10-membered aromatic heterocycle, said aromatic carbocycle or heterocycle being optionally substituted with 1, 2, or 3 substituents each independently selected from the group consisting of —F, —Cl, —Br, —OCH$_3$, —OCF$_3$, —CN, —C$_{1-6}$alkyl optionally substituted by up to 3 halogen, hydroxyl, or —OC$_{1-4}$alkyl groups, —S(O)C$_{1-4}$alkyl, —S(O)$_2$C$_{1-4}$alkyl, —C(O)N(R$^9$)$_2$, —CH$_2$C(O)N(R$^9$)$_2$, —S(O)$_2$NHC$_{1-4}$alkyl, —S(O)$_2$N(C$_{1-4}$alkyl)$_2$, —NHC$_{1-4}$alkyl, —N(C$_{1-4}$alkyl)$_2$, —NHC(O)C$_{1-4}$alkyl, —CH$_2$NHC(O)C$_{1-4}$alkyl, —NHC(O)CF$_3$ and NHS(O)$_2$C$_{1-4}$alkyl.

19. An NMT inhibitor as claimed in claim 1, which comprises an isotope atom or in which L is —(CHR$^{12}$)$_m$— or —(CHR$^{12}$)$_m$O—, and one R$^{12}$ is a terminal C$_{1-6}$alkynyl optionally substituted by up to 3 —F, —Cl, —Br, I, —OH, —OCH$_3$, —OCF$_3$ or —CN groups.

20. An NMT inhibitor as claimed in claim 3, wherein X is —O— and L is —(CH$_2$)$_m$.

21. An NMT inhibitor as claimed in claim 1, wherein said compound is 1-(5-(3, 4-difluoro-2-(2-(1,3,5-trimethyl-1H-pyrazol-4-yl)ethoxy)phenyl)-1-methyl-1H-indazol-3-yl)-N,N-dimethylmethanamine or a salt thereof.

22. An NMT inhibitor as claimed in claim 1, wherein said compound is 1-(5-(3, 4-difluoro-2-(2-(1,3,5-trimethyl-1H-pyrazol-4-yl)ethoxy)phenyl)-1-methyl-1H-indazol-3-yl)-N,N-dimethylmethanamine.

23. A pharmaceutical composition as claimed in claim 17, wherein said compound is 1-(5-(3, 4-difluoro-2-(2-(1,3,5-trimethyl-1H-pyrazol-4-yl)ethoxy)phenyl)-1-methyl-1H-indazol-3-yl)-N,N-dimethylmethanamine or a salt thereof.

24. A pharmaceutical composition as claimed in claim 17, wherein said compound is 1-(5-(3, 4-difluoro-2-(2-(1,3,5-trimethyl-1H-pyrazol-4-yl)ethoxy)phenyl)-1-methyl-1H-indazol-3-yl)-N,N-dimethylmethanamine.

\* \* \* \* \*